(12) United States Patent
Kischel et al.

(10) Patent No.: US 11,925,684 B2
(45) Date of Patent: Mar. 12, 2024

(54) COMPOSITIONS COMPRISING CROSS-SPECIES-SPECIFIC ANTIBODIES AND USES THEREOF

(71) Applicant: AMGEN RESEARCH (MUNICH) GMBH, Munich (DE)

(72) Inventors: Roman Kischel, Munich (DE); Tobias Raum, Munich (DE); Bernd Schlereth, Munich (DE); Doris Rau, Munich (DE); Ronny Cierpka, Munich (DE); Peter Kufer, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 634 days.

(21) Appl. No.: 16/116,293

(22) Filed: Aug. 29, 2018

(65) Prior Publication Data
US 2019/0070290 A1    Mar. 7, 2019

Related U.S. Application Data

(63) Continuation of application No. 13/567,672, filed on Aug. 6, 2012, now abandoned, which is a continuation of application No. 12/083,351, filed as application No. PCT/EP2006/009782 on Oct. 10, 2006, now Pat. No. 8,236,308.

(60) Provisional application No. 60/724,781, filed on Oct. 11, 2005.

(51) Int. Cl.
| C07K 16/28 | (2006.01) |
|---|---|
| A61K 39/395 | (2006.01) |
| A61K 45/06 | (2006.01) |
| C07K 16/30 | (2006.01) |
| C07K 16/40 | (2006.01) |
| C07K 16/46 | (2006.01) |
| A61K 39/00 | (2006.01) |

(52) U.S. Cl.
CPC ........ *A61K 39/39558* (2013.01); *A61K 45/06* (2013.01); *C07K 16/2809* (2013.01); *C07K 16/30* (2013.01); *C07K 16/40* (2013.01); *C07K 16/468* (2013.01); *A61K 2039/505* (2013.01); *C07K 2317/31* (2013.01); *C07K 2317/34* (2013.01); *C07K 2317/56* (2013.01); *C07K 2317/622* (2013.01)

(58) Field of Classification Search
None
See application file for complete search history.

(56) References Cited

U.S. PATENT DOCUMENTS

| 5,260,203 A | 11/1993 | Ladner et al. |
|---|---|---|
| 5,714,350 A | 2/1998 | Co et al. |
| 6,407,213 B1 | 6/2002 | Carter et al. |
| 8,236,308 B2 | 8/2012 | Kischel et al. |
| 2002/0142000 A1 | 10/2002 | Digan et al. |
| 2002/0147312 A1 | 10/2002 | O'Keefe et al. |
| 2005/0201994 A1 | 9/2005 | Korman et al. |
| 2006/0034835 A1 | 2/2006 | Adams et al. |
| 2006/0084264 A1 | 4/2006 | Baskaran et al. |
| 2006/0210564 A1 | 9/2006 | Kumagai et al. |

FOREIGN PATENT DOCUMENTS

| EP | 0623679 A1 | 11/1994 |
|---|---|---|
| WO | 1991/09968 A1 | 7/1991 |
| WO | 1992/10755 A1 | 6/1992 |
| WO | WO-1995/16037 | 6/1995 |
| WO | 1998/52976 A1 | 11/1998 |
| WO | WO-1999/54440 A1 | 10/1999 |
| WO | WO-1999/60023 A1 | 11/1999 |
| WO | 2000/34317 A2 | 6/2000 |
| WO | 2002/66514 A2 | 8/2002 |
| WO | 2002/79415 A2 | 10/2002 |
| WO | 2004/106381 A1 | 12/2004 |
| WO | WO-2004/106380 A2 | 12/2004 |
| WO | WO-2004/106383 A1 | 12/2004 |
| WO | WO-2005/061547 A2 | 7/2005 |
| WO | WO-2005/077982 A1 | 8/2005 |
| WO | WO-2005/118635 A2 | 12/2005 |
| WO | WO-2006/084264 A2 | 8/2006 |
| WO | WO-2007/008943 A2 | 1/2007 |
| WO | 2007/042261 A2 | 4/2007 |

(Continued)

OTHER PUBLICATIONS

Abramowicz et al., High-dose glucocorticosteroids increase the procoagulant effects of OKT3, *Kidney Int.* 46:1596-602 (1994).

(Continued)

*Primary Examiner* — Zachary S Skelding
(74) *Attorney, Agent, or Firm* — MARSHALL, GERSTEIN & BORUN LLP

(57) ABSTRACT

The present invention relates to uses of bispecific antibodies exhibiting cross-species specificity for evaluating the in vivo safety and/or activity and/or pharmacokinetic profile of the same in non-human species and humans. The present invention moreover relates to methods for evaluating the in vivo safety and/or activity and/or pharmacokinetic profile of said bispecific antibodies exhibiting cross-species specificity. The present invention also relates to methods of measuring the biological activity and/or efficacy of such bispecific antibodies exhibiting cross-species specificity. In addition, the present invention relates to pharmaceutical compositions comprising bispecific single chain antibodies exhibiting cross-species specificity and to methods for the preparation of pharmaceutical compositions comprising said bispecific single chain antibodies exhibiting cross-species specificity for the treatment of diseases.

16 Claims, 41 Drawing Sheets

Figure 3:
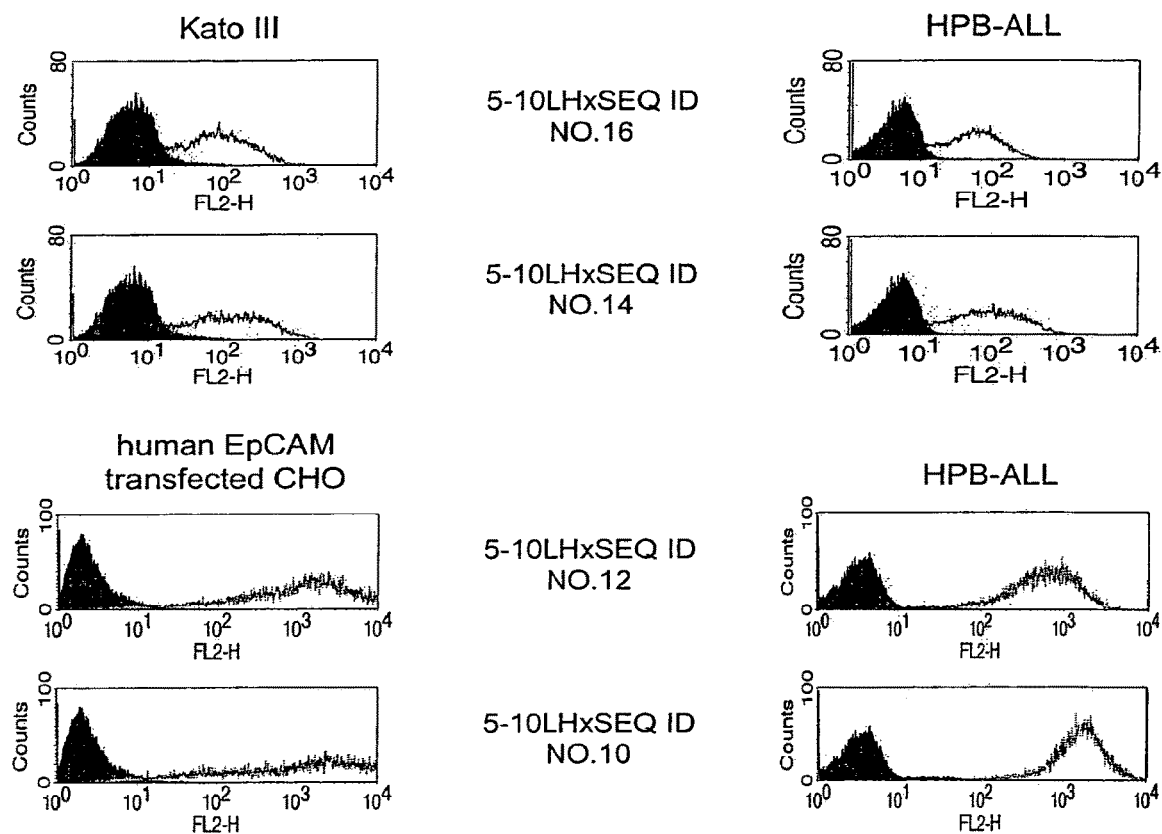

Specification includes a Sequence Listing.

(56) References Cited

FOREIGN PATENT DOCUMENTS

| WO | 2008/119567 A2 | 10/2008 |
| WO | WO-2010/042904 A2 | 4/2010 |
| WO | 2014/106383 A1 | 7/2014 |
| WO | 2016/030819 A1 | 3/2016 |

OTHER PUBLICATIONS

Approved Labeling for cetuximab, pp. 1-18, 2004, Imclone Systems Incorporated and Bristol-Myers Squibb Company.

Baca et al., Antibody humanization using monovalent phage display, *J. Biol. Chem.* 272:10678-84 (1997).

BD Bioscences package inset for SP34 antibody dated Dec. 27, 2001, p. 1.

Bevilacqua et al., Endothelial-leukocyte adhesion molecules in human disease, *Annu. Rev. Med.* 45:361-78 (1994).

Bibollet-Ruche et al., The quality of chimpanzee T-cell activation and simian immunodeficiency virus/human immunodeficiency virus susceptibility achieved via antibody-mediated T-cell receptor/CD3 stimulation is a function of the anti-CD3 antibody isotype, *J. Virol.* 82:10271-8 (2008).

Bortoletto et al., Optimizing anti-CD3 affinity for effective T cell targeting against tumor cells, *Eur. J. Immunol.* 32:3102-7 (2002).

Brok et al., An extensive monoclonal antibody panel for the phenotyping of leukocyte subsets in the common marmoset and the cotton-top tamarin, *Cytometry.* 45:294-303 (2001).

Buckner et al., Priming B cell-mediated anti-HIV envelope responses by vaccination allows for the long-term control of infection in macaques exposed to a R5-tropic SHIV, *Virology.* 320:167-80 (2004).

Burlingham, "Critical analysis of monoclonal antibody therapy in transplantation," (1992), *CRC Press,* Chapter 1, pp. 1 and 10.

Buysmann et al., Activation and increased expression of adhesion molecules on peripheral blood lymphocytes is a mechanism for the immediate lymphocytopenia after administration of OKT3, *Blood.* 87:404-411 (1996).

Chatenoud, CD3-specific antibodies restore self-tolerance: mechanisms and clinical applications, *Curr. Opin. Immunol.* 17:632-7 (2005).

Colman, Effects of amino acid sequence changes on antibody-antigen interactions, *Res. Immunol.* 145:33-6 (1994).

Office Action Received in the corresponding European Patent Application No. EP 06 806 155.5, dated Mar. 24, 2010.

Davis et al., Affinity improvement of single antibody VH domains: residues in all three hypervariable regions affect antigen binding, *Immunotechnology.* 2:169-79 (1996).

Dhanji et al., The low affinity Fc receptor for IgG functions as an effective cytolytic receptor for self-specific CD8 T cells, *J. Immunol.* 174:1253-8 (2005).

Fagerholm et al., Lck tyrosine kinase is important for activation of the CD11a/CD18-integrins in human T lymphocytes, *Eur. J. Immunol.* 32:1670-8 (2002).

Flieger et al., A bispecific single-chain antibody directed against EpCAM/CD3 in combination with the cytokines interferon alpha and interleukin-2 efficiently retargets T and CD3+CD56+ natural-killer-like T lymphocytes to EpCAM-expressing tumor cells, *Cancer Immunol. Immunother.* 49:441-8 (2000).

Gallart et al., Anti-Sia-lb (anti-Gd) cold agglutinins bind the domain NeuNAc alpha2-3Gal in sialyl Lewis(x), sialyl Lewis(a), and related carbohydrates on nucleated cells and in soluble cancer-associated mucins, *Blood.* 90:1576-87 (1997).

Giavedoni et al., Phenotypic changes associated with advancing gestation in maternal and fetal baboon lymphocytes, *J. Reprod. Immunol.* 64:121-32 (2004).

Gil et al., Recruitment of Nck by CD3 epsilon reveals a ligand-induced conformational change essential for T cell receptor signaling and synapse formation, *Cell.* 109:901-12 (2002).

Grun et al., Research Report, MDC Berlin-Buch, 2002, p. 126.

Harlow et al., Antibodies, A Laboratory Manual, Cold Spring Harbor Laboratory, pp. 567-569 (1988).

Hexham et al., Influence of relative binding affinity on efficacy in a panel of anti-CD3 scFv immunotoxins, *Mol. Immunol.* 38:397-408 (2001).

Holt et al., Domain antibodies: proteins for therapy, *Trends Biotechnol.* 21:484-90 (2003).

International Search Report for PCT International Application No. PCT/EP2006/009782, dated Nov. 7, 2007 (6 pgs.).

Jacobs et al., Efficiency of T cell triggering by anti-CD3 monoclonal antibodies (mAb) with potential usefulness in bispecific mAb generation, *Cancer Immunol. Immunother.* 44:257-64 (1997).

Kerr et al., Heteroconjugate antibody-directed killing of autologous human renal carcinoma cells by in vitro-activated lymphocytes, *J. Immunol.* 144:4060-7 (1990).

Knechtle et al., FN18-CRM9 immunotoxin promotes tolerance in primate renal allografts, *Transplantation.* 63:1-6 (1997).

Koulova et al., Identification of the anti-CD3-unresponsive subpopulation of CD4+, CD45RA+ peripheral T lymphocytes, *J. Immunol.* 145:2035-43 (1990).

Kroesen et al., Approaches to lung cancer treatment using the CD3 x EGP-2-directed bispecific monoclonal antibody BIS-1, *Cancer Immunol. Immunother.* 45:203-6 (1997).

Kroesen et al., Phase I study of intravenously applied bispecific antibody in renal cell cancer patients receiving subcutaneous interleukin 2, *Br. J. Cancer.* 70:652-61 (1994).

Krummel et al., Thirty-six views of T-cell recognition, *Philos. Trans. R. Soc. Lond. B. Biol. Sci.* 355:1071-6 (2000).

Kufer et al., Construction and biological activity of a recombinant bispecific single-chain antibody designed for therapy of minimal residual colorectal cancer, *Cancer Immunol. Immunother.* 45:193-7 (1997).

Lammers et al., Monoclonal antibody 9C4 recognizes epithelial cellular adhesion molecule, a cell surface antigen expressed in early steps of erythropoiesis, *Experimental Hematology.* 30:537-545 (2002).

Loffler et al., A recombinant bispecific single-chain antibody, CD19 x CD3, induces rapid and high lymphoma-directed cytotoxicity by unstimulated T lymphocytes, *Blood.* 95:2098-103 (2000).

Lutterbuese et al., European Journal of Cancer, (Oct., 1999) vol. 35, No. Suppl. 5, pp. S58, Abstract 112.

Luwor et al., The tumor-specific de2-7 epidermal growth factor receptor (EGFR) promotes cells survival and heterodimerizes with the wild-type EGFR, *Oncogene.* 23:6095-104 (2004).

Mack et al., Biologic properties of a bispecific single-chain antibody directed against 17-1A (EpCAM) and CD3: tumor cell-dependent T cell stimulation and cytotoxic activity, *J. Immunol.* 158:3965-70 (1997).

Mamot et al., Epidermal growth factor receptor (EGFR)-targeted immunoliposomes mediate specific and efficient drug delivery to EGFR- and EGFRvIII-overexpressing tumor cells, *Cancer Res.* 63:3154-61 (2003).

Mansfield et al., Marmoset models commonly used in biomedical research, *Comp. Med.* 53:383-92 (2003).

McDyer et al., IL-2 receptor blockade inhibits late, but not early, IFN-gamma and CD40 ligand expression in human T cells: disruption of both IL-12-dependent and -independent pathways of IFN-gamma production, *J. Immunol.* 169:2736-46 (2002).

McLaughlin et al., An EGP-2/Ep-CAM-expressing transgenic rat model to evaluate antibody-mediated immunotherapy, *Cancer Immunol. Immunother.* 48:303-311 (1999).

Modjtahedi et al., Targeting of cells expressing wild-type EGFR and type-III mutant EGFR (EGFRvIII) by anti-EGFR MAb ICR62: a two-pronged attack for tumour therapy, *Int. J. Cancer.* 105:273-80 (2003).

Mourad et al., Humanized IgG1 and IgG4 anti-CD4 monoclonal antibodies: effects on lymphocytes in the blood, lymph nodes, and renal allografts in cynomolgus monkeys, *Transplantation.* 65:632-41 (1998).

Nevell et al., In Vivo T-Cell ablation by a holo-immunotoxin directed at human CD3, *Proceedings of the National Academy of Sciences of USA, National Academy of Science, Washington D.C.,* 89:2585-9 (1992).

(56) References Cited

OTHER PUBLICATIONS

Offner et al., Epithelial tight junction proteins as potential antibody targets for pancarcinoma therapy, *Cancer Immunol. Immunother.* 54:431-45 (2005).
Perez-Soler et al., HER1/EGFR inhibitor-associated rash: future directions for management and investigation outcomes from the HER1/EGFR inhibitor rash management forum, *Oncologist.* 10:345-56 (2005).
Pritsch et al., Can isotype switch modulate antigen-binding affinity and influence clonal selection? *Eur. J. Immunol.* 30:3387-95 (2000).
Rogers et al., Identification and characterization of macaque CD89 (immunoglobulin A Fc receptor), *Immunology.* 113:178-86 (2004).
Rudikoff et al., Single amino acid substitution altering antigen-binding specificity, *Proc. Natl. Acad. Sci. USA.* 79:1979-83 (1982).
Salmeron et al., A confirmational epitope expressed upon associate of CD3-Epsilon with either CD3-Delta or CD3-gamma is the main target for recognition by anti-CD3 monoclonal antibodies, *Journal of Immunol.* 147:3047-52 (2006).
Santis et al., Regulation of tumor necrosis factor (TNF)-alpha synthesis and TNF receptors expression in T lymphocytes through the CD2 activation pathway, *Eur. J. Immunol.* 22:3155-60 (1992).
Schlereth et al., Eradication of tumors from a human colon cancer cell line and from ovarian cancer metastases in immunodeficient mice by a single-chain Ep-CAM-/CD3-bispecific antibody construct, *Cancer Res.* 65:2882-9 (2005).
Schlereth et al., T-cell activation and B-cell depletion in chimpanzees treated with a bispecific anti-CD19/anti-CD3 single-chain antibody construct, *Cancer Immunol. Immunother.* 55:503-14 (2006).
Schmidt et al., Epidermal growth factor receptor signaling intensity determines intracellular protein interactions, ubiquitination, and internalization, *Proc. Natl. Acad. Sci. USA.* 100:6505-10 (2003).
Segaert et al., Clinical signs, pathophysiology and management of skin toxicity during therapy with epidermal growth factor receptor inhibitors, *Ann. Oncol.* 16:1425-33 (2005).
Summary: Methods used for the sequencing of SP34, sequence data relating to antibody SP34 with alignments, Opposition document D17, pp. 1-4, dated Mar. 22, 2013.
Szymczak et al., The CD3epsilon proline-rich sequence, and its interaction with Nck, is not required for T cell development and function, *J. Immunol.* 175:270-5 (2005).
The U.S. Department of Health and Human Services Food and Drug Administration, Center for Biologics Evaluation and Research, "Points to consider in the manufacture and testing of monoclonal antibody products for human use," pp. 1-50, Feb. 28, 1997.
Tonbo biosciences, "FITC anti-human CD3 (OKT3)" technical data sheet, 2013, p. 1 (Year 2013).
Traunecker et al., Bispecific single chain molecules (Janusins) target cytotoxic lymphocytes on HIV infected cells, *EMBO. J.* 10:3655-9 (1991).
Vajdos et al., Comprehensive functional maps of the antigen-binding site of an anti-ErbB2 antibody obtained with shotgun scanning mutagenesis, *J. Mol. Biol.* 320:415-428 (2002).
Weiner et al., The role of T cell activation in anti-CD3 x antitumor bispecific antibody therapy, *J. Immunol.* 152:2385-92 (1994).
Wolf et al., BiTEs: bispecific antibody constructs with unique anti-tumor activity, *Drug Discov. Today.* 10:1237-44 (2005).
Yoshino et al., Upgrading of flow cytometric analysis for absolute counts, cytokines and other antigenic molecules of cynomolgus monkeys (*Macaca fascicularis*) by using anti-human cross-reactive antibodies, *Exp. Anim.* 49:97-110 (2000).
Mack et al., A small bispecific antibody construct expressed as a functional single-chain molecule with high tumor cell cytotoxicity, Proc. Natl. Acad. Sci. USA., 92:7021-7025 (1995).
Milstein et al., Continuous cultures of fused cells secreting antibody of predefined specificity, Nature, 256:495-497 (1975).
Naundorf et al., In vitro and in vivo activity of MT201, a fully human monoclonal antibody for pancarcinoma treatment, Int. J. Cancer, 100:101-110 (2002).

Nooij et al., Polymorphism for RhT3, a CD3-like cell surface antigen, expressed on rhesus monkey T lymphocytes, Immunology, 59(4):611-620 (1986).
Passlick et al., The 17-1A antigen is expressed on primary, metastatic and disseminated non-small cell lung carcinoma cells, Int. J. Cancer, 87:548-552 (2000).
Pfeiffer et al., Lipopolysaccharide and ceramide docking to CD14 provokes ligand-specific receptor clustering in rafts, Eur. J. Immunol., 31:3153-3164 (2001).
Report from Patent Seekers.
Request for correction of the decision.
Rogers et al., IgG Fc Receptor III Homologues in Nonhuman Primate Species: Genetic Characterization and Li and Interactions, J. Immunol., 177:3848-3856 2006.
Sancho et al., CD3-zeta surface expression is required for CD4-p56lck-mediated upregulation of T cell antigen receptor-CD3 signaling in T cells, J. Biol. Chem., 267:7871-7879 (1992).
Sandusky et al., Use of monoclonal antibodies to human lymphocytes to identify lymphocyte subsets in lymph nodes of the rhesus monkey and the dog, J. Med. Primatol., 15:441-451 (1986).
Schlereth et al., T-cell activation and B-cell depletion in chimpanzees treated with a bispecific anti-CD19/anti-CD3 single-chain antibody construct, Cancer Immunol. Immunother., 20:1-12 (2005).
Sequence alignment of SP34 and CRIS-7 to SEQ ID Nos. 2, 110, 168 and 6, 8 respectively.
Sequence data relating to antibody SP34.
Sequence of SP34.
SP34 binding experiments prepared by F. Hoffmann-La Roche AG.
SP34 product insert.
Szala et al., Molecular cloning of cDNA for the carcinoma-associated antigen GA733-2, Proc. Natl. Acad. Sci. USA., 87:3542-3546 (1990).
Technical data sheet for SP34-2 (purified mouse anti-human CD3).
Technical report prepared by Janssen Biotech Inc.
Tunnacliffe et al., The majority of human CD3 epitopes are conferred by the epsilon chain, Int. Immunol. 1 (5):546-550 (1989).
Uda et al., CD3 polymorphism in cynomolgus monkeys (*Macaca fascicularis*), J. Med Primatol., 30:141-147 (2001).
Uda et al., Detection of CD3epsilon polymorphism in cynomolgus monkeys by a method based on RFLP, J. Med. Primatol., 33:34-37 (2004).
Uda et al., Identification of an amino acid responsible for the CD3 polymorphism in cynomolgus monkeys (*Macaca fascicularis*), J. Med. Primatol., 32:105-110 (2003).
Uemura et al., MN/CA IX/G250 as a potential target for immunotherapy of renal cell carcinomas, Br. J. Cancer, 81:741-746 (1999).
Uniprot Database Accession No. P07766, CD3E - T-Cell surface glycoprotein CD3 epsilon chain precursor, excerpt on CD3epsilon, Jul. 3, 2019.
Wildman et al., Implications of natural selection in shaping 99.4% nonsynonymous DNA identity between humans and chimpanzees: enlarging genus *Homo*, Proc. Natl. Acad. Sci. USA., 100:7181-7188 (2003).
Wilson et al., Selection of monoclonal antibodies for the identification of lymphocyte surface antigens in the New World primate *Saguinus oedipus oedipus* (cotton top tamarin), J. Immunol. Methods, 178:195-200 (1994).
Zapata et al., Biochemical differences in the alphabeta T cell receptor.CD3 surface complex between CD8+ and CD4+ human mature T lymphocytes, J. Biol. Chem., 279(23):24485-244992 (2004).
Zapata et al., Conformational and biochemical differences in the TCR.CD3 complex of CD8(+) versus CD4(+) mature lymphocytes revealed in the absence of CD3gamma, J. Biol. Chem., 274:35119-35128 (1999).
Actual data sheet for SP34.
Alberola-Ila et al., Stimulation through the TCR/CD3 complex up-regulates the CD2 surface expression on human T lymphocytes, J. Immunol., 146(4):1085-1092 (1991).
Alignment of SP34 variable domains with SEQ ID Nos. 2 and 4 from the patent.

(56) References Cited

OTHER PUBLICATIONS

Amino acid sequence alignment of SP34 with SEQ ID Nos. 2 and 4 of WO 2007/042261, cited in connection with the Opposition to European Patent No. 2 155 783 by Affimed Therapeutics Ag, dated Apr. 29, 2014.
Amino acid Sequence Alignments for SP34 and CRIS7.
Annex A of Submission in opposition proceedings of EP2370467.
Armengol et al., Thyroid autoimmune disease, Demonstration of thyroid antigen-specific B cells and recombination-activating gene expression in chemokine-containing active intrathyroidal germinal centers, Am. J. Pathol., 159(3):861-873 (2001).
Arnett et al., Crystal structure of a human CD3-epsilon/delta dimer in complex with a UCHT1 single-chain antibody fragment, Proc. Natl. Acad. Sci. USA., 101:16268-16273 (2004).
Balzar et al., The biology of the 17-1A antigen (Ep-CAM), J. Mol. Med., 77:699-712 (1999).
BD Pharmigen Safety Sheet on SP34 (product #556611).
BD Pharmingen Data Sheet on SP34 (product #556611).
BD Pharmingen: Technical Data Sheet for SP34 (Dated May 13, 2003).
Beasley et al., Carbonic anhydrase IX, an endogenous hypoxia marker, expression in head and neck squamous cell carcinoma and its relationship to hypoxia, necrosis, and microvessel density, Cancer Res., 61:5262-5267 (2001).
Bonner et al., Epidermal growth factor receptor as a therapeutic target in head and neck cancer, Semin. Radiat. Oncol., 12:11-20 (2002).
Bugelski et al., Preclinical development of keliximab, a Primatized anti-CD4 monoclonal antibody, in human CD4 transgenic mice: characterization of the model and safety studies, Hum. Exp. Toxicol., 19:230-243 (2000).
CDR sequence comparison of CD3e antibodies of the patent and prior art.
Chapman Kathryn NC3RS Biological Workshop Report (2006).
Chapman, Kathryn, "Opportunities for reducing the use of non-human primates in the development of monoclonal antibodies—a Workshop report", National Centre of Replacement, Refinement, and Reduction of Animals in Research, May 2006.
Cheson et al., Report of an international workshop to standardize response criteria for non-Hodgkin's lymphomas. NCI Sponsored International Working Group, J. Clin. Oncol., 17:1244 (1999).
Chia et al., Prognostic significance of a novel hypoxia-regulated marker, carbonic anhydrase IX, in invasive breast carcinoma, J. Clin. Oncol., 19:3660-3668 (2001).
Cited document D35 in D20.
Cited document D41 in D20.
Claim of Invention (Letters to inventors).
Claim of invention receipt confirmation.
Data regarding SEQ ID No. 12 of the patent.
Decision of the Opposition Division of Oct. 19, 2016 pertaining to European Patent No. 2155783.
Declaration by Catherine Jean McMahan.
Declaration of Dr. M. Engelhard.
Declaration of Inventors.
Determination of SP34 antibody affinity to full length and N1-27 CD3.
Email from BD Biosciences confirming (i) the date of availability of SP34 and SP34-2 and (ii) that their binding specificities are identical.
Email from BO Biosciences confirming (i) the date of availability of SP34 and SP34-2 and (ii) that their binding specificities are identical, cited in connection with the Opposition to European Patent No. 2 155 783 by GenMab A/S, dated Apr. 29, 2014.
Experimental data filed by opponents in parallel case on binding of SP34 to mutated FSE.
Experimental data filed by opponents in parallel case on SP34 epitope mapping to human CD3.
Extract from Catalogue produced by Biosource.
Extract from publication entitled Leucocyte Typing III, edited by McMichael.
Extract from USPTO website/assignment.
Fogler et al., Enhanced cytotoxicity against colon carcinoma by combinations of noncompeting monoclonal antibodies to the 17-1A antigen, Cancer Res., 48:6303-6308 (1988).
Ikezumi et al., The sialoadhesin (CD169) expressing a macrophage subset in human proliferative glomerulonephritis, Nephrol. Dial. Transplant., 20:2704-2713 (2005).
International Application No. PCT/EP2006/009782, International Preliminary Report on Patentability, dated Apr. 15, 2008.
Invention Report.
Kaufmann, Selection and coamplification of heterologous genes in mammalian cells, Methods Enzymol., 185:537-566 (1990).
Kiyota et al., Anti-epidermal growth factor receptor monoclonal antibody 225 upregulates p27(KIP1) and p15(INK4B) and induces G1 arrest in oral squamous carcinoma cell lines, Oncology, 63:92-98 (2002).
Kjer-Nielsen et al., Crystal structure of the human T cell receptor CD3 epsilon gamma heterodimer complexed to the therapeutic mAb OKT3, Proc. Natl. Acad. Sci. USA., 101:7675-80 (2004).
Kuan et al., EGFRvIII as a promising target for antibody-based brain tumor therapy, Brain Tumor Pathol., 17:71-78 (2000).
Kufer et al., Minimal costimulatory requirements for T cell priming and TH1 differentiation: activation of naive human T lymphocytes by tumor cells armed with bifunctional antibody constructs, Cancer Immunity, 1:10 (2001).
Lara-Marquez et al., Selective gene expression and activation-dependent regulation of vasoactive intestinal peptide receptor type 1 and type 2 in human T cells, J. Immunol., 166(4):2522-2530 (2001).
Letter filed on Mar. 16, 2016 by Janssen Biotech Inc. in Opposition against European Patent No. 2155783.
Liu et al., Induction of apoptosis and activation of the caspase cascade by anti-EGF receptor monoclonal antibodies in DiFi human colon cancer cells do not involve the c-jun N-terminal kinase activity, Br. J. Cancer, 82:1991-1999 (2000).
Longcaster et al., Carbonic anhydrase (CA IX) expression, a potential new intrinsic marker of hypoxia: correlations with tumor oxygen measurements and prognosis in locally advanced carcinoma of the cervix, Cancer Res., 61:6394-6399 (2001).

FIGURE 1
Anti-CD3
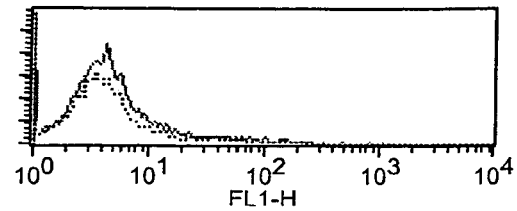
OKT-3
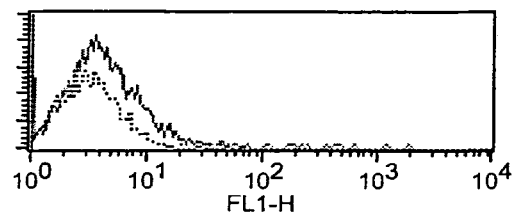
Ig comprising
SEQ ID NOs.
6 and 8
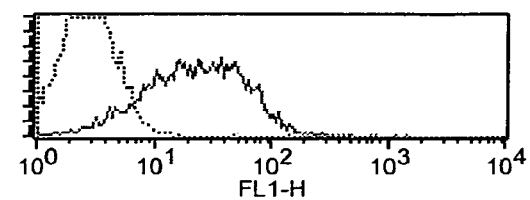
Ig comprising
SEQ ID NOs.
2 and 4
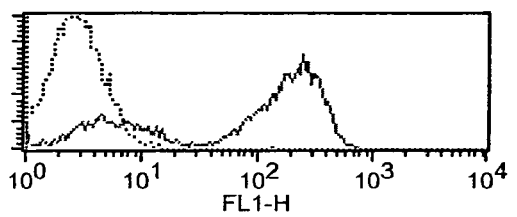
UCHT-1
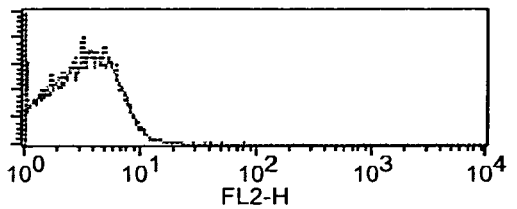

FIGURE 2
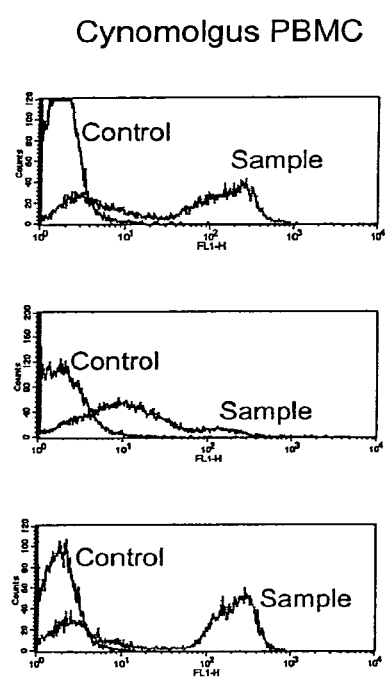
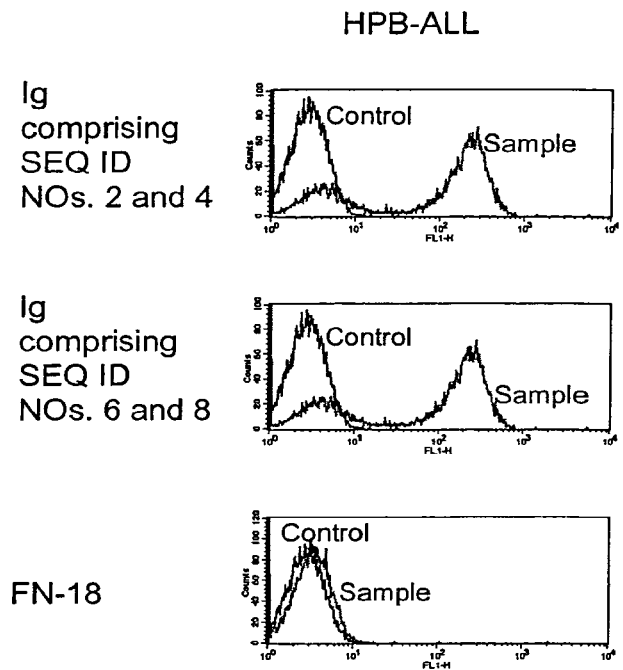
Cynomolgus PBMC
HPB-ALL
Ig comprising SEQ ID NOs. 2 and 4
Ig comprising SEQ ID NOs. 6 and 8
FN-18

FIGURE 6

```
human EpCAM    (1)    QEECVCENYKLAVNCFVNNNRQCQCTSVGAQNTVICSKLAAKCLVMKAEMNGSKLGRRAKPEGALQNNDG
cyno  EpCAM    (1)    QKECVCENYKLAVNCFLNDNGQCQCTSIGAQNTVLCSKLAAKCLVMKAEMNGSKLGRRAKPEGALQNNDG 71                                                                    140
human EpCAM    (71)   LYDPDCDESGLFKAKQCNGTSTCWCVNTAGVRRTDKDTEITCSERVRTYWIIIELKHKAREKPYDSKSLR
cyno  EpCAM    (71)   LYDPDCDESGLFKAKQCNGTSTCWCVNTAGVRRTDKDTEITCSERVRTYWIIIELKHKAREKPYDVQSLR 141                                                                   210
human EpCAM   (141)   TALQKEITTRYQLDPKFITSILYENNVITIDLVQNSSQKTQNDVDIADVAYYFEKDVKGESLFHSKKMDL
cyno  EpCAM   (141)   TALEEAIKTRYQLDPKFITNILYEDNVITIDLVQNSSQKTQNDVDIADVAYYFEKDVKGESLFHSKKMDL 211                                          280
human EpCAM   (211)   TVNGEQLDLDPGQTLIYYVDEKAPEFSMQGLK
cyno  EpCAM   (211)   RVNGEQLDLDPGQTLIYYVDEKAPEFSMQGLK
```

FIGURE 11

```
SEQ ID NO.2      EVKLLESGGGLVQPKGSLKLSCAASGFTFN
hu3-73           EVQLVESGGGLVQPGGSLKLSCAASGFTFS

I                        II
SEQ ID NO.2      TYAMN WVRQAPGKGLEWV A RIRSKYNNYAT
hu3-73           GSAMH WVRQASGKGLEWV G RIRSKANSYAT

SEQ ID NO.2      YYADSVKD RFTISRDDSQSILYLQMNNLKT
hu3-73           AYAASVKG RFTISRDDSKNTAYLQMNSLKT

III
SEQ ID NO.2      EDTAMYYCVR HGNFGNSYVSWFAY WGQGTL
hu3-73/FR4huJ1   EDTAVYYCTR --------------  WGQGTL

SEQ ID NO.2      VTVSA
hu3-73           VTVSS
```

FIGURE 12

```
         E   V   Q   L   L   E   S   G   G   L   V   Q   P   G   G   S   L   K   L
  1   GAGGTGCAGC TGCTCGAGTC TGGAGGAGGA TTGGTGCAGC CTGGAGGGTC ATTGAAACTC
      CTCCACGTCG ACGAGCTCAG ACCTCCTCCT AACCACGTCG GACCTCCCAG TAACTTTGAG

S   C   A   A   S   G   F   T   F   N   T   Y   A   M   N   W   V   R   Q   A
 61   TCATGTGCAG CCTCTGGATT CACCTTCAAT ACCTACGCCA TGAACTGGGT CCGCCAGGCT
      AGTACACGTC GGAGACCTAA GTGGAAGTTA TGGATGCGGT ACTTGACCCA GGCGGTCCGA

P   G   K   G   L   E   W   V   A   R   I   R   S   K   Y   N   N   Y   A   T
121   CCAGGAAAGG GTTTGGAATG GGTTGCTCGC ATAAGAAGTA AATATAATAA TTATGCAACA
      GGTCCTTTCC CAAACCTTAC CCAACGAGCG TATTCTTCAT TTATATTATT AATACGTTGT

Y   Y   A   D   S   V   K   D   R   F   T   I   S   R   D   D   S   K   N   T
181   TATTATGCCG ATTCAGTGAA AGACAGGTTC ACCATCTCCA GAGATGATTC AAAAAACACT
      ATAATACGGC TAAGTCACTT TCTGTCCAAG TGGTAGAGGT CTCTACTAAG TTTTTTGTGA

A   Y   L   Q   M   N   N   L   K   T   E   D   T   A   V   Y   Y   C   V   R
241   GCCTATCTAC AAATGAACAA CTTGAAAACT GAGGACACTG CCGTGTACTA CTGTGTGAGA
      CGGATAGATG TTTACTTGTT GAACTTTTGA CTCCTGTGAC GGCACATGAT GACACACTCT

~
         H   G   N   F   G   N   S   Y   V   S   W   F   A   Y   W   G   Q   G   T   L
301   CATGGGAACT TCGGTAATAG CTACGTTTCC TGGTTTGCTT ACTGGGGCCA AGGGACTCTG
      GTACCCTTGA AGCCATTATC GATGCAAAGG ACCAAACGAA TGACCCCGGT TCCCTGAGAC

V   T   V   S   S
361   GTCACCGTCT CCTCA
      CAGTGGCAGA GGAGT
```

FIGURE 15

```
                1                                         40
human CD3ε     -DGNEEMGGITQTPYKVSISGTTVILTCPQYPGSEILWQH
cyno  CD3ε     QDGNEEMGSITQTPYQVSISGTTVILTCSQHLGSEAQWQH 41   46                 47                71
                     abcdefghk
human CD3ε     NDKNIGGDEDDKNIGSDEDHLSLKEFSELEQSGYYVCYPR
cyno  CD3ε     NGKNKG---------DSGDQLFLPEFSEMEQSGYYVCYPR
                                        E-F-loop 72                      96
human CD3ε     GSKPEDANFYLYLRARVCENCMEMD
cyno  CD3ε     GSNPEDASHHLYLKARVCENCMEMD
```

FIGURE 16

| | |
|---|---|
| 1 | QDGNEEMGSITQT |
| 2 | GNEEMGSITQTPY |
| 3 | EEMGSITQTPYQV |
| 4 | MGSITQTPYQVSI |
| 5 | SITQTPYQVSISG |
| 6 | TQTPYQVSISGTT |
| 7 | TPYQVSISGTTVI |
| 8 | YQVSISGTTVILT |
| 9 | VSISGTTVILTSS |
| 10 | ISGTTVILTSSQH |
| 11 | GTTVILTSSQHLG |
| 12 | TVILTSSQHLGSE |
| 13 | ILTSSQHLGSEAQ |
| 14 | TSSQHLGSEAQWQ |
| 15 | SQHLGSEAQWQHN |
| 16 | HLGSEAQWQHNGK |
| 17 | GSEAQWQHNGKNK |
| 18 | EAQWQHNGKNKGD |
| 19 | QWQHNGKNKGDSG |
| 20 | QHNGKNKGDSGDQ |
| 21 | NGKNKGDSGDQLF |
| 22 | KNKGDSGDQLFLP |
| 23 | KGDSGDQLFLPEF |
| 24 | DSGDQLFLPEFSE |
| 25 | GDQLFLPEFSEME |
| 26 | QLFLPEFSEMEQS |
| 27 | FLPEFSEMEQSGY |
| 28 | PEFSEMEQSGYYV |
| 29 | FSEMEQSGYYVSY |
| 30 | EMEQSGYYVSYPR |
| 31 | EQSGYYVSYPRGS |
| 32 | SGYYVSYPRGSNP |
| 33 | YYVSYPRGSNPED |
| 34 | VSYPRGSNPEDAS |
| 35 | YPRGSNPEDASHH |
| 36 | RGSNPEDASHHLY |
| 37 | SNPEDASHHLYLK |
| 38 | PEDASHHLYLKAR |
| 39 | DASHHLYLKARVS |
| 40 | SHHLYLKARVSEN |
| 41 | HLYLKARVSENSM |
| 42 | YLKARVSENSMEM |
| 43 | LKARVSENSMEMD |

FIGURE 17

| | |
|---|---|
| 1 | DGNEEMGGITQTP |
| 2 | NEEMGGITQTPYK |
| 3 | EMGGITQTPYKVS |
| 4 | GGITQTPYKVSIS |
| 5 | ITQTPYKVSISGT |
| 6 | QTPYKVSISGTTV |
| 7 | PYKVSISGTTVIL |
| 8 | KVSISGTTVILTS |
| 9 | SISGTTVILTSPQ |
| 10 | SGTTVILTSPQYP |
| 11 | TTVILTSPQYPGS |
| 12 | VILTSPQYPGSEI |
| 13 | LTSPQYPGSEILW |
| 14 | SPQYPGSEILWQH |
| 15 | QYPGSEILWQHND |
| 16 | PGSEILWQHNDKN |
| 17 | SEILWQHNDKNIG |
| 18 | ILWQHNDKNIGGD |
| 19 | WQHNDKNIGGDED |
| 20 | HNDKNIGGDEDDK |
| 21 | DKNIGGDEDDKNI |
| 22 | NIGGDEDDKNIGS |
| 23 | GGDEDDKNIGSDE |
| 24 | DEDDKNIGSDEDH |
| 25 | DDKNIGSDEDHLS |
| 26 | KNIGSDEDHLSLK |
| 27 | IGSDEDHLSLKEF |
| 28 | SDEDHLSLKEFSE |
| 29 | EDHLSLKEFSELE |
| 30 | HLSLKEFSELEQS |
| 31 | SLKEFSELEQSGY |
| 32 | KEFSELEQSGYYV |
| 33 | FSELEQSGYYVSY |
| 34 | ELEQSGYYVSYPR |
| 35 | EQSGYYVSYPRGS |
| 36 | SGYYVSYPRGSKP |
| 37 | YYVSYPRGSKPED |
| 38 | VSYPRGSKPEDAN |
| 39 | YPRGSKPEDANFY |
| 40 | RGSKPEDANFYLY |
| 41 | SKPEDANFYLYLR |
| 42 | PEDANFYLYLRAR |
| 43 | DANFYLYLRARVS |
| 44 | NFYLYLRARVSEN |
| 45 | YLYLRARVSENSM |
| 46 | YLRARVSENSMEM |
| 47 | LRARVSENSMEMD |

FIGURE 18
(A)
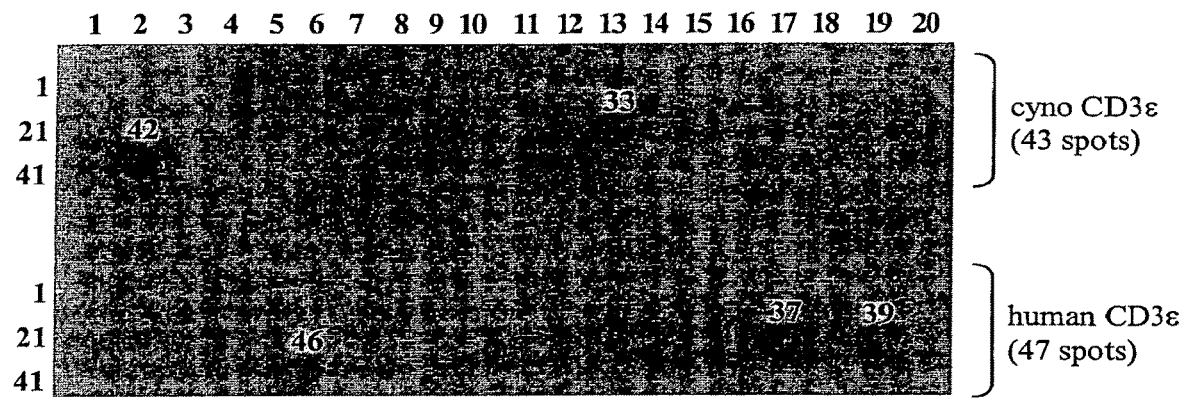
(B)
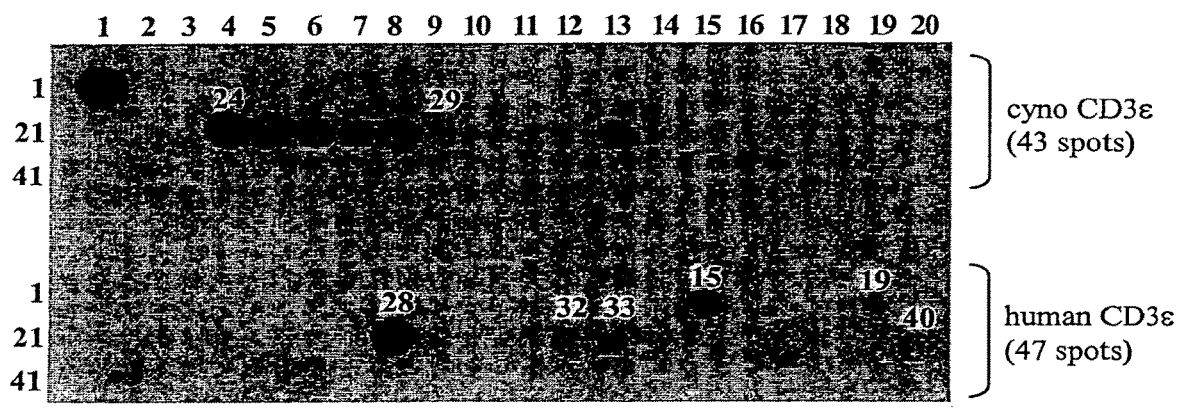

FIGURE 24
(A)
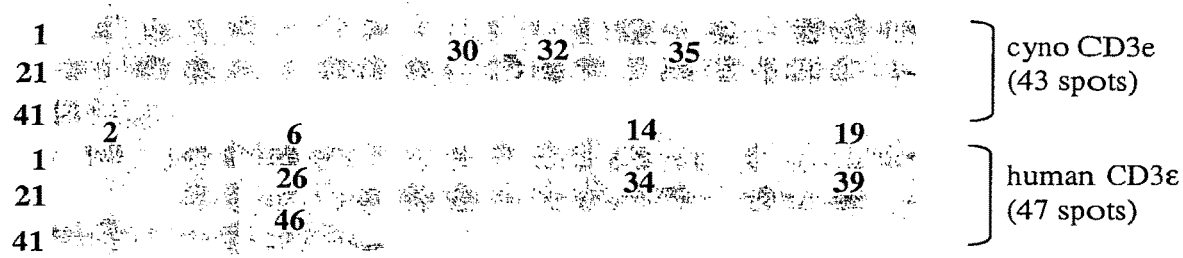
(B)
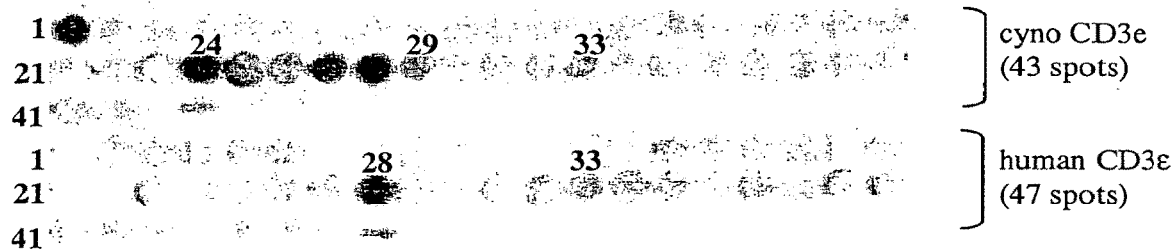

Figure 26:
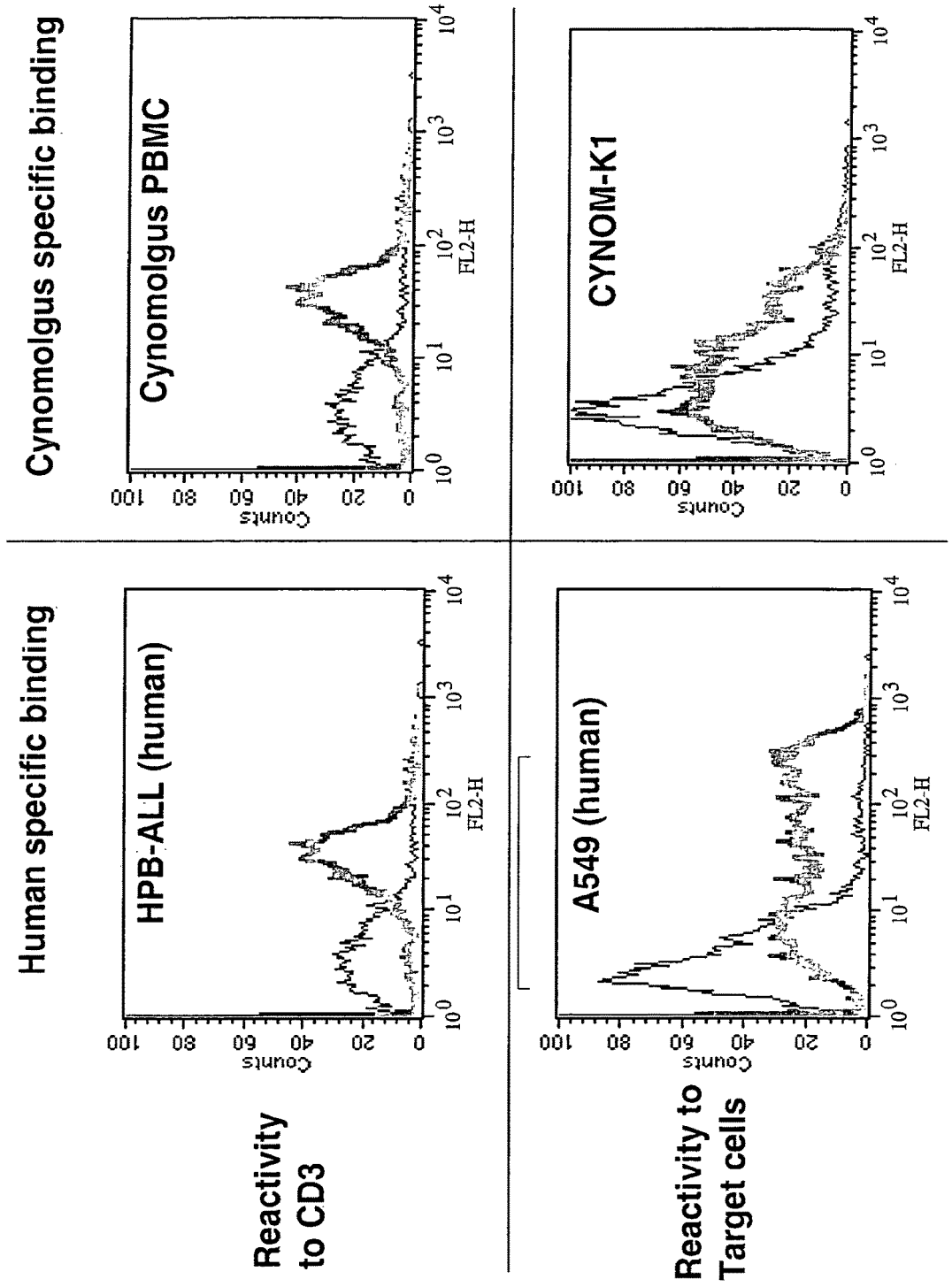

FIGURE 26 CAIX HL x SEQ ID NO. 194

Figure 29:
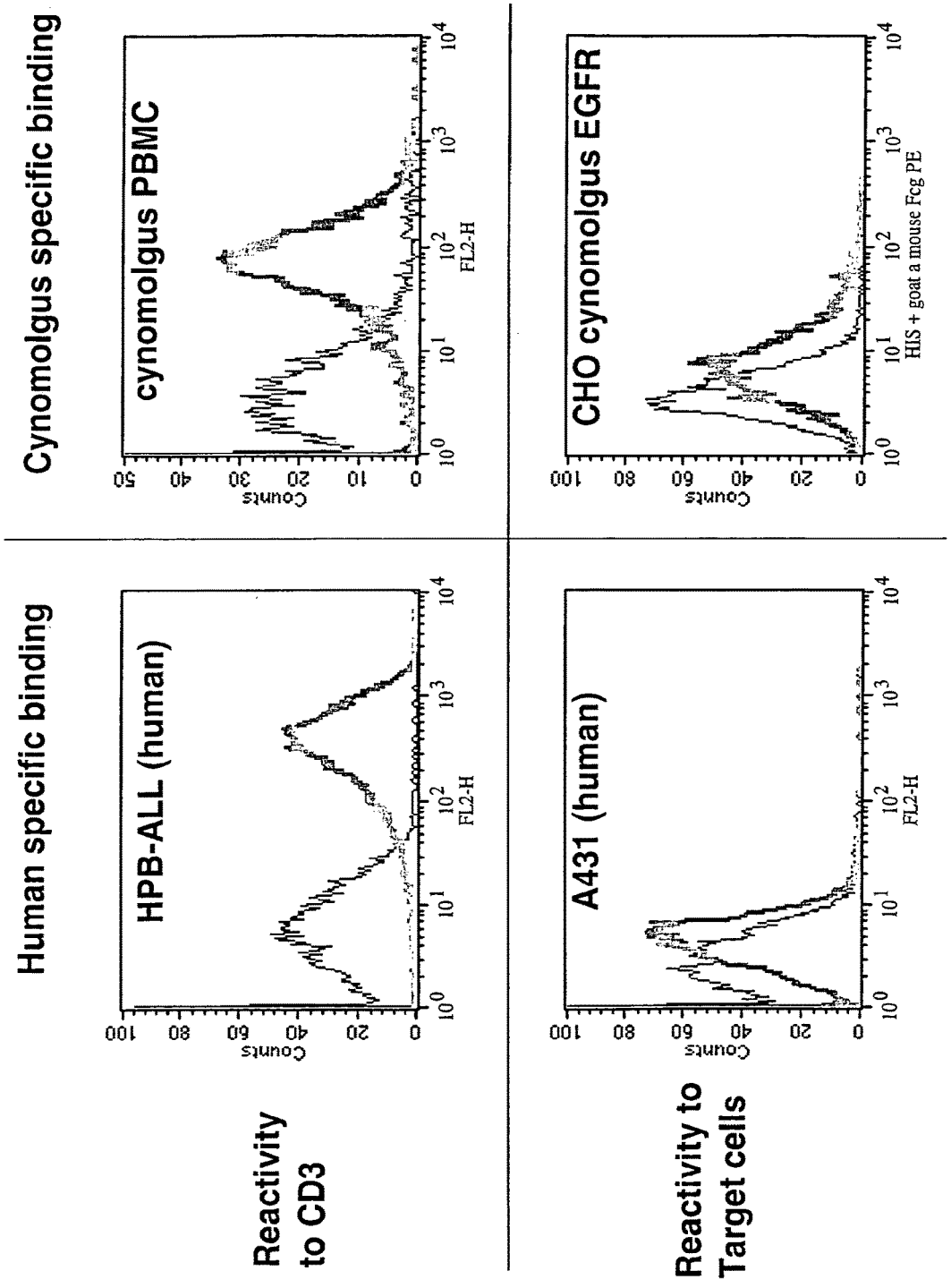

FIGURE 29  EGFR HL x SEQ ID NO. 170

Figure 30:
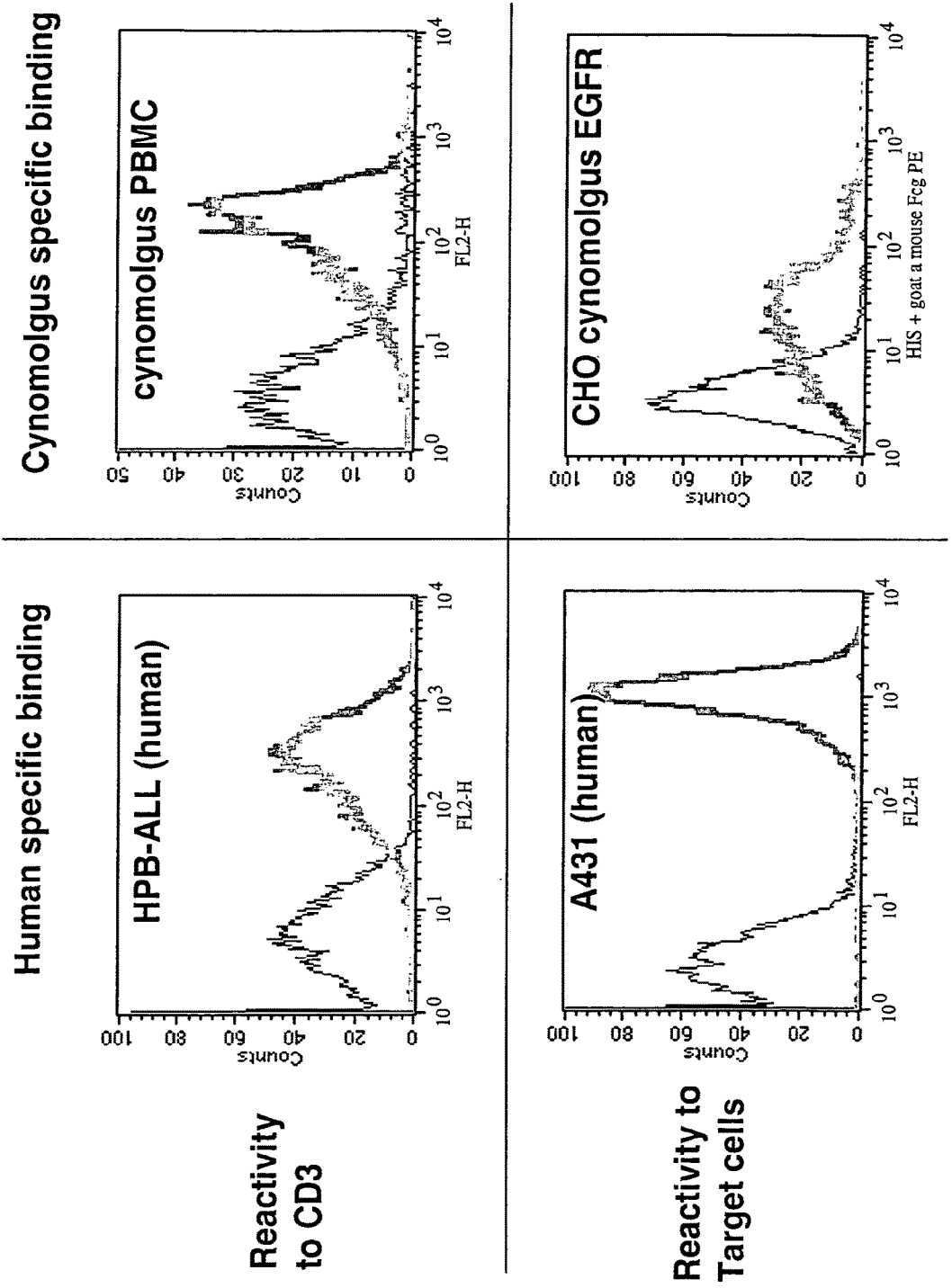

FIGURE 30    EGFR LH x SEQ ID NO. 170

Figure 32:
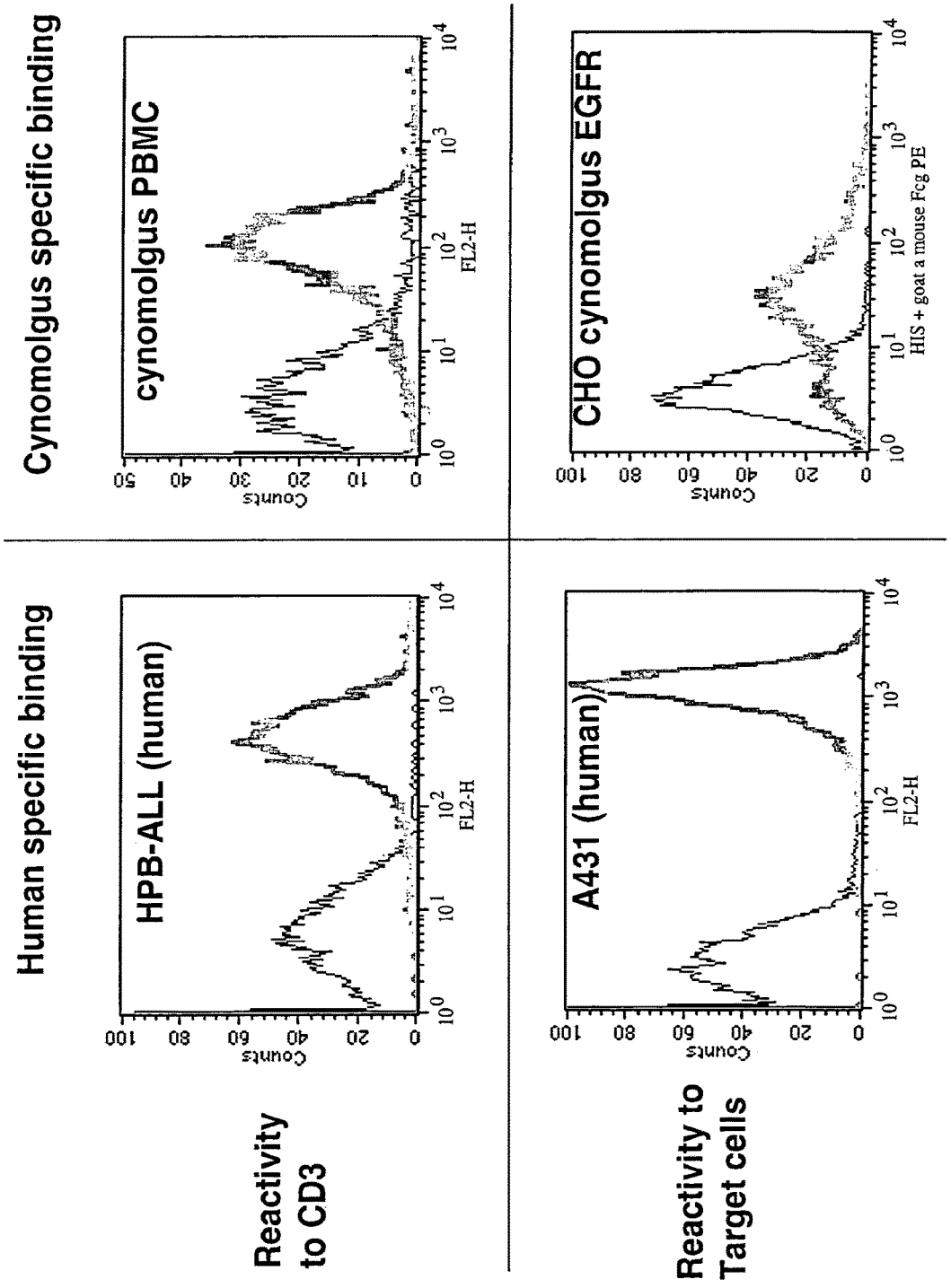

FIGURE 32  EGFR LH x SEQ ID NO. 194

Figure 33:
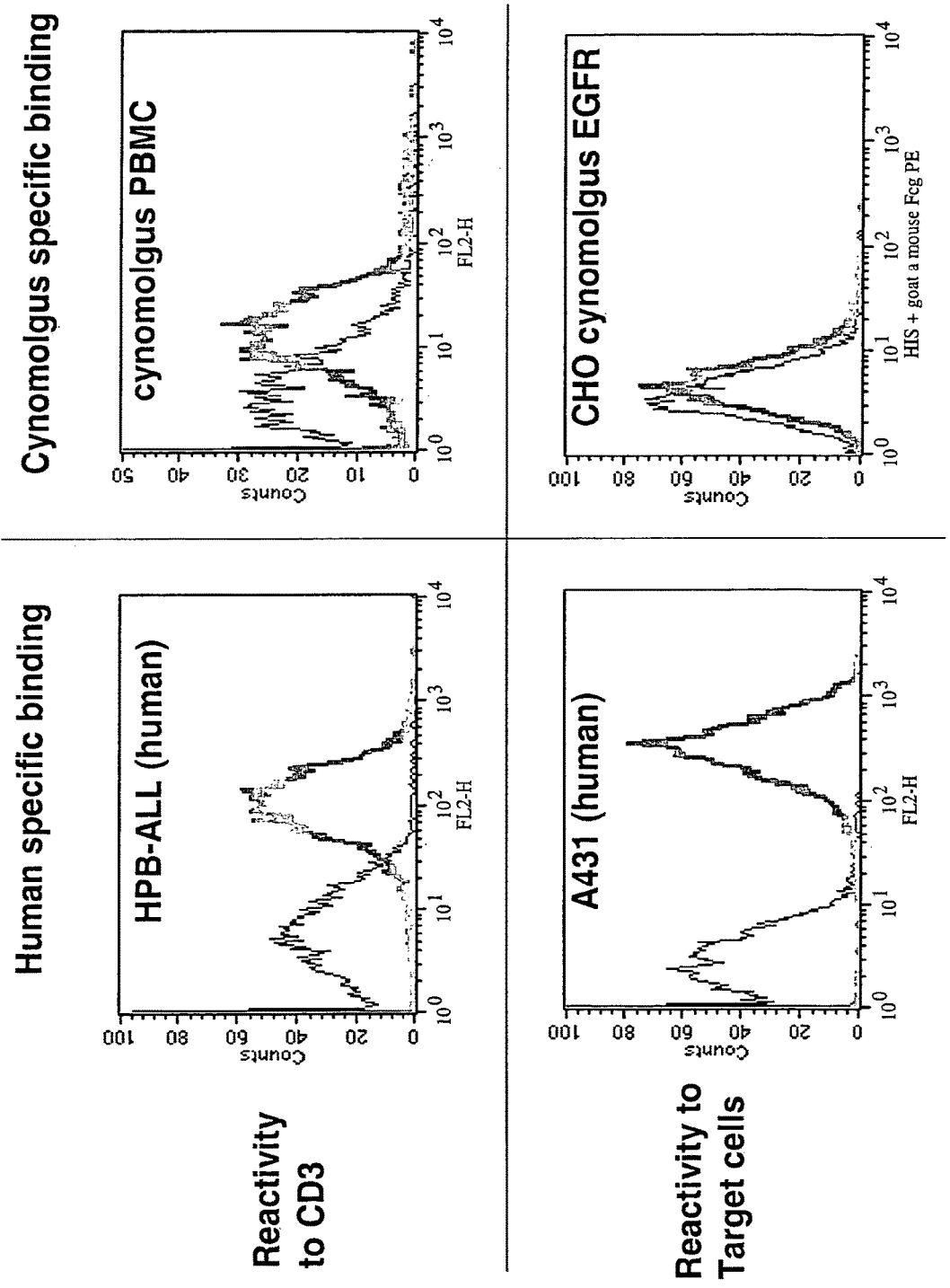

FIGURE 33   SEQ ID NO. 170 x EGFR HL

Figure 34:
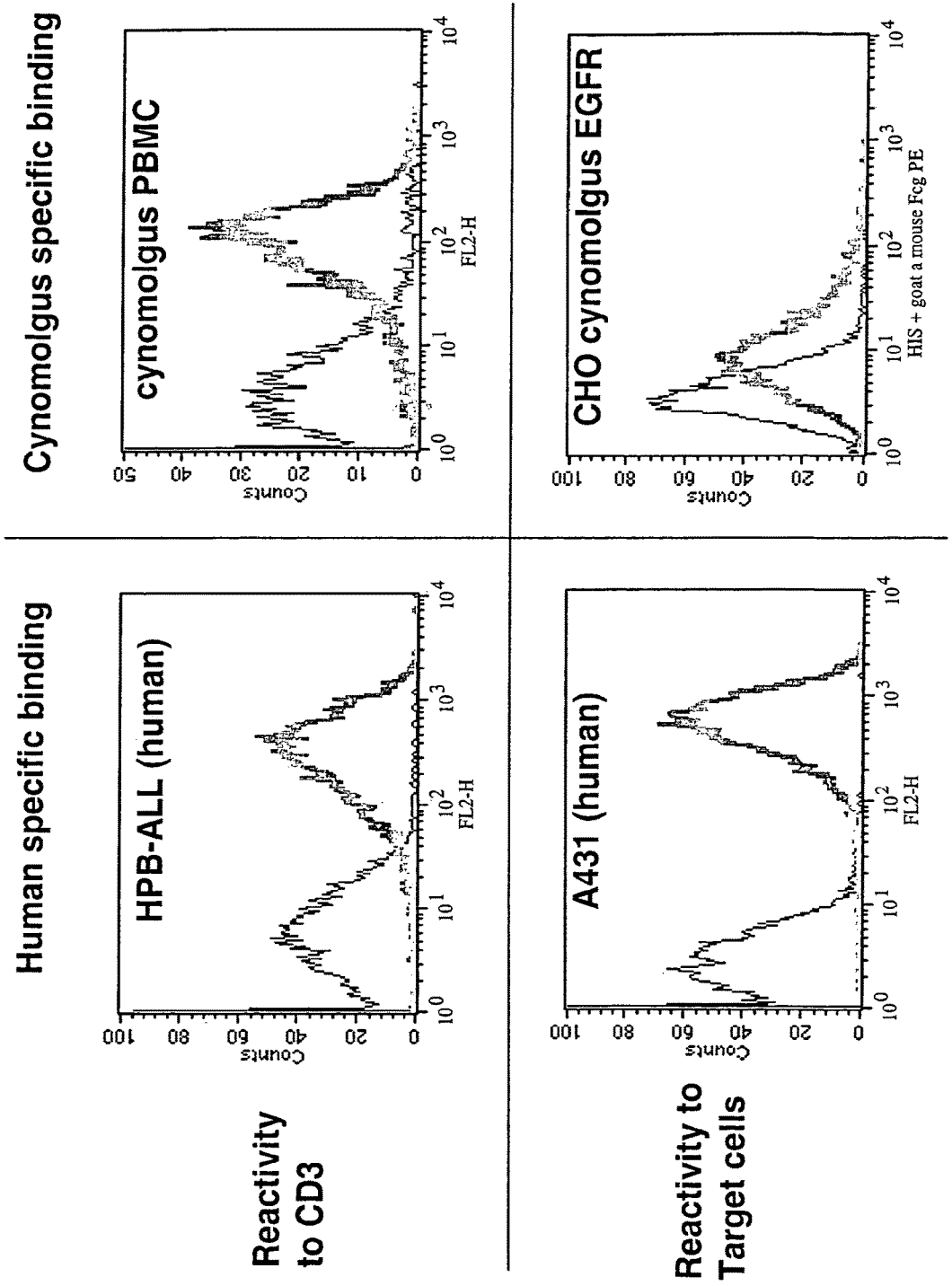

FIGURE 34   SEQ ID NO. 170 x EGFR LH

Figure 36:
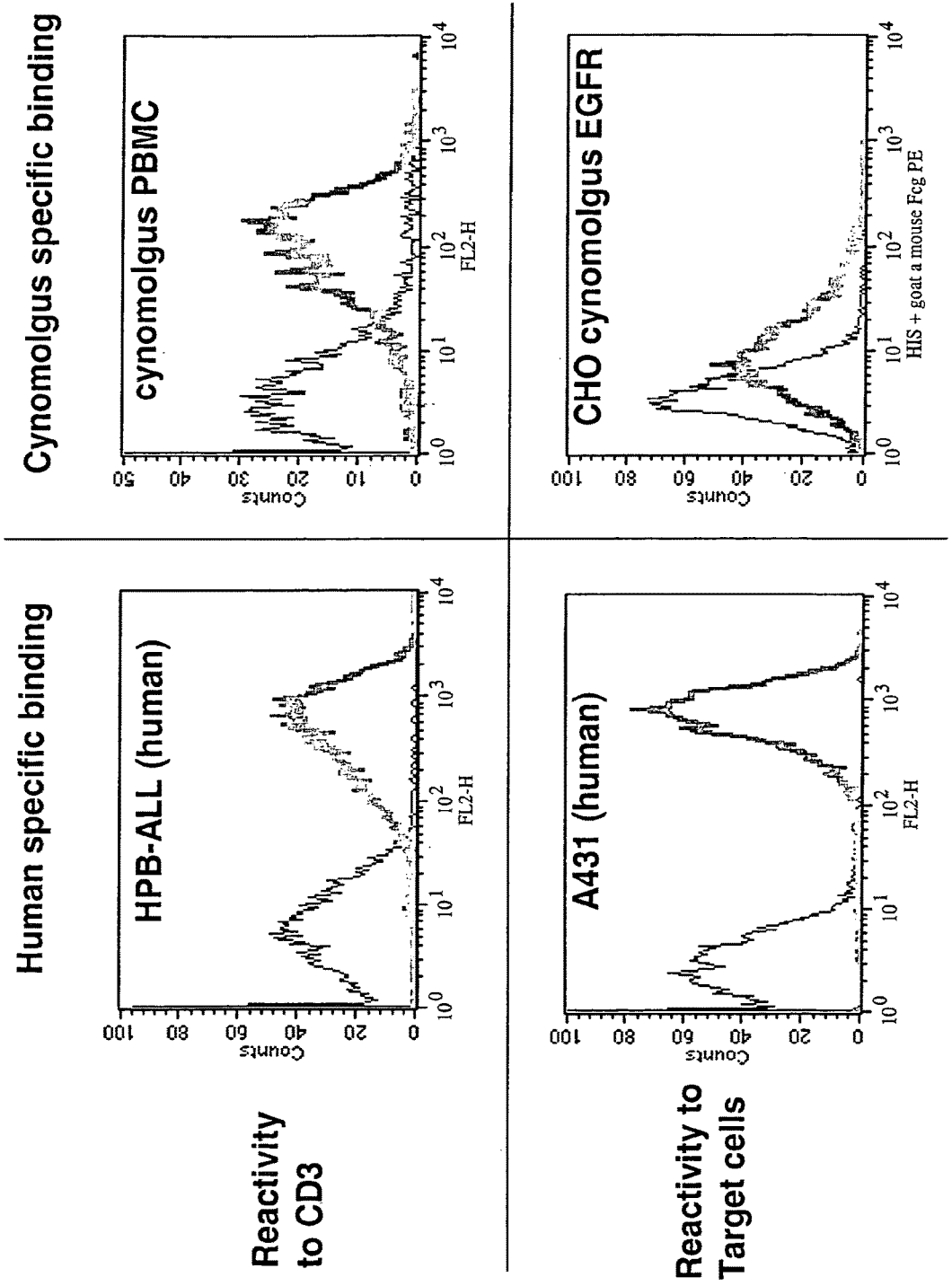

FIGURE 36   SEQ ID NO. 194 x EGFR LH

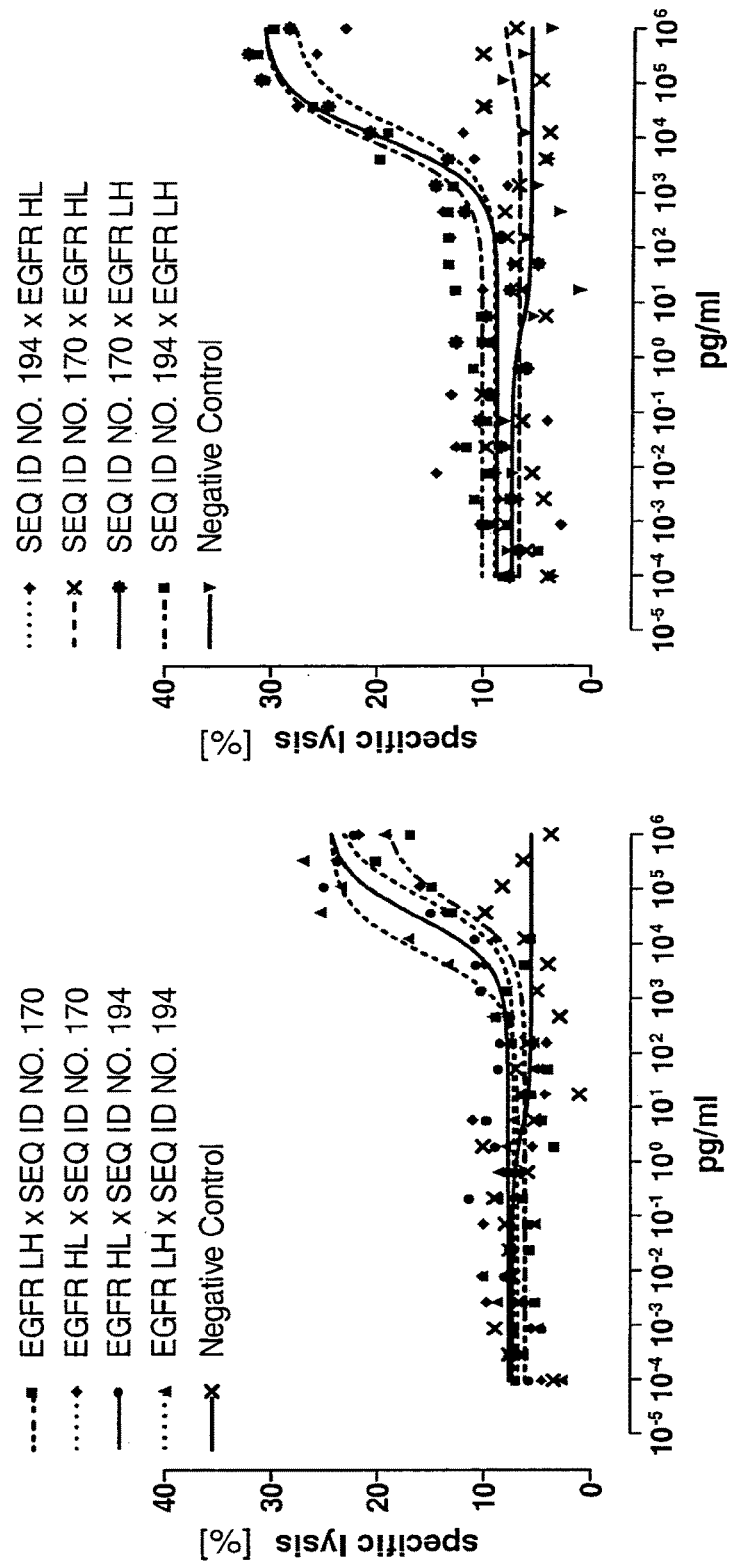

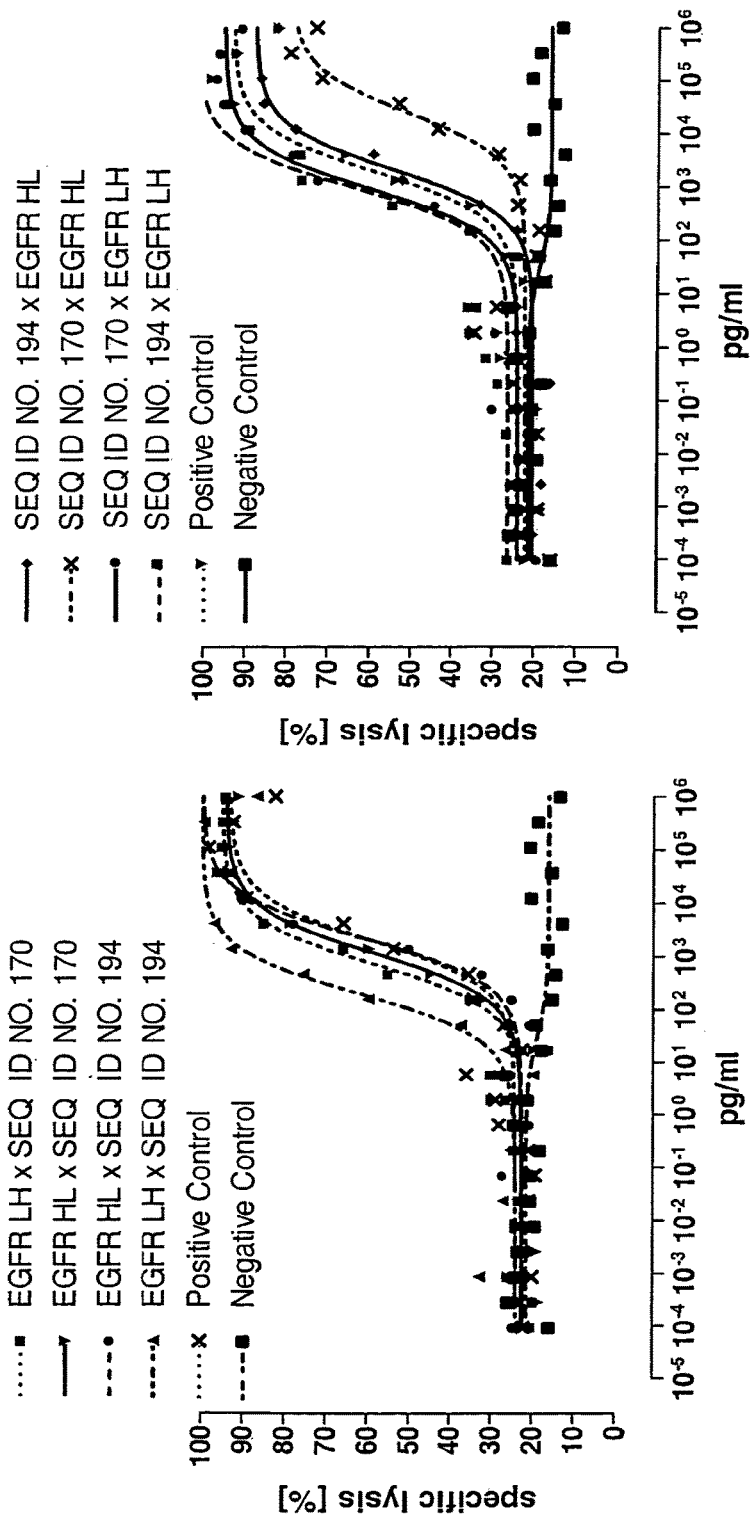

COMPOSITIONS COMPRISING CROSS-SPECIES-SPECIFIC ANTIBODIES AND USES THEREOF

The Sequence Listing, which is a part of the present disclosure, is submitted concurrently with the specification as a text file. The name of the text file containing the Sequence Listing is "47403B_SubSeqlisting.txt", which was created on Nov. 19, 2018 and is 302,853 bytes in size. The subject matter of the Sequence Listing is incorporated herein in its entirety by reference.

The present invention relates to uses of bispecific antibodies exhibiting cross-species specificity for evaluating the in vivo safety and/or activity and/or pharmacokinetic profile of the same in non-human species and humans. The present invention moreover relates to methods for evaluating the in vivo safety and/or activity and/or pharmacokinetic profile of said bispecific antibodies exhibiting cross-species specificity. The present invention also relates to methods of measuring the biological activity and/or efficacy of such bispecific antibodies exhibiting cross-species specificity. In addition, the present invention relates to pharmaceutical compositions comprising bispecific single chain antibodies exhibiting cross-species specificity and to methods for the preparation of pharmaceutical compositions comprising said bispecific single chain antibodies exhibiting cross-species specificity for the treatment of diseases.

In order to be marketed, any new candidate medication must pass through rigorous testing. Roughly, this testing can be subdivided into preclinical and clinical phases: Whereas the latter—further subdivided into the generally known clinical phases I, II and III—is performed in human patients, the former is performed in animals. Generally, the aim of pre-clinical testing is to prove that the drug candidate works and is efficacious and safe. Specifically, the purpose of these animal studies is to prove that the drug is not carcinogenic, mutagenic or teratogenic, as well as to understand the pharmacokinetic of the drug. Only when the safety in animals and possible effectiveness of the drug candidate has been established in preclinical testing will this drug candidate be approved for clinical testing in humans.

The behavior of a small molecule drug candidate, e.g. a new anthracycline-based antineoplastic agent, in animals will in many cases be indicative of the expected behavior of this drug candidate upon administration to humans. As a result, the data obtained from such preclinical testing will therefore generally have a high predictive power for the human case. However, such compatibility is not to be expected with all types of drug candidates; certain molecular formats would be expected to behave one way in animals and another way in humans. In such cases, the predictive power of preclinical tests—and hence the likelihood of approval of the drug candidate for clinical testing—is greatly reduced.

One format of drug candidate which often acts differently in animals than in humans is an antibody. Generally, antibodies function by way of highly specific recognition of— usually proteinaceous—target molecules. Most antibody drug candidates are monoclonal antibodies; they recognize only a single site, or epitope, on their target molecule. However, while this discriminatory ability inherent to monoclonal antibodies and fragments thereof makes these compounds very interesting candidates for drug development, it also complicates their preclinical testing. This is because of species-dependent variations in the sequence of the target molecule bound by such antibodies. A monoclonal antibody or fragment thereof which specifically recognizes and binds to, say, molecule Y via epitope X in humans, will often fail to specifically recognize and bind to the corresponding molecule Y' in a non-human species since the corresponding epitope X' may be different from its human counterpart X. Thus, monoclonal antibodies (e.g. against human antigens) by design tend to have limited reactivity to phylogenetically distant species such as rodents, except in the very rare cases in which the antigen is highly conserved. Even among the group of monoclonal antibodies with reactivity to human and primate antigens, there are numerous examples of antibodies which react only with the human and chimpanzee antigen homologs. This has also been observed for anti-CD3 monoclonal antibodies. One of the most widely used and best characterized monoclonal antibodies specific for the CD3 complex is OKT-3 which reacts with chimpanzee CD3 but not with the CD3 homolog of other primates, such as macaques, or with dog CD3 (Sandusky et al., J. Med. Primatol. 15 (1986), 441-451). The anti-CD3 monoclonal antibody UCHT-1 is also reactive with CD3 from chimpanzee but not with CD3 from macaques (own data; see the following Examples). On the other hand, there are also examples of monoclonal antibodies which recognize macaque antigens, but not their human counterparts. One example of this group is monoclonal antibody FN-18 directed to CD3 from macaques (Uda et al., J. Med. Primatol. 30 (2001), 141-147). Interestingly, it has been found that peripheral lymphocytes from about 12% of cynomolgus monkeys lacked reactivity with anti-rhesus monkey CD3 monoclonal antibody (FN-18) due to a polymorphism of the CD3 antigen in macaques. Uda et al. described a substitution of two amino acids in the CD3 sequence of cynomolgus monkeys which are not reactive with FN-18 antibodies, as compared to CD3 derived from animals which are reactive with FN-18 antibodies (Uda et al., J Med Primatol. 32 (2003), 105-10; Uda et al., J Med Primatol. 33 (2004), 34-7).

Similar difficulties with the high specificity of monoclonal antibodies in preclinical animal testing are observed with bispecific antibodies, for example a recombinant bispecific single chain antibody of the general type disclosed in, for example, U.S. Pat. No. 5,260,203. This added difficulty is due to the fact that a bispecific antibody, for example a bispecific single chain antibody, comprises two distinct binding domains, either one of which—or both—may fail to recognize the non-human counterpart of its human target molecule. Effectively, the risk that e.g. a bispecific single chain antibody, will fail to recognize its intended respective target molecules in an animal is twice as high as with a monospecific antibody or fragment thereof.

There exist several known strategies for countering such problems.

One known approach is to perform preclinical testing of the (bispecific) antibody drug candidate or fragment thereof in a chimpanzee model. The chimpanzee is the closest genetic relative to human, identical to the latter in over 99% of its genome, so the chimpanzee variant of a molecule specifically bound by a (bispecific) antibody drug candidate or fragment thereof is very likely to be identical to the human variant of this molecule. The danger of non-recognition of this molecule by the (bispecific) antibody drug candidate or fragment thereof in chimpanzee is therefore minimized. However, testing in chimpanzees is very expensive and fraught with ethical problems. Furthermore, chimpanzees are endangered animals so that the number of animals which can be used in experimentation is very limited. For most developers of (bispecific) antibody therapeutics, such preclinical testing in chimpanzees is therefore precluded.

The above approach is described e.g. in Schlereth et al. (Cancer Immunol. Immunother. 20 (2005), 1-12). In this study, the biological activity of a clinical drug candidate, bispecific single chain antibody CD19×CD3, has been tested in chimpanzee. CD19×CD3 antibody, previously described in WO 99/54440 for therapeutic administration in humans, is a bispecific single chain antibody specifically binding to human B cell antigen CD19 and human T cell antigen CD3. The authors of this paper found that this bispecific single chain antibody bound to both human and chimpanzee variants of the CD3 and CD19 molecule. However, no reactivity of said bispecific single chain antibody to B and T cells from other species, i.e. mouse, beagle dog, and non-chimpanzee primates (cynomolgus, rhesus and baboon), could be found, again confirming the extreme species sensitivity of monoclonal antibodies.

Another approach adapts the molecule used in preclinical testing to the animal used for this testing. According to this approach, the requisite safety information is obtained in preclinical studies by constructing so-called "surrogate" antibodies for administration to test animals. Generally, such a surrogate antibody is an antibody which has been modified so as to specifically recognize and bind to the test animal counterpart of the target molecule bound by the non-surrogate antibody, i.e. the actual drug candidate in humans. Thus, in approaches using such "surrogate" antibodies, two different molecules have to be separately developed and investigated: the clinical drug candidate and a candidate for preclinical testing in an animal species corresponding to the target specificity of the clinical candidate. The major drawback of such surrogate approaches is that the surrogate antibody for preclinical testing has been modified vis-à-vis the actual drug candidate antibody. Therefore, the data obtained in preclinical testing using a surrogate antibody are often not directly applicable to the human case. As explained above, this reduced applicability ultimately reduces the predictive power of any preclinical study using these approaches.

While the above approach adapts the drug candidate to match the animal used for testing, other known approaches do exactly the converse; according to these other known approaches, the animal used for testing is adapted to the drug candidate intended for administration to humans.

One example of the adaptation of the test animal to the drug candidate intended for administration to humans, is the creation of a transgenic animal expressing the human molecule specifically bound by the (bispecific) antibody or fragment thereof instead of the non-human molecule which is endogenous to its own species. In this way, the (bispecific) antibody or fragment thereof administered in preclinical trials will encounter and bind to the human antigen in the transgenic test animal. For example, in a study designed by Bugelski et al. (Bugelski et al., Hum Exp Toxicol. 19 (2000), 230-243), preclinical safety assessment of monoclonal antibody Keliximab has been carried out in a human CD4 transgenic mouse in order to support chronic treatment of rheumatoid arthritis in human patients. Keliximab is a monoclonal antibody with specificity for human and chimpanzee CD4. The authors conclude that the use of transgenic mice expressing human proteins provides a useful alternative to studies in chimpanzees with biopharmaceutical agents having limited cross-species specificity (Bugelski et al., Hum Exp Toxicol. 19 (2000), 230-243). However, creation of transgenic animals for test purposes is very labor- and therefore cost-intensive.

In the same vein, an alternative approach often employed is to inject a non-transgenic test animal with human cells expressing the molecule to be specifically bound by the (bispecific) antibody or fragment thereof being tested. However, while avoiding the costs and time associated with constructing transgenic animal species, this approach presents other problems. For one, in approaches using e g immunocompetent mice, foreign cells introduced into the animal are often recognized by the immune system of the test animal and are systematically eliminated. Although immunodeficient mice allow the injection and growth of non-syngeneic cells, for instance in xenograft tumor models, the applicability of the data obtained for the drug candidate in such studies is limited due to the phylogenetic distance between rodents and humans. In addition, multiple blood extractions are problematic in lower animals, say a mouse. However, such multiple blood extractions are essential for the determination of pharmacokinetic parameters and the continuous testing of blood parameters for evaluating the biological effects of a drug candidate in preclinical animal testing.

In summary, there are two main approaches of obtaining preclinical data on safety and toxicity of a drug candidate for administration in humans. One way is the application of the clinical drug candidate to transgenic animal models, mostly mouse models. However, preclinical data are of limited explanatory power due to the fact that rodents are less related to humans compared to primates. Another way is the testing of surrogate molecules in a relevant animal species. These surrogate molecules are specific for the animals used and are therefore different from the clinical drug candidate developed for administration in humans. The problem is that the clinical drug candidate cannot directly be applied in an animal other than chimpanzees which is closely related to humans and has highly predictive power when used in preclinical testing. Existing methods for obtaining meaningful preclinical data regarding a (bispecific) antibody or fragment thereof undergoing testing as a drug candidate either match this antibody to the test animal, in which case the data obtained are often of only limited applicability for the drug candidate or, conversely, match the test animal to the antibody, in which case ethical and/or cost difficulty arise/s and, in the worst case, the applicability of the data obtained for the drug candidate may still be limited.

It is therefore an aim of the invention to provide a solution to the problems outlined above.

The solution to these problems is the provision of bispecific single chain antibodies exhibiting cross-species specificity which bind to human and non-chimpanzee primate target molecules and therefore can be used both for preclinical evaluation of safety, activity and/or pharmacokinetic profile of said bispecific antibody in primates and—in the identical form—as drugs in humans.

Accordingly, one aspect of the invention relates to the use of a bispecific single chain antibody comprising a first binding domain binding to a non-chimpanzee primate CD3, and a second binding domain binding to a cell surface antigen antigen, wherein said first binding domain binds to human and non-chimpanzee primate CD3, for evaluating the (in vivo) safety and/or activity and/or pharmacokinetic profile of said bispecific single chain antibody in humans, comprising (i) administering said bispecific single chain antibody to a non-chimpanzee primate, (ii) measuring said (in vivo) safety and/or activity and/or pharmacokinetic profile of said bispecific single chain antibody in said non-chimpanzee primate, and (iii) evaluating the (in vivo) safety and/or activity and/or pharmacokinetic profile of said bispecific single chain antibody in humans.

In another aspect, the invention relates to a method for evaluating the biological activity/safety/toxicity of a bispecific single chain antibody as defined above, comprising
(i) administering said bispecific single chain antibody to a non-chimpanzee primate,
(ii) measuring the in vivo safety and/or activity and/or pharmacokinetic profile of said bispecific single chain antibody in said non-chimpanzee primate,
(iii) evaluating the in vivo safety and/or activity and/or pharmacokinetic profile of said bispecific single chain antibody in the non-chimpanzee primate, and
(iv) determining an effective and non-toxic dose of said bispecific single chain antibody and administering said dose to humans.

In particular, it is an aim of the invention to provide means and methods which improve the predictive value of data obtained in preclinical animal testing for the administration of the drug candidate to humans.

As used herein, a "bispecific single chain antibody" denotes a single polypeptide chain comprising two binding domains. Each binding domain comprises one variable region from an antibody heavy chain ("VH region"), wherein the VH region of the first binding domain specifically binds to said first molecule, i.e. the CD3 molecule, and the VH region of the second binding domain specifically binds to a cell surface antigen, as defined in more detail below. The two binding domains are optionally linked to one another by a short polypeptide spacer generally comprising on the order of 5 amino acids. Each binding domain may additionally comprise one variable region from an antibody light chain ("VL region"), the VH region and VL region within each of the first and second binding domains being linked to one another via a polypeptide linker, for example of the type disclosed and claimed in EP 623679 B1, but in any case long enough to allow the VH region and VL region of the first binding domain and the VH region and VL region of the second binding domain to pair with one another such that, together, they are able to specifically bind to the respective first and second molecules.

As used herein, the term "binds" or related expressions such as "binding" or "reactivity with/to" etc. refer to the ability of the first and/or second binding domains of the bispecific single chain antibody as defined herein to discriminate between the respective first and/or second molecule to such an extent that, from a pool of a plurality of different molecules as potential binding partners, only said respective first and/or second molecule is/are bound, or is/are significantly bound. Such binding measurements can be routinely performed e.g. on a Biac ore apparatus.

More specifically, the first binding domain of the bispecific single chain antibody as defined herein binds to human CD3 and to non-chimpanzee primate CD3. The term "non-chimpanzee primate" is explained in more detail below. As evident to the person skilled in the art, it is not excluded from the scope of the invention that the first binding domain of the bispecific single chain antibodies exhibiting cross-species specificity as defined herein may also bind, e.g., to chimpanzee CD3. On the other hand, it is apparent that binding domains which only bind to human CD3, but not to non-chimpanzee primate CD3, are excluded from the scope of the invention. This applies mutatis mutandis to binding domains which only bind to non-chimpanzee primate CD3, but not to human CD3, such as e.g. those of monoclonal antibody FN-18.

The second binding domain of the bispecific single chain antibodies as defined herein binds to a cell surface antigen, preferably a tumor antigen, as set forth below. Preferably, both binding molecules of the bispecific single chain antibodies as defined herein are binding to their respective human and non-chimpanzee primate target molecules. The second binding domain, thus, binds to a human cell surface antigen and to the corresponding homolog of the cell surface antigen in a non-chimpanzee primate. The identification and determination of homologs of human cell surface antigens in non-chimpanzee primates is well known to the person skilled in the art and can be carried out e.g. by sequence alignments.

The term "cross-species specificity" or "interspecies specificity" as used herein means binding of at least one of the two binding domains, preferably of both binding domains, of the bispecific single chain antibody described herein to the same target molecule in humans and non-chimpanzee primates. Thus, "cross-species specificity" or "interspecies specificity" is to be understood as an interspecies reactivity to the same molecule X, but not to a molecule other than X. Cross-species specificity of a monoclonal antibody recognizing e.g. human CD3, to a non-chimpanzee primate CD3, e.g. macaque CD3, can be determined, for instance, by FACS analysis. The FACS analysis is carried out in a way that the respective monoclonal antibody is tested for binding to human and non-chimpanzee primate cells, e.g. macaque cells, expressing said human and non-chimpanzee primate CD3 antigens, respectively. An appropriate assay is shown in the following examples. For the generation of the first binding domain of the bispecific single chain antibodies as defined herein, e.g. monoclonal antibodies binding to both the human and non-chimpanzee CD3 (e.g. macaque CD3) can be used. Similarly, for the generation of the second binding domain of the bispecific single chain antibodies as defined herein, monoclonal antibodies binding to both of the respective human and non-chimpanzee primate cell surface antigens can be utilized. Appropriate binding domains for the bispecific single chain antibodies as defined herein can be derived from cross-species specific monoclonal antibodies by recombinant methods described in the art. A monoclonal antibody binding to a human cell surface antigen and to the homolog of said cell surface antigen in a non-chimpanzee primate can be tested by FACS assays as set forth above. It is evident to those skilled in the art that cross-species specific monoclonal antibodies can also be generated by hybridoma techniques described in the literature (Milstein and Köhler, Nature 256 (1975), 495-7). For example, mice may be alternately immunized with human and non-chimpanzee primate CD3. From these mice, cross-species specific antibody-producing hybridoma cells are isolated via hybridoma technology and analysed by FACS as set forth above. The generation and analysis of bispecific single chain antibodies exhibiting cross-species specificity as described herein is shown in the following examples. The advantages of the bispecific single chain antibodies exhibiting cross-species specificity include the points enumerated below.

As used herein, "human" and "man" refers to the species Homo sapiens. A "human" molecule is therefore the variant of that molecule as it is naturally expressed in Homo sapiens. As far as the medical uses of the constructs described herein are concerned, human patients are to be treated with the same.

As used herein, a "non-chimpanzee primate" or "non-chimp primate" or grammatical variants thereof refers to any primate other than chimpanzee, i.e. other than an animal of belonging to the genus *Pan*, and including the species *Pan paniscus* and *Pan troglodytes*, also known as *Anthropopithecus troglodytes* or *Simia satyrus*. A "primate", "primate species", "primates" or grammatical variants thereof denote/s an order of eutherian mammals divided into the two suborders of prosimians and anthropoids and comprising man, apes, monkeys and lemurs. Specifically, "primates" as used herein comprises the suborder Strepsirrhini (non-tarsier prosimians), including the infraorder Lemuriformes (itself including the superfamilies Cheirogaleoidea and Lemuroidea), the infraorder Chiromyiformes (itself including the family Daubentoniidae) and the infraorder Lorisiformes (itself including the families Lorisidae and Galagidae). "Primates" as used herein also comprises the suborder Haplorrhini, including the infraorder Tarsiiformes (itself including the family Tarsiidae), the infraorder Simiiformes (itself including the Platyrrhini, or New World monkeys, and the Catarrhini, including the Cercopithecidea, or Old-World Monkeys).

The non-chimpanzee primate species may be understood within the meaning of the invention to be a lemur, a tarsier, a gibbon, a marmoset (belonging to New World Monkeys of the family Cebidae) or an Old-World Monkey (belonging to the superfamily Cercopithecoidea).

As used herein, an "Old-World Monkey" comprises any monkey falling in the superfamily Cercopithecoidea, itself subdivided into the families: the Cercopithecinae, which are mainly African but include the diverse genus of macaques which are Asian and North African; and the Colobinae, which include most of the Asian genera but also the African colobus monkeys.

Specifically, within the subfamily Cercopithecinae, an advantageous non-chimpanzee primate may be from the Tribe Cercopithecini, within the genus *Allenopithecus* (Allen's Swamp Monkey, *Allenopithecus nigroviridis*); within the genus *Miopithecus* (Angolan Talapoin, *Miopithecus talapoin*; Gabon Talapoin, *Miopithecus ogouensis*); within the genus *Erythrocebus* (Patas Monkey, *Erythrocebus patas*); within the genus *Chlorocebus* (Green Monkey, *Chlorocebus sabaceus*; Grivet, *Chlorocebus aethiops*; Bale Mountains Vervet, *Chlorocebus djamdjamensis*; Tantalus Monkey, *Chlorocebus tantalus*; Vervet Monkey, *Chlorocebus pygerythrus*; Malbrouck, *Chlorocebus cynosuros*); or within the genus *Cercopithecus* (Dryas Monkey or Salongo Monkey, *Cercopithecus dryas*; Diana Monkey, *Cercopithecus diana*; Roloway Monkey, *Cercopithecus roloway*; Greater Spot-nosed Monkey, *Cercopithecus nictitans*; Blue Monkey, *Cercopithecus mitis*; Silver Monkey, *Cercopithecus doggetti*; Golden Monkey, *Cercopithecus kandti*; Sykes's Monkey, *Cercopithecus albogularis*; Mona Monkey, *Cercopithecus mona*; Campbell's Mona Monkey, *Cercopithecus campbelli*; Lowe's Mona Monkey, *Cercopithecus lowei*; Crested Mona Monkey, *Cercopithecus pogonias*; Wolfs Mona Monkey, *Cercopithecus wolfs*; Dent's Mona Monkey, *Cercopithecus denti*; Lesser Spot-nosed Monkey, *Cercopithecus petaurista*; White-throated Guenon, *Cercopithecus erythrogaster*; Sclater's Guenon, *Cercopithecus sclateri*; Red-eared Guenon, *Cercopithecus erythrotis*; Moustached Guenon, *Cercopithecus cephus*; Red-tailed Monkey, *Cercopithecus ascanius*; L'Hoest's Monkey, *Cercopithecus lhoesti*; Preuss's Monkey, *Cercopithecus preussi*; Sun-tailed Monkey, *Cercopithecus solatus*; Hamlyn's Monkey or Owl-faced Monkey, *Cercopithecus hamlyni*; De Brazza's Monkey, *Cercopithecus neglectus*).

Alternatively, an advantageous non-chimpanzee primate, also within the subfamily Cercopithecinae but within the Tribe Papionini, may be from within the genus *Macaca* (Barbary Macaque, *Macaca sylvanus*; Lion-tailed Macaque, *Macaca silenus*; Southern Pig-tailed Macaque or Beruk, *Macaca nemestrina*; Northern Pig-tailed Macaque, *Macaca leonina*; Pagai Island Macaque or Bokkoi, *Macaca pagensis*; Siberut Macaque, *Macaca siberu*; Moor Macaque, *Macaca maura*; Booted Macaque, *Macaca ochreata*; Tonkean Macaque, *Macaca tonkeana*; Heck's Macaque, *Macaca hecki*; Gorontalo Macaque, *Macaca nigriscens*; Celebes Crested Macaque or Black "Ape", *Macaca nigra*; Cynomolgus monkey or Crab-eating Macaque or Long-tailed Macaque or Kera, *Macaca fascicularis*; Stump-tailed Macaque or Bear Macaque, *Macaca arctoides*; Rhesus Macaque, *Macaca mulatta*; Formosan Rock Macaque, *Macaca cyclopis*; Japanese Macaque, *Macaca fuscata*; Toque Macaque, *Macaca sinica*; Bonnet Macaque, *Macaca radiata*; Barbary Macaque, *Macaca sylvanmus*; Assam Macaque, *Macaca assamensis*; Tibetan Macaque or Milne-Edwards' Macaque, *Macaca thibetana*; Arunachal Macaque or Munzala, *Macaca munzala*); within the genus *Lophocebus* (Gray-cheeked Mangabey, *Lophocebus albigena; Lophocebus albigena albigena; Lophocebus albigena osmani; Lophocebus albigena johnstoni*; Black Crested Mangabey, *Lophocebus aterrimus*; Opdenbosch's Mangabey, *Lophocebus opdenboschi*; Highland Mangabey, *Lophocebus kipunji*); within the genus *Papio* (Hamadryas Baboon, *Papio hamadryas*; Guinea Baboon, *Papio papio*; Olive Baboon, *Papio anubis*; Yellow Baboon, *Papio cynocephalus*; Chacma Baboon, *Papio ursinus*); within the genus *Theropithecus* (Gelada, *Theropithecus gelada*); within the genus *Cercocebus* (Sooty Mangabey, *Cercocebus atys; Cercocebus atys atys; Cercocebus atys lunulatus*; Collared Mangabey, *Cercocebus torquatus*; Agile Mangabey, *Cercocebus agilis*; Golden-bellied Mangabey, *Cercocebus chrysogaster*; Tana River Mangabey, *Cercocebus galeritus*; Sanje Mangabey, *Cercocebus sanjei*); or within the genus *Mandrillus* (Mandrill, *Mandrillus sphinx*; Drill, *Mandrillus leucophaeus*).

Most preferred is *Macaca fascicularis* (also known as Cynomolgus monkey and, therefore, in the Examples named "Cynomolgus") and *Macaca mulatta* (rhesus monkey, named "rhesus").

Within the subfamily Colobinae, an advantageous non-chimpanzee primate may be from the African group, within the genus *Colobus* (Black Colobus, *Colobus satanas*; Angola Colobus, *Colobus angolensis*; King Colobus, *Colobus polykomos*; Ursine Colobus, *Colobus vellerosus*; Mantled Guereza, *Colobus guereza*); within the genus *Piliocolobus* (Western Red Colobus, *Piliocolobus badius; Piliocolobus badius badius; Piliocolobus badius temminckii; Piliocolobus badius waldronae*; Pennant's Colobus, *Piliocolobus pennantii; Piliocolobus pennantii pennantii; Piliocolobus pennantii epieni; Piliocolobus pennantii bouvieri*; Preuss's Red Colobus, *Piliocolobus preussi*; Thollon's Red Colobus, *Piliocolobus tholloni*; Central African Red Colobus, *Piliocolobus foai; Piliocolobus foai foai; Piliocolobus foai ellioti; Piliocolobus foai oustaleti; Piliocolobus foai semlikiensis; Piliocolobus foai parmentierorum*; Ugandan Red Colobus, *Piliocolobus tephrosceles*; Uzyngwa Red Colobus, *Piliocolobus gordonorum*; Zanzibar Red Colobus, *Piliocolobus kirkii*; Tana River Red Colobus, *Piliocolobus rufomitratus*); or within the genus *Procolobus* (Olive Colobus, *Procolobus verus*).

Within the subfamily Colobinae, an advantageous non-chimpanzee primate may alternatively be from the Langur (leaf monkey) group, within the genus *Semnopithecus* (Nepal Gray Langur, *Semnopithecus schistaceus*; Kashmir Gray Langur, *Semnopithecus ajax*; Tarai Gray Langur, *Semnopithecus hector*; Northern Plains Gray Langur, *Semnopithecus entellus*; Black-footed Gray Langur, *Semnopithecus hypoleucos*; Southern Plains Gray Langur, *Semnopithecus dus-*

*sumieri*; Tufted Gray Langur, *Semnopithecus priam*); within the *T. vetulus* group or the genus *Trachypithecus* (Purple-faced Langur, *Trachypithecus vetulus*; Nilgiri Langur, *Trachypithecus johnii*); within the *T. cristatus* group of the genus *Trachypithecus* (Javan Lutung, *Trachypithecus auratus*; Silvery Leaf Monkey or Silvery Lutung, *Trachypithecus cristatus*; Indochinese Lutung, *Trachypithecus germaini*; Tenasserim Lutung, *Trachypithecus barbei*); within the *T. obscurus* group of the genus *Trachypithecus* (Dusky Leaf Monkey or Spectacled Leaf Monkey, *Trachypithecus obscurus*; Phayre's Leaf Monkey, *Trachypithecus phayrei*); within the *T. pileatus* group of the genus *Trachypithecus* (Capped Langur, *Trachypithecus pileatus*; Shortridge's Langur, *Trachypithecus shortridgei*; Gee's Golden Langur, *Trachypithecus geei*); within the *T. francoisi* group of the genus *Trachypithecus* (Francois' Langur, *Trachypithecus francoisi*; Hatinh Langur, *Trachypithecus hatinhensis*; White-headed Langur, *Trachypithecus poliocephalus*; Laotian Langur, *Trachypithecus laotum*; Delacour's Langur, *Trachypithecus delacouri*; Indochinese Black Langur, *Trachypithecus ebenus*); or within the genus *Presbytis* (Sumatran Surili, *Presbytis melalophos*; Banded Surili, *Presbytis femoralis*; Sarawak Surili, *Presbytis chrysomelas*; White-thighed Surili, *Presbytis siamensis*; White-fronted Surili, *Presbytis frontata*; Javan Surili, *Presbytis comata*; Thomas's Langur, *Presbytis thomasi*; Hose's Langur, *Presbytis hosei*; Maroon Leaf Monkey, *Presbytis rubicunda*; Mentawai Langur or Joja, *Presbytis potenziani*; Natuna Island Surili, *Presbytis natunae*).

Within the subfamily Colobinae, an advantageous non-chimpanzee primate may alternatively be from the Odd-Nosed group, within the genus *Pygathrix* (Red-shanked Douc, *Pygathrix nemaeus*; Black-shanked Douc, *Pygathrix nigripes*; Gray-shanked Douc, *Pygathrix cinerea*); within the genus *Rhinopithecus* (Golden Snub-nosed Monkey, *Rhinopithecus roxellana*; Black Snub-nosed Monkey, *Rhinopithecus bieti*; Gray Snub-nosed Monkey, *Rhinopithecus brelichi*; Tonkin Snub-nosed Langur, *Rhinopithecus avunculus*); within the genus *Nasalis* (Proboscis Monkey, *Nasalis larvatus*); or within the genus *Simias* (Pig-tailed Langur, *Simias concolor*). As used herein, the term "marmoset" denotes any New World Monkeys of the genus *Callithrix*, for example belonging to the Atlantic marmosets of subgenus *Callithrix* (sic!) (Common Marmoset, *Callithrix (Callithrix) jacchus*; Black-tufted Marmoset, *Callithrix (Callithrix) penicillata*; Wied's Marmoset, *Callithrix (Callithrix) kuhlii*; White-headed Marmoset, *Callithrix (Callithrix) geoffroyi*; Buffy-headed Marmoset, *Callithrix (Callithrix) flaviceps*; Buffy-tufted Marmoset, *Callithrix (Callithrix) aurita*); belonging to the Amazonian marmosets of subgenus *Mico* (Rio Acari Marmoset, *Callithrix (Mico) acariensis*; Manicore Marmoset, *Callithrix (Mico) manicorensis*; Silvery Marmoset, *Callithrix (Mico) argentata*; White Marmoset, *Callithrix (Mico) leucippe*; Emilia's Marmoset, *Callithrix (Mico) emiliae*; Black-headed Marmoset, *Callithrix (Mico) nigriceps*; Marca's Marmoset, *Callithrix (Mico)marcai*; Black-tailed Marmoset, *Callithrix (Mico) melanura*; Santarem Marmoset, *Callithrix (Mico) humeralifera*; Maues Marmoset, *Callithrix (Mico) mauesi*; Gold-and-white Marmoset, *Callithrix (Mico) chrysoleuca*; Hershkovitz's Marmoset, *Callithrix (Mico) intermedia*; Satéré Marmoset, *Callithrix (Mico) saterei*); Roosmalens' Dwarf Marmoset belonging to the subgenus *Callibella* (*Callithrix (Callibella) humilis*); or the Pygmy Marmoset belonging to the subgenus *Cebuella* (*Callithrix (Cebuella) pygmaea*).

As used herein, CD3 denotes a molecule expressed as part of the T cell receptor and has the meaning as typically ascribed to it in the prior art. In human, it encompasses in individual or independently combined form all known CD3 subunits, for example CD3 epsilon, CD3 delta, CD3 gamma, CD3 zeta, CD3 alpha and CD3 beta. The non-chimpanzee primate CD3 antigens as referred to herein are, for example, *Macaca fascicularis* CD3 and *Macaca mulatta* CD3. In *Macaca fascicularis*, it encompasses CD3 epsilon FN-18 negative and CD3 epsilon FN-18 positive, CD3 gamma and CD3 delta. In *Macaca mulatta*, it encompasses CD3 epsilon, CD3 gamma and CD3 delta. Preferably, said CD3 as used herein is CD3 epsilon.

The human CD3 epsilon is indicated in GenBank Accession No. NM_000733 and comprises SEQ ID NO. 134. The human CD3 gamma is indicated in GenBank Accession No. NM_000073 and comprises SEQ ID NO. 142. The human CD3 delta is indicated in GenBank Accession No. NM_000732 and comprises SEQ ID NO. 143.

The CD3 epsilon "FN-18 negative" of *Macaca fascicularis* (i.e. CD3 epsilon not recognized by monoclonal antibody FN-18 due to a polymorphism as set forth above) is indicated in GenBank Accession No. AB073994 and comprises SEQ ID NO. 136.

The CD3 epsilon "FN-18 positive" of *Macaca fascicularis* (i.e. CD3 epsilon recognized by monoclonal antibody FN-18) is indicated in GenBank Accession No. AB073993 and comprises SEQ ID NO. 135. The CD3 gamma of *Macaca fascicularis* is indicated in GenBank Accession No. AB073992 and comprises SEQ ID NO. 144. The CD3 delta of *Macaca fascicularis* is indicated in GenBank Accession No. AB073991 and comprises SEQ ID NO. 145.

The nucleic acid sequences and amino acid sequences of the respective CD3 epsilon, gamma and delta homologs of *Macaca mulatta* can be identified and isolated by recombinant techniques described in the art (Sambrook et al. Molecular Cloning: A Laboratory Manual; Cold Spring Harbor Laboratory Press, 3$^{rd}$ edition 2001). This applies mutatis mutandis to the CD3 epsilon, gamma and delta homologs of other non-chimpanzee primates as defined herein.

As pointed out above and as disclosed herein, it is envisaged that the first binding domain of the bispecific single chain antibody comprised in the inventive pharmaceutical composition leads to an epitope of human and non-chimpanzee primate CD3 which comprises the amino acid sequence "phenylalanine (F)—serine (S)—glutamic acid (E)". The person skilled in the art is readily in the position to deduce an epitope detected by a given antibody/binding molecule and/or (as in the present invention) a given "binding domain" of a single chain construct by methods known in the art, said methods are also illustrated in the appended examples and may comprise Western blot analysis, epitope mapping or pepspot analysis and the like.

The epitope to be detected by said first binding domain is preferably in the range of 15 amino acids +/−3 amino acids. Envisaged are (but not limiting) 18, 17, 16, 15, 14, 13, 12, 11, 10, 9, 8, 7, 6, 5, 4 or 3 amino acids in said epitope comprising the "F-S-E" stretch/"F-S-E" core epitope.

As shown in the following Examples, the minimum core epitope of human and non-chimpanzee primate CD3 bound by the first binding domain of the bispecific single chain antibody as defined herein is an epitope comprising the amino acid residues "FSE". More specifically, the minimum epitope comprises the amino acid residues "FSEXE" (SEQ ID NOs. 202 and 204), wherein the substitution of methionine to leucine is a conserved amino acid substitution between two neutral, non-polar amino acid residues. The minimum epitope may be part of a discontinuous epitope. As used herein, the term "discontinuous epitope" is to be understood as at least two non-adjacent amino acid sequence stretches within a given polypeptide chain, here e.g. CD3 (preferably CD3 epsilon), which are simultaneously bound by an antibody. These amino acid stretches might be of different length and may also be involved in the interaction of antibody and antigen. Accordingly, in addition to the minimum (core) epitope as defined above, the bispecific single chain antibody may simultaneously bind to one, two or even more non-adjacent epitopes. This (these) non-adjacent epitope(s) in combination with the minimal (core) epitope could represent the contact site between antigen and antibody. According to this definition, such simultaneous binding may be of the polypeptide in linear form. Here, one may imagine the polypeptide forming an extended loop, in one region of which the two sequences for example are more or less in parallel and in proximity of one another. Non-adjacent epitopes in the linear sequence could form a three dimensional structure leading to a close proximity of these epitopes. In this state they are simultaneously bound by the bispecific single chain antibody as defined herein. According to this definition, simultaneous binding of the at least two sequence stretches of the polypeptide indicated above (including the minimum (core) epitope) may also take the form of antibody binding to a conformational epitope. Here, the mature polypeptide has already formed its tertiary conformation as it normally exists in vivo. In this tertiary conformation, the polypeptide chain is folded in such a manner as to bring the at least two sequence stretches indicated above into spatial proximity, for example, on the outer surface of a particular region of mature, folded polypeptide, where they are then recognized by virtue of their three-dimensional conformation in the context of the surrounding polypeptide sequences.

The term "cell surface antigen" as used herein denotes a molecule which is displayed on the surface of a cell. In most cases, this molecule will be located in or on the plasma membrane of the cell such that at least part of this molecule remains accessible from outside the cell in tertiary form. A non-limiting example of a cell surface molecule which is located in the plasma membrane is a transmembrane protein comprising, in its tertiary conformation, regions of hydrophilicity and hydrophobicity. Here, at least one hydrophobic region allows the cell surface molecule to be embedded, or inserted in the hydrophobic plasma membrane of the cell while the hydrophilic regions extend on either side of the plasma membrane into the cytoplasm and extracellular space, respectively. Non-limiting examples of a cell surface molecules which are located on the plasma membrane are proteins which have been modified at a cysteine residue to bear a palmitoyl group, proteins modified at a C-terminal cysteine residue to bear a farnesyl group or proteins which have been modified at the C-terminus to bear a glycosyl phosphatidyl inositol ("GPI") anchor. These groups allow covalent attachment of proteins to the outer surface of the plasma membrane, where they remain accessible for recognition by extracellular molecules such as antibodies.

The "tumor antigen" as used herein may be understood as those antigens that are presented on tumor cells. These antigens can be presented on the cell surface with an extracellular part which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. Non-limiting examples of tumor antigens as used herein are EpCAM (Naundorf, Int. J. Cancer 100/1 (2002), 101-110), EGFR (Liu, Br. J. Cancer 82/12 (2000), 1991-1999; Bonner, Semin. Radiat. Oncol. 12 (2002), 11-20; Kiyota, Oncology 63/1 (2002), 92-98; Kuan, Brain Tumor Pathol. 17/2 (2000), 71-78), EGFRvIII (Kuan, Brain Tumor Pathol. 17/2 (2000), 71-78), or Carboanhydrase IX (MN/CA IX) (Uemura, Br. J. Cancer 81/4 (1999), 741-746; Longcaster, Cancer Res. 61/17 (2001), 6394-6399; Chia, J. Clin. Oncol. 19/16 (2001), 3660-3668; Beasley, Cancer Res. 61/13 (2001), 5262-5267).

The corresponding sequences of the human and non-chimpanzee primate nucleic acid and amino acid sequences can be found e.g. in NCBI databases.

A cross-species-specific monoclonal antibody binding to a human cell surface antigen (preferably a tumor antigen) and to the homolog of said cell surface antigen (preferably a tumor antigen) in a non-chimpanzee primate can be generated as set out above. "Homologs" as used herein refer to genes (encoding e.g. CD3, CD3 epsilon, cell surface antigens or tumor antigens) which encode gene products with similar or identical biological function in different species and which genes can be attributed to a common precursor gene. Cross-species specificity of said monoclonal antibody to the human and non-chimpanzee primate tumor antigen can be tested by FACS assays as set forth above. Alternatively, immunohistochemistry, radioimmunoassay, or ELISA assays may be used as known to the person skilled in the art. The second binding domain of the bispecific single chain antibody exhibiting cross-species specificity as described herein can for example be derived from such cross-species specific monoclonal antibodies by recombinant techniques described in the following examples.

The term "evaluating the in vivo safety and/or activity and/or pharmacokinetic profile" of the bispecific single chain antibody as used herein may be understood as set forth below. Before a new candidate medication can be marketed it must pass through rigorous testing, which may be roughly subdivided into preclinical testing in animals and clinical phases in human patients. The aim of preclinical testing in animals is to prove that the drug candidate is safe and efficacious (see e.g. the Preclinical safety evaluation of biotechnology-derived pharmaceuticals; ICH Harmonised Tripartite Guideline; ICH Steering Committee meeting on Jul. 16, 1997).

The term "drug", "drug candidate" or "pharmaceutical composition" as used herein refers to bispecific single chain antibodies defined herein.

The biological activity of the bispecific single chain antibody as defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the bispecific single chain antibody as defined herein, using e.g. standardized NCI response criteria. The success or in vivo efficacy of the therapy using a bispecific single chain antibody as defined herein refers to the effectiveness of the bispecific single chain antibody as defined herein for its intended purpose, i.e. the ability of the bispecific antibody to cause its desired effect, i.e.

depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment [Cheson B D, Horning S J, Coiffier B, Shipp M A, Fisher R I, Connors J M, Lister T A, Vose J, Grillo-Lopez A, Hagenbeek A, Cabanillas F, Klippensten D, Hiddemann W, Castellino R, Harris N L, Armitage J O, Carter W, Hoppe R, Canellos G P. Report of an international workshop to standardize response criteria for non-Hodgkin's lymphomas. NCI Sponsored International Working Group. J Clin Oncol. 1999 April; 17(4): 1244]), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs is the predictable modulation of pharmacokinetic properties. To this end, a pharmacokinetic profile of the drug candidate, i.e. a profile of the pharmacokinetic parameters that effect the ability of a particular drug to treat a given condition, is established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above. "Half-life" means the time where 50% of an administered drug are eliminated through biological processes, e.g. metabolism, excretion, etc.

By "hepatic first-pass metabolism" is meant the propensity of a drug to be metabolized upon first contact with the liver, i.e. during its first pass through the liver.

"Volume of distribution" means the degree of retention of a drug throughout the various compartments of the body, like e.g. intracellular and extracellular spaces, tissues and organs, etc. and the distribution of the drug within these compartments.

"Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered.

"Bioavailability" means the amount of a drug in the blood compartment.

"Lag time" means the time delay between the administration of the drug and its detection and measurability in blood or plasma.

"Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetik parameters of the bispecific single chain antibodies exhibiting cross-species specificity which may be determined in preclinical animal testing in non-chimpanzee primates as outlined above are also set forth e.g. in the publication by Schlereth et al. (Cancer Immunol. Immunother. 20 (2005), 1-12).

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviating to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance haematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The term "effective and non-toxic dose" as used herein refers to a tolerable dose of the bispecific single chain antibody as defined herein which is high enough to cause depletion of pathologic cells, tumor elimination, tumor shrinkage or stabilisation of disease without or essentially without major toxic effects. Such effective and non-toxic doses may be determined e.g. by dose escalation studies described in the art and should be below the dose inducing severe adverse side events (dose limiting toxicity, DLT).

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

It has been surprisingly found that it is possible to generate bispecific antibody-based therapeutics for humans wherein the identical molecule can also be used in preclinical animal testing. This is due to the unexpected identification of bispecific single chain antibodies which, in addition to binding to human antigens (and due to genetic similarity likely to chimpanzee counterparts), also bind to the homologs of said antigens of non-chimpanzee primates, such as macaques. Thus, the need to construct a surrogate bispecific single chain antibody for testing in a phylogenetic distant (from humans) species disappears. As a result, the very same bispecific single chain antibody can be used in animal preclinical testing as is intended to be administered to humans in clinical testing as well as following market approval. The ability to use the same molecule for preclinical animal testing as in later administration to humans virtually eliminates, or at least greatly reduces, the danger that the data obtained in preclinical animal testing are not applicable to the human case. In short, obtaining preclinical safety data in animals using the same molecule as will actually be administered to humans does much to ensure the applicability of the data to a human-relevant scenario. In contrast, in conventional approaches using surrogate molecules, said surrogate antibodies have to be molecularly adapted to the animal test system used for preclinical safety assessment. Thus, the surrogate antibody to be used in human therapy in fact differs in sequence and also likely in structure from the one used in preclinical testing in pharmacokinetic parameters and/or biological activity, with the consequence that data obtained in preclinical animal testing have limited applicability/transferability to the human case. The use of surrogate molecules requires the construction, production, purification and characterization of a completely new antibody construct. This leads to additional development costs and time necessary to obtain that molecule. In sum, surrogates have to be developed separately in addition to the actual drug to be used in human therapy, so that two lines of development for two bispecific single chain antibody molecules have to be carried out. Therefore, a major advantage of the bispecific antibody-based constructs exhibiting cross-species specificity described herein is that the identical molecule can be used for therapeutics in humans and in preclinical animal testing.

On the other hand, it is also no longer necessary to adapt the test animal to the bispecific antibody-drug candidate intended for administration to humans, such as e.g. the creation of transgenic animals producing the human molecules bound by the bispecific antibody. The bispecific single chain antibodies exhibiting cross-species specificity according to the uses and methods of invention can be directly used for preclinical testing in non-chimpanzee primates, without any genetic manipulation of the animals. As well known to those skilled in the art, approaches in which the test animal is adapted to the drug candidate always bear the risk that the results obtained in the preclinical safety testing are less representative and predictive for humans due to the modification of the animal. For example, in transgenic animals, the proteins encoded by the transgenes are often highly over-expressed. Thus, data obtained for the biological activity of an antibody against this protein antigen may be limited in their predictive value for humans in which the protein is expressed at much lower, more physiological levels.

A further advantage of the uses of the bispecific single chain antibody exhibiting cross-species specificity of the invention lies in the avoidance of chimpanzee as a species for animal testing. Chimpanzees are the closest relatives to humans and were recently grouped into the family of hominids based on the genome sequencing data (Wildman et al., PNAS 100 (2003), 7181). Therefore, data obtained with chimpanzee is generally considered to be highly predictive for humans. However, due to their status as endangered species, the number of chimpanzees which can be used for medical experiments is highly restricted. As stated above, maintenance of chimpanzees for animal testing is therefore both costly and ethically problematic. The uses of the bispecific single chain antibody of the invention avoids both financial burden and ethical objection during preclinical testing without prejudicing the quality, i.e. applicability, of the animal testing data obtained. In light of this, the uses of bispecific single chain antibodies exhibiting cross-species specificity and methods according to the invention for preclinical animal testing in non-chimpanzee primates provides for a reasonable alternative for studies in chimpanzees.

A further advantage of the bispecific single chain antibody of the invention is the ability of extracting multiple blood samples when using it as part of animal preclinical testing, for example in the course of pharmacokinetic animal studies. Multiple blood extractions can be much more readily obtained with a non-chimpanzee primate than with lower animals, say a mouse. The extraction of multiple blood samples allows continuous testing of blood parameters for the determination of the biological effects induced by the bispecific single chain antibody of the invention. Furthermore, the extraction of multiple blood samples enables the researcher to evaluate the pharmacokinetic profile of the bispecific single chain antibody as defined herein. In addition, potential side effects which may be induced by said bispecific single chain antibody reflected in blood parameters can be measured in different blood samples extracted during the course of the administration of said antibody. This allows the determination of the potential toxicity profile of the bispecific single chain antibody as defined herein.

The advantages of the pharmaceutical compositions comprising bispecific single chain antibodies exhibiting cross-species specificity, uses of said bispecific antibodies and methods according to the invention may be briefly summarized as follows:

First, the bispecific single chain antibody exhibiting cross-species specificity used in preclinical testing is the same as the one used in human therapy. Thus, it is no longer necessary to develop two independent molecules which may differ in their pharmacokinetic properties and biological activity. This is highly advantageous in that e.g. the pharmacokinetic results are more directly transferable and applicable to the human setting than e.g. in conventional surrogate approaches.

Second, the uses of the bispecific antibody exhibiting cross-species specificity and methods according to the invention for the preparation of therapeutics in human is less cost- and labor-intensive than surrogate approaches.

Third, chimpanzee as a species for animal testing is avoided.

Fourth, multiple blood samples can be extracted for extensive pharmacokinetic studies.

A further aspect of the invention relates to a method of determining the biological activity and/or efficacy of a bispecific single chain antibody as defined above, wherein said bispecific single chain antibody is administered to a non-chimpanzee primate and the in vivo activity is measured.

Preferably, said in vivo activity is T cell activation, tumor target cell depletion, cytotoxicity, toxicity, occurrence of adverse side effects, and/or cytokine release. Methods for the determination of said in vivo activity are set forth e.g. in WO 99/54440.

The present invention in another aspect also provides for a pharmaceutical composition for the treatment of a human patient, comprising a bispecific single chain antibody which comprises
(i) a first binding domain binding to a non-chimpanzee primate CD3, and
(ii) a second binding domain binding to a cell surface antigen,
wherein said first binding domain binds to human and non-chimpanzee primate CD3.

In accordance with this invention, the term "pharmaceutical composition" relates to a composition for administration to a patient, preferably a human patient. Preferably, the pharmaceutical composition comprises suitable formulations of carriers, stabilizers and/or excipients. In a preferred embodiment, the pharmaceutical composition comprises a composition for parenteral, transdermal, intraluminal, intraarterial, intrathecal and/or intranasal administration or by direct injection into tissue. It is in particular envisaged that said composition is administered to a patient via infusion or injection. Administration of the suitable compositions may be effected by different ways, e.g., by intravenous, intraperitoneal, subcutaneous, intramuscular, topical or intradermal administration. The composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, liposomes, etc. Compositions comprising such carriers can be formulated by well known conventional methods. These compositions can be administered to the subject at a suitable dose which can be determined e.g. by dose escalating studies by administration of increasing doses of the bispecific single chain antibody exhibiting cross-species specificity described herein to non-chimpanzee primates, for instance macaques. As set forth above, the bispecific single chain antibody exhibiting cross-species specificity described herein can be advantageously used in identical form in preclinical testing in non-chimpanzee primates and as drug in humans. These compositions can also be administered in combination with other proteinaceous and non-proteinaceous drugs. These drugs may be administered simultaneously with the composition comprising the bispecific single chain antibody as defined herein or separately before or after administration of said bispecific antibody in timely defined intervals and doses. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the composition of the present invention might comprise proteinaceous carriers, like, e.g., serum albumin or immunoglobulin, preferably of human origin. It is envisaged that the composition of the invention might comprise, in addition to the bispecific single chain antibody as defined herein, further biologically active agents, depending on the intended use of the composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art.

According to a preferred embodiment of the pharmaceutical composition of the invention, the first binding domain of the bispecific single chain antibody as defined herein binds to an epitope of human and non-chimpanzee primate CD3 comprising the amino acid sequence "FSE". The minimum core epitope comprising the amino acid residues "FSE", the minimum epitope comprising the amino acid sequence "FSEXE" (SEQ ID NOs. 202 and 204; wherein "X" corresponds to a leucine (L) or to a methionine (M)) or non-adjacent epitopes as defined herein are preferably 18, 17, 16, 15, 14, 13, 12, 11, 10, 9, 8, 7, 6, 5, 4 or 3 amino acid residues in length. Preferably, said epitopes are 13 amino acid residues in length. Even more preferrred, the epitope with the "FSEXE" (SEQ ID NOs. 202 and 204; wherein "X" corresponds to a leucine (L) or to a methionine (M))—motif comprises the amino acid sequence "EFSELEQSGYYVC" (SEQ ID NO. 195) of human CD3 epsilon. In cynomolgus CD3 epsilon, the corresponding epitope reads "EFSEMEQSGYYVC" (SEQ ID NO. 201). The substitution of methionine to leucine is a conserved amino acid substitution between two neutral, non-polar amino acid residues. The corresponding sequence of the preferred epitope "EFSEXEQSGYYVC" wherein X represents L (Leucine) or M (Methionine) is depicted in SEQ ID NO. 207. As shown in the following Examples, the bispecific single chain antibody as defined herein not only binds to this epitope, but also to amino-acid stretches non-adjacent to said minimal epitope. For example, the bispecific single chain antibody as defined herein in addition to the minimum core epitope may simultaneously bind to (an) epitope(s) of human CD3 epsilon contained in said CD3 epsilon chain. Accordingly, said epitope may additionally comprise the amino acid sequence "QYPGSEILWQHND" (SEQ ID NO. 203). Also additional or (further) epitopes of cynomolgus CD3 epsilon contained in said chain may be detected by the binding molecule or molecule comprising the binding domains as defined therein. These additional or further sequences may comprise the amino acid sequence "QDGNEEMGSITQT" (SEQ ID NO. 199) and "YYVSYPRGSNPED" (SEQ ID NO. 200). Thus, the minimal epitope is most likely part of a discontinuous epitope or a conformational epitope. As evident to a person skilled in the art, the scope of the present invention includes bispecific single chain antibodies not only binding to this minimum (core) epitope, but also to one, two or even more non-adjacent amino acid sequence stretches within CD3 (preferably CD3 epsilon). Based on the results shown in the following Examples it is concluded that cross-species specific anti-CD3 antibodies contact CD3 epsilon in the area of amino acid residues 57-61 of both cynomolgus and human CD3 epsilon comprising the amino acid stretches FSEME (SEQ ID NO. 206) and FSELE (SEQ ID NO. 205) of cynomolgus and human CD3 epsilon, respectively, with the motif FSE forming the epitope core. This result—although plausible because of the accessibility of the E-F-loop (amino acids 56-62) of human CD3 epsilon (Kjer-Nielsen et al., PNAS 101 (2004), p. 7675-80) comprising the amino acids FSELE (SEQ ID NO. 205) or FSEME (SEQ ID NO. 206)—is surprising since there is no overlap of this newly defined epitope with the known epitope on the CD3 epsilon-chain of anti-CD3 antibodies OKT-3 and UCHT-1 (Kjer-Nielsen et al., loc.cit; Arnett et al., PNAS 101 (2004), p. 16268-73) which have so far been regarded as representative of all anti-CD3 antibodies thought to form a single family with the same or a very similar epitope. In summary, the epitopes "FSE" and "FSEXE" (SEQ ID NO. 204) are distinct from the epitopes recognized by UCHT-1 or OKT-3 (Kjer-Nielsen et al., PNAS 101 (2004), p. 7675-80; Arnett et al., PNAS 101 (2004), p. 16268-73) and are unique for cross-species specific anti-CD3 antibodies binding to human and macaque CD3. Preferably, the minimum epitope comprises the amino acid sequence "FSEXE" (SEQ ID NO.

204), wherein X represents L (Leucine) or M (Methionine) and stands for a substitution of non-polar, neutral amino acid residues.

It is envisaged that in the pharmaceutical composition of the invention, said first binding domain of the bispecific single chain antibody of the pharmaceutical composition of the invention is located C-terminally to the second binding domain. However, also part of this invention is a bispecific construct, wherein the "first binding domain to a non-chimpanzee primate CD3" is located N-terminally to the herein defined "second binding domain to a cell surface antigen".

As shown in the following examples, the advantages as described hereinabove are realizable not only when the first binding domain (binding to CD3) is located C-terminally to the second binding domain, i.e. closer to the C-terminus of the bispecific single chain antibody than the second binding domain, but also when the first binding domain (binding to CD3) is located N-terminally to the second binding domain, i.e. closer to the N-terminus of the bispecific single chain antibody than the second binding domain. The arrangement of the binding domains in the bispecific single chain antibody defined herein may therefore be one in which the first binding domain is located C-terminally to the second binding domain. The arrangement of the V chains may be VH (cell surface antigen)-VL (cell surface antigen)-VL(CD3)-VH(CD3), VH(cell surface antigen)-VL(cell surface antigen)-VH(CD3)-VL(CD3), VL(cell surface antigen)-VH(cell surface antigen)-VL(CD3)-VH(CD3) or VL(cell surface antigen)-VH(cell surface antigen)-VH(CD3)-VL(CD3). For an arrangement, in which the first binding domain is located N-terminally to the second binding domain, the following orders are possible: VH (CD3)-VL(CD3)-VL(cell surface antigen)-VH(cell surface antigen), VH(CD3)-VL(CD3)-VH (cell surface antigen)-VL(cell surface antigen), VL(CD3)-VH(CD3)-VL(cell surface antigen)-VH(cell surface antigen) or VL(CD3)-VH(CD3)-VH(cell surface antigen)-VL (cell surface antigen). As used herein, "N-terminally to" or "C-terminally to" and grammatical variants thereof denote relative location within the primary amino acid sequence rather than placement at the absolute N- or C-terminus of the bispecific single chain antibody. Hence, as a non-limiting example, a first binding domain which is "located C-terminally to the second binding domain" simply denotes that the first binding domain is located to the carboxyl side of the second binding domain within the bispecific single chain antibody, and does not exclude the possibility that an additional sequence, for example a His-tag, or another proteinaceous or non-proteinaceous compound such as a radioisotope, is located at the ultimate C-terminus of the bispecific single chain antibody.

In another preferred embodiment of the pharmaceutical composition, the second binding domain binds to a cell surface antigen and to the non-chimpanzee primate homolog of said cell surface antigen.

According to this embodiment of the invention, both the first and second binding domains of the bispecific single chain antibody described herein specifically bind to both human and non-chimpanzee primate variants of said first and second molecules, respectively. In light of the above statements, this is particularly advantageous since sufficient (cross-species) specificity exists on both sides of the bispecific single chain antibody, thus ensuring interspecies compatibility with respect to both first and second molecules and hence optimal extrapolability of the data obtained in pre-clinical animal studies to the case of administration in humans.

Preferably, said cell surface antigen is a tumor antigen. Even more preferred, said tumor antigen is EpCAM (Naundorf, Int. J. Cancer 100/1 (2002), 101-110), EGFR (Liu, Br. J. Cancer 82/12 (2000), 1991-1999; Bonner, Semin. Radiat. Oncol. 12 (2002), 11-20; Kiyota, Oncology 63/1 (2002), 92-98; Kuan, Brain Tumor Pathol. 17/2 (2000), 71-78), EGFRvIII (Kuan, Brain Tumor Pathol. 17/2 (2000), 71-78), or Carboanhydrase IX (MN/CA IX) (Uemura, Br. J. Cancer 81/4 (1999), 741-746; Longcaster, Cancer Res. 61/17 (2001), 6394-6399; Chia, J. Clin. Oncol. 19/16 (2001), 3660-3668; Beasley, Cancer Res. 61/13 (2001), 5262-5267).

Particularly preferred as cell surface antigen and/or tumor antigen is EpCAM. As shown in the following Examples, the present application for the first time provides for the nucleic acid and amino acid sequences of the extracellular domain of cynomolgus EpCAM shown in SEQ ID NOs. 47 and 48, respectively. Said sequences are essential tools for the generation and characterization of the bispecific single chain antibodies as defined herein exhibiting cross-species specificity to human and cynomolgus EpCAM.

In a further preferred embodiment of the pharmaceutical composition of the invention, the first binding domain comprises a VH region having an amino acid sequence as shown in any of SEQ ID NOs. 2, 110 or 6. It is envisaged and preferred that the VH region of the first binding domain comprises at least a third CDR (CDR-H3) comprising an amino acid sequence as set out in SEQ ID NO. 112 or CDR-H3* comprising an amino acid sequence as set out in SEQ ID NO. 113. The first binding domain may additionally comprise a second CDR (CDR-H2) comprising an amino acid sequence as set out in SEQ ID NO. 114. Further, the first binding domain may in addition comprise a first CDR (CDR-H1) comprising an amino acid sequence as set out in SEQ ID NO. 115. The VH region of the first binding domain thus may comprise one, two or all three of the mentioned CDRs. The mentioned CDRs are included for example in the VH regions shown in SEQ ID NOs. 2 and 110.

Alternatively, it is envisaged that the VH region of the first binding domain comprises a third CDR (CDR-H3) comprising an amino acid sequence as set out in SEQ ID NO. 119. Preferably, the first binding domain additionally comprises a second CDR (CDR-H2) comprising an amino acid sequence as set out in SEQ ID NO. 120. Especially preferred, the first binding domain additionally comprises a first CDR (CDR-H1) comprising an amino acid sequence as set out in SEQ ID NO. 121. The VH region of the first binding domain thus may comprise one, two or all three of the mentioned CDRs. The above-indicated CDRs are included for example in the VH region shown in SEQ ID NO. 6.

In another preferred embodiment of the pharmaceutical composition, the first binding domain comprises a VL region having an amino acid sequence as shown in any of SEQ ID NOs. 4, 148, 168 or 8. It is envisaged and preferred that the VL region of the first binding domain comprises at least a third CDR (CDR-L3) comprising an amino acid sequence as set out in SEQ ID NO. 116. The VL region may further comprise a second CDR (CDR-L2) comprising an amino acid sequence as set out in SEQ ID NO. 117. The VL region may in addition comprise a first CDR (CDR-L1) comprising an amino acid sequence as set out in SEQ ID NO. 118. The VL region of the first binding domain thus may comprise one, two or all three of the mentioned CDRs. The above-indicated CDRs are included for example in the VL regions shown in SEQ ID NOs. 4, 148 and 168.

Alternatively, it is envisaged that the VL region of the first binding domain comprises a third CDR (CDR-L3) comprising an amino acid sequence as set out in SEQ ID NO. 164.

Preferably, the first binding domain additionally comprises a second CDR (CDR-L2) comprising an amino acid sequence as set out in SEQ ID NO. 165. Especially preferred, the first binding domain additionally comprises a first CDR (CDR-L1) comprising an amino acid sequence as set out in SEQ ID NO. 166. The VL region of the first binding domain thus may comprise one, two or all three of the mentioned CDRs. The above-indicated CDRs are included for example in the VL region shown in SEQ ID NO. 8.

Preferably, the first binding domain comprises CDR-L1 (SEQ ID NO. 118), CDR-L2 (SEQ ID NO. 117), and CDR-L3 (SEQ ID NO. 116) and CDR-H1 (SEQ ID NO. 115), CDR-H2 (SEQ ID NO. 114) and CDR-H3 (SEQ ID NO. 112) or CDR-H3* comprising the amino acid sequence "VSWFAY" (SEQ ID NO. 113).

Alternatively, the first binding domain comprises CDR-L1 (SEQ ID NO. 166), CDR-L2 (SEQ ID NO. 165), and CDR-L3 (SEQ ID NO. 164) and CDR-H1 (SEQ ID NO. 121), CDR-H2 (SEQ ID NO. 120) and CDR H3 (SEQ ID NO. 119).

Even more preferred, the VH region of the first binding domain comprises or consists of the amino acid sequence shown in SEQ ID NO. 2 and the VL region of the first binding domain comprises or consists of the amino acid sequence shown SEQ ID NO. 4; or the VH region of the first binding domain comprises or consists of the amino acid sequence shown in SEQ ID NO. 110 and the VL region of the first binding domain comprises or consists of the amino acid sequence shown in SEQ ID NO. 148; or the VH region of the first binding domain comprises or consists of the amino acid sequence shown in SEQ ID NO. 110 and the VL region of the first binding domain comprises or consists of the amino acid sequence shown in SEQ ID NO. 168, or the VH region of the first binding domain comprises or consists of the amino acid sequence shown in SEQ ID NO. 6 and the VL region of the first binding domain comprises or consists of the amino acid sequence shown in SEQ ID NO. 8. Or the VH region of the first binding domain comprises or consists of the amino acid sequence shown in SEQ ID NO. 2 and the VL region of the first binding domain comprises or consists of the amino acid sequence shown in SEQ ID NO. 148. Or the VH region of the first binding domain comprises or consists of the amino acid sequence shown in SEQ ID NO. 110 and the VL region of the first binding domain comprises or consists of the amino acid sequence shown in SEQ ID NO. 4. Or the VH region of the first binding domain comprises or consists of the amino acid sequence shown in SEQ ID NO. 2 and the VL region of the first binding domain comprises or consists of the amino acid sequence shown in SEQ ID NO. 168.

As set forth above, the order of the variable regions of the first binding domain may be VH-VL or VL-VH. Both arrangements are within the scope of the invention. For a first binding domain comprising the VH of SEQ ID NO. 2 and the VL of SEQ ID NO. 4, the VH-VL arrangement is shown in SEQ ID NOs. 9 and 10, whereas the VL-VH arrangement is depicted in SEQ ID NOs. 11 and 12.

For a first binding domain comprising the VH of SEQ ID NO. 110 and the VL of SEQ ID NO. 148, the VH-VL arrangement is shown in SEQ ID NOs. 146 and 147. For a first binding domain comprising the VH of SEQ ID NO. 110 and the VL of SEQ ID NO. 168, the VH-VL arrangement is shown in SEQ ID NOs. 169 and 170, whereas the VL-VH arrangement is depicted in SEQ ID NOs. 193 and 194. For a first binding domain comprising the VH of SEQ ID NO. 6 and the VL of SEQ ID NO. 8, the VH-VL arrangement is shown in SEQ ID NOs. 13 and 14, whereas the VL-VH arrangement is depicted in SEQ ID NOs. 15 and 16.

Similarly, the order of the variable regions of the second binding domain may be VH-VL or VL-VH. Both arrangements are within the scope of the invention. For example, the VH-VL arrangement of a second binding domain exhibiting cross-species specificity to human and cynomolgus EpCAM is shown in SEQ ID NOs. 53 and 54, whereas the VL-VH arrangement is depicted in SEQ ID NOs. 55 and 56.

In a particularly preferred embodiment of the pharmaceutical composition of the invention, the bispecific single chain antibody as defined herein comprises an amino acid sequence selected from the group consisting of:
  (a) an amino acid sequence as depicted in any of SEQ ID NOs. 38, 40, 124, 42 or 44;
  (b) an amino acid sequence encoded by a nucleic acid sequence as shown in SEQ ID NOs. 37, 39, 125, 41 or 43;
  (c) an amino acid sequence encoded by a nucleic acid sequence hybridizing under stringent conditions to the complementary nucleic acid sequence of (b);
  (d) an amino acid sequence encoded by a nucleic acid sequence which is degenerate as a result of the genetic code to a nucleotide sequence of (b); and
  (e) an amino acid sequence at least 85% identical, more preferred at least 90% identical, most preferred at least 95% identical to the amino acid sequence of (a) or (b).

In the above-indicated preferred embodiment, only the first binding domain (binding to CD3) exhibits cross-species specificity.

Most preferably, the bispecific single chain antibody as defined herein comprises an amino acid sequence selected from the group consisting of:
  (a) an amino acid sequence as depicted in any of SEQ ID NOs. 66, 68, 74, 76, 122, 70, 72, 78, 80, 172, 174, 176, 178, 180, 182, 184, 186, 188, 190, or 192;
  (b) an amino acid sequence encoded by a nucleic acid sequence as shown in SEQ ID NOs. 65, 67, 73, 75, 123, 69, 71, 77, 79, 171, 173, 175, 177, 179, 181, 183, 185, 187, 189, or 191;
  (c) an amino acid sequence encoded by a nucleic acid sequence hybridizing under stringent conditions to the complementary nucleic acid sequence of (b);
  (f) an amino acid sequence encoded by a nucleic acid sequence which is degenerate as a result of the genetic code to a nucleotide sequence of (b); and
  (g) an amino acid sequence at least 85% identical, more preferred at least 90% identical, most preferred at least 95% identical to the amino acid sequence of (a) or (b).

In this above-indicated embodiment, both the first and second binding domains exhibit cross-species specificity.

In another preferred embodiment of the pharmaceutical composition, the non-chimpanzee primate is a baboon, marmoset or an old world monkey.

In an even more preferred embodiment of the pharmaceutical composition, the old world monkey is a monkey of the macaque genus.

Most preferably, the monkey of the macaque genus is Assamese macaque (*Macaca assamensis*), Barbary macaque (*Macaca sylvanus*), Bonnet macaque (*Macaca radiata*), Booted or Sulawesi-Booted macaque (*Macaca ochreata*), Sulawesi-crested macaque (*Macaca nigra*), Formosan rock macaque (*Macaca cyclopsis*), Japanese snow macaque or Japanese macaque (*Macaca fuscata*), Cynomolgus monkey or crab-eating macaque or long-tailed macaque or Java macaque (*Macaca fascicularis*), Lion-tailed macaque (*Macaca silenus*), Pigtailed macaque (*Macaca nemestrina*), Rhesus macaque (*Macaca mulatta*), Tibetan macaque (*Macaca thibetana*), Tonkean macaque (*Macaca tonkeana*), Toque macaque (*Macaca sinica*), Stump-tailed macaque or Red-faced macaque or Bear monkey (*Macaca arctoides*), or Moor macaque (*Macaca maurus*).

Preferably, the non-chimpanzee primate CD3 comprises or consists of an amino acid sequence shown in SEQ ID NOs. 135, 136, 144, or 145.

According to a further embodiment of the pharmaceutical composition of the invention, at least one of said first or second binding domains is human, humanized, CDR-grafted and/or deimmunized.

The term "human" antibody as used herein is to be understood as meaning that the bispecific single chain antibody as defined herein, comprises (an) amino acid sequence(s) contained in the human germline antibody repertoire. For the purposes of definition herein, said bispecific single chain antibody may therefore be considered human if it consists of such (a) human germline amino acid sequence(s), i.e. if the amino acid sequence(s) of the bispecific single chain antibody in question is (are) identical to (an) expressed human germline amino acid sequence(s). A bispecific single chain antibody as defined herein may also be regarded as human if it consists of (a) sequence(s) that deviate(s) from its (their) closest human germline sequence(s) by no more than would be expected due to the imprint of somatic hypermutation. Additionally, the antibodies of many non-human mammals, for example rodents such as mice and rats, comprise VH CDR3 amino acid sequences which one may expect to exist in the expressed human antibody repertoire as well. Any such sequence(s) of human or non-human origin which may be expected to exist in the expressed human repertoire would also be considered "human" for the purposes of the present invention.

As used herein, the term "humanized", "humanization", "human-like" or grammatically related variants thereof are used interchangeably to refer to a bispecific single chain antibody comprising in at least one of its binding domains at least one complementarity determining region ("CDR") from a non-human antibody or fragment thereof. Humanization approaches are described for example in WO 91/09968 and U.S. Pat. No. 6,407,213. As non-limiting examples, the term encompasses the case in which a variable region of at least one binding domain comprises a single CDR region, for example the third CDR region of the VH, from another non-human animal, for example a rodent, as well as the case in which a or both variable region/s comprise at each of their respective first, second and third CDRs the CDRs from said non-human animal. In the event that all CDRs of a binding domain of the bispecific single chain antibody have been replaced by their corresponding equivalents from, for example, a rodent, one typically speaks of "CDR-grafting", and this term is to be understood as being encompassed by the term "humanized" or grammatically related variants thereof as used herein. The term "humanized" or grammatically related variants thereof also encompasses cases in which, in addition to replacement of one or more CDR regions within a VH and/or VL of the first and/or second binding domain further mutations (e.g. substitutions) of at least one single amino acid residue/s within the framework ("FR") regions between the CDRs has/have been effected such that the amino acids at that/those positions correspond/s to the amino acid/s at that/those position/s in the animal from which the CDR regions used for replacement is/are derived. As is known in the art, such individual mutations are often made in the framework regions following CDR-grafting in order to restore the original binding affinity of the non-human antibody used as a CDR-donor for its target molecule. The term "humanized" may further encompass (an) amino acid substitution(s) in the CDR regions from a non-human animal to the amino acid(s) of a corresponding CDR region from a human antibody, in addition to the amino acid substitutions in the framework regions as described above.

As used herein, the term "deimmunized," "deimmunization" or grammatically related variants thereof denotes modification of the first and/or second binding domain vis-à-vis an original wild type construct by rendering said wild type construct non-immunogenic or less immunogenic in humans. Deimmunization approaches are shown e.g. in WO 00/34317, WO 98/52976, WO 02/079415 or WO 92/10755. The term "deimmunized" also relates to constructs, which show reduced propensity to generate T cell epitopes. In accordance with this invention, the term "reduced propensity to generate T cell epitopes" relates to the removal of T-cell epitopes leading to specific T-cell activation. Furthermore, "reduced propensity to generate T cell epitopes" means substitution of amino acids contributing to the formation of T cell epitopes, i.e. substitution of amino acids, which are essential for formation of a T cell epitope. In other words, "reduced propensity to generate T cell epitopes" relates to reduced immunogenicity or reduced capacity to induce antigen independent T cell proliferation. The term "T cell epitope" relates to short peptide sequences which can be released during the degradation of peptides, polypeptides or proteins within cells and subsequently be presented by molecules of the major histocompatibility complex (MHC) in order to trigger the activation of T cells; see inter alia WO 02/066514. For peptides presented by MHC class II such activation of T cells can then give rise to an antibody response by direct stimulation of T cells to produce said antibodies. "Reduced propensity to generate T-cell epitopes" and/or "deimmunization" may be measured by techniques known in the art. Preferably, de-immunization of proteins may be tested in vitro by T cell proliferation assay. In this assay PBMCs from donors representing >80% of HLA-DR alleles in the world are screened for proliferation in response to either wild type or de-immunized peptides. Ideally cell proliferation is only detected upon loading of the antigen-presenting cells with wild type peptides. Alternatively, one may test deimmunization by expressing HLA-DR tetramers representing all haplotypes. These tetramers may be tested for peptide binding or loaded with peptides substitute for antigen-presenting cells in proliferation assays. In order to test whether deimmunized peptides are presented on HLA-DR haplotypes, binding of e.g. fluorescence-labeled peptides on PBMCs can be measured. Furthermore, deimmunization can be proven by determining whether antibodies against the deimmunized molecules have been formed after administration in patients. Preferably, antibody derived molecules are deimmunized in the framework regions and most of the CDR regions are not modified in order to generate reduced propensity to induce T cell epitope so that the binding affinity of the CDR regions is not affected. Even elimination of one T cell epitope results in reduced immunogenicity.

The invention also provides for a pharmaceutical composition comprising a nucleic acid sequence encoding a bispecific single chain antibody as defined herein.

The invention further relates to a pharmaceutical composition comprising a vector which comprises a nucleic acid sequence as defined above. Preferably said vector further comprises a regulatory sequence which is operably linked to said nucleic acid sequence defined above. More preferably, said vector is an expression vector.

In a further aspect, the invention relates to a pharmaceutical composition comprising a host transformed or transfected with a vector defined above.

A further aspect of the invention relates to a pharmaceutical composition as defined hereinabove, further comprising a proteinaceous compound capable of providing an activation signal for immune effector cells.

Preferably, the pharmaceutical composition further comprises suitable formulations of carriers, stabilizers and/or excipients.

In another aspect, the invention relates to a process for the production of a pharmaceutical composition as defined above, said process comprising culturing a host as defined above under conditions allowing the expression of the bispecific single chain antibody as defined hereinabove and recovering the produced bispecific single chain antibody from the culture.

A further aspect of the invention relates to a use of a bispecific single chain antibody as defined hereinabove or as produced by the process as defined hereinabove, a nucleic acid molecule as defined hereinabove, a vector as defined hereinabove or a host as defined hereinabove for the preparation of a pharmaceutical composition for the prevention, treatment or amelioration of a disease. Another aspect of the invention relates to a method for the prevention, treatment or amelioration of a disease in a subject in the need thereof, said method comprising the step of administration of an effective amount of a pharmaceutical composition of the invention or as produced according by the process set forth above.

Preferably, said disease is a proliferative disease, a tumorous disease, or an immunological disorder. Even more preferred, said tumorous disease is a malignant disease, preferably cancer. Cross-species specific bispecific single chain antibodies as defined herein with specificity for EpCAM, EGFR or EGFRvIII can be used for the therapy of epithelial cancers and tumors. Cross-species specific bispecific single chain antibody constructs as defined herein with specificity for CAIX can be used for the treatment of tumors with hypoxical regions or areas. Moreover, said CAIX constructs may be used for the treatment of renal or cervical carcinomas. In another preferred embodiment of the uses or methods of the invention, said pharmaceutical composition as defined hereinabove is suitable to be administered in combination with an additional drug, i.e. as part of a co-therapy. In said co-therapy, an active agent may be optionally included in the same pharmaceutical composition as the bispecific single chain antibody, or may be included in a separate pharmaceutical composition. In this latter case, said separate pharmaceutical composition is suitable for administration prior to, simultaneously as or following administration of said pharmaceutical composition comprising the bispecific single chain antibody. The additional drug or pharmaceutical composition may be a non-proteinaceous compound or a proteinaceous compound. In the case that the additional drug is a proteinaceous compound, it is advantageous that the proteinaceous compound be capable of providing an activation signal for immune effector cells.

Preferably, said proteinaceous compound or non-proteinaceous compound may be administered simultaneously or non-simultaneously with a bispecific single chain antibody as defined hereinabove, a nucleic acid molecule as defined hereinabove, a vector as defined as defined hereinabove, or a host as defined as defined hereinabove. Preferably, said subject to be treated is a human.

In a further aspect, the invention relates to a kit comprising a bispecific single chain antibody as defined hereinabove, a nucleic acid molecule as defined hereinabove, a vector as defined hereinabove, or a host as defined hereinabove.

These and other embodiments are disclosed and encompassed by the description and Examples of the present invention. Recombinant techniques and methods in immunology are described e.g. in Sambrook et al. Molecular Cloning: A Laboratory Manual; Cold Spring Harbor Laboratory Press, 3$^{rd}$ edition 2001; Lefkovits; Immunology Methods Manual; The Comprehensive Sourcebook of Techniques; Academic Press, 1997; Golemis; Protein-Protein Interactions: A Molecular Cloning Manual; Cold Spring Laboratory Press, 2002. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under http://www.ncbi.nlm.nih.qov/PubMed/medline.html. Further databases and addresses, such as http://www.ncbi.nim.nih.qov/, http://www.infobioaen.fr/, http://www.fmi.ch/bioloqv/research tools.html, http://www.tiqr.orQ/.are known to the person skilled in the art and can also be obtained using, e.g., http://www.lvcos.com The Figures show:

FIG. 1: Identification of cross-species specific antibodies to macaque CD3: Cross-species specificity of an anti-CD3 antibody shown in SEQ ID NO.162 described in WO 99/54440, OKT-3, an Ig comprising SEQ ID NOs. 6 and 8, an Ig comprising SEQ ID NOs. 2 and 4 and UCHT-1 to macaque (cynomolgus) CD3 were tested with Flow Cytometry as described in Example 1. An immunoglobulin (Ig) comprising SEQ ID NOs. 6 and 8 and an Ig comprising SEQ ID NOs. 2 and 4 show cross-species specificity to macaque CD3. In contrast, the anti-CD3 antibody shown in SEQ ID NO.162, OKT-3 and UCHT-1 fail to bind to macaque CD3.

FIG. 2: FACS assay for binding of an Ig comprising SEQ ID NOs. 2 and 4, an Ig comprising SEQ ID NOs. 6 and 8 and monoclonal antibody (mAb) FN-18 to HPB-ALL cells and PBMC of *Macaca fascicularis* (cynomolgus). HPB-ALL cells express the human CD3 complex. Cells stained with the respective antibodies are shown in comparison to unstained cells. Strong antigen binding on human as well as on cynomolgus cells was detected for the Ig comprising SEQ ID NOs. 2 and 4. For the Ig comprising SEQ ID NOs. 6 and 8, strong binding to human cells but weaker binding to cynomolgus cells was observed. For FN-18, strong binding to cynomolgus cells could be observed, whereas no binding to human cells could be detected.

FIG. 3: FACS assay for binding of 5-10LH×SEQ ID NO.12, 5-10LH×SEQ ID NO.10, 5-10LH×SEQ ID NO.16 and 5-10LH×SEQ ID NO.14 to human Kato III cells expressing EpCAM or human EpCAM transfected CHO cells and to HPB-ALL cells. Cells bound by the respective constructs (depicted as non-filled curves) are shown in comparison to cells incubated only with the detection antibodies (depicted as filled curves). Antigen binding of all bispecific constructs was clearly detectable for the anti human EpCAM specificity as well as for the anti CD3 specificities on the HPB-ALL cell line positive for human CD3.

Figure 4:
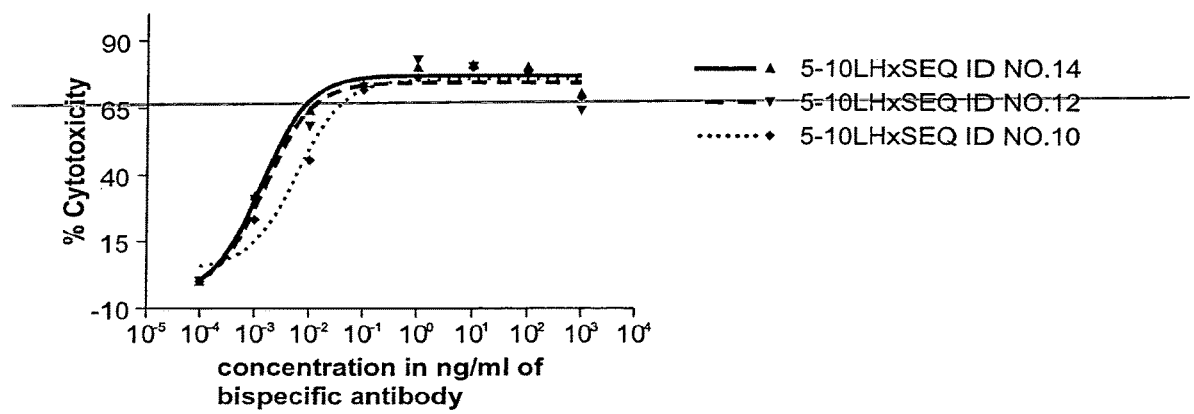

FIG. 4: Cytotoxicity assay for 5-10LH×SEQ ID NO.12, 5-10LH×SEQ ID NO.10 and 5-10LH×SEQ ID NO.14 with human Kato III cells as target cells and human PBMC as effector cells. All constructs showed cytotoxic activity.

Figure 5:
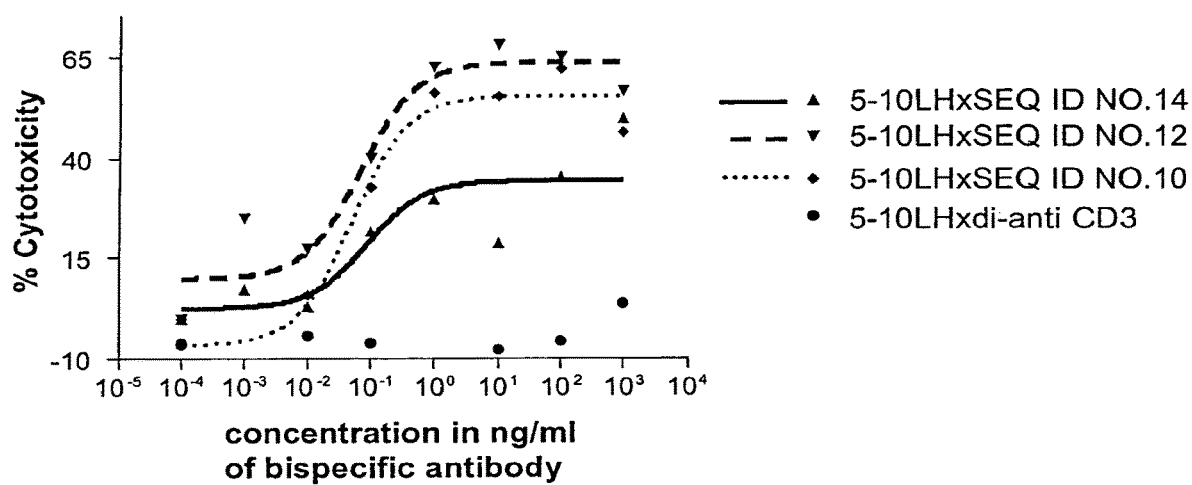

FIG. 5: Cytotoxicity assay for 5-10LH×SEQ ID NO.12, 5-10LH×SEQ ID NO.10, and 5-10LH×SEQ ID NO.14 with Kato III cells as target cells and cynomolgus PBMC as effector cells. 5-10LH×SEQ ID NO.14, 5-10LH×SEQ ID NO.12 and 5-10LH×SEQ ID NO.10 showed cytotoxic activity. 5-10LH×di-anti CD3 (deimmunised anti-CD3 antibody shown in SEQ ID NO.163) which fails to bind to cynomolgus CD3 was used as a negative control.

FIG. 6: Amino acid sequence alignment of the extracellular portion of the cynomolgus EpCAM antigen (also shown in SEQ ID NO. 48) and the human EpCAM antigen.

Figure 7:
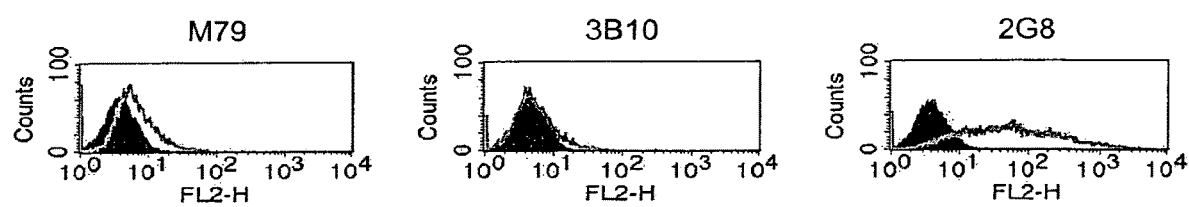

FIG. 7: FACS assay for the detection of the cynomolgus EpCAM antigen on transfected CHO cells. Supernatants of three different anti human EpCAM hybridomas (M79, 3B10, 2G8) were tested for binding. Transfectants (depicted as non-filled curves) as compared to untransfected cells (depicted as filled curves) showed binding only with the supernatant of the 2G8 hybridoma which is therefore recognized as antibody cross-species specific for human and cynomolgus EpCAM.

Figures 8, 8A:
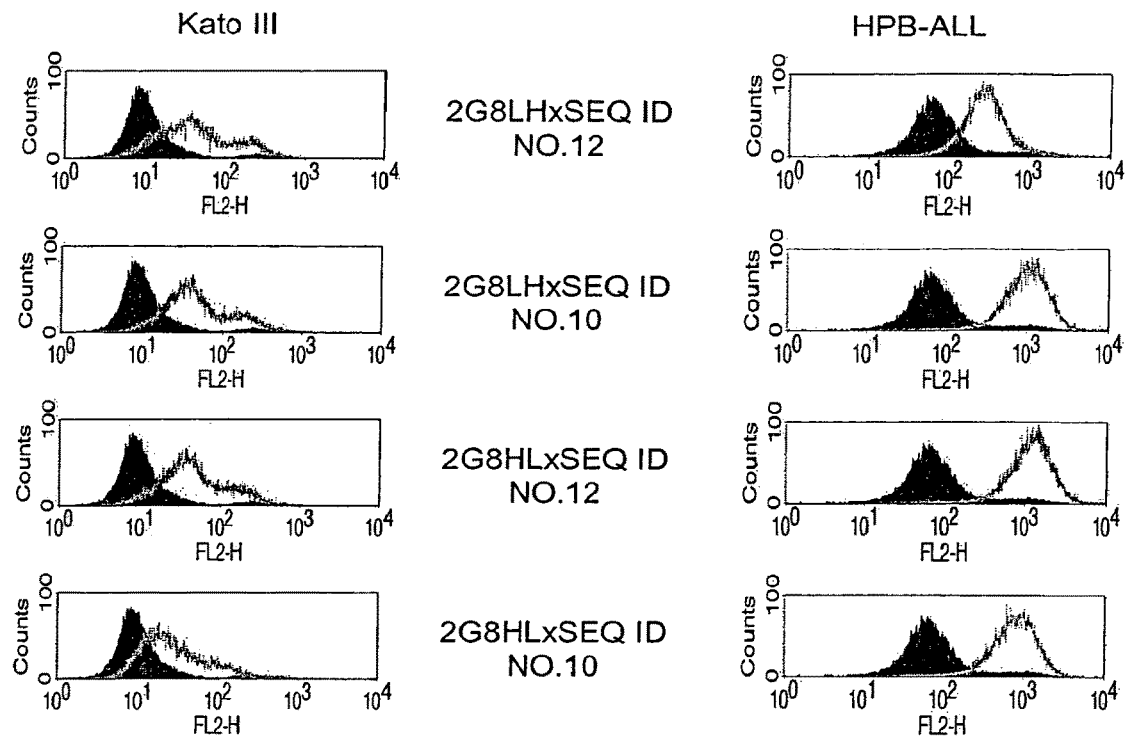
Figure 8B:
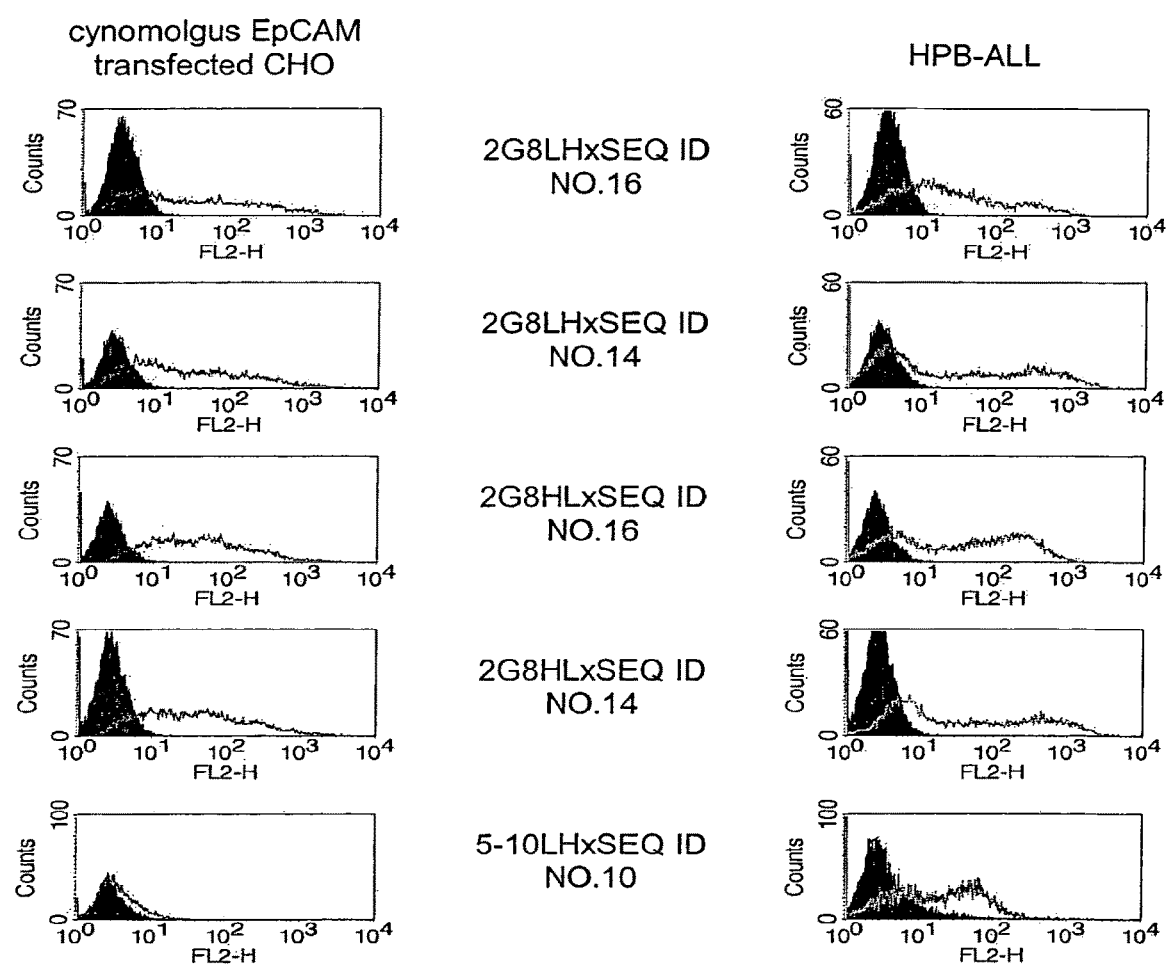

FIG. 8: FACS assay for binding of 2G8LH×SEQ ID NO.12, 2G8LH×SEQ ID NO.10, 2G8LH×SEQ ID NO.16, 2G8LH×SEQ ID NO.14, 2G8HL×SEQ ID NO.12, 2G8HL×SEQ ID NO.10, 2G8HL×SEQ ID NO.16 and 2G8HL×SEQ ID NO.14 on Kato III (FIG. 8A) cells or cynomolgus EpCAM transfected CHO cells (FIG. 8B) and HPB-ALL cells. Antigen binding was clearly detectable for the anti EpCAM specificities as well as for the anti CD3 specificities. As a negative control for binding to cynomolgus EpCAM, the 5-10LH×SEQ ID NO.10 construct was included which shows binding to human CD3 (on HPB-ALL cells) but no binding to cynomolgus EpCAM (cynomolgus EpCAM transfected CHO cells).

Figure 9:
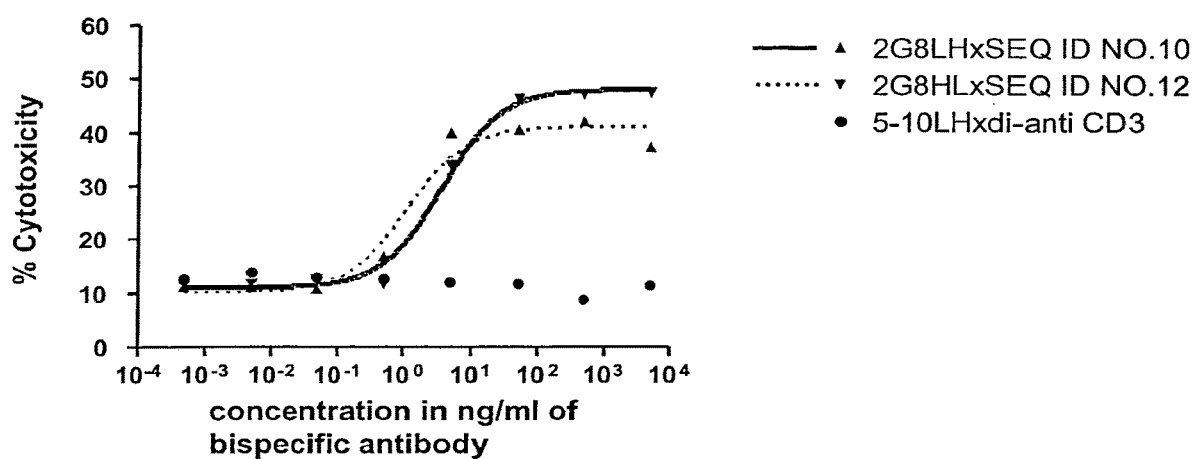

FIG. 9: Cytotoxicity assay for 2G8LH×SEQ ID NO.10 and 2G8HL×SEQ ID NO.12 with cynomolgus EpCAM transfected CHO cells as target cells and human PBMC as effector cells. 2G8LH×SEQ ID NO.10 and 2G8HL×SEQ ID NO.12 showed cytotoxic activity. 5-10LH×di-anti CD3 (deimmunised anti-CD3 antibody shown in SEQ ID NO.163) was included as negative control. 5-10LH fails to bind to cynomolgus EpCAM.

Figure 10:
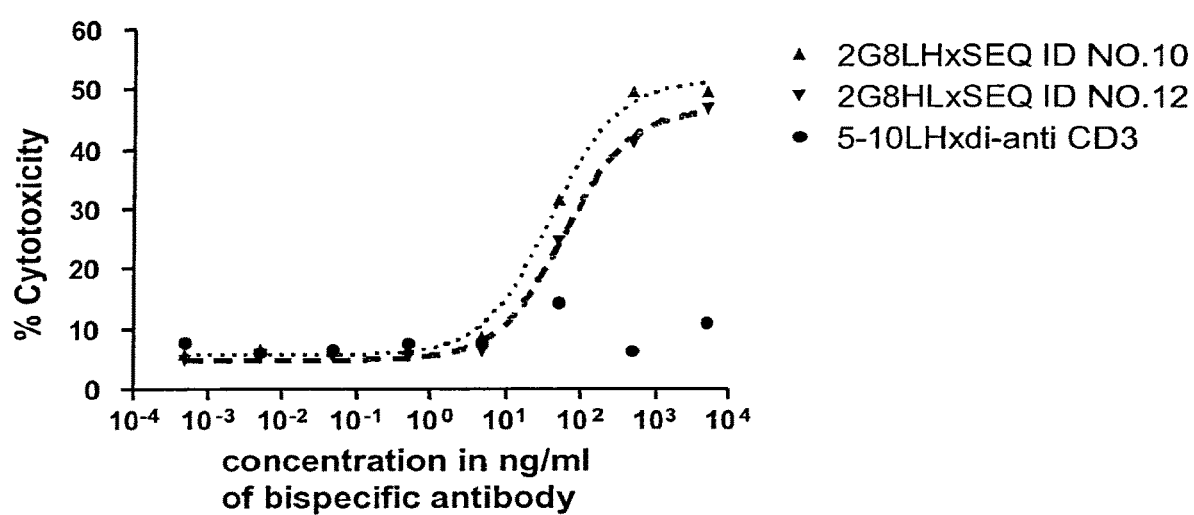

FIG. 10: Cytotoxicity assay for 2G8LH×SEQ ID NO.10 and 2G8HL×SEQ ID NO.12 with cynomolgus EpCAM transfected CHO cells as target cells and cynomolgus PBMC as effector cells. 2G8LH×SEQ ID NO.10 and 2G8HL×SEQ ID NO.12 showed cytotoxic activity. 5-10LH×di-anti CD3 (deimmunised anti-CD3 antibody shown in SEQ ID NO.163) was included as negative control. This construct fails to bind to cynomolgus CD3 and cynomolgus EpCAM.

FIG. 11: Amino acid comparison of SEQ ID NO. 2 and human VH segment (hu)3-73.

FIG. 12: Amino acid and nucleotide sequences of a cross-species specific human-like VH region (also shown in SEQ ID NOs. 110 and 111, respectively).

Figure 13:
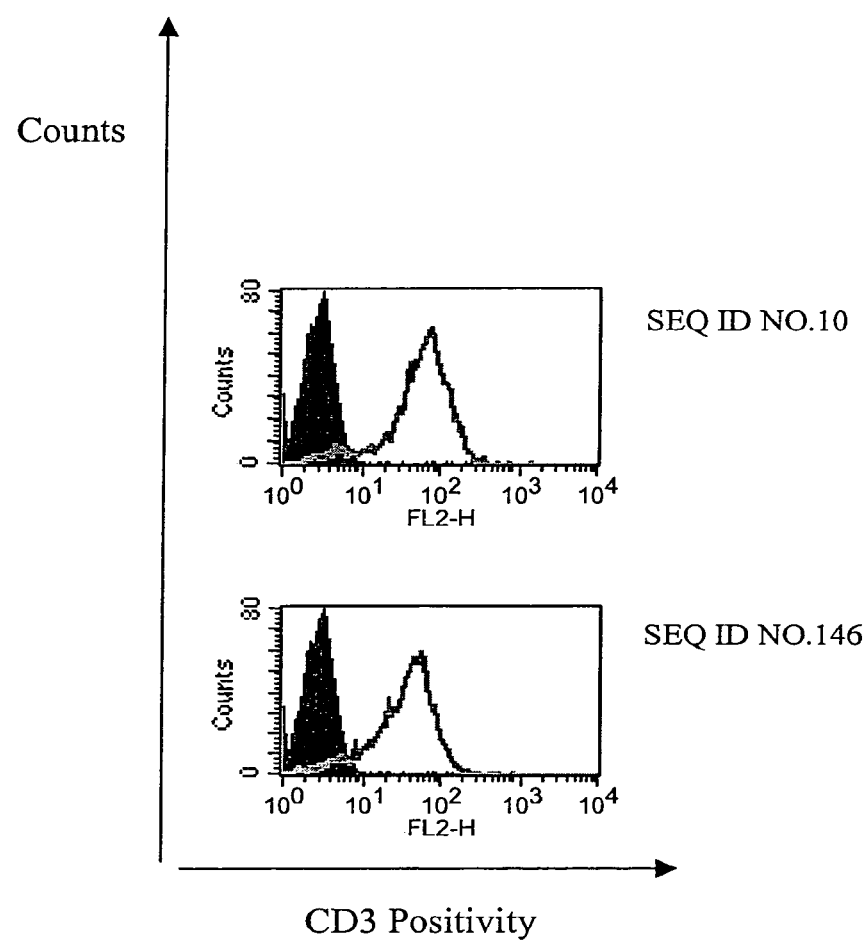

FIG. 13: FACS analysis of a scFv comprising the human-like VH chain shown in SEQ ID NO. 110 and the VL chain shown in SEQ ID NO: 148. The complete scFv amino acid sequence is shown in SEQ ID NO.146. The control scFv of SEQ ID NO.10 shows a clear shift on human CD3 positive HPB-All cells and thus binds to human CD3. The scFv depicted in SEQ ID NO. 146 also shows clear binding to said CD3 positive human cells.

Figure 14:
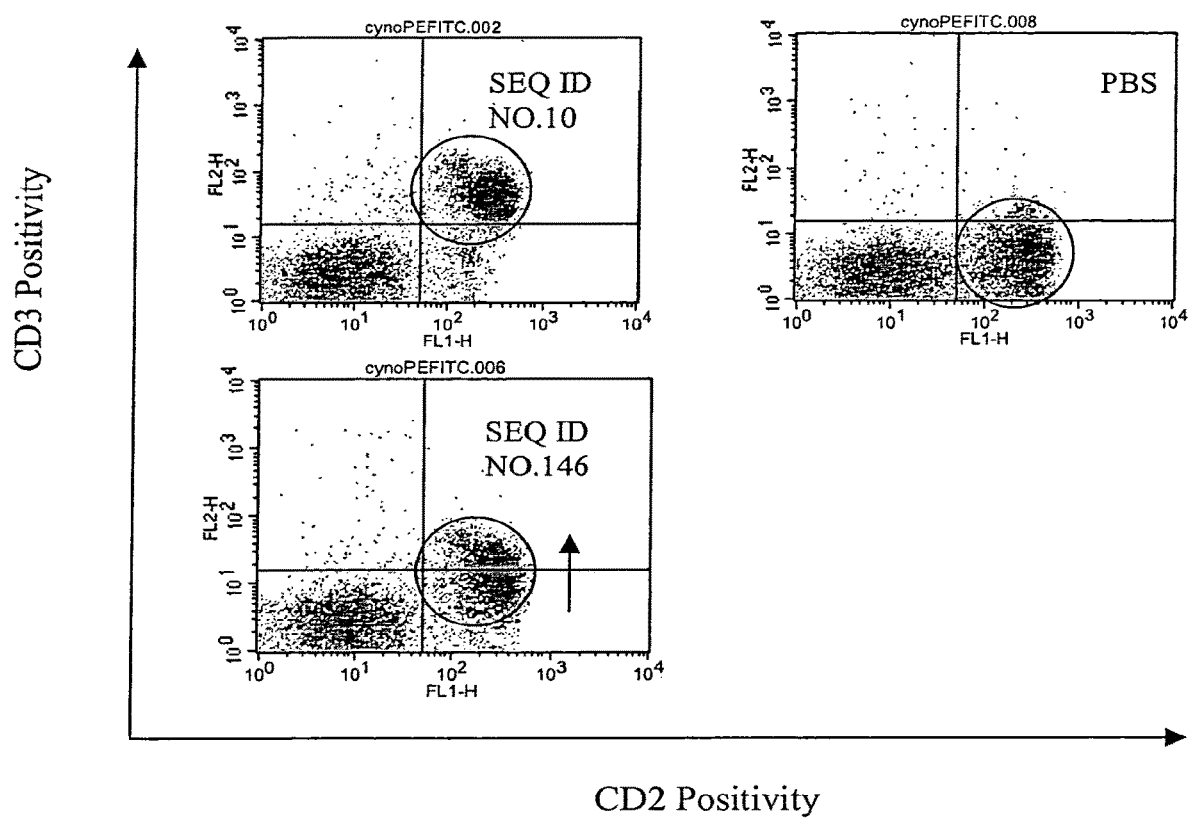

FIG. 14: Binding analysis of the scFv of SEQ ID NO. 146. The control scFv of SEQ ID NO. 10 shows a clear shift on cynomolgus CD3 positive T cells and thus binds to cynomolgus CD3 positive cells. Also the scFv of SEQ ID NO: 146 shows clear binding to cynomolgus CD3 positive cells.

FIG. 15: Alignment of amino acid sequences of human and cynomolgus CD3 epsilon.

FIG. 16: Amino acid sequences of the 13mer peptides derived from cynomolgus CD3 epsilon (43 peptide-spots).

FIG. 17: Amino acid sequences of the 13mer peptides derived from human CD3 epsilon (47 peptide-spots).

FIG. 18: Pepspots developed by enhanced chemiluminescence (A) Control pepspot with horseradish-peroxidase conjugated goat-anti-mouse IgG (B) Pepspot with cross-species specific anti-CD3 antibody I corresponding to an immunoglobulin (Ig) comprising the VH chain shown in SEQ ID NO. 2 and the VL chain shown in SEQ ID NO. 4.

Figure 19:
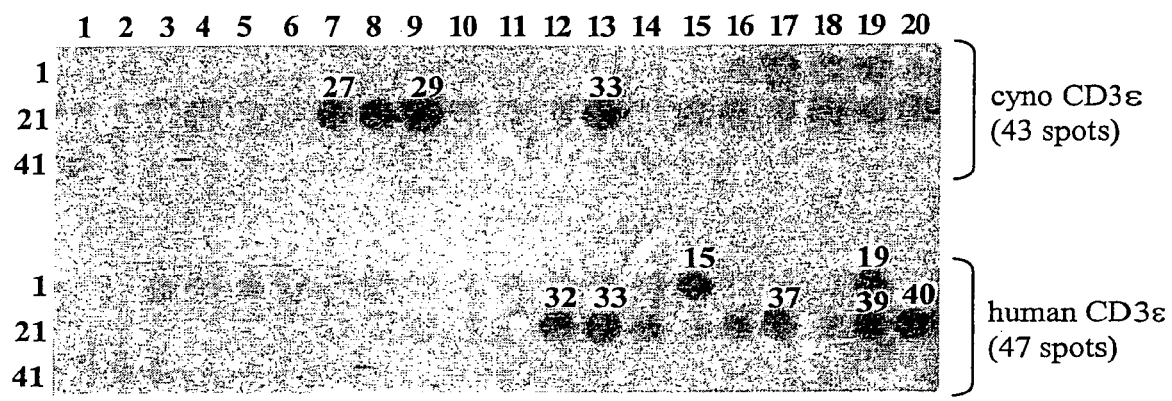

FIG. 19: Pepspot with cross-species specific anti-CD3 antibody II corresponding to an immunoglobulin (Ig) comprising the VH chain shown in SEQ ID NO. 6 and the VL chain shown in SEQ ID NO. 8.

Figure 20:
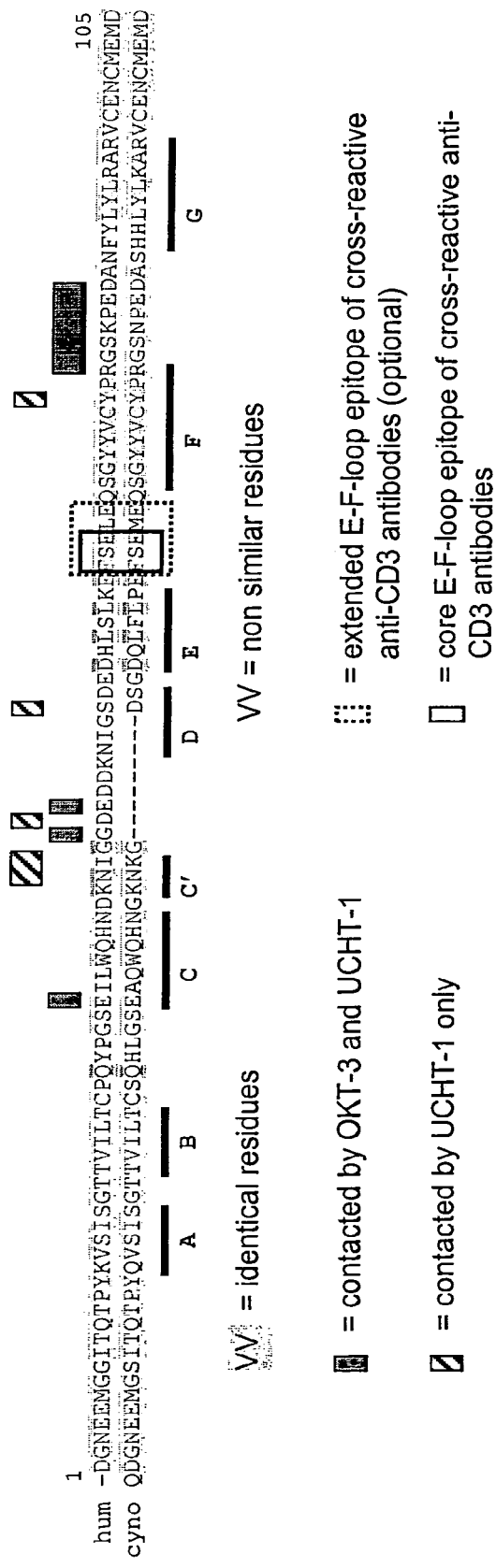

FIG. 20: Contact residues of OKT-3 and UCHT-1 and E-F-loop epitope of cross-species specific anti-CD3 antibodies I and II referred to in FIGS. 18 and 19, respectively, on cynomolgus and human CD3 epsilon.

Figure 21:
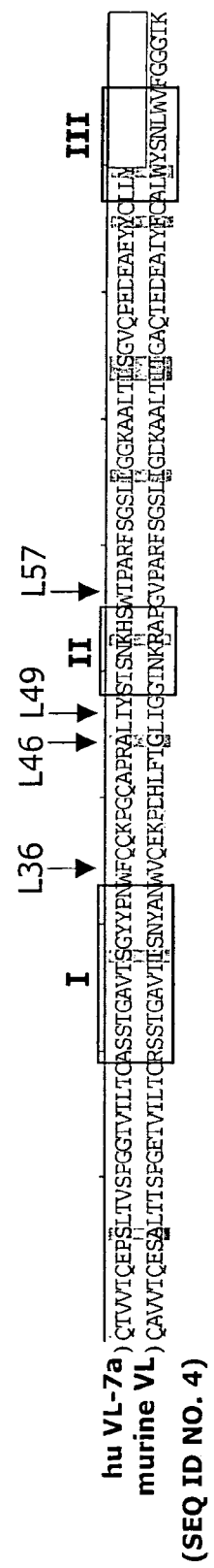

FIG. 21: Amino acid sequence comparison of the murine VL shown in SEQ ID NO. 4 to the human germline lambda 7a segment.

Figure 22:
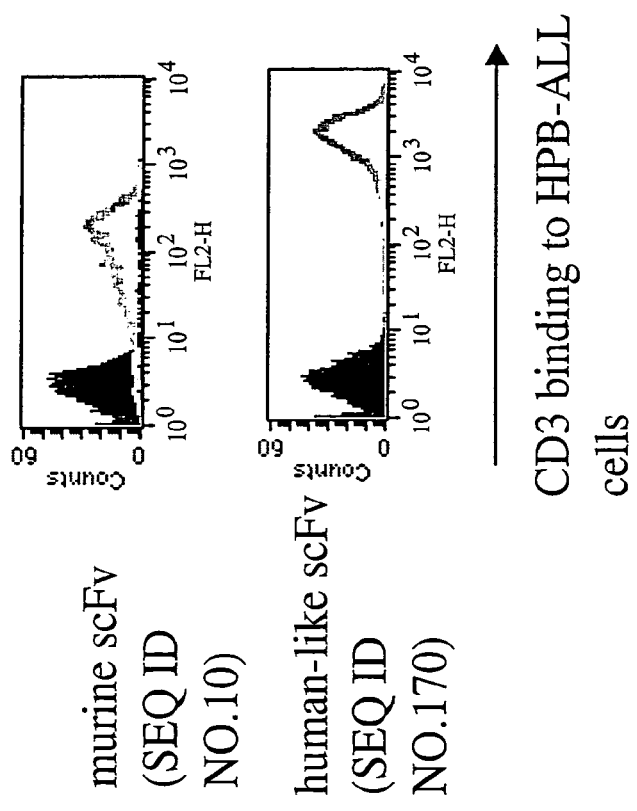

FIG. 22: Binding of the murine scFv shown in SEQ ID NO. 10 and the human-like scFv shown in SEQ ID NO. 170 to human CD3-positive HPB-ALL cells.

Figure 23:
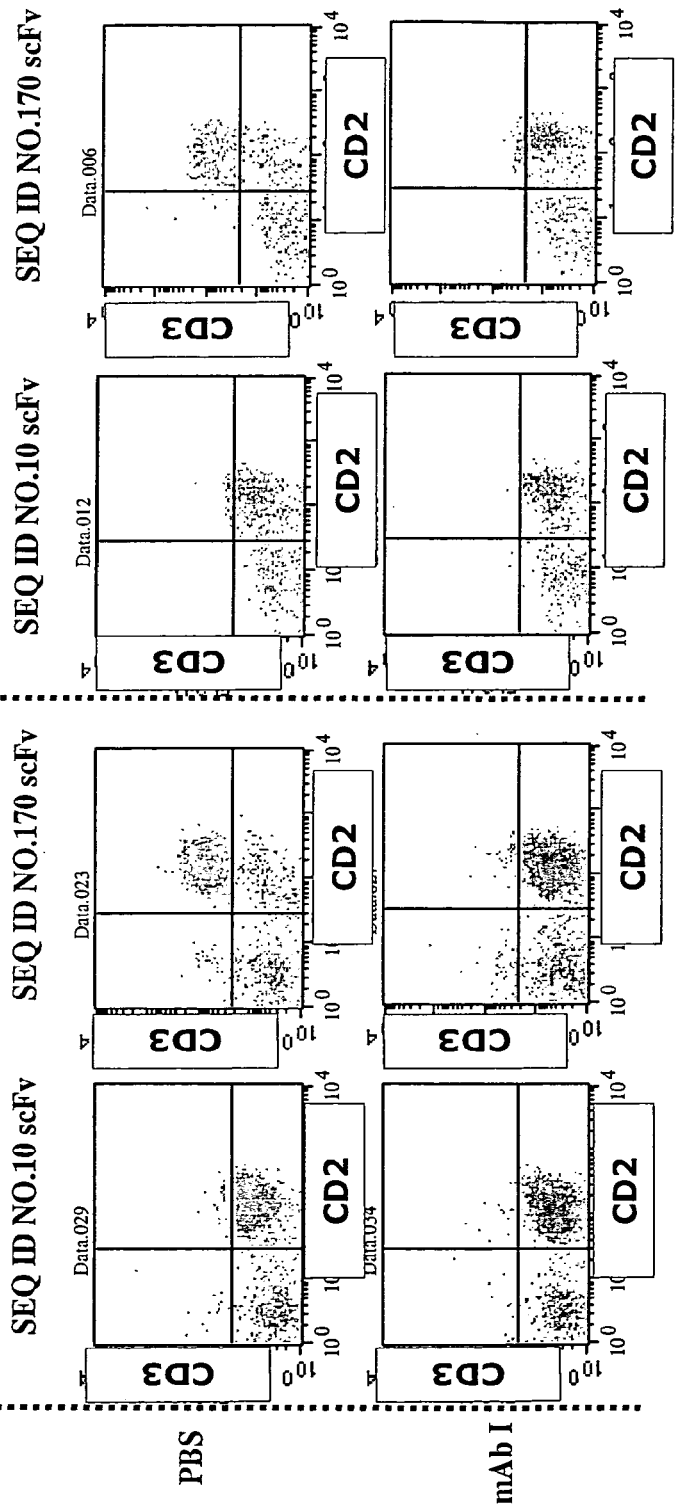

FIG. 23: Upper Panel: Equal binding of the murine scFv shown in SEQ ID NO. 10 and the human-like scFv shown in SEQ ID NO. 170 to human and cynomolgus T cells in PBMCs. Lower Panel: When preincubated with 10 μg/ml of the murine IgG antibody mAb I described in Example 1 having the same binding specificity as the scFvs (i.e. for CD3 epsilon), the shifts of cells stained with the above-mentioned murine scFv or the human-like scFv decrease significantly, underlining the similar binding region of the scFvs and the original murine antibody mAb I.

FIG. 24: Pepspots developed by the alkaline phosphatase detection system (A) Control pepspot with alkaline phosphatase conjugated goat-anti-mouse IgG (B) Pepspot with cross-species specific anti-CD3 antibody comprising the human-like VH shown in SEQ ID NO. 110 and the human-like VL shown in SEQ ID NO. 168 as described in Example 18.

Figure 25:
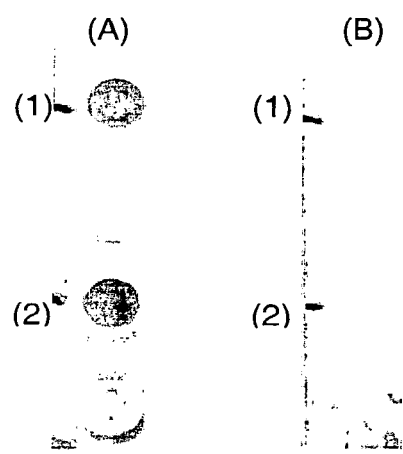

FIG. 25: Dot Blot Assay with the cross-species specific anti-CD3 antibody comprising the human-like VH of SEQ ID NO. 110 and the human-like VL of SEQ ID NO. 168 as described in Example 19 in (A) and the anti-CD3 murine IgG1 antibody UCHT1 (B) binding to the blotted peptides "biotin-linker-EFSELEQSGYYVC" (1) and "EFSELE-QSGYYVC-biotin" (2) derived from human CD3 epsilon FIG. 26: FACS binding analysis of cross-species specific bispecific single chain construct CAIX HL×SEQ ID NO. 194 to HPB-ALL (human CD3+), cynomolgus PBMC (cynomolgus CD3+), A549 (human CAIX+) and CYNOM-K1 (cynomolgus CAIX+) cells, respectively. The FACS staining was performed as described in Example 23. The thick line represents cells incubated with 1 μg/ml purified monomeric protein that were subsequently incubated with the anti-his antibody and the PE labeled detection antibody. The thin histogram line reflects the negative control: cells only incubated with the anti-his antibody and the detection antibody.

Figure 27:
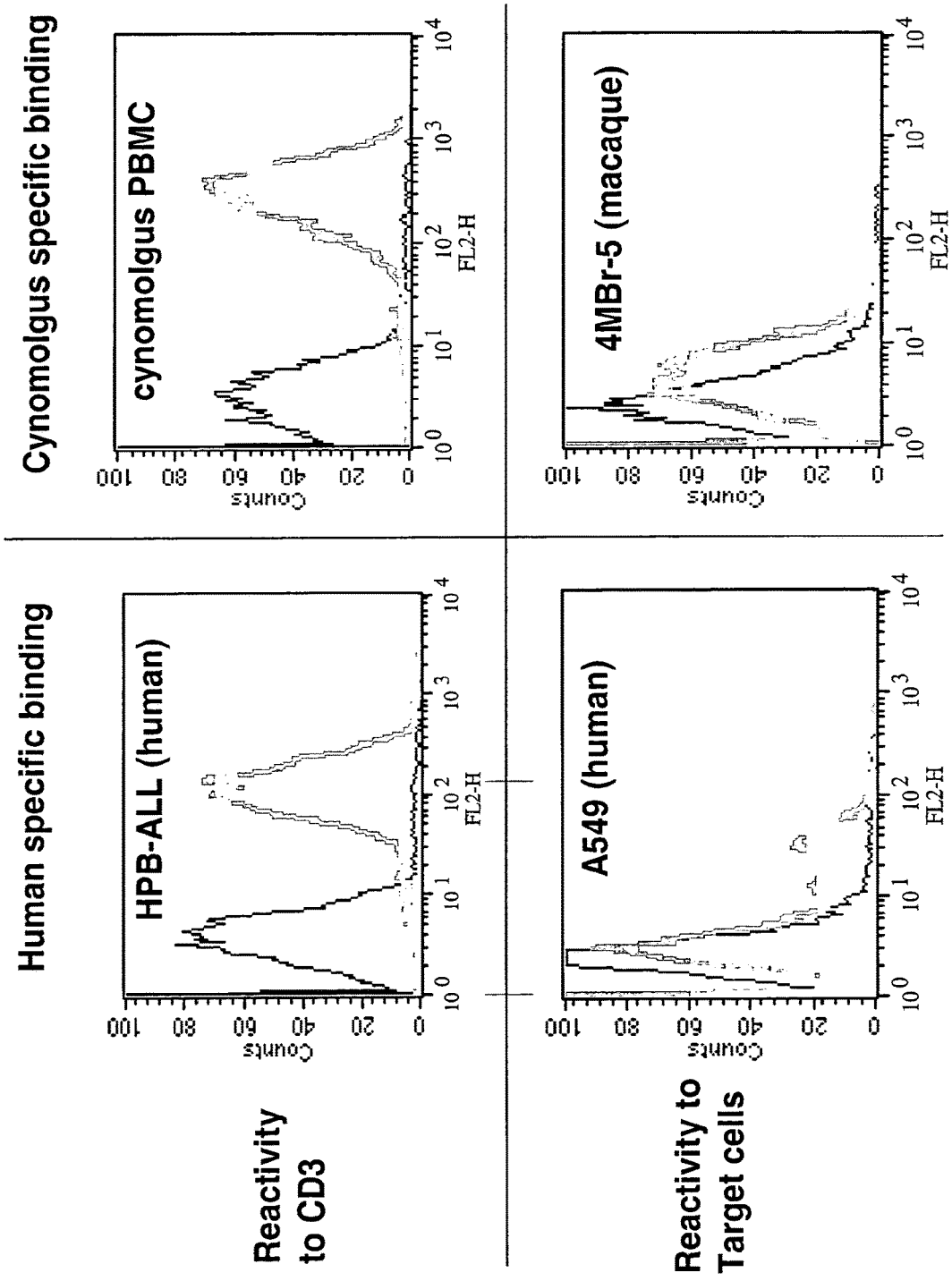

FIG. 27: FACS binding analysis of cross-species specific bispecific single chain construct CAIX HL×SEQ ID NO. 170 to HPB-ALL (human CD3+), cynomolgus PBMC (cynomolgus CD3+), A549 (human CAIX+) and 4MBr-5 (macaque CAIX+) cells, respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

Figure 28:
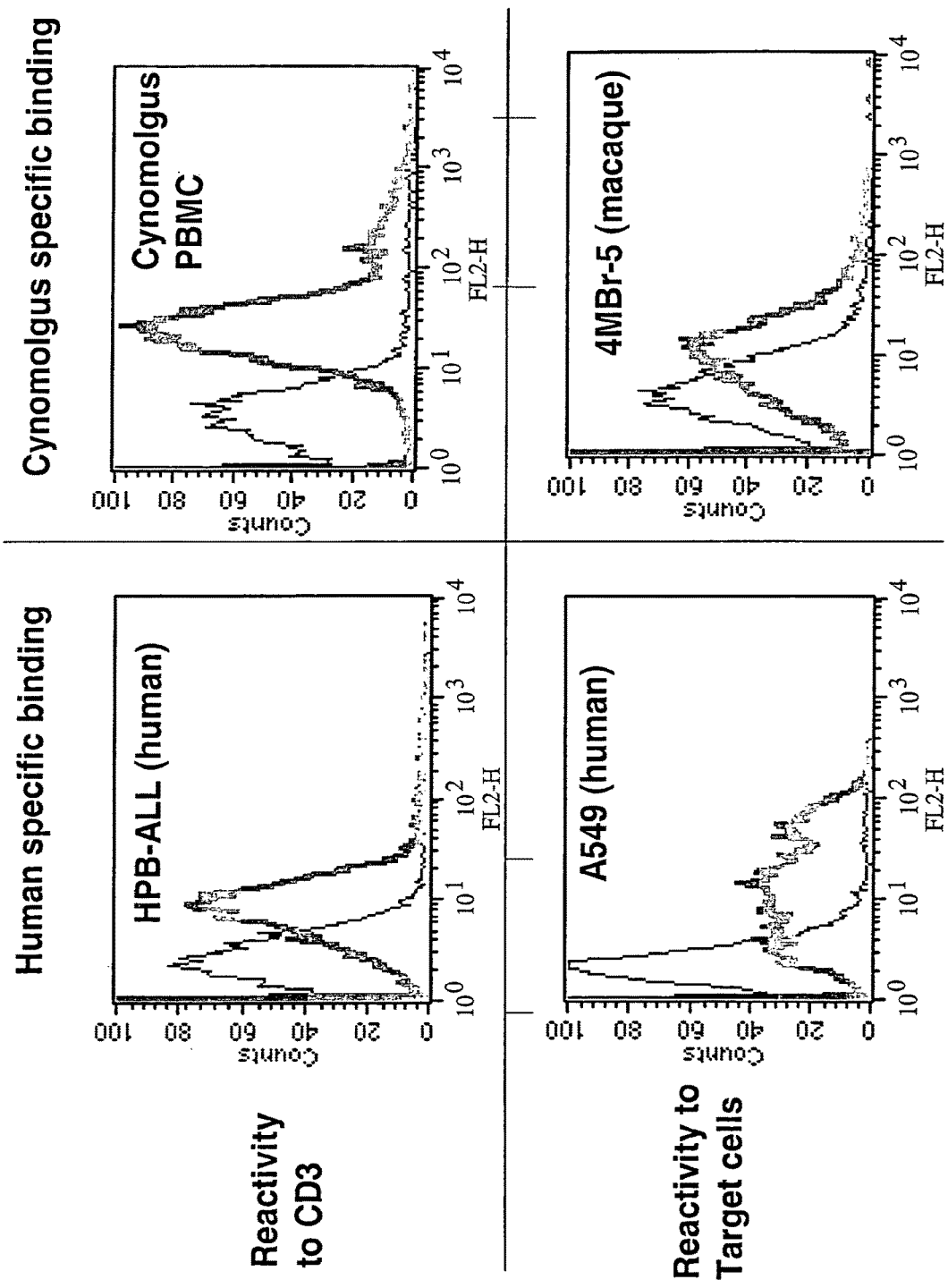

FIG. 28: FACS binding analysis of cross-species specific bispecific single chain construct CAIX LH×SEQ ID NO. 170 to HPB-ALL (human CD3+), cynomolgus PBMC (cynomolgus CD3+), A549 (human CAIX+) and 4MBr-5 (macaque CAIX+) cells, respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

FIG. 29: FACS binding analysis of cross-species specific bispecific single chain construct EGFR HL×SEQ ID NO. 170 to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

FIG. 30: FACS binding analysis of cross-species specific bispecific single chain construct EGFR LH×SEQ ID NO. 170 to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

Figure 31:
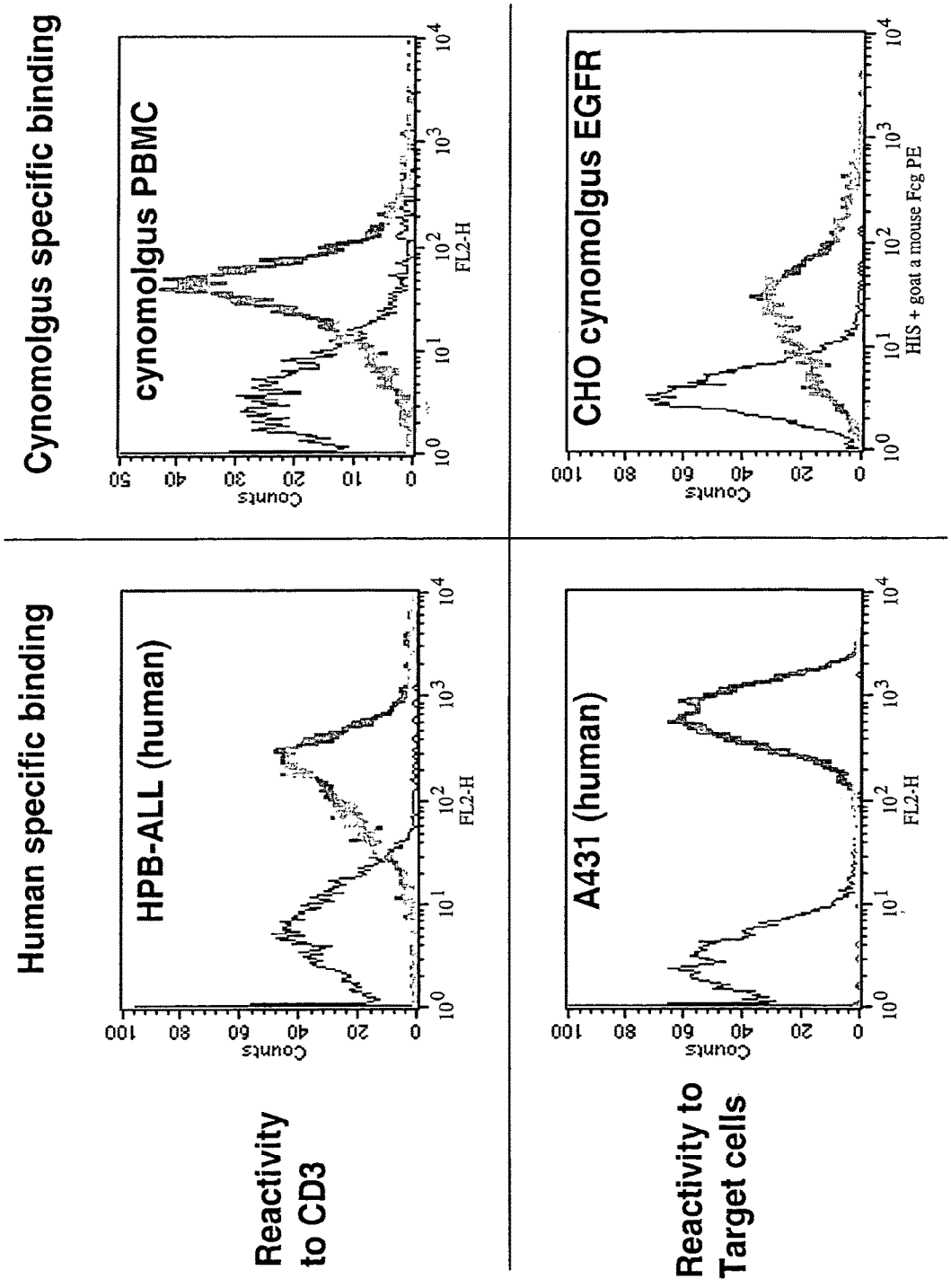

FIG. 31: FACS binding analysis of cross-species specific bispecific single chain construct EGFR HL×SEQ ID NO. 194 to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

FIG. 32: FACS binding analysis of cross-species specific bispecific single chain construct EGFR LH×SEQ ID NO. 194 to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

FIG. 33: FACS binding analysis of cross-species specific bispecific single chain construct SEQ ID NO. 170×EGFR HL to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

FIG. 34: FACS binding analysis of cross-species specific bispecific single chain construct SEQ ID NO. 170×EGFR LH to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

Figure 35:
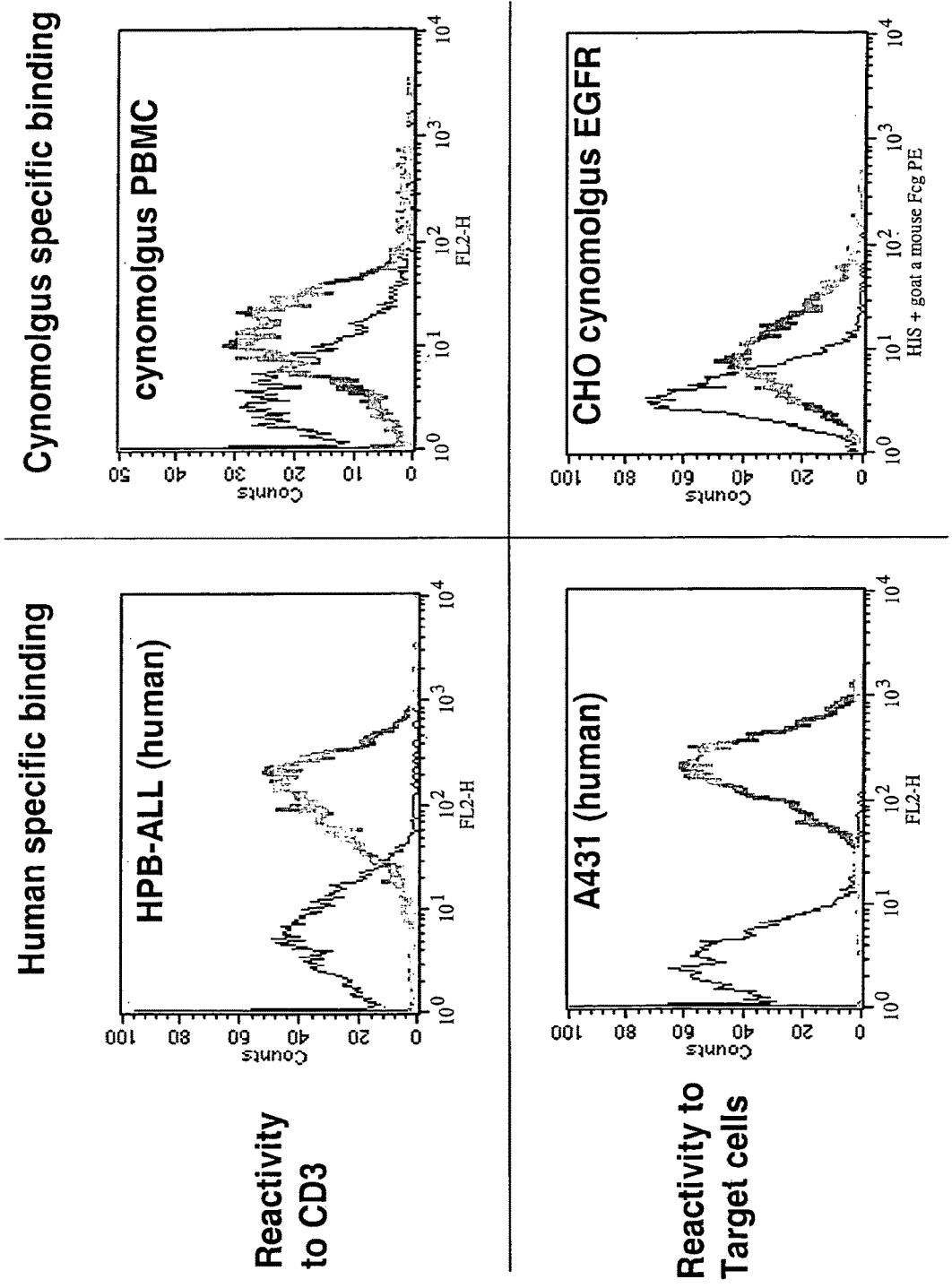

FIG. 35: FACS binding analysis of cross-species specific bispecific single chain construct SEQ ID NO. 194×EGFR HL to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

FIG. 36: FACS binding analysis of cross-species specific bispecific single chain construct SEQ ID NO. 194×EGFR LH to HPB-ALL (human CD3+), cynomolgus PBMC (cynomolgus CD3+), A431 (human EGFR+) and CHO cells transfected with cynomolgus EGFR (cynomolgus EGFR+), respectively. The FACS staining was performed as described in Example 23. The thick line represents cells incubated with 1 µg/ml purified monomeric protein that were subsequently incubated with the anti-his antibody and the PE labeled detection antibody. The thin histogram line reflects the negative control: cells only incubated with the anti-his antibody and the detection antibody.

Figure 37:
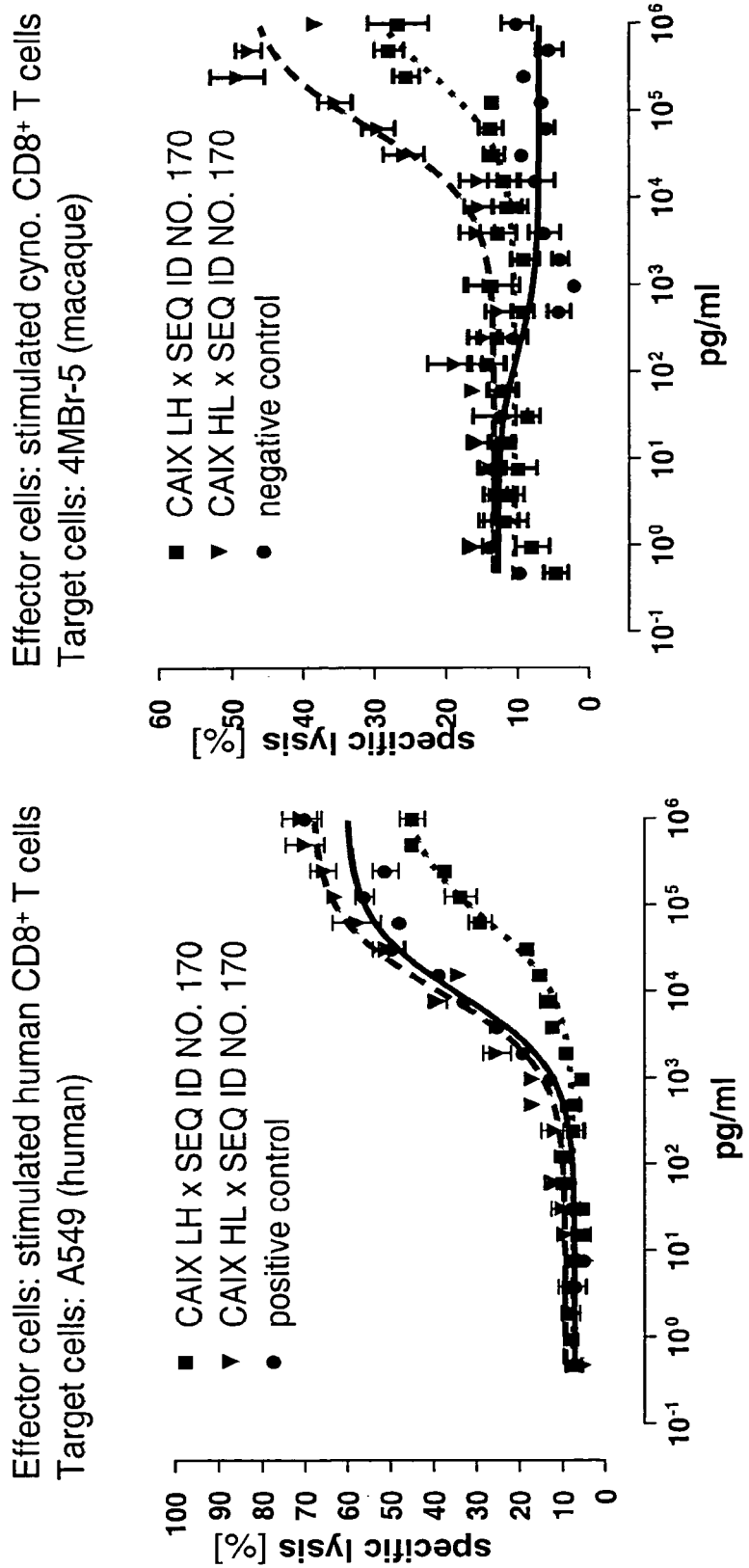

FIG. 37: Cytotoxic activity induced by CAIX and CD3 cross-species specific bispecific single chain antibody constructs redirected to indicated target cell lines. Stimulated CD8 positive T cells from human and cynomolgus origin were used as effector cells, respectively. The assay was performed as described in Examples 24 and 25. In the left panel of FIG. 37, a bispecific single chain antibody with a variable domain reactive with CAIX and a de-immunized human CD3-specific variable domain has been used as a positive control. In the right panel, the same construct has been used as a negative control.

Figure 38:
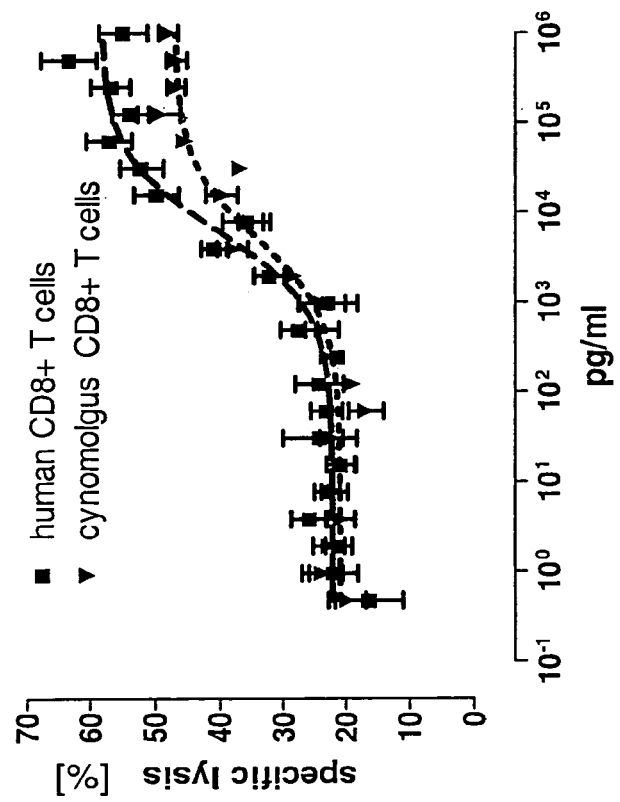

FIG. 38: Cytotoxic activity induced by the CAIX and CD3 cross-species specific bispecific single chain antibody construct CAIX HL×SEQ ID NO. 194 redirected to target cell line A549. Stimulated CD8 positive T cells from human and cynomolgus origin were used as effector cells, respectively. The assay was performed as described in Examples 24 and 25.

FIG. 39: Cytotoxic activity induced by EGFR and CD3 cross-species specific bispecific single chain antibody constructs redirected to CHO cells transfected with cynomolgus EGFR as target cell line. Stimulated CD8 positive T cells from cynomolgus origin were used as effector cells. The measurements shown in this figure were performed in a single assay. The assay was performed as described in Example 24. A bispecific single chain antibody with a variable domain reactive with EGFR and a de-immunized human CD3-specific variable domain (EGFR LH×di-anti CD3) has been used as a negative control.

FIG. 40: Cytotoxic activity induced by EGFR and CD3 cross-species specific bispecific single chain antibody constructs redirected to human A431 as target cell line. Stimulated CD8 positive T cells from human origin were used as effector cells. The measurements shown in this figure were performed in a single assay. The assay was performed as described in Example 24. A bispecific single chain antibody with a variable domain reactive with EGFR and a de-immunized human CD3-specific variable domain (EGFR LH×di-anti CD3) has been used as a positive control. As a negative control, an irrelevant bispecific single chain antibody has been used.

The following Examples illustrate the invention:

Example 1: Flow Cytometric Analysis of Cross-Species Specific Antibodies

Cross-species specificity of anti-human CD3 antibodies to macaque CD3 (CD3 of *Macaca fascicularis*, in the following also named "Cynomolgus") was tested by flow cytometric analysis. Antibodies tested were an anti-CD3 antibody as described in WO 99/54440 (as shown in SEQ ID NO. 162 of the present application), monoclonal antibody (mAb) OKT-3 (Jansen-Cilag), UCHT-1-PE (BD PharMingen, San Diego, California), an immunoglobulin (Ig) comprising the VH and VL chains shown in SEQ ID NOs. 2 and 4, respectively, and an Ig comprising the VH and VL chains shown in SEQ ID NOs. 6 and 8, respectively. $2 \times 10^5$ cells (macaque T cell lines of *Macaca fascicularis* and *Macaca mulatta*, respectively, as kindly provided by H. Fickenscher, Heidelberg, Germany) per sample were stained for 30 minutes at 4° C. in 25 µl of PBS/1% FCS/0.05% $NaN_3$ containing working dilutions of monoclonal antibodies (as determined individually by titration). Cells were washed two times in PBS/1% FCS/0.05% $NaN_3$ and a secondary antibody was added where necessary. After the addition of the secondary antibody, cells were washed again two times in the same solution and 10.000 living cells were acquired. A FACS Calibur flow cytometer and the CellQuest software from Becton Dickinson were used to collect and analyze the data. Non viable cells were excluded using forward and side scatter electronic gating. Isotype control or secondary antibody only were used as a negative control. As can be seen from FIG. 1, only the Ig comprising the VH and VL chains shown in SEQ ID NOs. 2 and 4, respectively, and the Ig comprising the VH and VL chains shown in SEQ ID NOs. 6 and 8, respectively, showed cross-species specificity for a non-chimpanzee primate CD3, i.e. macaque CD3.

Example 2: FACS Assay for Binding of an Ig Comprising SEQ ID NOs. 2 and 4, an Ig Comprising SEQ ID NOs. 6 and 8 and mAb FN18 to HPB-ALL Cells and Cynomolgus PBMC Binding of an Ig comprising SEQ ID NOs. 2 and 4, an Ig comprising SEQ ID NOs. 6 and 8 and mAb FN18 to the cynomolgus CD3 antigen on cynomolgus PBMC and to the human CD3 antigen on HPB-ALL cells (DSMZ No. ACC 483) was tested using an FACS assay. For that purpose, $2.5 \times 10^5$ cells were incubated with the FITC-conjugated Ig comprising SEQ ID NOs. 6 and 8 and the FITC-conjugated Ig comprising SEQ ID NOs. 2 and 4 diluted 1:25 in 50 µl PBS with 2% FCS, respectively. The incubation with the FITC-conjugated mAb FN18 antibody (Biosource International) was performed in 50 µl of undiluted antibody. The samples were measured on a FACSscan (BD biosciences, Heidelberg, FRG). The results for the assay are shown in FIG. 2. Strong antigen binding on human as well as on cynomolgus cells was detected for the Ig comprising SEQ ID NOs. 2 and 4. For the Ig comprising SEQ ID NOs. 6 and 8, strong binding to human cells but weaker binding to cynomolgus cells was observed. For FN18, strong binding to cynomolgus cells could be observed whereas no binding to human cells could be detected.

Example 3: Sequence Determination of the Variable Regions of Two Anti-Human CD3 Antibodies Exhibiting Species Specificity for Non-Human Primates For the sequence determination of the variable regions of the cross-species specific anti-CD3 Igs of Examples 1 and 2, PCR (denaturation at 93° C. for 5 min, annealing at 58° C. for 1 min, elongation at 72° C. for 1 min for the first cycle; denaturation at 93° C. for 1 min, annealing at 58° C. for 1 min, elongation at 72° C. for 1 min for 30 cycles; terminal extension at 72° C. for 5 min) was used to amplify the coding sequences of the variable regions of the antibodies. As the sequence of the 5' region of the variable regions is not known, instead of a single primer a set of 5' primers was used in combination with a constant 3' primer whereby the 3' primer was chosen according to the isotype of the respective antibody and there were two different sets of primers for the 5' region, one for the light chain variable region and the other for the heavy chain variable region. The primer combinations used in the PCR reactions are given below.

```
Heavy chain variable region:
5' primer:
                                        (SEQ ID NO. 81)
5'-SAGGTGCAGCTCGAGGAGTCAGGACCT-3'

(SEQ ID NO. 82)
5'-GAGGTCCAGCTCGAGCAGTCTGGACCT-3'

(SEQ ID NO. 83)
5'-CAGGTCCAACTCGAGCAGCCTGGGGCT-3'

(SEQ ID NO. 84)
5'-GAGGTTCAGCTCGAGCAGTCTGGGGCA-3'

(SEQ ID NO. 85)
5'-GARGTGAAGCTCGAGGAGTCTGGAGGA-3'

(SEQ ID NO. 86)
5'-GAGGTGAAGCTTCTCGAGTCTGGAGGT-3'

(SEQ ID NO. 87)
5'-GAAGTGAAGCTCGAGGAGTCTGGGGGA-3'

(SEQ ID NO. 88)
5'-GAGGTTCAGCTCGAGCAGTCTGGAGCT-3'

(SEQ ID NO. 89)
5'-GGGCTCGAGCACCATGGRATGSAGCTGKGTMATSCTCTT-3'

(SEQ ID NO. 90)
5'-GGGCTCGAGCACCATGRACTTCGGGYTGAGCTKGGTTTT-3'
```

-continued (SEQ ID NO. 91)
5'-GGGCTCGAGCACCATGGCTGTCTTGGGGCTGCTCTTCT-3'

3' primer:
(SEQ ID NO. 92)
5'-GAGGAATTCGAACTGGACAGGGATCCAGAGTTCC-3'

(SEQ ID NO. 93)
5'-CGGAATTCGAATGACATGGACATCTGGGTCATCC-3'

Light chain variable region:
5' primer:
(SEQ ID NO. 94)
5'-CCAGTTCCGAGCTCGTTGTGACTCAGGAATCT-3'

(SEQ ID NO. 95)
5'-CCAGTTCCGAGCTCGTGTTGACGCAGCCGCCC-3'

(SEQ ID NO. 96)
5'-CCAGTTCCGAGCTCGTGCTCACCCAGTCTCCA-3'

(SEQ ID NO. 97)
5'-CCAGTTCCGAGCTCCAGATGACCCAGTCTCCA-3'

(SEQ ID NO. 98)
5'-CCAGATGTGAGCTCGTGATGACCCAGACTCCA-3'

(SEQ ID NO. 99)
5'-CCAGATGTGAGCTCGTCATGACCCAGTCTCCA-3'

(SEQ ID NO. 100)
5'-CCAGTTCCGAGCTCGTGATGACACAGTCTCCA-3'

(SEQ ID NO. 101)
5'-GGGGAGCTCCACCATGGAGACAGACACACTCCTGCTAT-3'

(SEQ ID NO. 102)
5'-GGGGAGCTCCACCATGGATTTTCAAGTGCAGATTTTCAG-3'

(SEQ ID NO. 103)
5'-GGGGAGCTCCACCATGGAGWCACAKWCTCAGGTCTTTRTA-3'

(SEQ ID NO. 104)
5'-GGGGAGCTCCACCATGKCCCCWRCTCAGYTYCTKGT-3'

3' primer:
(SEQ ID NO. 105)
5'-GAGGAATTCGAACTGCTCACTGGATGGTGGG-3'

(SEQ ID NO. 106)
5'-CGGAATTCGAACAAACTCTTCTCCACAGTGTGACC-3'

All PCR products with a length between 350 and 700 base pairs were isolated, purified and sequenced with the respective 3' primer according to standard protocols (Sambrook, Molecular Cloning; A Laboratory Manual, Cold Spring Harbor Laboratory Press, Cold Spring Harbor, New York (1989)(2001)).

The obtained sequences were examined for functional variable region coding sequences and for the heavy chain and the light chain of each antibody a sequence coding for the variable region was obtained. The nucleotide and amino acid sequences of the heavy and light chain variable regions of the cross-species specific anti-CD3 antibodies are described in SEQ ID NOs. 1 through 8 in the sequence listing included in the description, respectively.

Example 4: Cloning of Anti Human EpCAM and CD3 Cross-Species Specific Bispecific Single Chain Antibodies To generate bispecific single chain antibodies comprising the aforementioned CD3 cross-species specificities, the amplified variable regions had to be modified by PCR to obtain the corresponding single chain Fv antibody fragments. To determine suitable arrangements of the light and heavy chain variable regions in the single chain Fv antibody, two different single chain Fv antibodies were generated for each antibody. To this end, a two-step fusion PCR was used to amplify the sequence coding for the variable regions. A set of appropriate primers was designed to perform the PCR-based cloning steps, finally resulting in a single chain antibody connecting the two variable domains with a 15 amino acid linker ([Gly$_4$Ser]$_3$) in the order VH-Linker-VL and VL-Linker-VH. The corresponding nucleotide and amino acid sequences are described in SEQ ID NO. 9 through 12 and in SEQ ID NO. 13 through 16 of the sequence listing included in the description.

In short the following primer combinations were used:
For VL-VH scFv antibody shown in SEQ ID NOs. 11 and 12: SEQ ID NOs. 17 to 20.
For VH-VL scFv antibody shown in SEQ ID NOs. 9 and 10: SEQ ID NOs. 21 to 24.
For VL-VH scFv antibody shown in SEQ ID NOs. 15 and 16: SEQ ID NOs. 25 to 28.
For VH-VL scFv antibody shown in SEQ ID NOs. 13 and 14: SEQ ID NOs. 29 to 32.

To generate the single chain antibody, two PCRs with the respective primer combinations were performed. During this PCR overlapping complementary sequences were introduced into the PCR-products stemming from the respective linker primers that combined to form the coding sequence of the 15 amino acid linker during the subsequent fusion PCR. The amplified VH and VL domains were fused in a next PCR in which only the outer primers and both PCR-products were required. The resulting scFv antibody is flanked at the 5' end with a small Ser(Gly$_4$)Ser linker preceded by the restriction enzyme recognition site for BspEI and at the 3' end with a 6 histidine affinity tag followed by a stop codon and by the restriction enzyme recognition site for SalI. The second single chain Fv antibody was an anti human EpCAM specificity designated "5-10" which is described in SEQ ID NO. 33 and 34 of the sequence listing included in the description. To accomplish the fusion of the single chain Fv antibodies and to allow for eukaryotic expression, the coding sequence of the single chain Fv antibodies was then cloned via BspEI (5' to the Ser(Gly$_4$)Ser linker) and SalI into the pEFDHFR expression vector (pEFDHFR was described in Mack et al. Proc. Natl. Acad. Sci. USA 92 (1995) 7021-7025) containing the coding sequence for the human EpCAM specific single chain Fv antibody 5-10 and the restriction enzyme recognition site for BspEI. The coding sequence of an murine immunoglobulin leader peptide is described in SEQ ID NO. 35 and 36 of the sequence listing included in the description, preceded by a Kozak translation initiation consensus sequence and the restriction enzyme recognition site for EcoRI. Single clones of the constructs were isolated and sequenced with primers complementary to flanking regions in the vector according to standard protocols (Sambrook, Molecular Cloning; A Laboratory Manual, Cold Spring Harbor Laboratory Press, Cold Spring Harbor, New York (1989) (2001)). For further experiments a clone of each construct was selected. The nucleotide and amino acid sequences are described for 5-10LH×SEQ ID NO.12 in SEQ ID NOs. 37 and 38, for 5-10LH×SEQ ID NO.10 in SEQ ID NOs. 39 and 40, for 5-10LH×SEQ ID NO.16 in SEQ ID NOs. 41 and 42 and for 5-10LH×SEQ ID NOs.14 in SEQ ID NO. 43 and 44 of the sequence listing included in the description.

Example 5: Expression of the 5-10LH×SEQ ID NO.12, 5-10LH×SEQ ID NO.10, 5-10LH×SEQ ID NO.16 and 5-10LH×SEQ ID NO.14 Bispecific Single Chain Antibodies in CHO Cells The plasmids with the sequences coding for the bispecific single chain antibodies were transfected into DHFR deficient CHO cells for eukaryotic expression of the construct as described in Kaufmann R. J. (1990) Methods Enzymol. 185, 537-566). Gene amplification of the construct was induced by increasing concentrations of Methotrexat (MTX) to a final concentration of up to 500 nM MTX. The transfected cells were then expanded and 1 liter of supernatant produced. The construct was finally purified out of the culture supernatant as described in Kufer et al. Cancer immunity Vol. 1, p. 10 (2001).

Example 6: FACS Assay for Binding of 5-10LH×SEQ ID NO.12, 5-10LH×SEQ ID NO.10, 5-10LH×SEQ ID NO.16 and 5-10LH×SEQ ID NO.14 to Kato III Cells or Human EpCAM Transfected CHO Cells and to HPB-ALL Cells Binding of the bifunctional constructs to the EpCAM antigen on human Kato III cells expressing EpCAM (ATCC No. HTB-103) or on human EpCAM transfected CHO cells and to the human CD3 antigen on HPB-ALL cells was tested using an FACS assay. For that purpose $2.5 \times 10^5$ cells were incubated with 50 µl of cell culture supernatant containing the construct. The binding of the construct was detected with an anti-His antibody (Penta-His Antibody, BSA free, obtained from Qiagen GmbH, Hilden, FRG) at 2 µg/ml in 50 µl PBS with 2% FCS. As a second step reagent a R-Phycoerythrin-conjugated affinity purified F(ab')2 fragment, goat anti-mouse IgG, Fc-gamma fragment specific antibody, diluted 1:100 in 50 µl PBS with 2% FCS (obtained from Dianova, Hamburg, FRG) was used. The samples were measured on a FACSscan (BD biosciences, Heidelberg, FRG). Antigen binding was clearly detectable for the anti human EpCAM specificity as well as for the anti CD3 specificities on the cell line positive for human CD3 (see FIG. 3).

Example 7: Cytotoxicity Assay for 5-10LH×SEQ ID NO. 12, 5-10LH×SEQ ID NO.10, and 5-10LH×SEQ ID NO.14 with Kato III Cells as Target Cells and Human PBMC as Effector Cells Bioactivity of 5-10LH×SEQ ID NO.12, 5-10LH×SEQ ID NO.10, and 5LH-10×SEQ ID NO.14 was analyzed by FACS-based in vitro cytotoxicity assays using the human EpCAM positive Kato III cells as target cells and human PBMCs as effector cells. Target cells were washed twice with PBS and labeled with PKH26 dye (Sigma-Aldrich, Germany) according to the manufacturer's instructions. Labeled target cells were washed twice with RPMI/10% FCS and mixed with freshly isolated effector cells at an E:T ratio of 10:1. Two times $10^4$ target and $2 \times 10^5$ effector cells in a volume of 50 µl RPMI/10% FCS were added per well in a 96-well round bottom plate. Ten-fold serial dilutions of different bispecific single chain constructs were prepared in RPMI/10% FCS to obtain a starting concentration of 1000 ng/ml in the final reaction volume. 50 µl of the different solutions were added in triplicates to the corresponding wells. Individual cytotoxicity mixtures were incubated for 24 to 48 hours at 37° C., 5% $CO_2$.

Subsequently the measurement of cytotoxic activity was performed. To this end, Propidium iodide (PI) was added to a final concentration of 1 µg/ml per well and plates were incubated for 10 minutes at room temperature. The number of PKH and PI positive and negative target cells was determined by FACS. Cytotoxicity was measured as the ratio of PKH-positive and PI negative (living target cells) over the mean of living target cells (PKH-positive and PI negative) in the control containing no construct according to the formula: cytotoxicity (%)=[(PI-negative cells/mean of PI-negative cells in control)×100]. Sigmoidal dose response killing curves were analyzed by Prism Software (GraphPad Software Inc., San Diego, USA) and the BiTE concentration calculated that induced half maximal killing (EC50 value). The results of this assay are shown below in FIG. 4. All constructs showed cytotoxic activity. The resulting EC50 values for 5-10LH×SEQ ID NO.14, 5-10LH×SEQ ID NO.12 and 5-10LH×SEQ ID NO.10 were 1.3 pg/ml, 1.5 pg/ml and 5.8 pg/ml respectively.

Example 8: Cytotoxicity Assay for 5-10LH×SEQ ID NO.12, 5-10LH×SEQ ID NO.10, and 5-10LH×SEQ ID NO.14 with Kato III Cells as Target Cells and Cynomolgus PBMC as Effector Cells Bioactivity of 5-10LH×SEQ ID NO.12, 5-10LH×SEQ ID NO.10, and 5-10LH×SEQ ID NO.14 was analyzed by FACS-based in vitro cytotoxicity assays using the human EpCAM positive Kato III cells as target cells and cynomolgus PBMCs as effector cells.

Target cells were washed twice with PBS and labeled with PKH26 dye (Sigma-Aldrich, Germany) according to the manufacturer's instructions. Labeled target cells were washed twice with RPMI/10% FCS and mixed with freshly isolated effector cells at an E:T ratio of 10:1. Two times $10^4$ target and $2 \times 10^5$ effector cells in a volume of 50 µl RPMI/10% FCS were added per well in a 96-well round bottom plate. Ten-fold serial dilutions of different Bispecific single chain antibodies were prepared in RPMI/10% FCS to obtain a starting concentration of 1000 ng/ml in the final reaction volume. 50 µl of the different solutions were added in triplicates to the corresponding wells. Individual cytotoxicity mixtures were incubated for 24 to 48 hours at 37° C., 5% $CO_2$.

Subsequently the measurement of cytotoxic activity was performed. To this end, propidium iodide (PI) was added to a final concentration of 1 µg/ml per well and plates were incubated for 10 minutes at room temperature. The number of PKH and PI positive and negative target cells was determined by FACS. Cytotoxicity was measured as the ratio of PKH-positive and PI negative (living target cells) over the mean of living target cells (PKH-positive and PI negative) in the control containing no construct according to the formula: cytotoxicity (%)=[(PI-negative cells/mean of PI-negative cells in control)×100]. Sigmoidal dose response killing curves were analyzed by Prism Software (GraphPad Software Inc., San Diego, USA) and the bispecific single chain antibody concentration calculated that induced half maximal killing (EC50 value). The results of this assay are shown below in FIG. 5. 5-10LH×SEQ ID NO.14, 5-10LH×SEQ ID NO.12 and 5-10LH×SEQ ID NO.10 showed cytotoxic activity. The resulting EC50 values for 5-10LH×SEQ ID NO.14, 5-10LH×SEQ ID NO.12 and 5-10LH×SEQ ID NO.10 were 87 pg/ml, 69 pg/ml and 52 pg/ml respectively. 5-10LH×di-anti CD3 (deimmunised anti-CD3 antibody as shown in SEQ ID NO.163) showed no activity. This is due to the fact that di-anti CD3 antibody only binds to human CD3, but not to cynomolgus CD3.

Example 9: Sequence Determination of the Cynomolgus EpCAM Antigen and Generation of Cynomolgus EpCAM Transfected CHO Cells To obtain the cynomolgus EpCAM antigen for testing of cross-species specificity of anti human EpCAM antibodies, first the coding sequence of the cynomolgus EpCAM antigen had to be determined. To this end, colon tissue samples of 3 animals were used in parallel for the isolation of total RNA and cDNA synthesis by random-primed reverse transcription, which were performed according to standard protocols (Sambrook, Molecular Cloning; A Laboratory Manual, Cold Spring Harbor Laboratory Press, Cold Spring Harbor, New York (1989) (2001)). A PCR (denaturation at 93° C. for 5 min, annealing at 58° C. for 1 min, elongation at 72° C. for 1 min for the first cycle; denaturation at 93° C. for 1 min, annealing at 58° C. for 1 min, elongation at 72° C. for 1 min for 35 cycles; terminal extension at 72° C. for 5 min) was used to amplify the coding sequence of the EpCAM antigen. As the coding sequence of the cynomolgus EpCAM antigen was not known, appropriate primers (5' primer described in SEQ ID NO. 45, 3' primer described in SEQ ID NO. 46) for the PCR reaction were designed according to the known coding sequence of the human EpCAM antigen (Szala S. et al., Proc Natl Acad Sci USA. 87 (1990); p. 3542-6). Primers were also designed as to allow for expression of the coding sequence of the entire antigen. For the 3 samples, PCR of 960 base pairs were isolated, purified and subcloned via XbaI and SalI, into pEFDHFR. Multiple clones for each sample were sequenced according to standard protocols (Sambrook, Molecular Cloning; A Laboratory Manual, Cold Spring Harbor Laboratory Press, Cold Spring Harbor, New York (1989)(2001)) using appropriate sequencing primers complementary to flanking sequences in the vector.

The novel nucleotide and amino acid sequences of the cynomolgus EpCAM antigen are described in SEQ ID NOs. 47 and 48 in the sequence listing included in the description, respectively.

The obtained sequences were examined by comparison with the coding sequence of the human EpCAM antigen. As shown in FIG. 6, there is a high degree of sequence homology between the coding sequence of the human EpCAM antigen and the sequences obtained from the colon samples of the 3 cynomolgus monkeys.

To generate a cell line positive for cynomolgus EpCAM, a clone of the aforementioned coding sequence of the cynomolgus EpCAM antigen subcloned into pEFDHFR with a verified nucleotide sequence was transfected into DHFR deficient CHO cells for eukaryotic expression of the construct as described in Kaufmann R. J. (1990) Methods Enzymol. 185, 537-566). Gene amplification of the construct was induced by increasing concentrations of MTX to a final concentration of up to 500 nM MTX. The transfected cells were then tested for expression of cynomolgus EpCAM using an FACS assay. For that purpose, a number of $2.5 \times 10^5$ cells was incubated with 50 µl supernatant three different mouse anti human EpCAM hybridomas (M79—Fogler et al., Cancer Res. 48 (1988); p. 6303-8; 3B10—Passlick et al. Int. J. Cancer 87 (2000), p. 548-552; 2G8—Balzar et al., J. Mol. Med. 77 (1999), p. 699-712). The binding of the antibodies was detected with a R-Phycoerythrin-conjugated affinity purified F(ab')2 fragment, goat anti-mouse IgG, Fc-gamma fragment specific antibody, diluted 1:100 in 50 µl PBS with 2% FCS (obtained from Dianova, Hamburg, FRG) was used. The samples were measured on a FACSscan (BD biosciences, Heidelberg, FRG). The anti EpCAM antibody 2G8 was recognized as cross-species specific and the expression of cynomolgus EpCAM was confirmed (see FIG. 7). Transfectants (depicted as non-filled curves) as compared to untransfected cells (depicted as filled curves) showed binding only with the supernatant of the 2G8 hybridoma which is therefore recognized as antibody species specific for human and cynomolgus EpCAM.

Example 10: Sequence Determination of the Variable Regions of an Anti Human EpCAM Antibody Cross-Species Specific for Non-Human Primates For the sequence determination of the variable regions of the anti-EpCAM antibody 2G8, the respective hybridoma cell line was used for isolation of total RNA and cDNA synthesis by random-primed reverse transcription, which were performed according to standard protocols (Sambrook, Molecular Cloning; A Laboratory Manual, Cold Spring Harbour Laboratory Press, Cold Spring Harbour, New York (1989) (2001)). A PCR (denaturation at 93° C. for 5 min, annealing at 58° C. for 1 min, elongation at 72° C. for 1 min for the first cycle; denaturation at 93° C. for 1 min, annealing at 58° C. for 1 min, elongation at 72° C. for 1 min for 30 cycles; terminal extension at 72° C. for 5 min) was used to amplify the coding sequences of the variable regions of the antibody. As the sequence of the 5' region of the variable regions is not known the aforementioned set of 5' primers was used in combination with a constant 3' primer whereby the 3' primer was chosen according to the isotype of the antibody.

```
Heavy chain variable region:
3' primer:
                                  (SEQ ID NO. 107)
5'-TATGCAACTAGTACAACCACAATCCCTGGG-3'

Light chain variable region:
3' primer:
                                  (SEQ ID NO. 108)
5'-GCGCCGTCTAGAATTAACACTCATTCCTGTTGAA-3'
```

All PCR products with a length between 350 and 700 base pairs were isolated, purified and sequenced with the respective 3' primer according to standard protocols (Molecular Cloning; A Laboratory Manual, Cold Spring Harbor Laboratory Press, Cold Spring Harbor, New York (1989)(2001)).

The obtained sequences were examined for functional variable region coding sequences and for the heavy chain and the light chain of the antibody a sequence coding for the variable region was isolated. The nucleotide and amino acid sequences of the variable regions are described in SEQ ID NOs. 49 through 52 in the sequence listing included in the description, respectively.

Example 11: Cloning of EpCAM and CD3 Cross-Species Specific Bispecific Single Chain Antibodies To generate bispecific single chain antibody molecules comprising the aforementioned CD3 cross-species specificity and the aforementioned EpCAM cross-species specificity, the amplified variable regions of the 2G8 antibody had to be modified by PCR to obtain the corresponding single chain Fv antibody fragments. Two single chain Fv antibodies with different arrangements of the light and heavy chain variable regions were generated. To this end, a two-step fusion PCR was used to amplify the sequence coding for the variable regions. A set of appropriate primers was designed to perform the PCR-based cloning steps, finally resulting in a 2G8 single chain antibody connecting the two variable domains with a 15 amino acid linker ([Gly$_4$Ser]$_3$) in the order VH-Linker-VL and VL-Linker-VH. The nucleotide and amino acid sequences are described in SEQ ID NOs. 53 through 56 of the sequence listing included in the description, respectively.

In short the following primer combinations were used:
For 2G8 VL-VH scFv antibody (hereafter designated as 2G8LH shown in SEQ ID NOs. 55 and 56): SEQ ID NOs. 57 to 60.
For 2G8 VH-VL scFv antibody (hereafter designated as 2G8HL shown in SEQ ID NOs. 53 and 54): SEQ ID NOs. 61 to 64.

To generate the single chain antibody, two PCRs with the respective primer combinations were performed. During this PCR, overlapping complementary sequences were introduced into the PCR-products (stemming from the respective linker primers that combined to form the coding sequence of the 15 amino acid linker during the subsequent fusion PCR). The amplified VH and VL domains were fused in this fusion PCR in which only the outer primers and both PCR-products were required. The resulting scFv antibody is flanked at the 5' end with the restriction enzyme recognition site for BsrGI and at the 3' end with the restriction enzyme recognition site for BspEI. The coding sequence of the EpCAM specific single chain Fv antibodies was then cloned via BsrGI and BspEI into the pEFDHFR expression vectors described above replacing the 5-10LH scFv. Single clones of the constructs were isolated and sequenced with primers complementary to flanking regions in the vector according to standard protocols (Sambrook, Molecular Cloning; A Laboratory Manual, Cold Spring Harbor Laboratory Press, Cold Spring Harbor, New York (1989)(2001)). For further experiments a clone of each construct was selected. The nucleotide and amino acid sequences are described for 2G8LH×SEQ ID NO.12 in SEQ ID NOs. 65 and 66, for 2G8LH×SEQ ID NO.10 in SEQ ID NOs. 67 and 68, for 2G8LH×SEQ ID NO.16 in SEQ ID NOs. 69 and 70, for 2G8LH×SEQ ID NO.14 in SEQ ID NOs. 71 and 72, for 2G8HL×SEQ ID NO.12 in SEQ ID NOs. 73 and 74, for 2G8HL×SEQ ID NO.10 in SEQ ID NOs. 75 and 76, for 2G8HL×SEQ ID NO.16 in SEQ ID NOs. 77 and 78, and for 2G8HL×SEQ ID NO.14 in SEQ ID NOs. 79 and 80 of the sequence listing included in the description.

Example 12: Expression of the 2G8LH×SEQ ID NO.12, 2G8LH×SEQ ID NO.10, 2G8LH×SEQ ID NO.16, 2G8LH×SEQ ID NO.14, 2G8HL×SEQ ID NO.12, 2G8HL×SEQ ID NO.10, 2G8HL×SEQ ID NO.16 and 2G8HL×SEQ ID NO.14 Bispecific Single Chain Antibodies in CHO Cells The plasmids with the sequences coding for the bispecific single chain antibodies were transfected into DHFR deficient CHO cells for eukaryotic expression of the construct as described in Kaufmann R. J. (1990) Methods Enzymol. 185, 537-566). Gene amplification of the construct was induced by increasing concentrations of MTX to a final concentration of up to 500 nM MTX. The transfected cells were then expanded and 1 liter of supernatant produced. The construct was finally purified out of the culture supernatant as described in Kufer et al. Cancer Immunity Vol. 1, p. 10 (2001).

Example 13: FACS Assay for Binding of 2G8LH×SEQ ID NO.12, 2G8LH×SEQ ID NO.10, 2G8LH×SEQ ID NO.16, 2G8LH×SEQ ID NO.14, 2G8HL×SEQ ID NO.12, 2G8HL×SEQ ID NO.10, 2G8HL×SEQ ID NO.16 and 2G8HL×SEQ ID NO.14 on Kato III Cells or Cynomolgus EpCAM Transfected CHO Cells and HPB-ALL Cells Binding of the bifunctional constructs from cell culture supernatants or binding of purified bifunctional constructs to the human EpCAM antigen on Kato III cells or cynomolgus EpCAM transfected CHO cells and to the CD3 antigen on HPB-ALL cells was tested using an FACS assay. For that purpose 2.5×10$^5$ cells were incubated with 50 μl supernatant or with 5 μg/ml of the purified constructs in 50 μl PBS with 2% FCS. The binding of the constructs was detected with an anti-His antibody (Penta-His Antibody, BSA free, obtained from Qiagen GmbH, Hilden, FRG) at 2 μg/ml in 50 μl PBS with 2% FCS. As a second step reagent a R-Phycoerythrin-conjugated affinity purified F(ab')2 fragment, goat anti-mouse IgG, Fc-gamma fragment specific antibody, diluted 1:100 in 50 μl PBS with 2% FCS (obtained from Dianova, Hamburg, FRG) was used. The samples were measured on a FACSscan (BD biosciences, Heidelberg, FRG). Antigen binding was clearly detectable for the anti EpCAM specificities as well as for the anti CD3 specificities (see FIG. 8). As a negative control for binding to cynomolgus EpCAM, the 5-10LH×SEQ ID NO.10 construct was included which shows binding on human CD3 (HPB-ALL cells) but no binding to cynomolgus EpCAM (cynomolgus EpCAM transfected CHO cells). The 5-10LH part only binds to human EpCAM.

Example 14: Cytotoxicity Assay for 2G8LH×SEQ ID NO.10 and 2G8HL×SEQ ID NO.12 with Cynomolgus EpCAM Transfected CHO Cells as Target Cells and Human PBMC as Effector Cells Bioactivity of selected bispecific single chain antibodies was analyzed by FACS-based in vitro cytotoxicity assays using the cynomolgus EpCAM transfected CHO cells as target cells and human PBMCs as effector cells.

Target cells were washed twice with PBS and labeled with PKH26 dye (Sigma-Aldrich, Germany) according to the manufacturer's instructions. Labeled target cells were washed twice with RPMI/10% FCS and mixed with freshly isolated effector cells at an E:T ratio of 10:1. 2×10$^4$ target and 2×10$^5$ effector cells in a volume of 50 μl RPMI/10% FCS were added per well in a 96-well round bottom plate. Ten-fold serial dilutions of different bispecific single chain antibodies were prepared in RPMI/10% FCS to obtain a starting concentration of 5000 ng/ml in the final reaction volume. 50 μl of the different solutions were added in triplicates to the corresponding wells and incubated for 24 to 48 hours at 37° C., 5% CO$_2$.

Subsequently, the measurement of cytotoxic activity was performed. To this end propidium iodide (PI) was added to a final concentration of 1 μg/ml per well and plates were incubated for 10 minutes at room temperature. The number of PKH and PI positive target cells was determined by FACS. Cytotoxicity was measured as the ratio of PI positive (dead cells) over total number of target cells (PKH-positive) according to the formula: cytotoxicity (%)=[(PI-positive cells/PKH-positive cells)×100]. Sigmoidal dose response killing curves were analyzed by Prism Software (GraphPad Software Inc., San Diego, USA) and the bispecific single chain antibody concentration calculated that induced half maximal killing (EC50 value). The results of this assay are shown below in FIG. 9. The resulting EC50 values for 2G8LH×SEQ ID NO.10 and 2G8HL×SEQ ID NO.12 were 1103 pg/ml and 3638 pg/ml, respectively. 5-10LH×di-anti CD3 (deimmunised version of the anti-CD3 antibody as shown in SEQ ID NO.163 binding to human CD3, but not to cynomolgus CD3) was included as negative control and showed no activity. This is due to the fact that 5-10LH only binds to human EpCAM but lacks cross-species specificity to cynomolgus EpCAM.

Example 15: Cytotoxicity Assay for 2G8LH×SEQ ID NO.10 and 2G8HL×SEQ ID NO.12 with Cynomolgus EpCAM Transfected CHO Cells as Target Cells and Cynomolgus PBMC as Effector Cells Bioactivity of selected bispecific single chain antibodies was analyzed by FACS-based in vitro cytotoxicity assays using the cynomolgus EpCAM transfected CHO cells as target cells and cynomolgus PBMCs as effector cells.

Target cells were washed twice with PBS and labeled with PKH26 dye (Sigma-Aldrich, Germany) according to the manufacturer's instructions. Labeled target cells were washed twice with RPMI/10% FCS and mixed with freshly isolated effector cells at an E:T ratio of 10:1. $2 \times 10^4$ target and $2 \times 10^5$ effector cells in a volume of 50 µl RPMI/10% FCS were added per well in a 96-well round bottom plate. Ten-fold serial dilutions of different bispecific single chain antibodies were prepared in RPMI/10% FCS to obtain a starting concentration of 5000 ng/ml in the final reaction volume. 50 µl of the different solutions were added in triplicates to the corresponding wells. Individual cytotoxicity mixtures were incubated for 24 to 48 hours at 37° C., 5% $CO_2$.

Subsequently the measurement of cytotoxic activity was performed as described in Example 14. The resulting EC50 values for 2G8LH×SEQ ID NO.10 and 2G8HL×SEQ ID NO.12 were 39810 pg/ml and 60350 pg/ml respectively. 5-10LH×di-anti CD3 (deimmunised version of the anti-CD3 antibody as shown in SEQ ID NO.163) was included as negative control and showed no activity. Di-anti CD3 only binds to human CD3, but fails to bind to macaque/cynomolgus CD3. 5-10LH only binds to human EpCAM but lacks cross-species specificity to cynomolgus EpCAM.

Example 16: Generation of a Human-Like CD3 Antibody Fragment that Binds to Human and Cynomolgus CD3

1. Determination of a Correlating Human VH

The amino acid sequence of the murine VH chain shown in SEQ ID NO. 2 was aligned to the repertoire of human VH germline sequences (http://vbase.mrc-cpe.catmac.uk) using the Vector NTI DNA analysis software. On the basis of this analysis, the human VH segment 3-73 was chosen as a template sequence (see FIG. 11). Definitions of CDRs and frameworks are according to the Kabat numbering scheme.

The corresponding amino acid residues that differ between the VH chain shown in SEQ ID NO. 2 and the human VH segment 3-73 within the framework regions were mutated on the DNA level towards the human residues. However, the construct retained potentially crucial framework residues of the original murine VH sequence (according to the Kabat numbering scheme): H-30, H-41, H49, H82b, H-93 (see FIG. 12). In this way, an amino acid sequence was designed that was identical to the murine VH chain shown in SEQ ID NO. 2 sequence within its CDRs. The corresponding amino acid sequence is shown in SEQ ID NO. 110, whereas the corresponding nucleic acid sequence is shown in SEQ ID NO. 111; see also FIG. 12. The N-terminal VH sequence was changed to "EVQLLE" to generate a suitable N-terminal cloning site (see FIG. 12).

2. Gene Synthesis and Cloning of the Human-Like VH Region

The afore-mentioned human-like VH region was gene synthesized (Entelechon, Germany) and subcloned via the restriction sites XhoI and BstEII into a suitable bacterial expression vector. This vector already contained the sequence coding for a VL chain (amino acid sequence shown in SEQ ID NO. 148; N-terminus in comparison to the original VL shown in SEQ ID NO. 4 slightly changed for cloning reasons) pairing with the human like VH region followed by a Flag and a His-6 Tag and preceded by a leader sequence that directs the functional scFv into the periplasma of *E. coli*. The functional domain arrangement after cloning was Leader sequence-VH-$(G_4S)_3$-VL-Flag-His6.

3. Functional Analysis of scFv Constructs having the Original Murine VH Shown in SEQ ID NO.2/VL Shown in SEQ ID NO.4 in Comparison to the Human-Like VH Shown in SEQ ID NO.110/VL Shown in SEQ ID NO. 148

Plasmid DNA encoding a) for the original murine VH (SEQ ID NO. 2) and VL (SEQ ID NO. 4) and b) for the human-like VH (SEQ ID NO. 110) combined with the VL (SEQ ID NO. 148) was each transformed into *E. coli* TG1 according to standard protocols. The nucleotide and amino acid sequences of the VH-VL scFv comprising the original murine VH (SEQ ID NO. 2) and VL (SEQ ID NO. 4) are shown in SEQ ID NOs. 9 and 10, respectively. The nucleotide and amino acid sequences of the VH-VL scFv comprising the human-like VH (SEQ ID NO. 110) and the VL (SEQ ID NO. 148) are shown in SEQ ID NOs. 147 and 146, respectively.

Expression of different clones was performed in *E. coli* TG-1 in 96-well format. 100 µl LB/0.1% glucose were inoculated with 10 µl of an overnight culture of single clones and grown for 4 h at 37° C. After addition of IPTG to a final concentration of 1 mM, the culture was grown at 30° C. for another 18-20 h. Per well, 40 µl of BEL-buffer (400 mM boric acid, 320 mM NaCl, 4 mM EDTA pH 8.0+2.5 mg/ml lysozyme) were added and shaken at room temperature for 1 h. Cellular debris was eliminated by centrifugation and supernatants were tested in flow cytometric experiments.

The human T cell line HPB-All and T cells in cynomolgus peripheric blood mononuclear cells (PBMC) were used as human CD3 and cynomolgus CD3 positive cells, respectively. Typically 100,000 cells were incubated with 50 µl of the scFv containing bacterial supernatants and incubated for 30 min on ice.

Afterwards the cells were washed three times with PBS and subsequently resuspended in 50 µl PBS containing anti-His antibody (Pentahis, Roche) and further incubated on ice for 30 min. Then the cells were washed three times with PBS and incubated with a PE labeled anti mouse IgG antibody for 30 more min. on ice (in this step cynomolgus PBMCs were coincubated with anti-CD2 FITC to identify the T cells in the PBMC mixture). After washing the cells for one time the cells were resuspended in a suitable buffer and positivity of cell bound antibody construct determined in a flow cytometer (FACScalibur) and analyzed. The control scFv of SEQ ID NO. 10 shows a clear shift on human CD3 positive cells as well as on cynomolgus CD3 positive cells indicative of binding to both human and cynomolgus CD3. The scFv shown in SEQ ID NO. 146 containing the human-like VH also shows clear binding to CD3 positive human (see FIG. 13) and cynomolgus cells (see FIG. 14).

4. Determination of a Correlating Human VL

The amino acid sequence of the murine VH chain shown in SEQ ID NO. 2 was aligned to the repertoire of human VL germline sequences (http://vbase.mrc-cpe.cam.ac.uk) using the Vector NTI DNA analysis software. On the basis of this analysis, the human Vlambda segment 7a was chosen as a template sequence (see FIG. 21). Definitions of CDRs and frameworks are according to the Kabat numbering scheme.

The corresponding amino acid residues that differ between the murine VL chain shown in SEQ ID NO. 4 and the human Vlambda segment 7a within the framework regions were mutated on the DNA level towards the human residues. However, the construct retained potentially crucial framework residues of the original murine Vlambda sequence (according to the Kabat numbering scheme): L 36, L 46, L 49, L 57 (see FIG. 21). In this way, an amino acid sequence was designed that was identical to the murine VL chain shown in SEQ ID NO. 4 sequence within its CDRs. The corresponding amino acid sequence of the generated human-like VL is shown in SEQ ID NO. 168, whereas the corresponding nucleic acid sequence is shown in SEQ ID NO. 167. The N-terminal VL sequence was changed to "EL" to generate a suitable N-terminal cloning site.

5. Gene Synthesis and Cloning of the Human-Like VL Region

The above-mentioned human-like VL region was gene synthesized (Entelechon, Germany) and subcloned via the restriction sites SacI and BsiWI into a suitable bacterial expression vector. This vector already contained the sequence coding for the above-mentioned human-like VH chain (amino acid sequence shown in SEQ ID NO. 110) pairing with the human-like VL region (amino acid sequence shown in SEQ ID NO. 168) followed by a Flag and a His-6 Tag and preceded by a leader sequence that directs the functional scFv into the periplasma of *E. coli*. The functional domain arrangement after cloning was Leader sequence-VH-(G$_4$S)$_3$ linker-VL-Flag tag-His6 tag.

6. Functional Analysis of scFv Constructs having the Human-Like VH Shown in SEQ ID NO. 110 Combined with the Human-Like VL Shown in SEQ ID NO. 168

Plasmid DNA encoding a) for the original murine VH (SEQ ID NO. 2) and VL (SEQ ID NO. 4) and b) for the human-like VH (SEQ ID NO. 110) combined with the human-like VL (SEQ ID NO. 168) was each transformed into *E. coli* TG1 according to standard protocols. The nucleotide and amino acid sequences of the VH-VL scFv comprising the original murine VH (SEQ ID NO. 2) and VL (SEQ ID NO. 4) are shown in SEQ ID NOs. 9 and 10, respectively. The nucleotide and amino acid sequences of the VH-VL scFv comprising the human-like VH (SEQ ID NO. 110) and the human-like VL (SEQ ID NO. 168) are shown in SEQ ID NOs. 169 and 170, respectively. The nucleotide and amino acid sequences of the VL-VH scFv comprising the human-like VL (SEQ ID NO. 168) and the human-like VH (SEQ ID NO. 110) are shown in SEQ ID NOs. 193 and 194, respectively. Due to different cloning strategies, the amino acid sequence of the VL-VH scFv of SEQ ID NO. 194 shows three amino acid exchanges in comparison to the one of the VH-VL scFv of SEQ ID NO. 170, however, without affecting the binding capacity and specificity of said scFv.

Expression of different clones was performed in *E. coli* TG-1 in 96-well format. 100 µl LB/0.1% glucose were inoculated with 10 µl of an overnight culture of single clones and grown for 4 h at 37° C. After addition of IPTG to a final concentration of 1 mM, the culture was grown at 30° C. for another 18-20 h. Per well, 40 µl of BEL-buffer (400 mM boric acid, 320 mM NaCl, 4 mM EDTA pH 8.0+2.5 mg/ml lysozyme) were added and shaken at room temperature for 1 h. Cellular debris was eliminated by centrifugation and supernatants were tested in flow cytometric experiments.

The human T cell line HPB-ALL and human and cynomolgus T cells in peripheral blood mononuclear cells (PBMCs) were used as human CD3 and cynomolgus CD3 positive cells, respectively.

Typically 100,000 cells were incubated with 50 µl of the scFv containing bacterial supernatants and incubated for 30 min on ice.

a) HPB-ALL cells were washed three times with PBS and subsequently resuspended in 50 µl PBS containing anti-His antibody (Pentahis, Roche) and further incubated on ice for 30 mM. Then the cells were washed three times with PBS and incubated with a PE labeled anti mouse IgG antibody for 30 more min. on ice. After washing the cells for one time the cells were resuspended in a suitable buffer and positivity of cell bound antibody construct determined in a flow cytometer (FACScalibur) and analyzed.

b) Human and cynomolgus PBMCs (containing T cells) were washed three times with PBS and subsequently resuspended in 50 µl PBS containing biotinylated anti-His antibody (biotinylated Pentahis, Roche) and further incubated on ice for 30 min. Then the cells were washed three times with PBS and incubated with PE labeled Streptavidin for 30 more min. on ice. In this step, PBMCs were coincubated with anti-CD2 FITC to identify the T cells in the PBMC mixture.

After washing the cells from a) or b) for one time the cells were resuspended in a suitable buffer and positivity of cell bound antibody construct determined in a flow cytometer (FACScalibur) and analyzed.

The control scFv of SEQ ID NO. 10 (murine VH of SEQ ID NO.4—murine VL of SEQ ID NO. 2) shows a clear shift on human CD3 positive cells as depicted in FIG. 22. The shift on human and cynomolgus T cells is less pronounced, most probably due to the less sensitive detection system (FIG. 23).

The human-like scFv of SEQ ID NO. 170 (human-like VH of SEQ ID NO.110—human-like VL of SEQ ID NO. 168) shows a positive shift on HPB-ALL cells (FIG. 22) and clear shifts on human as well as cynomolgus T cells (FIG. 23, upper panel).

When preincubated with 10 µg/ml of the murine IgG antibody mAb I described in Example 1 having the same specificity as the scFvs (i.e. for CD3 epsilon), the shifts of cells stained with the above-mentioned murine scFv or the human-like scFv decrease significantly, underlining the similar binding region of the scFvs and the original murine antibody; see FIG. 23 lower panel.

Example 17: Determination of an Epitope for Cross-Species Specific Anti-CD3 Antibodies Binding Both Human and Cynomolgus CD3 Epsilon In order to determine the epitope of human and cynomolgus CD3 epsilon bound by cross-species specific anti-CD3 antibodies, epitope mapping was carried out with antibody I (Ig comprising the VH chain shown in SEQ ID NO. 2 and the VL chain shown in SEQ ID NO. 4) and antibody II (Ig comprising the VH chain shown in SEQ ID NO. 6 and the VL chain shown in SEQ ID NO. 8), both binding to human and cynomolgus CD3 epsilon; see also FIG. 1. For the peptide-spotting ("pepspot") analysis, overlapping 13mer peptides derived from the amino acid sequences of human and cynomolgus CD3 epsilon (see FIG. 15) were covalently linked to a Whatman 50 cellulose-β-alanine-membrane via the C-terminus while the acetylated N-terminus remained free. In the peptides, the amino acid cystein—wherever occurring in the corresponding CD3 epsilon sequence—was exchanged by the amino acid serin. The individual 13mer peptides generated (by JPT Peptide Technologies GmbH) are shown in FIGS. 16 and 17. For cynomolgus CD3 epsilon, 43 spots have been tested, whereas for the human CD3 epsilon 47 spots have been tested. The length of the overlapping sequence of two adjacent peptides was set to be 11 amino acids.

The pepspot experiments were performed as follows. According to the manufacturer's protocol, the membrane was rinsed with methanol for 1 min, washed with 1×TBS and blocked with 1×TBS/1% (w/v) blocking reagent (BM Chemiluminescence Blotting Substrate (POD) of Roche Diagnostics GmbH) for 3 h. All incubation and washing steps were performed on an orbital shaker at room temperature, except for the overnight incubation of the primary antibody. Directly after discarding the blocking solution, the membranes were incubated overnight with 5 or 3 μg/ml of cross-species specific anti-CD3 antibodies as set forth above in 1×TBS/0.5% (w/v) blocking reagent at 4° C. on an orbital shaker. After washing 4 times with 1×TBS/0.05% Tween for 15 min, detection of bound anti-CD3 antibody was accomplished by incubation for 2 h with a commercially available horseradish-peroxidase-conjugated anti-IgG (F(ab)$_2$ specific) antibody or an alkaline phosphatase-labeled anti-IgG antibody (diluted according to the manufacturer's recommendation in 1×TBS/0.5% blocking reagent, respectively). Subsequently, the membranes were washed 6 times with 1×TBS/0.05% Tween for 15 min. Horseradish-peroxidase was visualized by enhanced chemiluminescence (luminescence substrate solution A and starting solution B mixed 100:1; BM Chemiluminescence Blotting Substrate (POD) of Roche Diagnostics GmbH) and a BioMax Film (Kodak). Alkaline phosphatase was visualized using 5-bromo-4-chloro-indolyl phosphate/nitro blue tetrazolium liquid substrate system (Sigma).

To exclude unspecific binding of horseradish-peroxidase-conjugated secondary antibody, the membrane was incubated with secondary antibody only. All other steps were performed as in the experiment above.

The control pepspot assay (see FIG. 18(A)) showed signals on spots 33 and 42 of cynomolgus CD3 epsilon and on spots 37, 39 and 46 of human CD3 epsilon. These signals are regarded as unspecific and will not be mentioned further.

1. Anti-CD3 Antibody I (Ig Comprising the VH Chain Shown in SEQ ID NO. 2 and the VL Chain Shown in SEQ ID NO. 4)

(i) Binding on Cynomolgus CD3 Epsilon

Strong binding signals of cross-species specific anti-CD3 antibody I (Ig comprising the VH chain shown in SEQ ID NO. 2 and the VL chain shown in SEQ ID NO. 4) to peptides derived from cynomolgus CD3 epsilon were detected on spot 1 as well as on the stretch of peptide-spots 24-29 (FIG. 18(B)). The latter corresponds to amino acid residues 47-69 of cynomolgus CD3 epsilon (see FIG. 15). All 13mer peptides covering this region contain one minimal amino acid motif 56-59 (EFSE). Spot 1 corresponds to amino acid residues 1-13 (QDGNEEMGSITQT) of cynomolgus CD3 epsilon.

(ii) Binding on Human CD3 Epsilon

Cross-species specific anti-CD3 antibody I bound to peptide-spots 15, 28, 32, 33 and 40 derived from human CD3 epsilon (see FIG. 18(B)). The stretch of peptide-spots 28 to 33 corresponds to the amino acid residues 47-69 of human CD3 epsilon and comprises the minimal amino acid motif 57-59 (FSE). Spots 15 and 40 correspond to amino acid residues 30-42 (QYPGSEILWQHND) and 71-83 (RG-SKPEDANFYLY), respectively.

2. Anti-CD3 Antibody II (Ig Comprising the VH Chain Shown in SEQ ID NO. 6 and the VL Chain Shown in SEQ ID NO. 8)

(i) Binding on Cynomolgus CD3 Epsilon

The pepspot analysis with cross-species specific anti-CD3 antibody II (Ig comprising the VH chain shown in SEQ ID NO. 6 and the VL chain shown in SEQ ID NO. 8) showed strong signals to cynomolgus CD3 epsilon on the stretch of peptide-spots 27-29 as well as on spot 33 (see FIG. 19). The stretch spanning spots 27 and 29 corresponds to the amino acid residues 53-69 of cynomolgus CD3 epsilon (see FIG. 15), wherein the 13mer peptides have the minimal stretch of amino acids 57-61 (FSEME) in common. Spot 33 correlates with amino acid residues 65-77 (YYVSYPRGSNPED).

(ii) Binding on Human CD3 Epsilon

Cross-reactive anti-CD3 antibody II bound the peptide-spots 15, 19, 32 and 33, 37, 39 and 40 of human CD3 epsilon (see FIG. 19). Spot 19 corresponds to amino acid residues 38-46d (WQHNDKNIGGDED) of human CD3 epsilon (see FIG. 15). The small stretch of spots 32 to 33 corresponds to amino acid residues 55-69 containing the minimal peptide FSELE (amino acids 57-61). The spots 37 and 39 match amino acid residues 65-77 (YYVSYPRGSKPED) and 69-81 (YPRGSKPEDANFY) of human CD3 epsilon, respectively. The correlations of spots 15 and 40 are already mentioned above.

In summary, both cross-species specific anti-CD3 antibodies recognize discontinous epitopes on human and cynomolgus CD3 epsilon. Regarding cynomolgus CD3 epsilon both cross-species specific anti-CD3 antibodies recognized a clear overlapping stretch of peptide-spots 27-29 (see FIG. 16). All 13mer peptides covering this region contain one minimal peptide FSEME (amino acid residues 57-61 of cynomolgus CD3 epsilon). The peptide-intersection on human CD3 epsilon bound by both antibodies can be determined for spots 32 and 33 (see FIG. 17). This section contains the minimal peptide FSELE corresponding to residues 57-61 of human CD3 epsilon.

Based on these results it is concluded that cross-species specific CD3 antibody fragments contact CD3 epsilon in the area of amino acid residues 57-61 of both cynomolgus and human CD3 epsilon comprising, the amino acid stretches FSEME and FSELE of cynomolgus and human CD3 epsilon, respectively, with the motif FSE forming the epitope core. This result—although plausible because of the accessibility of the E-F-loop (amino acids 56-62; see FIG. 15) of human CD3 epsilon (Kjer-Nielsen et al., PNAS 101 (2004), p. 7675-80) comprising the amino acids FSELE or FSEME—is nevertheless surprising since there is no overlap of this newly defined epitope with the known epitope on the CD3 epsilon-chain of anti-CD3 antibodies OKT3 and UCHT1 (see FIG. 17; Kjer-Nielsen et al., loc.cit; Arnett et al., PNAS 101 (2004), p. 16268-73) which have so far been regarded as representative of all anti-CD3 antibodies thought to form a single family with the same or a very similar epitope.

Example 18: Determination of the Epitope for the Human-Like Cross-Species Specific Anti-CD3 Antibody Binding Both to Human and Cynomolgus CD3 Epsilon The epitope mapping of the human-like cross-species specific anti-CD3 antibody fragment described in Example 16 (SEQ ID NO. 170) was carried out by peptide-spotting ("pepspot") analysis as described in Example 17. For this purpose, said single chain Fv fragment shown in SEQ ID NO. 170 was converted into a full IgG antibody with a murine gamma1 heavy chain comprising the VH region as shown in SEQ ID NO. 110 and a kappa light chain comprising the VL region as shown in SEQ ID NO. 168. The procedure of the pepspot experiment was identical to the protocol used in Example 17.

The pepspot membrane was incubated with 4 µg/ml of the mentioned IgG1 antibody, and an alkaline phosphatase-labeled goat-anti-mouse IgG antibody detecting bound CD3 antibody. A second membrane was incubated with alkaline phosphatase-labeled goat-anti-mouse IgG antibody alone to reveal unspecific binding of the detection antibody.

The following signals detected in the control pepspot assay (see FIG. 24(A)) have been regarded as unspecific and will not be mentioned further: the stained spot-stretches 10-13, 15-19, 30-32, 35-41 of cynomolgus CD3 epsilon and 2-6, 14-19, 26, 34-39 and 46 of human CD3 epsilon.

(i) Binding on Cynomolgus CD3 Epsilon

The cross-species specific anti-CD3 antibody (murine IgG1 comprising the VH chain shown in SEQ ID NO. 110 and the VL chain shown in SEQ ID NO. 168) bound to the peptide-spots 1 and 33 as well as to the amino acid stretch of peptide-spots 24-29 (FIG. 24(B)) derived from cynomolgus CD3 epsilon. The stretch spanning spots 24 and 29 corresponds to the amino acid residues 47-69 of cynomolgus CD3 epsilon (see FIGS. 15 and 16), wherein the 13mer peptides have the minimal stretch of amino acids 56-59 (EFSE) in common. Spot 1 and spot 33 correspond to amino acid residues 1-13 ("QDGNEEMGSITQT"; SEQ ID NO. 199) and 65-77 ("YYVSYPRGSNPED"; SEQ ID NO. 200) of cynomolgus CD3 epsilon, respectively.

(ii) Binding on Human CD3 Epsilon

Binding signals of the mentioned cross-species specific anti-CD3 IgG1 antibody to peptides derived from human CD3 epsilon (see FIG. 24(B)) were found on spots 28 and 33, which correspond to the amino acid residues 47-59 and 57-69 of human CD3 epsilon (see FIG. 17), respectively. The two stained spots comprise the minimal amino acid motif 57-59 (FSE).

The human-like cross-species specific anti-CD3 antibody recognizes the same discontinuous epitopes on human and cynomolgus CD3 epsilon as antibody I and II described in Examples 1 and 17. Binding signals of said human-like antibody on the peptide membrane reveal the peptide-intersections corresponding to the amino acid sequence "FSEME" (amino acid residues 57-61) of cynomolgus CD3 epsilon and those corresponding to amino acid sequence "FSELE" (amino acid residues 57-61) of human CD3 epsilon as core region. This is in line with the epitope determined for the cross-species specific anti-CD3 antibodies I and II on both cynomolgus and human CD3 epsilon (see Example 17).

Example 19: Verification of the Identified Epitope on Human CD3 Epsilon for the Human-Like Cross-Species Specific Anti-CD3 Antibody To verify the epitope of the human-like cross-species specific anti-CD3 antibody fragment described in Example 16 on human CD3 epsilon, the identified binding region as determined in Experiment 18 was further analyzed by a dot-blotting assay using a 13mer peptide covering the defined binding area of amino acid residues "FSELE" on human CD3 epsilon. This peptide comprises the amino acid sequence "EFSELEQSGYYVC" (SEQ ID NO. 195) of human CD3 epsilon. The peptide exists in two forms and is either biotinylated N- or C-terminally. In case of the N-terminal labelling, a short linker connects the peptide with the biotin. As described in Example 18, the antibody fragment was converted to a murine IgG format with a murine gamma1 heavy chain comprising the VH region as shown in SEQ ID NO. 110 and a kappa light chain comprising the VL region as shown in SEQ ID NO. 168. The dot blotting was performed as follows. The Minifold I Spot Blot System from Schleicher & Schuell was used for immobilizing the peptides on a nitrocellulose membrane (Protran BA 85, 0.45 µm). 75 µg of each peptide in 100 µl TBS were filtered through the membrane using vacuum. After the filtration step the membrane was blocked with 1×TBS/1% (w/v) blocking reagent (BM Chemiluminescence Blotting Substrate (POD) of Roche Diagnostics GmbH) for 2 h. All incubation and washing steps were performed on an orbital shaker at room temperature, except for the overnight incubation of the primary antibody. Directly after discarding the blocking solution, the membrane was incubated overnight with 3 µg/ml of the above-mentioned anti-CD3 antibody in 1×TBS/0.5% (w/v) blocking reagent at 4° C. on an orbital shaker. As a control, the anti-CD3 murine IgG1 antibody UCHT1 (BD Biosciences) binding to human CD3 epsilon was applied to a second membrane blotted with the same amounts of the two peptides. After washing three times with 1×TBS/0.05% Tween for 10 min, detection of bound anti-CD3 antibody was accomplished by incubation for 2 h with a commercially available alkaline phosphatase-conjugated anti-IgG antibody (diluted according to the manufacturer's recommendation in 1×TBS/0.5% blocking reagent). Subsequently, the membranes were washed three times with 1×TBS/0.05% Tween for 10 min. Alkaline phosphatase was visualized using 5-bromo-4-chloro-indolyl phosphate/nitro blue tetrazolium liquid substrate system (Sigma).

The mentioned CD3 specific antibody comprising the VH region shown in SEQ ID NO. 110 and the VL region shown in SEQ ID NO. 168 bound to both forms of the peptide "EFSELEQSGYYVC" (SEQ ID NO. 195) blotted to the membrane (see FIGS. 25(A)(1) and (2)), whereas no binding could be obtained for the anti-CD3 murine IgG antibody UCHT1 (see FIGS. 25(B)(1) and (2)). The epitope recognized by anti-CD3 antibody UCHT1 is described e.g. in Kjer-Nielsen et al., loc.cit; Arnett et al., PNAS (2204), p. 16268-73.

These results support the identification of the newly defined epitope of the herein-described anti-CD3 antibody (with the VH region shown in SEQ ID NO. 110 and the VL region shown in SEQ ID NO. 168). Said epitope corresponds to the amino acid residues "EFSELEQSGYYVC" (SEQ ID NO. 195) on the human CD3 epsilon chain and comprises the amino acid stretch "FSELE".

Example 20: Generation of CHO Cells Transfected with Cynomolgus EGFR

A shock frozen piece of EGFR positive cynomolgus colon was used to obtain the total RNA that was isolated according to the instructions of the kit manual (Qiagen, RNeasy Mini Kit). The obtained RNA was used for cDNA synthesis by random-primed reverse transcription. For cloning of the full length sequence of the EGFR antigen the following oligonucleotides were used:

```
5' EGFR AG XbaI
                              (SEQ ID NO. 197)
5'-GGTCTAGAGCATGCGACCCTCCGGGACGGCCGGG-3'

3' EGFR AG SalI
                              (SEQ ID NO. 198)
5'-TTTTAAGTCGACTCATGCTCCAATAAATTCACTGCT-3'.
```

A PCR (denaturation at 93° C. for 5 min, annealing at 58° C. for 1 min, elongation at 72° C. for 2 min for the first cycle; denaturation at 93° C. for 1 min, annealing at 58° C. for 1 min, elongation at 72° C. for 2 min for 30 cycles; terminal extension at 72° C. for 5 min) was used to amplify the coding sequence. The PCR product was subsequently digested with XbaI and SalI, ligated into the appropriately digested expression vector pEF-DHFR, and transformed into E. coli. The afore-mentioned procedures were carried out according to standard protocols (Sambrook, Molecular Cloning; A Laboratory Manual, 3rd edition, Cold Spring Harbour Laboratory Press, Cold Spring Harbour, New York (2001)). A clone with sequence-verified nucleotide sequence was transfected into DHFR deficient CHO cells for eukaryotic expression of the construct. Eukaryotic protein expression in DHFR deficient CHO cells was performed as described in Kaufmann R. J. (1990) Methods Enzymol. 185, 537-566. Gene amplification of the construct was induced by increasing concentrations of MTX to a final concentration of up to 20 nM MTX.

Example 21: Generation of EGFR and CD3 Cross-Species Specific Bispecific Single Chain Antibodies Generally, bispecific single chain antibody molecules, each comprising a domain with a binding specificity for the human and the cynomolgus CD3 antigen as well as a domain with a binding specificity for the human and the cynomolgus EGFR antigen, were designed as set out in the following Table 1:

TABLE 1

Formats of anti-CD3 and anti-EGFR cross-species specific bispecific single chain antibody molecules

| SEQ ID (nucl/prot) | Formats of protein constructs (N → C) |
|---|---|
| 171/172 | EGFR HL x SEQ ID NO. 170 |
| 173/174 | EGFR LH x SEQ ID NO. 170 |
| 175/176 | EGFR HL x SEQ ID NO. 194 |
| 177/178 | EGFR LH x SEQ ID NO. 194 |
| 179/180 | SEQ ID NO. 170 x EGFR HL |
| 181/182 | SEQ ID NO. 194 x EGFR HL |
| 183/184 | SEQ ID NO. 170 x EGFR LH |
| 185/186 | SEQ ID NO. 194 x EGFR LH |

The afore-mentioned constructs containing the variable light-chain (L) and variable heavy-chain (H) domains reactive with the human and cynomolgus EGFR derived from murine hybridomas were obtained by gene synthesis and subsequent cloning into an expression vector comprising the CD3 specific VH and VL combinations reactive with the human and cynomolgus CD3. Herein, SEQ ID NO. 170 corresponds to amino acid sequence of the anti-CD3 VH-VL scFv comprising the human-like VH (SEQ ID NO. 110) and the human-like VL (SEQ ID NO. 168). SEQ ID NO. 194 corresponds to the amino acid sequence of the anti-CD3 VL-VH scFv comprising the human-like VL (SEQ ID NO. 168) and the human-like VH (SEQ ID NO. 110). The constructs were then transfected into DHFR-deficient CHO-cells by electroporation.

Example 22: Expression and Purification of the EGFR and CD3 Cross-Species Specific Bispecific Single Chain Antibodies The bispecific single chain antibodies were expressed in chinese hamster ovary cells (CHO). Eukaryotic protein expression in DHFR deficient CHO cells was performed as described in Kaufmann R. J. (1990) Methods Enzymol. 185, 537-566. Gene amplification of the constructs were induced by increasing concentrations of MTX to a final concentration of up to 20 nM MTX. After two passages of stationary culture the cells were grown in roller bottles with CHO modified MEM medium for 7 days before harvest. The cells were removed by centrifugation and the supernatant containing the expressed protein was stored at −20° C.

Akta® FPLC System (Pharmacia) and Unicorn® Software were used for chromatography. All chemicals were of research grade and purchased from Sigma (Deisenhofen) or Merck (Darmstadt) Immobilized metal affinity chromatography ("IMAC") was performed using a Fractogel® column (Merck) which was loaded with $ZnCl_2$ according to the protocol provided by the manufacturer. The column was equilibrated with buffer A2 (20 mM sodium phosphate buffer pH 7.5, 0.4 M NaCl) and the cell culture supernatant (500 ml) was applied to the column (10 ml) at a flow rate of 3 ml/min. The column was washed with buffer A2 to remove unbound sample. Bound protein was eluted using a two step gradient of buffer B2 (20 mM sodium phosphate buffer pH 7.5, 0.4 M NaCl, 0.5 M Imidazol) according to the following:

Step 1: 20% buffer B2 in 6 column volumes;
Step 2: 100% buffer B2 in 6 column volumes.

Eluted protein fractions from step 2 were pooled for further purification.

Gel filtration chromatography was performed on a Sephadex S200 HiPrep column (Pharmacia) equilibrated with PBS (Gibco). Eluted protein samples (flow rate 1 ml/min) were subjected to standard SDS-PAGE and Western Blot for detection. Prior to purification, the column was calibrated for molecular weight determination (molecular weight marker kit, Sigma MW GF-200). Protein concentrations were determined using protein assay dye (MicroBCA, Pierce) and IgG (Biorad) as standard protein.

The bispecific single chain antibodies were isolated in a two step purification process of IMAC and gel filtration. The main product had a molecular weight of about 52 kDa under native conditions as determined by gel filtration in PBS. This molecular weight corresponds to the bispecific single chain antibody. All constructs were purified according to this method.

Purified bispecific single chain antibody protein was analyzed in SDS PAGE under reducing conditions performed with pre-cast 4-12% Bis Tris gels (Invitrogen). Sample preparation and application were performed according to the protocol provided by the manufacturer. The molecular weight was determined with MultiMark protein standard (Invitrogen). The gel was stained with colloidal Coomassie (Invitrogen protocol). The purity of the isolated protein was >95% as determined by SDS-PAGE.

Western Blot was performed using an Optitran® BA-S83 membrane and the Invitrogen Blot Module according to the protocol provided by the manufacturer. The antibodies used were directed against the His Tag (Penta His, Qiagen) and Goat-anti-mouse Ig labeled with alkaline phosphatase (AP) (Sigma), and BCIP/NBT (Sigma) as substrate. The bispecific single chain antibody could be specifically detected by Western Blot. A single band was detected at 52 kD corresponding to the purified bispecific molecule.

Example 23: Flow Cytometric Binding Analysis of the EGFR and CD3 Cross-Species Specific Bispecific Antibodies In order to test the functionality of the cross-species specific bispecific antibody constructs with regard to binding capability to human and cynomolgus EGFR and CD3, respectively, a FACS analysis was performed. For this purpose the EGFR positive epidermoid carcinoma A431 cells (ATCC, CRL-1555) and CD3 positive human T cell leukemia cell line HPB-ALL (DSMZ, Braunschweig, ACC483) were used to check the binding to human antigens. The binding reactivity to cynomolgus antigens was tested by using the generated cynomolgus EGFR transfectants described in Example 20 and cynomolgus PBMCs which were obtained by Ficoll density gradient centrifugation. 200,000 cells of the respective cell population were incubated for 30 min on ice with 50 µl of the purified protein of the cross-species specific bispecific antibody constructs (1 µg/ml). The cells were washed twice in PBS and binding of the construct was detected with an unlabeled murine Penta His antibody (diluted 1:20 in 50 µl PBS with 2% FCS; Qiagen; Order No. 34660). After washing, bound anti His antibodies were detected with an Fc gamma-specific antibody (Dianova) conjugated to phycoerythrin, diluted 1:100 in 50 µl PBS with 2% FCS. Fresh culture medium was used as a negative control.

Cells were analyzed by flow cytometry on a FACS-Calibur apparatus (Becton Dickinson, Heidelberg). FACS staining and measuring of the fluorescence intensity were performed as described in Current Protocols in Immunology (Coligan, Kruisbeek, Margulies, Shevach and Strober, Wiley-Interscience, 2002).

The binding ability of several domain arrangements were clearly detectable as shown in FIGS. 29 to 36. In FACS analysis, all constructs with different arrangement of VH and VL domains specific for EGFR and CD3 showed binding to CD3 and EGFR compared to the negative control using culture medium and 1. and 2. detection antibody. In summary, the cross-species specificity of the bispecific antibody to human and cynomolgus CD3 and EGFR antigens could clearly be demonstrated.

Example 24: Bioactivity of EGFR and CD3 Cross-Species Specific Bispecific Single Chain Antibodies Bioactivity of the generated bispecific single chain antibodies was analyzed by chromium 51 release in vitro cytotoxicity assays using the EGFR positive cell lines described in Example 23; see also FIGS. 39 and 40. As effector cells stimulated human CD8 positive T cells or stimulated cynomolgus PBMCs were used, respectively.

The generation of the stimulated CD8+ T cells was performed as follows:

A Petri dish (85 mm diameter, Nunc) was pre-coated with a commercially available anti-CD3 specific antibody in a final concentration of 1 µg/ml for 1 hour at 37° C. Unbound protein was removed by one washing step with PBS. The fresh PBMC's were isolated from peripheral blood (30-50 ml human blood or 10 ml cynomolgus blood) by Ficoll gradient centrifugation according to standard protocols. 3-5×10$^7$ PBMCs were added to the precoated petri dish in 50 ml of RPMI 1640/10% FCS/IL-2 20 U/ml (Proleukin, Chiron) and stimulated for 2 days. At the third day the cells were collected, washed once with RPMI 1640. IL-2 was added to a final concentration of 20 U/ml and cultivated again for one day. The CD8+ CTLs were isolated by depleting CD4+ T cells an CD56+ NK cells.

Target cells were washed twice with PBS and labeled with 11.1 MBq $^{51}$Cr in a final volume of 100 µl RPMI with 50% FCS for 45 minutes at 37° C. Subsequently the labeled target cells were washed 3 times with 5 ml RPMI and then used in the cytotoxicity assay. The assay was performed in a 96 well plate in a total volume of 250 µl supplemented RPMI (as above) with an E:T ratio of 10:1 corresponding to 1000 target cells and 10000 effector cells per well. 1 µg/ml of the cross-species specific bispecific single chain antibody molecules and 20 threefold dilutions thereof were applied. The assay time was 18 hours and cytotoxicity was measured as relative values of released chromium in the supernatant related to the difference of maximum lysis (addition of Triton-X) and spontaneous lysis (without effector cells). All measurements were done in quadruplicates. Measurement of chromium activity in the supernatants was performed with a Wizard 3 gammacounter (Perkin Elmer Life Sciences GmbH, Köln, Germany). Analysis of the experimental data was performed with Prism 4 for Windows (version 4.02, GraphPad Software Inc., San Diego, California, USA). Sigmoidal dose response curves typically had $R^2$ values >0.90 as determined by the software. $EC_{50}$ values calculated by the analysis program were used for comparison of bioactivity.

As shown in FIGS. 39 and 40, all of the generated cross-species specific bispecific single chain antibody constructs revealed cytotoxic activity against human EGFR positive target cells elicited by human CD8+ cells and cynomolgus EGFR positive target cells elicited by cynomolgus CD8+ cells. In FIG. 39, a bispecific single chain antibody with a variable domain reactive with EGFR and a de-immunized human CD3-specific variable domain (EGFR LHxdi-anti CD3) has been used as a negative control. In FIG. 40, the same construct (EGFR LHxdi-anti CD3) has been used as a positive control. As a negative control, an irrelevant bispecific single chain antibody has been used.

Example 25: Generation and Characterization of Carboanhydrase IX (CAIX) and CD3 Cross-Species Specific Bispecific Single Chain Antibodies

TABLE 2

Formats of CAIX and CD3 cross-species specific bispecific single chain antibodies

| SEQ ID (nucl/prot) | Formats of protein constructs (N → C) |
|---|---|
| 189/190 | CAIX HL x SEQ ID NO. 170 |
| 191/192 | CAIX LH x SEQ ID NO. 170 |
| 187/188 | CAIX HL x SEQ ID NO. 194 |

In analogy to the afore-mentioned Examples, Carboanhydrase IX (CAIX/MN) and CD3 cross-species specific bispecific single chain antibodies containing the variable light-chain (L) and variable heavy-chain (H) domains reactive with the human and cynomolgus CAIX antigen were created and subsequently cloned into an expression vector comprising the CD3 specific VH and VL combinations reactive with the human and cynomolgus CD3. The experiments were carried out in essence as described in Examples 20 to 24, with the following exceptions:

The FACS binding experiments were performed with the CAIX positive human lung carcinoma cell line A549 (ATCC, CCL-185) to assess the binding capability to the human CAIX antigen. The cross-species specificity to cynomolgus tissue was tested by deploying the cynomolgus skin cell line CYNOM-K1 (National Institute for Cancer Research (IST) of Genova, Italy, ECACC 90071809) or the rhesus monkey epithelial cell line 4MBr-5 (ATCC, CCL-208). The same changes in cell lines apply to the cytotoxicity assays performed with the CAIX and CD3 cross-species specific bispecific single chain antibodies.

As depicted in FIGS. 26 to 28, the generated CAIX and CD3 cross-species specific bispecific single chain antibodies demonstrated binding to both the human and cynomolgus antigens and proved to be fully cross-species specific. The cytolytic bioactivity of the analysed constructs is shown in FIGS. 37 and 38. In the left panel of FIG. 37, a bispecific single chain antibody with a variable domain reactive with CAIX and a de-immunized human CD3-specific variable domain has been used as a positive control. In the right panel, the same construct has been used as a negative control.

APPENDIX

| SEQ ID NO. | DESIGNATION | SOURCE | TYPE | SEQUENCE |
|---|---|---|---|---|
| 1 | VH | Murine | NA | gaggtgaagcttctcgagtctg gaggaggattggtgcagcctaa agggtcattgaaactctcatgt gcagcctctggattccacttca atacctacgccatgaactgggt ccgccaggctccaggaaaggt ttggaatgggttgctcgcataa gaagtaaatataataattatgc aacatattatgccgattcagtg aaagacaggttcaccatctcca gagatgattcacaaagcattct ctatctacaaatgaacaacttg aaaactgaggacacagccatgt actactgtgtgagacatgggaa cttcggtaatagctacgtttcc tggtttgcttactggggccaag ggactctggtcactgtctctgc a |
| 2 | VH | Murine | AA | EVKLLESGGGLVQPKGSLKLSC AASGFTFNTYAMNWVRQAPGKG LEWVARIRSKYNNYATYYADSV KDRFTISRDDSQSILYLQMNNL KTEDTAMYYCVRHGNFGNSYVS WFAYWGQGTLVTVSA |
| 3 | VL | Murine | NA | caggctgttgtgactcaggaat ctgcactcaccacatcacctgg tgaaacagtcacactcacttgt cgctcaagtactggggctgtta caactagtaactatgccaactg ggtccaagaaaaaccagatcat ttattcactggtctaataggtg gtaccaacaagcgagctccagg tgtgcctgccagattctcaggc tccctgattggagacaaggctg ccctcaccatcacaggggcaca gactgaggatgaggcaatatat ttctgtgctctatggtacagca acctctgggtgttcggtggagg aaccaaactgactgtccta |
| 4 | VL | Murine | AA | QAVVTQESALTTSPGETVTLTC RSSTGAVTTSNYANWVQEKPDH LFTGLIGGTNKRAPGVPARFSG SLIGDKAALTITGAQTEDEAIY FCALWYSNLWVFGGGTKLTVL |
| 5 | VH | Murine | NA | caggtccagctgcagcagtctg gggctgaactggcaagacctgg ggcctcagtgaagatgtcctgc aaggcttctggctacacccttta ctagatctacgatgcactgggt aaaacagaggcctggacagggt ctggaatggattggatacatta atcctagcagtgcttatactaa ttacaatcagaaattcaaggac aaggccacattgactgcagaca aatcctccagtacagcctacat gcaactgagtagcctgacatct gaggactctgcagtctattact gtgcaagtccgcaagtccacta tgattacaacgggtttccttac tggggccaagggactctggtca ctgtctctgca |
| 6 | VH | Murine | AA | QVQLQQSGAELARPGASVKMSC KASGYTFTRSTMHWVKQRPGQG LEWIGYINPSSAYTNYNQKFKD KATLTADKSSTAYMQLSSLTS EDSAVYYCASPQVHYDYNGFPY WGQGTLVTVSA |
| 7 | VL | Murine | NA | caagttgttctcacccagtctc cagcaatcatgtctgcatttcc aggggagaaggtcaccatgacc tgcagtgccagctcaagtgtaa gttacatgaactggtaccagca gaagtcaggcacctcccccaaa agatggatttatgactcatcca aactggcttctggagtccctgc tcgcttcagtggcagtgggtct gggacctcttattctctcacaa tcagcagcatggagactgaaga tgctgccacttattactgccag cagtggagtcgtaacccaccca cgttcggaggggggaccaagct acaaattaca |
| 8 | VL | Murine | AA | QVVLTQSPAIMSAFPGEKVTMT CSASSSVSYMNWYQQKSGTSPK RWIYDSSKLASGVPARFSGSGS GTSYSLTISSMETEDAATYYCQ QWSRNPPTFGGGTKLQIT |
| 9 | VH-VL scFv | artificial | NA | gaggtgaagcttctcgagtctg gaggaggattggtgcagcctaa agggtcattgaaactctcatgt gcagcctctggattccacttca atacctacgccatgaactgggt ccgccaggctccaggaaaggt ttggaatgggttgctcgcataa gaagtaaatataataattatgc aacatattatgccgattcagtg aaagacaggttcaccatctcca gagatgattcacaaagcattct ctatctacaaatgaacaacttg aaaactgaggacacagccatgt actactgtgtgagacatgggaa cttcggtaatagctacgtttcc tggtttgcttactggggccaag |

APPENDIX-continued

| SEQ ID NO. | DESIGNATION | SOURCE | TYPE | SEQUENCE |
|---|---|---|---|---|
| | | | | ggactctggtcactgtctctgc aggtggtggtggttctggcggc ggcggctccggtggtggtggtt ctcaggctgttgtgactcagga atctgcactcaccacatcacct ggtgaaacagtcacactcactt gtcgctcaagtactggggctgt tacaactagtaactatgccaac tgggtccaagaaaaaccagatc atttattcactggtctaataggt gtaccaacaagcgagctcca ggtgtgcctgccagattctcag gctccctgattggagacaaggc tgccctcaccatcacaggggca cagactgaggatgaggcaatat atttctgtgctctatggtacag caacctctgggtgttcggtgga ggaaccaaactgactgtccta |
| 10 | VH-VL scFv | artificial | AA | EVKLLESGGGLVQPKGSLKLSC RSKYNNYATYYADSVKDRFTIS RDDSQSILYLQMNNLKTEDTAM YYCVRHGNFGNSYVSWFAYWGQ GTLVTVSAGGGGSGGGGSGGGG SQAVVTQESALTTSPGETVTLT CRSSTGAVTTSNYANWVQEKPD HLFTGLIGGTNKRAPGVPARFS GSLIGDKAALTITGAQTEDEAI YFCALWYSNLWVFGGGTKLTVL |
| 11 | VL-VH scFv | artificial | NA | caggctgttgtgactcaggaat ctgcactcaccacatcacctgg tgaaacagtcacactcacttgt cgctcaagtactggggctgtta caactagtaactatgccaactg gtccaagaaaaaccagatcat ttattcactggtctaataggtg taccaacaagcgagctccagg tgtgcctgccagattctcaggc tccctgattggagacaaggctg ccctcaccatcacaggggcaca gactgaggatgaggcaatatat ttctgtgctctatggtacagca acctctgggtgttcggtggagg aaccaaactgactgtcctaggt ggtggtggttctggcggcggcg gctccggtggtggtggttctga ggtgaagcttctcgagtctgga ggaggattggtgcagcctaaag ggtcattgaaactctcatgtgc agcctctggattcaccttcaat acctacgccatgaactgggtcc gccaggctccaggaaagggttt ggaatgggttgctcgcataaga agtaaatataataattatgcaa catattatgccgattcagtgaa agacaggttcaccatctccaga gatgattcacaaagcattctct atctacaaatgaacaacttgaa aactgaggacacagccatgtac tactgtgtgagacatgggaact tcggtaatagctacgtttcctg gttttgcttactggggccaaggg actctggtcactgtctctgca |
| 12 | VL-VH scFv | artificial | AA | QAVVTQESALTTSPGETVTLTC RSSTGAVTTSNYANWVQEKPDH LFTGLIGGTNKRAPGVPARFSG SLIGDKAALTITGAQTEDEAIY FCALWYSNLWVFGGGTKLTVLG GGGSGGGGSGGGGSEVKLLESG GGLVQPKGSLKLSCAASGFTFN TYAMNWVRQAPGKGLEWVARIR SKYNNYATYYADSVKDRFTISR DDSQSILYLQMNNLKTEDTAMY YCVRHGNFGNSYVSWFAYWGQG TLVTVSA |
| 13 | VH-VL scFv | artificial | NA | caggtccagctgcagcagtctg gggctgaactggcaagacctgg ggcctcagtgaagatgtcctgc aaggcttctggctacacccttta ctagatctacgatgcactgggt aaaacagaggcctggacaggt ctggaatggattggatacatta atcctagcagtgcttatactaa ttacaatcagaaatttcaaggac aaggccacattgactgcagaca atcctccagtacagcctacat gcaactgagtagcctgacatct gaggactctgcagtctattact gtgcaagtccgcaagtccacta tgattacaacgggtttccttac tggggccaagggactctggtca ctgtctctgcaggtggtggtgg ttctggcggcggcggctccggt ggtggtggttctcaagttgttc tcacccagtctccagcaatcat gtctgcatttccaggggagaag gtcaccatgacctgcagtgcca gctcaagtgtaagttacatgaa ctggtaccagcagaagtcaggc acctcccccaaaagatggattt atgactcatccaaactggcttc tggagtccctgctcgcttcagt ggcagtgggtctgggacctctt attctctcacaatcagcagcat ggagactgaagatgctgccact tattactgccagcagtggagtc gtaacccaccacgttcggagg ggggaccaagctacaaattaca |
| 14 | VH-VL scFv | artificial | AA | QVQLQQSGAELARPGASVKMSC KASGYTFTRSTMHWVKQRPGQG LEWIGYINPSSAYTNYNQKFKD KATLTADKSSSTAYMQLSSLTS EDSAVYYCASPQVHYDYNGFPY WGQGTLVTVSAGGGGSGGGGSG GGGSQVVLTQSPAIMSAFPGEK VTMTCSASSSVSYMNWYQQKSG TSPKRWIYDSSKLASGVPARFS GSGSGTSYSLTISSMETEDAAT YYCQQWSRNPPTFGGGTKLQIT |
| 15 | VL-VH scFv | artificial | NA | caagttgttctcacccagtctc cagcaatcatgtctgcatttcc aggggagaaggtcaccatgacc tgcagtgccagctcaagtgtaa gttacatgaactggtaccagca gaagtcaggcacctcccccaaa agatggatttatgactcatcca aactggcttctggagtccctgc tcgcttcagtggcagtgggtct gggacctcttattctctcacaa tcagcagcatggagactgaaga tgctgccacttattactgccag cagtggagtcgtaacccaccca cgttcggagggggaccaagct acaaattacaggtggtggtggt tctggcggcggcggctccggtg gtggtggttctcaggtccagct gcagcagtctggggctgaactg gcaagacctggggcctcagtga agatgtcctgcaaggcttctgg ctacaccttactagatctacg atgcactgggtaaaacagaggc ctggacagggtctggaatggat tggatacattaatcctagcagt gcttatactaattacaatcaga aattcaaggacaaggccacatt |

APPENDIX-continued

| SEQ ID NO. | DESIGNATION | SOURCE | TYPE | SEQUENCE |
|---|---|---|---|---|
| | | | | gactgcagacaaatcctccagt acagcctacatgcaactgagta gcctgacatctgaggactctgc agtctattactgtgcaagtccg caagtccactatgattacaacg ggtttccttactggggccaagg gactctggtcactgtctctgca |
| 16 | VL-VH scFv | artificial | AA | QVVLTQSPAIMSAFPGEKVTMT CSASSSVSYMNWYQQKSGTSPK RWIYDSSKLASGVPARFSGSGS GTSYSLTISSMETEDAATYYCQ QWSRNPPTFGGGTKLQITGGGG SGGGGSGGGGSQVQLQQSGAEL ARPGASVKMSCKASGYTFTRST MHWVKQRPGQGLEWIGYINPSS AYTNYNQKFKDKATLTADKSSS TAYMQLSSLTSEDSAVYYCASP QVHYDYNGFPYWGQGTLVTVSA |
| 17 | 5' LH | artificial | NA | acatccggaggtggtggatccc aggctgttgtgactcaggaatc tgc |
| 18 | 3' VL Linker | artificial | NA | ggagccgccgccgccagaacca ccaccacctaggacagtcagtt tggttcc |
| 19 | 5' VH Linker | artificial | NA | tctggcggcggcggctccggtg gtggtggttctgaggtgaagct tctcgagtctggaggaggattg gtgc |
| 20 | 3' LH | artificial | NA | agtgggtcgacctaatgatgat ggtgatgatgtgcagagacagt gaccagagtccc |
| 21 | 5' HL | artificial | NA | acatccggaggtggtggatccg aggtgaagcttctcgagtctgg aggaggattggtgc |
| 22 | 3' VH Linker | artificial | NA | ggagccgccgccgccagaacca ccaccacctgcagagacagtga ccagagtccc |
| 23 | 5' VL Linker | artificial | NA | tctggcggcggcggctccggtg gtggtggttctcaggctgttgt gactcaggaatctgc |
| 24 | 3' HL | artificial | NA | agtgggtcgacctaatgatgat ggtgatgatgtaggacagtcag tttggttcctcc |
| 25 | 5' LH | artificial | NA | acatccggaggtggtggatccc aagttgttctcacccagtctcc |
| 26 | 3' VL Linker | artificial | NA | ggagccgccgccgccagaacca ccaccacctgtaatttgtagct ggtccccc |
| 27 | 5' VH Linker | artificial | NA | tctggcggcggcggctccggtg gtggtggttctcaggtccagct gcagcagtctgg |
| 28 | 3' LH | artificial | NA | agtgggtcgacctaatgatgat ggtgatgatgtgcagagacagt gaccagagtccc |
| 29 | 5' HL | artificial | NA | acatccggaggtggtggatccc aggtccagctgcagcagtctgg |
| 30 | 3' VH Linker | artificial | NA | ggagccgccgccgccagaacca ccaccacctgcagagacagtga ccagagtccc |
| 31 | 5' VL Linker | artificial | NA | tctggcggcggcggctccggtg gtggtggttctcaagttgttct cacccagtctcc |
| 32 | 3' HL | artificial | NA | agtgggtcgacctaatgatgat ggtgatgatgtgtaatttgtag cttggtccccc |
| 33 | 5-10 LH scFv | artificial | NA | gagctcgtgatgacacagtctc catcctccctgactgtgacagc aggagagaaggtcactatgagc tgcaagtccagtcagagtctgt taaacagtggaaatcaaaagaa ctacttgacctggtaccagcag aaaccagggcagcctcctaaac tgtttgatctactgggcatcca tagggaatctggggtccctgat cgcttcacaggcagtggatctg gaacagatttcactctcaccat cagcagtgtgcaggctgaagac ctggcagtttattactgtcaga atgattatagttatccgctcac gttcggtgctgggaccaagctt gagatcaaaggtggtggtggtt ctggcggcggcggctccggtgg tggttctgaggtgcagctgctc gagcagtctggagctgagctgg taaggcctgggacttcagtgaa gatatcctgcaaggcttctgga tacgccttcactaactactggc taggttgggtaaagcagaggcc tggacatggacttgagtggatt ggagatatttccctgaagtggt aatatccactacaatgagaagt tcaagggcaaagccacactgac tgcagacaaatcttcgagcaca gcctatatgcagctcagtagcc tgacatttgaggactctgctgt ctatttctgtgcaagactgagg aactgggacgagcctatggact actggggccaagggaccacggt caccgtctcctcc |
| 34 | 5-10 LH scFv | artificial | AA | ELVMTQSPSSLTVTAGEKVTMS CKSSQSLLNSGNQKNYLTWYQQ KPGQPPKLLIYWASTRESGVPD RFTGSGSGTDFTLTISSVQAED LAVYYCQNDYSYPLTFGAGTKL EIKGGGGSGGGGSGGGGSEVQL LEQSGAELVRPGTSVKISCKAS GYAFTNYWLGWVKQRPGHGLEW IGDIFPGSGNIHYNEKFKGKAT LTADKSSSTAYMQLSSLTFEDS AVYFCARLRNWDEPMDYWGQGT TVTVSS |
| 35 | Leader peptide | mouse cDNA | NA | atgggatggagctgtatcatcc tcttcttggtagcaacagctac aggtgtacactcc |
| 36 | Leader peptide | mouse cDNA | AA | MGWSCIILFLVATATGVHS |
| 37 | 5-10 LHx SEQ ID NO.12 | artificial | NA | gagctcgtgatgacacagtctc catcctccctgactgtgacagc aggagagaaggtcactatgagc tgcaagtccagtcagagtctgt taaacagtggaaatcaaaagaa ctacttgacctggtaccagcag aaaccagggcagcctcctaaac tgtttgatctactgggcatcca tagggaatctggggtccctgat cgcttcacaggcagtggatctg gaacagatttcactctcaccat cagcagtgtgcaggctgaagac |

APPENDIX-continued

| SEQ ID NO. | DESIGNATION | SOURCE | TYPE | SEQUENCE |
|---|---|---|---|---|
| | | | | ctggcagtttattactgtcaga
atgattatagttatccgctcac
gttcggtgctgggaccaagctt
gagatcaaaggtggtggtggtt
ctggcggcggcggctccggtgg
tggtggttctgaggtgcagctg
ctcgagcagtctggagctgagc
tggtaaggcctgggacttcagt
gaagatatcctgcaaggcttct
ggatacgccttcactaactact
ggctaggttgggtaaagcagag
gcctggacatggacttgagtgg
attggagatattttccctggaa
gtggtaatatccactacaatga
gaagttcaagggcaaagccaca
ctgactgcagacaaatcttcga
gcacagcctatatgcagctcag
tagcctgacatttgaggactct
gctgtctatttctgtgcaagac
tgaggaactgggacgagcctat
ggactactggggccaagggacc
acggtcaccgtctcctccggag
gtggtggatcccaggctgttgt
gactcaggaatctgcactcacc
acatcacctggtgaaacagtca
cactcacttgtcgctcaagtac
tggggctgttacaactagtaac
tatgccaactgggtccaagaaa
aaccagatcatttattcactgg
tctaataggtggtaccaacaag
cgagctccaggtgtgcctgcca
gattctcaggctccctgattgg
agacaaggctgccctcaccatc
acaggggcacagactgaggatg
aggcaatatatttctgtgctct
atggtacagcaacctctgggtg
ttcggtggaggaaccaaactga
ctgtcctaggtggtggtggttc
tggcggcggcggctccggtggt
ggtggttctgaggtgaagcttc
tcgagtctggaggaggattggt
gcagcctaaagggtcattgaaa
ctctcatgtgcagcctctggat
tcaccttcaatacctacgccat
gaactgggtccgccaggctcca
ggaaagggttttggaatgggtt
ctcgcataagaagtaaatataa
taattatgcaacatattatgcc
gattcagtgaaagacaggttca
ccatctccagagatgattcaca
aagcattctctatctacaaatg
aacaacttgaaaactgaggaca
cagccatgtactactgtgtgag
acatgggaacttcggtaatagc
tacgttcctggttttgcttact
ggggccaagggactctggtcac
tgtctctgca |
| 38 SEQ ID NO. 12 | 5-10 LHx | arti-ficial | AA | ELVMTQSPSSLTVTAGEKVTMS
CKSSQSLLNSGNQKNYLTWYQQ
KPGQPPKLLIYWASTRESGVPD
RFTGSGSGTDFTLTISSVQAED
LAVYYCQNDYSYPLTFGAGTKL
EIKGGGGSGGGGSGGGGSEVQL
LEQSGAELVRPGTSVKISCKAS
GYAFTNYWLGWVKQRPGHGLEW
IGDIFPGSGNIHYNEKFKGKAT
LTADKSSSTAYMQLSSLTFEDS
AVYFCARLRNWDEPMDYWGQGT
TVTVSSGGGGSQAVVTQESALT
TSPGETVTLTCRSSTGAVTTSN
YANWVQEKPDHLFTGLIGGTNK
RAPGVPARFSGSLIGDKAALTI
TGAQTEDEAIYFCALWYSNLWV
FGGGTKLTVLGGGGSGGGGSGG
GGSEVKLLESGGGLVQPKGSLK |
| | | | | LSCAASGFTFNTYAMNWVRQAP
GKGLEWVARIRSKYNNYATYYA
DSVKDRFTISRDDSQSILYLQM
NNLKTEDTAMYYCVRHGNFGNS
YVSWFAYWGQGTLVTVSA |
| 39 SEQ ID NO. 10 | 5-10 LHx | arti-ficial | NA | gagctcgtgatgacacagtctc
catcctccctgactgtgacagc
aggagagaaggtcactatgagc
tgcaagtccagtcagagtctgt
taaacagtggaaatcaaaagaa
ctacttgacctggtaccagcag
aaaccagggcagcctcctaaac
tgttgatctactgggcatccac
tagggaatctggggtccctgat
cgcttcacaggcagtggatctg
gaacagatttcactctccaccat
cagcagtgtgcaggctgaagac
ctggcagtttattactgtcaga
atgattatagttatccgctcac
gttcggtgctgggaccaagctt
gagatcaaaggtggtggtggtt
ctggcggcggcggctccggtgg
tggtggttctgaggtgcagctg
ctcgagcagtctggagctgagc
tggtaaggcctgggacttcagt
gaagatatcctgcaaggcttct
ggatacgccttcactaactact
ggctaggttgggtaaagcagag
gcctggacatggacttgagtgg
attggagatattttccctggaa
gtggtaatatccactacaatga
gaagttcaagggcaaagccaca
ctgactgcagacaaatcttcga
gcacagcctatatgcagctcag
tagcctgacatttgaggactct
gctgtctatttctgtgcaagac
tgaggaactgggacgagcctat
ggactactggggccaagggacc
acggtcaccgtctcctccggag
gtggtggatccgaggtgaagct
tctcgagtctggaggaggattg
gtgcagcctaaagggtcattga
aactctcatgtgcagcctctgg
attcaccttcaatacctacgcc
atgaactgggtccgccaggctc
caggaaagggtttggaatgggt
tgctcgcataagaagtaaatat
aataattatgcaacatattatg
ccgattcagtgaaagacaggtt
caccatctccagagatgattca
caaagcattctctatctacaaa
tgaacaacttgaaaactgagga
cacagccatgtactactgtgtg
agacatgggaacttcggtaata
gctacgttcctggttttgcttac
tggggccaagggactctggtc
actgtctctgcaggtggtggtg
gttctggcggcggcggctccgg
tggtggtggttctcaggctgtt
gtgactcaggaatctgcactca
ccacatcacctggtgaaacagt
cactcacttgtcgctcaagt
actggggctgttacaactagta
actatgccaactgggtccaaga
aaaaccagatcatttattcact
ggtctaataggtggtaccaaca
agcgagctccaggtgtgcctgc
cagattctcaggctccctgatt
ggagacaaggctgccctcacca
tcacaggggcacagactgagga
tgaggcaatatatttctgtgct
ctatggtacagcaacctctggg
tgttcggtggaggaaccaaact
gactgtccta |

APPENDIX-continued

| SEQ ID NO. | DESIGNATION | SOURCE | TYPE | SEQUENCE |
|---|---|---|---|---|
| 40 | 5-10 LHx SEQ ID NO. 10 | artificial | AA | ELVMTQSPSSLTVTAGEKVTMS CKSSQSLLNSGNQKNYLTWYQQ KPGQPPKLLIYWASTRESGVPD RFTGSGSGTDFTLTISSVQAED LAVYYCQNDYSYPLTFGAGTKL EIKGGGGSGGGGSGGGGSEVQL LEQSGAELVRPGTSVKISCKAS GYAFTNYWLGWVKQRPGHGLEW IGDIFPGSGNIHYNEKFKGKAT LTADKSSSTAYMQLSSLTFEDS AVYFCARLRNWDEPMDYWGQGT TVTVSSGGGGSEVKLLESGGGL VQPKGSLKLSCAASGFTFNTYA MNWVRQAPGKGLEWVARIRSKY NNYATYYADSVKDRFTISRDDS QSILYLQMNNLKTEDTAMYYCV RHGNFGNSYVSWFAYWGQGTLV TVSAGGGGSGGGGSGGGGSQAV VTQESALTTSPGETVTLTCRSS TGAVTTSNYANWVQEKPDHLFT GLIGGTNKRAPGVPARFSGSLI GDKAALTITGAQTEDEAIYFCA LWYSNLWVFGGGTKLTVL |
| 41 | 5-10 LHx SEQ ID NO. 16 | artificial | NA | gagctcgtgatgacacagtctc catcctccctgactgtgacagc aggagagaaggtcactatgagc tgcaagtccagtcagagtctgt taaacagtggaaatcaaaagaa ctacttgacctggtaccagcag aaaccagggcagcctcctaaac tgttgatctactgggcatccac tagggaatctgggtccctgat cgcttcacaggcagtggatctg gaacagatttcactctcaccat cagcagtgtgcaggctgaagac ctggcagtttattactgtcaga atgattatagttatccgctcac gttcggtgctgggaccaagctt gagatcaaaggtggtggtggtt ctggcggcggcggctccggtgg tggtggttctgaggtgcagctg ctcgagcagtctggagctgagc tggtaaggcctggggacttcagt gaagatatcctgcaaggcttct ggatacgccttcactaactact ggctaggttgggtaaagcagag gcctggacatggacttgagtgg attggagatattttccctggaa gtggtaatatccactacaatga gaagttcaagggcaaagccaca ctgactgcagacaaatcttcga gcacagcctatatgcagctcag tagcctgacatttgaggactct gctgtctatttctgtgcaagac tgaggaactgggacgagcctat ggactactggggccaagggacc acggtcaccgtctcctccggag gtggtggatcccaggtccagct gcagctcctgcagcaatcatg tctgcatttccaggggagaagg tcaccatgacctgcagtgccag ctcaagtgtaagttacatgaac tggtaccagcagaagtcaggca cctcccccaaaagatggattta tgactcatccaaactggcttct ggagtccctgctcgcttcagtg gcagtgggtctgggacctctta ttctctcacaatcagcagcatg gagactgaagatgctgccactt attactgccagcagtggagtcg taacccacccacgttcggaggg gggaccaagctacaaattacag gtggtggtggttctggcggcgg cggctccggtggtggtggttct caggtccagctgcagcagtctg |
| 42 | 5-10 LHx SEQ ID NO. 16 | artificial | AA | ELVMTQSPSSLTVTAGEKVTMS CKSSQSLLNSGNQKNYLTWYQQ KPGQPPKLLIYWASTRESGVPD RFTGSGSGTDFTLTISSVQAED LAVYYCQNDYSYPLTFGAGTKL EIKGGGGSGGGGSGGGGSEVQL LEQSGAELVRPGTSVKISCKAS GYAFTNYWLGWVKQRPGHGLEW IGDIFPGSGNIHYNEKFKGKAT LTADKSSSTAYMQLSSLTFEDS AVYFCARLRNWDEPMDYWGQGT TVTVSSGGGGSQVVLTQSPAIM SAFPGEKVTMTCSASSSVSYMN WYQQKSGTSPKRWIYDSSKLAS GVPARFSGSGSGTSYSLTISSM ETEDAATYYCQQWSRNPPTFGG GTKLQITGGGGSGGGGSGGGGS QVQLQQSGAELARPGASVKMSC KASGYTFTRSTMHWVKQRPGQG LEWIGYINPSSAYTNYNQKFKD KATLTADKSSSTAYMQLSSLTS EDSAVYYCASPQVHYDYNGFPY WGQGTLVTVSA |
| 43 | 5-10 LHx SEQ ID NO. 14 | artificial | NA | gagctcgtgatgacacagtctc catcctccctgactgtgacagc aggagagaaggtcactatgagc tgcaagtccagtcagagtctgt taaacagtggaaatcaaaagaa ctacttgacctggtaccagcag aaaccagggcagcctcctaaac tgttgatctactgggcatccac tagggaatctgggtccctgat cgcttcacaggcagtggatctg gaacagatttcactctcaccat cagcagtgtgcaggctgaagac ctggcagtttattactgtcaga atgattatagttatccgctcac gttcggtgctgggaccaagctt gagatcaaaggtggtggtggtt ctggcggcggcggctccggtgg tggtggttctgaggtgcagctg ctcgagcagtctggagctgagc tggtaaggcctggggacttcagt gaagatatcctgcaaggcttct ggatacgccttcactaactact ggctaggttgggtaaagcagag gcctggacatggacttgagtgg attggagatattttccctggaa gtggtaatatccactacaatga gaagttcaagggcaaagccaca ctgactgcagacaaatcttcga gcacagcctatatgcagctcag tagcctgacatttgaggactct gctgtctatttctgtgcaagac tgaggaactgggacgagcctat ggactactggggccaagggacc acggtcaccgtctcctccggag gtggtggatcccaggtccagct |

APPENDIX-continued

| SEQ ID NO. | DESIGNATION | SOURCE | TYPE | SEQUENCE |
|---|---|---|---|---|
| | | | | gcagcagtctgggctgaactg gcaagacctggggcctcagtga agatgtcctgcaaggcttctgg ctacacctttactagatctacg atgcactgggtaaaacagaggc ctggacagggtctggaatggat tggatacattaatcctagcagt gcttatactaattacaatcaga aattcaaggacaaggccacatt gactgcagacaaatcctccagt acagcctacatgcaactgagta gcctgacatctgaggactctgc agtctattactgtgcaagtccg caagtccactatgattacaacg ggtttccttactggggccaagg gactctggtcactgtctctgca ggtggtggttctggcggcgga gcggctccggtggtggtggttc tcaagttgttctcacccagtct ccagcaatcatgtctgcatttc caggggagaaggtcaccatgac ctgcagtgccagctcaagtgta agttacatgaactggtaccagc agaagtcaggcacctcccccaa aagatggatttatgactcatcc aaactgcttctggagtccctg ctcgcttcagtggcagtgggtc tgggacctcttattctctcaca atcagcagcatggagactgaag atgctgccacttattactgcca gcagtggagtcgtaacccaccc acgttcggaggggggaccaagc tacaaattaca |
| 44 | 5-10 LHx SEQ ID NO. 14 | artificial | AA | ELVMTQSPSSLTVTAGEKVTMS CKSSQSLLNSGNQKNYLTWYQQ KPGQPPKLLIYWASTRESGVPD RFTGSGSGTDFTLTISSVQAED LAVYYCQNDYSYPLTFGAGTKL EIKGGGSGGGGSGGGGSEVQL LEQSGAELVRPGTSVKISCKAS GYAFTNYWLGVVKQRPGHGLEW IGDIFPGSGNIHYNEKFKGKAT LTADKSSSTAYMQLSSLTFEDS AVYFCARLRNWDEPMDYWGQGT TVTVSSGGGGSQVQLQQSGAEL ARPGASVKMSCKASGYTFTRST MHWVKQRPGQGLEWIGYINPSS AYTNYNQKFKDKATLTADKSSS TAYMQLSSLTSEDSAVYYCASP QVHYDYNGFPYWGQGTLVTVSA GGGGSGGGGSGGGGSQVVLTQS PAIMSAFPGEKVTMTCSASSSV SYMNWYQQKSGTSPKRWIYDSS KLASGVPARFSGSGSGTSYSLT ISSMETEDAATYYCQQWSRNPP TFGGGTKLQIT |
| 45 | 5'EpCAM | artificial | NA | ggtctagaccaccatggcgcc ccgcaggtcctcgcgttcgg |
| 46 | 3'EpCAM | artificial | NA | agtgggtcgacttatgcattga gttccctatgcatctcaccc |
| 47 | cynomolgus EpCAM extracellular portion | Cynomolgus cDNA | NA | cagaaagaatgtgtctgtgaaa actacaagctggccgtaaactg cttttgaatgacaatggtcaa tgccagtgtacttcgattggtg cacaaaatactgtcctttgctc aaagctggctgccaaatgtttg gtgatgaaggcagaaatgaacg gctcaaaacttgggagaagagc gaaacctgaaggggctctccag aacaatgatggcctttacgatc ctgactgcgatgagagcgggct cttttaaggccaagcagtgcaac |
| | | | | ggcacctccacgtgctggtgtg tgaacactgctggggtcagaag aactgacaaggacactgaaata acctgctctgagcgagtgagaa cctactggatcatcattgaatt aaaacacaaagcaagagaaaaa ccttatgatgttcaaagtttgc ggactgcacttgaggaggcgat caaaacgcgttacaactggat ccaaaatttatcacaaatattt tgtatgaggataatgttatcac tattgatctggttcaaaattct tctcagaaaactcagaatgatg tggacatagctgatgtggctta ttattttgaaaaagatgttaaa ggtgaatccttgtttcattcta agaaaatggacctgagagtaaa tggggaacaactggatctggat cctggtcaaactttaatttatt atgtcgatgaaaaagcacctga attctcaatgcagggtctaaaa |
| 48 | cynomolgus EpCAM extracellular portion | Cynomolgus cDNA | AA | QKECVCENYKLAVNCFLNDNGQ CQCTSIGAQNTVLCSKLAAKCL VMKAEMNGSKLGRRAKPEGALQ NNDGLYDPDCDESGLFKAKQCN GTSTCWCVNTAGVRRTDKDTEI TCSERVRTYWIIIELKHKAREK PYDVQSLRTALEEAIKTRYQLD PKFITNILYEDNVITIDLVQNS SQKTQNDVDIADVAYYFEKDVK GESLFHSKKMDLRVNGEQLDLD PGQTLIYYVDEKAPEFSMQGLK |
| 49 | 2G8 VH | Hybridoma | NA | gaggttcagctgcagcagtctg gggcagagcttgtgaggtcagg ggcctcagtcaagttgtcctgc acagcttctggcttcaacatta aagactactatttgcactgggt gaagcagaggcctgaacagggc ctggagtggattgctggattg atcttgagaatggtgatattaa atatgccccgaagtttcaggc aaggccactataactgcagaca catcctccaacacagcctacct gcagctcagcagcctgacatct gaggacactgccgtctattact gtaatcccattactacggtag taactacgactatgctatggac tactggggtcaaggaacctcag tcaccgtctcctca |
| 50 | 2G8 VH | Hybridoma | AA | EVQLQQSGAELVRSGASVKLSC TASGFNIKDYYLHWVKQRPEQG LEWIAWIDLENGDIKYAPKFQG KATITADTSSNTAYLQLSSLTS EDTAVYYCNPYYYGSNYDYAMD YWGQGTSVTVSS |
| 51 | 2G8 VL | Hybridoma | NA | gatgttgtgatgacccagactc cactcactttgtcggttaccat tggacaaccagcctctatctct tgcaagtcaagtcagagcctct tatatagtaatggaaaaaccta tttgaactggatattacagagg ccaggccagtctccaaagcgcc taatctatctggtgtctaaact ggactctggagtccctgacagg ttcactggcagtggatcaggaa cagattttacgctgaaaatcag cagagtggaggctgaggatttg ggagtttattactgcgtgcaag gtacacatttcctctcacgtt cggtgctgggaccaagctggag ctgaaa |

APPENDIX-continued

| SEQ ID NO. | DESIGNATION | SOURCE | TYPE | SEQUENCE |
|---|---|---|---|---|
| 52 | 2G8 VL | Hybridoma | AA | DVVMTQTPLTLSVTIGQPASIS CKSSQSLLYSNGKTYLNWILQR PGQSPKRLIYLVSKLDSGVPDR FTGSGSGTDFTLKISRVEAEDL GVYYCVQGTHFPLTFGAGTKLE LK |
| 53 | 2G8VH-VL scFv | artificial | NA | gaggttcagctgcagcagtctg gggcagagcttgtgaggtcagg ggcctcagtcaagttgtcctgc acagcttctggcttcaacatta aagactactatttgcactgggt gaagcagaggcctgaacaggc ctgagtggattgcctggattg atcttgagaatggtgatatta atatgccccgaagtttcaggc aaggccactataactgcagaca catcctccaacacagcctacct gcagctcagcagcctgacatct gaggacactgccgtctattact gtaatccctattactacggtag taactacgactatgctatggac tactggggtcaaggaacctcag tcaccgtcctcaggtggtgg tggttctggcggcggcggctcc ggtggtggtggttctgatgttg tgatgacccagactccactcac tttgtcggttaccattggacaa ccagcctctatctcttgcaagt caagtcagagcctcttatatag taatggaaaaacctatttgaac tggatattacagaggccaggcc agtctccaaagcgcctaatcta tctggtgtctaaactggactct ggagtccctgacaggttcactg gcagtggatcaggaacagattt tacgctgaaaatcagcagagtg gaggctgaggatttgggagttt attactgcgtgcaaggtacaca ttttcctctcacgttcggtgct gggaccaagctggagctgaaa |
| 54 | 2G8VH-VL scFv | artificial | AA | EVQLQQSGAELVRSGASVKLSC TASGFNIKDYYLHWVKQRPEQG LEWIAWIDLENGDIKYAPKFQG KATITADTSSNTAYLQLSSLTS EDTAVYYCNPYYYGSNYDYAMD YWGQGTSVTVSSGGGGSGGGGS GGGGSDVVMTQTPLTLSVTIGQ PASISCKSSQSLLYSNGKTYLN WILQRPGQSPKRLIYLVSKLDS GVPDRFTGSGSGTDFTLKISRV EAEDLGVYYCVQGTHFPLTFGA GTKLELK |
| 55 | 2G8VL-VH scFv | artificial | NA | gatgttgtgatgacccagactc cactcactttgtcggttaccat ggacaaccagcctctatctct tgcaagtcaagtcagagcctct tatatagtaatggaaaaaccta tttgaactggatattacagagg ccaggccagtctccaaagcgcc taatctatctggtgtctaaact ggactctggagtccctgacagg ttcactggcagtggatcaggaa cagattttacgctgaaaatcag cagagtggaggctgaggatttg ggagtttattactgcgtgcaag gtacacattttcctctcacgtt cggtgctgggaccaagctggag ctgaaaggtggtggttctg gcggcggcggctccggtggtgg tggttctgaggttcagctgcag cagtctggggcagagcttgtga ggtcaggggcctcagtcaagtt gtcctgcacagcttctggcttc aacattaaagactactatttgc actgggtgaagcagaggcctga acaggcctgagtggattgcc tggattgatcttgagaatggtg atattaaatatgccccgaagtt tcagggcaaggccactataact gcagacacatcctccaacacag cctacctgcagctcagcagcct gacatctgaggacactgccgtc tattactgtaatccctattact acggtagtaactacgactatgc tatggactactggggtcaagga acctcagtcaccgtcctcc |
| 56 | 2G8VL-VH scFv | artificial | AA | DVVMTQTPLTLSVTIGQPASIS CKSSQSLLYSNGKTYLNWILQR PGQSPKRLIYLVSKLDSGVPDR FTGSGSGTDFTLKISRVEAEDL GVYYCVQGTHFPLTFGAGTKLE LKGGGGSGGGGSGGGGSEVQLQ QSGAELVRSGASVKLSCTASGF NIKDYYLHWVKQRPEQGLEWIA WIDLENGDIKYAPKFQGKATIT ADTSSNTAYLQLSSLTSEDTAV YYCNPYYYGSNYDYAMDYWGQG TSVTVSS |
| 57 | 5'2G8 LH | artificial | NA | aggtgtacactccgatgttgtg atgacccagactccactcactt tgtcg |
| 58 | 3'2G8 VL Linker | artificial | NA | ggagccgccgccgccagaacca ccaccactttcagctccagct tggtcccagc |
| 59 | 5'2G8 VH Linker | artificial | NA | tctggcggcggcggctccggtg gtggtggttctgaggttcagct gcagcagtctgg |
| 60 | 3'2G8 LH | artificial | NA | acatccggaggagacggtgact gaggttcc |
| 61 | 5'2G8 HL | artificial | NA | aggtgtacactccgaggttcag ctgcagcagtctggg |
| 62 | 3'2G8 VH Linker | artificial | NA | ggagccgccgccgccagaacca ccaccactgaggagacggtga ctgaggttcc |
| 63 | 5'2G8 VL Linker | artificial | NA | tctggcggcggcggctccggtg gtggtggttctgatgttgtgat gacccagactccactcactttg tcg |
| 64 | 3'2G8 HL | artificial | NA | acatccggatttcagctccagc ttggtcccagc |
| 65 | 2G8LHx SEQ ID NO. 12 | artificial | NA | gatgttgtgatgacccagactc cactcactttgtcggttaccat ggacaaccagcctctatctct tgcaagtcaagtcagagcctct tatatagtaatggaaaaaccta tttgaactggatattacagagg ccaggccagtctccaaagcgcc taatctatctggtgtctaaact ggactctggagtccctgacagg ttcactggcagtggatcaggaa cagattttacgctgaaaatcag cagagtggaggctgaggatttg ggagtttattactgcgtgcaag gtacacattttcctctcacgtt cggtgctgggaccaagctggag ctgaaaggtggtggttctg gcggcggcggctccggtggtgg tggttctgaggttcagctgcag cagtctggggcagagcttgtga |

APPENDIX-continued

| SEQ ID NO. | DESIG- NATION | SOURCE | TYPE | SEQUENCE |
|---|---|---|---|---|
| | | | | ggtcaggggcctcagtcaagtt gtcctgcacagcttctggcttc aacattaaagactactatttgc actgggtgaagcagaggccta acagggcctggagtggattgcc tggattgatcttgagaatggtg atattaaatatgccccgaagtt tcagggcaaggccactataact gcagacacatcctccaacacag cctacctgcagctcagcagcct gacatctgaggacactgccgtc tattactgtaatcccattact acggtagtaactacgactatgc tatggactactggggtcaagga acctcagtcaccgtctcctccg gaggtggtggatcccaggctgt tgtgactcaggaatctgcactc accacatcacctggtgaaacag tcacactcacttgtcgctcaag tactggggctgttacaactagt aactatgccaactgggtccaag aaaaaccagatcatttattcac tggtctaataggtggtaccaac aagcgagctccaggtgtgcctg ccagattctcaggctcccgat tggagacaaggctgccctcacc atcacaggggcacagactgagg atgaggcaatatatttctgtgc tctatggtacagcaacctctgg gtgttcggtggagaaccaaac tgactgtcctaggtggtggtgg ttctggcggcggcggctccggt ggtggtggttctgaggtgaagc ttctcgagtctggaggaggatt ggtgcagcctaaagggtcattg aaactctcatgtgcagcctctg gattcaccttcaatacctacgc catgaactgggtccgccaggct ccaggaaagggtttggaatggg ttgctcgcataagaagtaaata taataattatgcaacatattat gccgattcagtgaaagacaggt tcaccatctccagagatgattc acaaagcattctctatctacaa atgaacaacttgaaaactgagg acacagccatgtactactgtgt gagacatgggaacttcggtaat agctacgtttcctggttttgctt actggggccaaggggactctggt cactgtctctgca |
| 66 | 2G8LHx SEQ ID NO. 12 | arti- ficial | AA | DVVMTQTPLTLSVTIGQPASIS CKSSQSLLYSNGKTYLNWILQR PGQSPKRLIYLVSKLDSGVPDR FTGSGSGTDFTLKISRVEAEDL GVYYCVQGTHFPLTFGAGTKLE LKGGGGSGGGGSGGGGSEVQLQ QSGAELVRSGASVKLSCTASGF NIKDYYLHWVKQRPEQGLEWIA WIDLENGDIKYAPKFQGKATIT ADTSSNTAYLQLSSLTSEDTAV YYCNPYYYGSNYDYAMDYWGQG TSVTVSSGGGGSQAVVTQESAL TTSPGETVTLTCRSSTGAVTTS NYANWVQEKPDHLFTGLIGGTN KRAPGVPARFSGSLIGDKAALT ITGAQTEDEAIYFCALWYSNLW VFGGGTKLTVLGGGGSGGGGS GGGSEVKLLESGGGLVQPKGSL KLSCAASGFTFNTYAMNWVRQA PGKGLEWVARIRSKYNNYATYY ADSVKDRFTISRDDSQSILYLQ MNNLKTEDTAMYYCVRHGNFGN SYVSWFAYWGQGTLVTVSA |
| 67 | 2G8LHx SEQ ID NO. 10 | arti- ficial | NA | gatgttgtgatgacccagactc cactcactttgtcggttaccat tggacaaccagcctctatctct tgcaagtcaagtcagagcctct tatatagtaatggaaaaaccta tttgaactggatattacagagg ccaggccagtctccaaagcgcc taatctatctggtgtctaaact ggactctggagtccctgacagg ttcactggcagtggatcaggaa cagattttacgctgaaaatcag cagagtggaggctgaggatttg ggagtttattactgcgtgcaag gtacacatttcctctcacgtt cggtgctgggaccaagctggag ctgaaaggtggtggttctg gcggcggcggctccggtggtgg tggttctgaggttcagctgcag cagtctggggcagagcttgtga ggtcaggggcctcagtcaagtt gtcctgcacagcttctggcttc aacattaaagactactatttgc actgggtgaagcagaggccta acagggcctggagtggattgcc tggattgatcttgagaatggtg atattaaatatgccccgaagtt tcagggcaaggccactataact gcagacacatcctccaacacag cctacctgcagctcagcagcct gacatctgaggacactgccgtc tattactgtaatcccattact acggtagtaactacgactatgc tatggactactggggtcaagga acctcagtcaccgtctcctccg gaggtggtggatccgaggtgaa gcttctcgagtctggaggagga ttggtgcagcctaaagggtcat tgaaactctcatgtgcagcctc tggattcaccttcaatacctac gccatgaactgggtccgccagg ctccaggaaagggtttggaatg ggttgctcgcataagaagtaaa tataataattatgcaacatatt atgccgattcagtgaaagacag gttcaccatctccagagatgat tcacaaagcattctctatctac aaatgaacaacttgaaaactga ggacacagccatgtactactgt gtgagacatgggaacttcggta atagctacgtttcctggttgc ttactggggccaaggggactct ggtcactgtctctgcaggtggtg gtggttctggcggcggcggctc cggtggtggtggttctcaggtc gttgtgactcaggaatctgcac tcaccacatcacctggtgaaac agtcacactcacttgtcgctca agtactggggctgttacaacta gtaactatgccaactgggtcca agaaaaaccagatcatttattc actggtctaataggtggtacca acaagcgagctccaggtgtgcc tgccagattctcaggctccctg attggagacaaggctgccctca ccatcacaggggcacagactga ggatgaggcaatatatttctgt gctctatggtacagcaacctct gggtgttcggtggaggaaccaa aactgactgtccta |
| 68 | 2G8LHx SEQ ID NO. 10 | arti- ficial | AA | DVVMTQTPLTLSVTIGQPASIS CKSSQSLLYSNGKTYLNWILQR PGQSPKRLIYLVSKLDSGVPDR FTGSGSGTDFTLKISRVEAEDL GVYYCVQGTHFPLTFGAGTKLE |

APPENDIX-continued

| SEQ ID NO. | DESIGNATION | SOURCE | TYPE | SEQUENCE |
|---|---|---|---|---|
| | | | | LKGGGGSGGGGSGGGGSEVQLQ QSGAELVRSGASVKLSCTASGF NIKDYYLHWVKQRPEQGLEWIA WIDLENGDIKYAPKFQGKATIT ADTSSNTAYLQLSSLTSEDTAV YYCNPYYYGSNYDYAMDYWGQG TSVTVSSGGGGSEVKLLESGGG LVQPKGSLKLSCAASGFTFNTY AMNWVRQAPGKGLEWVARIRSK YNNYATYYADSVKDRFTISRDD SQSILYLQMNNLKTEDTAMYYC VRHGNFGNSYVSWFAYWGQGTL VTVSAGGGGSGGGGSGGGGSQA VVTQESALTTSPGETVTLTCRS STGAVTTSNYANWVQEKPDHLF TGLIGGTNKRAPGVPARFSGSL IGDKAALTITGAQTEDEAIYFC ALWYSNLWVFGGGTKLTVL |
| 69 | 2G8LHx SEQ ID NO. 16 | artificial | NA | gatgttgtgatgacccagactc cactcactttgtcggttaccat tggacaaccagcctctatctct tgcaagtcaagtcagagcctct tatatagtaatggaaaaaccta tttgaactggatattacagagg ccaggccagtctccaaagcgcc taatctatctggtgtctaaact ggactctggagtccctgacagg ttcactggcagtggatcaggaa cagattttacgctgaaaatcag cagagtggaggctgaggatttg ggagtttattactgcgtgcaag gtacacattttcctctcacgtt cggtgctgggaccaagctgag ctgaaaggtggtggtggttctg gcggcggcggctccggtggtgg tggttctgaggttcagctgcag cagtctggggcagagcttgtga ggtcaggggcctcagtcaagtt gtcctgcacagcttctggcttc aacattaaagactactatttgc actgggtgaagcagaggcctga acagggcctggagtggattgcc tggattgatcttgagaatggtg atattaaatatgccccgaagtt tcagggcaaggccactataact gcagacacatcctccaacacag cctacctgcagctcagcagcct gacatctgaggacactgccgtc tattactgtaatccctattact acggtagtaactacgactatgc tatggactactggggtcaagga acctcagtcaccgtctcctccg gaggtggtggatcccaagttgt tctcacccagtccagcaatc atgtctgcatttccaggggaga aggtcaccatgacctgcagtgc cagctcaagtgtaagttacatg aactggtaccagcagaagtcag gcacctcccccaaaagatggat ttatgactcatccaaactggct tctggagtccctgctcgcttca gtggcagtgggtctggaacctc ttattctctcacaatcagcagc atggagactgaagatgctgcca cttattactgccagcagtggag tcgtaacccacccgttcgga gggggaccaagctacaaatta caggtggtggtggttctggcgg cggcggctccggtggtggtggt tctcaggtccagctgcagcagt ctggggctgaactggcaagacc tggggcctcagtgaagatgtcc tgcaaggcttctggctacacct tactagatctacgatgcactgg gtaaaacagaggcctggacaga |
| 70 | 2G8LHx SEQ ID NO. 16 | artificial | AA | DVVMTQTPLTLSVTIGQPASIS CKSSQSLLYSNGKTYLNWILQR PGQSPKRLIYLVSKLDSGVPDR FTGSGSGTDFTLKISRVEAEDL GVYYCVQGTHFPLTFGAGTKLE LKGGGGSGGGGSGGGGSEVQLQ QSGAELVRSGASVKLSCTASGF NIKDYYLHWVKQRPEQGLEWIA WIDLENGDIKYAPKFQGKATIT ADTSSNTAYLQLSSLTSEDTAV YYCNPYYYGSNYDYAMDYWGQG TSVTVSSGGGGSQVVLTQSPAI MSAFPGEKVTMTCSASSSVSYM NWYQQKSGTSPKRWIYDSSKLA SGVPARFSGSGSGTSYSLTISS METEDAATYYCQQWSRNPPTFG GGTKLQITGGGGSGGGGSGGGG SQVQLQQSGAELARPGASVKMS CKASGYTFTRSTMHWVKQRPGQ GLEWIGYINPSSAYTNYNQKFK DKATLTADKSSSTAYMQLSSLT SEDSAVYYCASPQVHYDYNGFP YWGQGTLVTVSA |
| 71 | 2G8LHx SEQ ID NO. 14 | artificial | NA | gatgttgtgatgacccagactc cactcactttgtcggttaccat tggacaaccagcctctatctct tgcaagtcaagtcagagcctct tatatagtaatggaaaaaccta tttgaactggatattacagagg ccaggccagtctccaaagcgcc taatctatctggtgtctaaact ggactctggagtccctgacagg ttcactggcagtggatcaggaa cagattttacgctgaaaatcag cagagtggaggctgaggatttg ggagtttattactgcgtgcaag gtacacattttcctctcacgtt cggtgctgggaccaagctggag ctgaaaggtggtggtggttctg gcggcggcggctccggtggtgg tggttctgaggttcagctgcag cagtctggggcagagcttgtga ggtcaggggcctcagtcaagtt gtcctgcacagcttctggcttc aacattaaagactactatttgc actgggtgaagcagaggcctga acagggcctggagtggattgcc tggattgatcttgagaatggtg atattaaatatgccccgaagtt tcagggcaaggccactataact gcagacacatcctccaacacag cctacctgcagctcagcagcct gacatctgaggacactgccgtc tattactgtaatccctattact acggtagtaactacgactatgc tatggactactggggtcaagga acctcagtcaccgtctcctccg gaggtggtggatcccaggtcca gctgcagcagtctggggctgaa ctggcaagacctggggcctcag tgaagatgtcctgcaaggcttc tggctacacctttactagatct acgatgcactgggtaaaacaga |

APPENDIX-continued

| SEQ ID NO. | DESIGNATION | SOURCE | TYPE | SEQUENCE |
|---|---|---|---|---|
| | | | | ggcctggacagggtctggaatg gattggatacattaatcctagc agtgcttatactaattacaatc agaaattcaaggacaaggccac attgactgcagacaaatcctcc agtacagcctacatgcaactga gtagcctgacatctgaggactc tgcagtctattactgtgcaagt ccgcaagtccactatgattaca acgggtttccttactggggcca agggactctggtcactgtctct gcaggtggtggtggttctggcg gcggcggctccggtggtggtgg ttctcaagttgttctcacccag tctccagcaatcatgtctgcat ttccaggggagaaggtcaccat gacctgcagtgccagctcaagt gtaagttacatgaactggtacc agcagaagtcaggcacctcccc caaaagatggatttatgactca tccaaactggcttctggagtcc ctgctcgcttcagtggcagtgg gtctgggacctcttattctctc acaatcagcagcatggagactg aagatgctgccacttattactg ccagcagtggagtcgtaaccca cccacgttcggaggggggacca agctacaaattaca |
| 72 | 2G8LHx SEQ ID NO. 14 | artificial | AA | DVVMTQTPLTLSVTIGQPASIS CKSSQSLLYSNGKTYLNWILQR PGQSPKRLIYLVSKLDSGVPDR FTGSGSGTDFTLKISRVEAEDL GVYYCVQGTHFPLTFGAGTKLE LKGGGGSGGGGSGGGGSEVQLQ QSGAELVRSGASVKLSCTASGF NIKDYYLHWVKQRPEQGLEWIA WIDLENGDIKYAPKFQGKATIT ADTSSNTAYLQLSSLTSEDTAV YYCNPYYYGSNYDYAMDYWGQG TSVTVSSGGGGSQVQLQQSGAE LARPGASVKMSCKASGYTFTRS TMHWVKQRPGQGLEWIGYINPS SAYTNYNQKFKDKATLTADKSS STAYMQLSSLTSEDSAVYYCAS PQVHYDYNGFPYWGQGTLVTVS AGGGGSGGGGSGGGGSQVVLTQ SPAIMSAFPGEKVTMTCSASSS VSYMNWYQQKSGTSPKRWIYDS SKLASGVPARFSGSGSGTSYSL TISSMETEDAATYYCQQWSRNP PTFGGGTKLQIT |
| 73 | 2G8HLx SEQ ID NO. 12 | artificial | NA | gaggttcagctgcagcagtctg gggcagagcttgtgaggtcagg ggcctcagtcaagttgtcctgc acagcttctggcttcaacatta aagactactatttgcactgggt gaagcagaggcctgaacagggc ctggagtggattgctggattg atcttgagaatggtgatattaa atatgccccgaagtttcagggc aaggccactataactgcagaca catcctccaacacagcctacct gcagctcagcagcctgacatct gaggacactgccgtctattact gtaatccctattactacggtag taactacgactatgctatggac tactggggtcaaggaacctcag tcaccgtctcctcaggtggtgg tggttctggcggcggcggctcc ggtggtggtggttctgatgttg tgatgacccagactccactcac tttgtcggttaccattggacaa ccagcctctatctcttgcaagt caagtcagagcctcttatatag |
| | | | | taatggaaaaacctatttgaac tggatattacagaggccaggcc agtctccaaagcgcctaatcta tctggtgtctaaactggactct ggagtccctgacaggttcactg gcagtggatcaggaacagattt tacgctgaaaatcagcagagtg gaggctgaggatttgggagttt attactgcgtgcaaggtacaca ttttcctctcacgttcggtgct gggaccaagctggagctgaaat ccggaggtggtggatcccaggc tgttgtgactcaggaatctgca ctcaccacatcacctggtgaaa cagtcacactcacttgtcgctc aagtactgggctgttacaact agtaactatgccaactgggtcc aagaaaaaccagatcatttatt cactggtctaataggtggtacc aacaagcgagctccaggtgtgc ctgccagattctcaggctccct gattgagacaaggctgccctc accatcacaggggcacagactg aggatgaggcaatatatttctg tgctctatggtacagcaacctc tgggtgttcggtggaggaacca aactgactgtcctaggtggtgg tggttctggcggcggcggctcc ggtggtggtggttctgaggtga agcttctcgagtctgggaggag attggtgcagcctaaagggtca ttgaaactctcatgtgcagcct ctggattcaccttcaatacccta cgccatgaactgggtccgccag gctccaggaaagggtttggaat gggttgctcgcataagaagtaa atataataattatgcaacatat tatgccgattcagtgaaagaca ggttcaccatctccagagatga ttcacaaagcattctctatcta caaatgaacaacttgaaaactg aggacacagccatgtactactg tgtgagacatgggaacttcggt aatagctacgtttcctggtttg cttactggggccaagggactct ggtcactgtctctgca |
| 74 | 2G8HLx SEQ ID NO. 12 | artificial | AA | EVQLQQSGAELVRSGASVKLSC TASGFNIKDYYLHWVKQRPEQG LEWIAWIDLENGDIKYAPKFQG KATITADTSSNTAYLQLSSLTS EDTAVYYCNPYYYGSNYDYAMD YWGQGTSVTVSSGGGGSGGGGS GGGGSDVVMTQTPLTLSVTIGQ PASISCKSSQSLLYSNGKTYLN WILQRPGQSPKRLIYLVSKLDS GVPDRFTGSGSGTDFTLKISRV EAEDLGVYYCVQGTHFPLTFGA GTKLELKGGGGSQAVVTQESA LTTSPGETVTLTCRSSTGAVTT SNYANWVQEKPDHLFTGLIGGT NKRAPGVPARFSGSLIGDKAAL TITGAQTEDEAIYFCALWYSNL WVFGGGTKLTVLGGGGSGGGGS GGGGSEVKLLESGGGLVQPKGS LKLSCAASGFTFNTYAMNWVRQ APGKGLEWVARIRSKYNNYATY YADSVKDRFTISRDDSQILYL QMNNLKTEDTAMYYCVRHGNFG NSYVSWFAYWGQGTLVTVSA |
| 75 | 2G8HLx SEQ ID NO. 10 | artificial | NA | gaggttcagctgcagcagtctg gggcagagcttgtgaggtcagg ggcctcagtcaagttgtcctgc acagcttctggcttcaacatta aagactactatttgcactgggt |

APPENDIX-continued

| SEQ ID NO. | DESIGNATION | SOURCE | TYPE | SEQUENCE |
|---|---|---|---|---|
| | | | | gaagcagaggcctgaacagggc ctggagtggattgcctggattg atcttgagaatggtgatattaa atatgccccgaagtttcagggc aaggccactataactgcagaca catcctccaacacagcctacct gcagctcagcagcctgacatct gaggacactgccgtctattact gtaatcctattactacggtag taactacgactatgctatggac tactggggtcaaggaacctcag tcaccgtctcctcaggtggtgg tggttctggcggcggcggctcc ggtggtggtggttctgatgttg tgatgacccagactccactcac tttgtcggttaccattggacaa ccagcctctatctcttgcaagt caagtcagagcctcttatatag taatggaaaaacctatttgaac tggatattacagaggccaggcc agtctccaaagcgcctaatcta tctggtgtctaaactggactct ggagtccctgacaggttcactg gcagtggatcaggaacagattt tacgctgaaaatcagcagagtg gaggctgaggatttgggagttt attactgcgtgcaaggtacaca ttttcctctcacgttcggtgct gggaccaagctggagctgaaat ccggaggtggtggatccgaggt gaagcttctcgagtctggagga ggattggtgcagcctaaaggt cattgaaactctcatgtgcagc ctctggattcaccttcaataccc tacgccatgaactgggtccgcc aggctccaggaaagggtttgga atgggttgctcgcataagaagt aaatataattatgcaacat attatgccgattcagtgaaaga caggttcaccatctccagagat gattcacaaagcattctctatc tacaaatgaacaacttgaaaac tgaggacacagccatgtactac tgtgtgagacatgggaacttcg gtaatagctacgtttcctggtt tgcttactggggccaaggact ctggtcactgtctctgcaggtg gtggtggttctggcggcggcgg ctccggtggtggtggttctcag gctgttgtgactcaggaatctg cactcaccacatcacctggtga aacagtcacactcacttgtcgc tcaagtactggggctgttacaa ctagtaactatgccaactgggt ccaagaaaaaccagatcattta ttcactggtctaataggtggta ccaacaagcgagctccaggtgt gcctgccagattctcaggctcc ctgattggagacaaggctgccc tcaccatcacaggggcacagac tgaggatgaggcaatatattc tgtgctctatggtacagcaacc tctggtgttcggtggagaac caaactgactgtccta |
| 76 | 2G8HLx SEQ ID NO. 10 | artificial | AA | EVQLQQSGAELVRSGASVKLSC TASGFNIKDYYLHWVKQRPEQG LEWIAWIDLENGDIKYAPKFQG KATITADTSSNTAYLQLSSLTS EDTAVYYCNPYYYGSNYDYAMD YWGQGTSVTVSSGGGGSGGGGS GGGGSDVVMTQTPLTLSVTIGQ PASISCKSSQSLLYSNGKTYLN WILQRPGQSPKRLIYLVSKLDS GVPDRFTGSGSGTDFTLKISRV EAEDLGVYYCVQGTHFPLTFGA GTKLELKSGGGGSEVKLLESGG GLVQPKGSLKLSCAASGFTFNT YAMNWVRQAPGKGLEWVARIRS KYNNYATYYADSVKDRFTISRD DSQSILYLQMNNLKTEDTAMYY CVRHGNFGNSYVSWFAYWGQGT LVTVSAGGGGSGGGGSGGGGSQ AVVTQESALTTSPGETVTLTCR SSTGAVTTSNYANWVQEKPDHL FTGLIGGTNKRAPGVPARFSGS LIGDKAALTITGAQTEDEAIYF CALWYSNLWVFGGGTKLTVL |
| 77 | 2G8HLx SEQ ID NO. 16 | artificial | NA | gaggttcagctgcagcagtctg gggcagagcttgtgaggtcagg ggcctcagtcaagttgtcctgc acagcttctggcttcaacatta agactactatttgcactgggt gaagcagaggcctgaacagggc ctggagtggattgcctggattg atcttgagaatggtgatattaa atatgccccgaagtttcagggc aaggccactataactgcagaca catcctccaacacagcctacct gcagctcagcagcctgacatct gaggacactgccgtctattact gtaatcctattactacggtag taactacgactatgctatggac tactggggtcaaggaacctcag tcaccgtctcctcaggtggtgg tggttctggcggcggcggctcc ggtggtggtggttctgatgttg tgatgacccagactccactcac tttgtcggttaccattggacaa ccagcctctatctcttgcaagt caagtcagagcctcttatatag taatggaaaaacctatttgaac tggatattacagaggccaggcc agtctccaaagcgcctaatcta tctggtgtctaaactggactct ggagtccctgacaggttcactg gcagtggatcaggaacagattt tacgctgaaaatcagcagagtg gaggctgaggatttgggagttt attactgcgtgcaaggtacaca ttttcctctcacgttcggtgct gggaccaagctggagctgaaat ccggaggtggtggatcccaagt tgttctcacccagtctccagca atcatgtctgcatttccagggg agaaggtcaccatgacctgcag tgccagctcaagtgtaagttac atgaactggtaccagcagaagt caggcacctcccccaaaagatg gatttatgactcatccaaactg gcttctgagtccctgctcgct tcagtggcagtgggtctgggac ctcttattctctcacaatcagc agcatggagactgaagatgctg ccacttattactgccagcagtg gagtcgtaacccaccacgttc ggaggggggaccaagctacaaa ttacaggtggtggttctgg cggcggcggctccggtggtggt ggttctcaggtccagctgcagc agtctggggctgaactggcaag acctggggcctcagtgaagatg tcctgcaaggcttctggctaca cctttactagatctacgatgca ctgggtaaaacagaggcctgga cagggtctggaatggattggat acattaatcctagcagtgctta tactaattacaatcagaaattc aaggacaaggccacattgactg cagacaaatcctccagtacagc ctacatgcaactgagtagcctg |

APPENDIX-continued

| SEQ ID NO. | DESIGNATION | SOURCE | TYPE | SEQUENCE |
|---|---|---|---|---|
| | | | | acatctgaggactctgcagtct attactgtgcaagtccgcaagt ccactatgattacaacgggttt ccttactggggccaagggactc tggtcactgtctctgca |
| 78 SEQ ID NO. 16 | 2G8HLx | artificial | AA | EVQLQQSGAELVRSGASVKLSC TASGFNIKDYYLHWVKQRPEQG LEWIAWIDLENGDIKYAPKFQG KATITADTSSNTAYLQLSSLTS EDTAVYYCNPYYYGSNYDYAMD YWGQGTSVTVSSGGGGSGGGGS GGGGSDVVMTQTPLTLSVTIGQ PASISCKSSQSLLYSNGKTYLN WILQRPGQSPKRLIYLVSKLDS GVPDRFTGSGSGTDFTLKISRV EAEDLGVYYCVQGTHFPLTFGA GTKLELKSGGGGSQVVLTQSPA IMSAFPGEKVTMTCSASSSVSY MNWYQQKSGTSPKRWIYDSSKL ASGVPARFSGSGSGTSYSLTIS SMETEDAATYYCQQWSRNPPTF GGGTKLQITGGGGSGGGGSGGG GSQVQLQQSGAELARPGASVKM SCKASGYTFTRSTMHWVKQRPG QGLEWIGYINPSSAYTNYNQKF KDKATLTADKSSSTAYMQLSSL TSEDSAVYYCASPQVHYDYNGF PYWGQGTLVTVSA |
| 79 SEQ ID NO. 14 | 2G8HLx | artificial | NA | gaggttcagctgcagcagtctg gggcagagcttgtgaggtcagg ggcctcagtcaagttgtcctgc acagcttctggcttcaacatta aagactactatttgcactgggt gaagcagaggcctgaacagggc ctggagtggattgcctggattg atcttgagaatggtgatattaa atatgcccgaagtttcagggc aaggccactataactgcagaca catcctccaacacagcctacct gcagctcagcagcctgacatct gaggacactgccgtctattact gtaatcccattactacggtag taactacgactatgctatggac tactgggtcaagggaacctcag tcaccgtctcctcaggtggtgg tggttctggcggcggcggctcc ggtggtggtggttctgatgttg tgatgacccagactccactcac tttgtcggttaccattggacaa ccagcctctatctcttgcaagt caagtcagagcctcttatatag taatggaaaaacctatttgaac tggatattacagaggccaggc agtctccaaagcgcctaatcta tctggtgtctaaactggactct ggagtccctgacaggttcactg gcagtggatcaggaacagattt tacgctgaaaatcagcagagtg gaggctgaggatttggagtttt attactgcgtgcaaggtacaca tttcctctcacgttcggtgct gggaccaagctggagctgaaat ccggaggtggtggatcccaggt ccagctgcagcagtctggggct gaactggcaagacctggggcct cagtgaagatgtcctgcaaggc ttctggctacaccttactaga tctacgatgcactgggtaaaac agaggcctgacagggtctgga atggattggatacattaatcct agcagtgcttatactaattaca atcagaaattcaaggacaaggc cacattgactgcagacaaatcc tccagtacagcctacatgcaac |

APPENDIX-continued

| SEQ ID NO. | DESIGNATION | SOURCE | TYPE | SEQUENCE |
|---|---|---|---|---|
| | | | | tgagtagcctgacatctgagga ctctgcagtctattactgtgca agtccgcaagtccactatgatt acaacgggtttccttactgggg ccaagggactctggtcactgtc tctgcaggtggtggtggttctg gcggcggcggctccggtggtgg tggttctcaagttgttctcacc cagtctccagcaatcatgtctg catttccaggggagaaggtcac catgacctgcagtgccagctca agtgtaagttacatgaactggt accagcagaagtcaggcacctc ccccaaaagatggatttatgac tcatccaaactggcttctggag tccctgctcgcttcagtggcag tgggtctgggacctcttattct ctcacaatcagcagcatggaga ctgaagatgctgccacttatta ctgccagcagtggagtcgtaac ccacccacgttcggaggggga ccaagctacaaattaca |
| 80 SEQ ID NO. 14 | 2G8HLx | artificial | AA | EVQLQQSGAELVRSGASVKLSC TASGFNIKDYYLHWVKQRPEQG LEWIAWIDLENGDIKYAPKFQG KATITADTSSNTAYLQLSSLTS EDTAVYYCNPYYYGSNYDYAMD YWGQGTSVTVSSGGGGSGGGGS GGGGSDVVMTQTPLTLSVTIGQ PASISCKSSQSLLYSNGKTYLN WILQRPGQSPKRLIYLVSKLDS GVPDRFTGSGSGTDFTLKISRV EAEDLGVYYCVQGTHFPLTFGA GTKLELKSGGGGSQVQLQQSGA ELARPGASVKMSCKASGYTFTR STMHWVKQRPGQGLEWIGYINP SSAYTNYNQKFKDKATLTADKS SSTAYMQLSSLTSEDSAVYYCA SPQVHYDYNGFPYWGQGTLVTV SAGGGGSGGGGSGGGGSQVVLT QSPAIMSAFPGEKVTMTCSASS SVSYMNWYQQKSGTSPKRWIYD SSKLASGVPARFSGSGSGTSYS LTISSMETEDAATYYCQQWSRN PPTFGGGTKLQIT |
| 81 | 5' primer VH | artificial | NA | 5'-SAGGTGCAGCTCGAGGAGT CAGGACCT-3' |
| 82 | 5' primer VH | artificial | NA | 5'-GAGGTCCAGCTCGAGCAGT CTGGACCT-3' |
| 83 | 5' primer VH | artificial | NA | 5'-CAGGTCCAACTCGAGCAGC CTGGGCT-3' |
| 84 | 5' primer VH | artificial | NA | 5'-GAGGTTCAGCTCGAGCAGT CTGGGGCA-3' |
| 85 | 5' primer VH | artificial | NA | 5'-GARGTGAAGCTCGAGGAGT CTGGAGGA-3' |
| 86 | 5' primer VH | artificial | NA | 5'-GAGGTGAAGCTTCTCGAGT CTGGAGGT-3' |
| 87 | 5' primer VH | artificial | NA | 5'-GAAGTGAAGCTCGAGGAGT CTGGGGGA-3' |
| 88 | 5' primer VH | artificial | NA | 5'-GAGGTTCAGCTCGAGCAGT CTGGAGCT-3' |
| 89 | 5' primer VH | artificial | NA | 5'-GGGCTCGAGCACCATGGRA TGSAGCTGKGTMATSCTCT |

APPENDIX-continued

| SEQ ID NO. | DESIGNATION | SOURCE | TYPE | SEQUENCE |
|---|---|---|---|---|
| 90 | 5' primer VH | artificial | NA | 5'-GGGCTCGAGCACCATGRACTTCGGGYTGAGCTKGGTTTT-3' |
| 91 | 5' primer VH | artificial | NA | 5'-GGGCTCGAGCACCATGGCTGTCTTGGGGCTGCTCTTCT-3' |
| 92 | 3' primer VH | artificial | NA | 5'-GAGGAATTCGAACTGGACAGGGATCCAGAGTTCC-3' |
| 93 | 3' primer VH | artificial | NA | 5'-CGGAATTCGAATGACATGGACATCTGGGTCATCC-3' |
| 94 | 5' primer VL | artificial | NA | 5'-CCAGTTCCGAGCTCGTTGTGACTCAGGAATCT-3' |
| 95 | 5' primer VL | artificial | NA | 5'-CCAGTTCCGAGCTCGTTGACGCAGCCGCCC-3' |
| 96 | 5' primer VL | artificial | NA | 5'-CCAGTTCCGAGCTCGTGCTCACCCAGTCTCCA-3' |
| 97 | 5' primer VL | artificial | NA | 5'-CCAGTTCCGAGCTCCAGATGACCCAGTCTCCA-3' |
| 98 | 5' primer VL | artificial | NA | 5'-CCAGATGTGAGCTCGTGATGACCCAGACTCCA-3' |
| 99 | 5' primer VL | artificial | NA | 5'-CCAGATGTGAGCTCGTCATGACCCAGTCTCCA-3' |
| 100 | 5' primer VL | artificial | NA | 5'-CCAGTTCCGAGCTCGTGATGACACAGTCTCCA-3' |
| 101 | 5' primer VL | artificial | NA | 5'-GGGGAGCTCCACCATGGAGACAGACACACTCCTGCTAT-3' |
| 102 | 5' primer VL | artificial | NA | 5'-GGGGAGCTCCACCATGGATTTTCAAGTGCAGATTTTCAG-3' |
| 103 | 5' primer VL | artificial | NA | 5'-GGGGAGCTCCACCATGGAGWCACAKWCTCAGGTCTTTRTA-3' |
| 104 | 5' primer VL | artificial | NA | 5'-GGGGAGCTCCACCATGKCCCCWRCTCAGYTYCTKGT-3' |
| 105 | 3' primer VL | artificial | NA | 5'-GAGGAATTCGAACTGCTCACTGGATGGTGGG-3' |
| 106 | 3' primer VL | artificial | NA | 5'-CGGAATTCGAACAAACTCTTCTCCACAGTGTGACC-3' |
| 107 | 3' primer VH | artificial | NA | 5'-TATGCAACTAGTACAACCACAATCCCTGGG-3' |
| 108 | 3' primer VL | artificial | NA | 5'-GCGCCGTCTAGAATTAACACTCATTCCTGTTGAA-3' |
| 109 | 5-10 LH x deimmunised (di) anti-CD3 | artificial | AA | ELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSGGGGSGGGGSEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK |
| 110 | Human-like VH | artificial | AA | EVQLLESGGGLVQPGGSLKLSCAASGFTFNTYAMNWVRQAPGKGLEWVARIRSKYNNYATYYADSVKDRFTISRDDSKNTAYLQMNNLKTEDTAVYYCVRHGNFGNSYVSWFAYWGQGTLVTVSS |
| 111 | Human-like VH | artificial | NA | gaggtgcagctgctcgagtctgaggaggattggtgcagcctggagggtcattgaaactctcatgtgcagcctctggattcaccttcaatacctacgccatgaactgggtccgccaggctccaggaaaggggttggaatgggttgctcgcataagaagtaaataataattatgcaacatatatgccgattcagtgaaagacaggttcaccatctccagagatgattcaaaaaacactgcctatctacaaatgaacaacttgaaaactgaggacactgccgtgtactactgtgtgagacatgggaacttcggtaatagctacgtttcctggtttgcttactggggccaagggactctggtcaccgtctcctca |
| 112 | VH: CDR3 | murine | AA | HGNFGNSYVSWFAY |
| 113 | VH: short CDR3 | murine | AA | VSWFAY |
| 114 | VH: CDR2 | murine | AA | RIRSKYNNYATYYADSVKD |
| 115 | VH: CDR1 | murine | AA | TYAMN |
| 116 | VL: CDR3 | murine | AA | ALWYSNLWV |
| 117 | VL: CDR2 | murine | AA | GTNKRAP |
| 118 | VL: CDR1 | murine | AA | RSSTGAVTTSNYAN |
| 119 | VH: CDR3 | murine | AA | PQVHYDYNGFPY |
| 120 | VH: CDR2 | murine | AA | YINPSSAYTNYNQKFKD |
| 121 | VH: CDR1 | murine | AA | GYTFTRSTMH |
| 122 | 2G8 LHx SEQ ID NO. 146 | artificial | AA | DVVMTQTPLTLSVTIGQPASISCKSSQSLLYSNGKTYLNWILQRPGQSPKRLIYLVSKLDSGVPDRFTGSGSGTDFTLKISRVEAEDLGVYYCVQGTHFPLTFGAGTKLELKGGGGSGGGGSGGGGSEVQLQSGAELVRSGASVKLSCTASGFNIKDYYLHWVKQRPEQGLEWIAWIDLENGDIKYAPKIFQGKATITADTSSNTAYLQLSSLTSEDTAVYYCNPYYYGSNYDYAMDYWGQGTSVTVSSGGGGSEVKLLESGGGLVQPGGSLKLSCAASGFTFNTYAMNWVRQAPGKGLEWVARIRSKYNNYATYYADSVKDRFTISRDDSKNTAYLQMNNLKTEDTAVYYCVRHGNFGNSYVSWFAYWGQGTLVTVSSGGGGSGGGGSGGGGSELVVTQESALTTSPGETVTLTCRSSTGAVTTSNYANWVQEKPDHL |

APPENDIX-continued

| SEQ ID NO. | DESIGNATION | SOURCE | TYPE | SEQUENCE |
|---|---|---|---|---|
| | | | | FTGLIGGTNKRAPGVPARFSGS LIGDKAALTITGAQTEDEAIYF CALWYSNLWVFGGGTKLTVLHH HHHH |
| 123 SEQ ID NO. 146 | 2G8 LHx | artificial | NA | gatgttgtgatgacccagactc cactcactttgtcggttaccat ggacaaccagcctctatctct tgcaagtcaagtcagagcctct tatatagtaatggaaaaaccta tttgaactggatattacagagg ccaggccagtctccaaagcgcc taatctatctggtgtctaaact ggactctggagtccctgacagg ttcactggcagtggatcaggaa cagattttacgctgaaaatcag cagagtggaggctgaggatttg ggagtttattactgcgtgcaag gtacacattttcctctcacgtt cggtgctgggaccaagctggag ctgaaaggtggtggttctgcg gcggcggcggctccggtggtgg tggttctgaggttcagctgcag cagtctggggcagagcttgtga ggtcagggggcctcagtcaagtt gtcctgcacagcttctggcttc aacattaaagactactatttgc actgggtgaagcagaggcctga acagggcctggagtggattgcc tggattgatcttgagaatggtg atattaaatatgccccgaagtt tcagggcaaggccactataact gcagacacatcctccaacacag cctacctgcagctcagcagcct gacatctgaggacactgccgtc tattactgtaatccctattact acggtagtaactacgactatgc tatgactactggggtcaagga acctcagtcaccgtctcctccg gaggtggtggatccgaggtgaa gcttctcgagtctggaggagga ttggtgcagcctggagggtcat tgaaactctcatgtgcagcctc tggattcaccttcaataacctac gccatgaactgggtccgccagg ctccaggaaagggtttggaatg ggttgctcgcataagaagtaaa tataataattatgcaacatatt atgccgattcagtgaaagacag gttcaccatctccagagatgat tcaaaaaacactgcctatctac aaatgaacaacttgaaaactga ggacactgccgtgtactactgt gtgagacatgggaacttcggta atagctacgtttcctggtttgc ttactggggccaagggactctg gtcaccgtctcctcaggtggtg gtggttctggcggcggcggctc cggtggtggtggttctgagctc gttgtgactcaggaatctgcac tcaccacatcacctggtgaaac agtcacactcacttgtcgctca agtactgggctgttacaacta gtaactatgccaactgggtcca agaaaaaccagatcatttattc actggtctaataggtggtacca acaagcgagcaccaggtgtgcc tgccagattctcaggctccctg attggagacaaggctgccctca ccatcacaggggcacagactga ggatgaggcaatatatttctgt gctctatggtacagcaacctct gggtgttcggtggaggaaccaa actgactgtcctactcatcac catcatcat |
| 124 SEQ ID NO. 146 | 5-10 LHx | artificial | AA | ELVMTQSPSSLTVTAGEKVTMS CKSSQSLLNSGNQKNYLTWYQQ KPGQPPKLLIYWASTRESGVPD RFTGSGSGTDFTLTISSVQAED LAVYYCQNDYSYPLTFGAGTKL EIKGGGGSGGGGSGGGGSEVQL LEQSGAELVRPGTSVKISCKAS GYAFTNYWLGWVKQRPGHGLEW IGDIFPGSGNIHYNEKFKGKAT LTADKSSSTAYMQLSSLTFEDS AVYFCARLRNWDEPMDYWGQGT TVTVSSGGGGSEVKLLESGGGL VQPGGSLKLSCAASGFTFNTYA MNWVRQAPGKGLEWVARIRSKY NNYATYYADSVKDRFTISRDDS KNTAYLQMNNLKTEDTAVYYCV RHGNFGNSYVSWFAYWGQGTLV TVSSGGGGSGGGGSGGGGSELV VTQESALTTSPGETVTLTCRSS TGAVTTSNYANWVQEKPDHLFT GLIGGTNKRAPGVPARFSGSLI GDKAALTITGAQTEDEAIYFCA LWYSNLWVFGGGTKLTVLHHHH HH |
| 125 SEQ ID NO. 146 | 5-10 LHx | artificial | NA | gagctcgtgatgacacagtctc catcctccctgactgtgacagc aggagagaaggtcactatgagc tgcaagtccagtcagagtctgt taaacagtggaaatcaaaagaa ctacttgacctggtaccagcag aaaaccagggcagcctcctaaac tgttgatctactgggcatccac tagggaatctggggtccctgat cgcttcacaggcagtggatctg gaacagatttcactctcaccat cagcagtgtgcaggctgaagac ctggcagtttattactgtcaga atgattatagttatccgctcac gttcggtgctgggaccaagctt gagatcaaaggtggtggtggtt ctggcggcggcggctccggtgg tggtggttctgaggtgcagctg ctcgagcagtctggagctgagc tggtaaggcctggagcttcagt gaagatatcctgcaaggcttct ggatacgccttcactaactact ggctaggttgggtaaagcagag gcctggacatggacttgagtgg attggagatatttccctggaa gtggtaatatccactacaatga gaagttcaagggcaaagccaca ctgactgcagacaaatcttcga gcacagcctatatgcagctcag tagcctgacatttgaggactct gctgtctatttctgtgcaagac tgaggaactgggacgagcctat ggactactggggccaagggacc acggtcaccgtctcctccggag gtggtggatccgaggtgaagct tctcgagtctggaggaggattg gtgcagcctggagggtcattga aactctcatgtgcagcctctgg attcaccttcaataccctacgcc atgaactgggtccgccaggctc caggaaagggtttggaatgggt tgctcgcataagaagtaaatat aataattatgcaacatattatg ccgattcagtgaaagacaggtt caccatctccagagatgattca aaaaacactgcctatctacaaa tgaacaacttgaaaactgagga cactgccgtgtactactgtgtg agacatgggaacttcggtaata gctacgtttcctggtttgctta ctggggccaagggactctggtc |

APPENDIX-continued

| SEQ ID NO. | DESIGNATION | SOURCE | TYPE | SEQUENCE |
|---|---|---|---|---|
| | | | | accgtctcctcaggtggtggtg gttctggcggcggcggctccgg tggtggtggttctgagctcgtt gtgactcaggaatctgcactca ccacatcacctggtgaaacagt cacactcacttgtcgctcaagt actggggctgttacaactagta actatgccaactgggtccaaga aaaaccagatcatttattcact ggtctaataggtggtaccaaca agcgagcaccaggtgtgcctgc cagattctcaggtccctgatt ggagacaaggtgccctcacca tcacaggggcacagactgagga tgaggcaatatatttctgtgct ctatggtacagcaacctctggg tgttcggtggaggcaccaaact gactgtcctacatcatcaccat catcat |
| 126 | FN18 VH | hybridoma | NA | caggtccagctgcagcagtctg aagctgaactggcaagacctgg ggcctcagtgaagatgtcctgc aaggcttctggctacaccttta ctgactacacgatacactggtt aaaacagaggcctggacaggt ctggactggattggatatttta atcctagcagtgaatctactga atacaatcggaaattcaaggac aggaccatattgactgcagaca gatcctcaaccacagcctacat gcaactgagcagcctgacatct gaggactctgcggtctattact gttcaaggaaaggggagaaact acttggtaaccgttactggtac ttcgatgtctggggcgcaggga cctcggtcaccgtctcctca |
| 127 | FN18 VH | hybridoma | AA | QVQLQQSEAELARPGASVKMSC KASGYTFTDYTIHWLKQRPGQG LDWIGYFNPSSESTEYNRKFKD RTILTADRSSTTAYMQLSSLTS EDSAVYYCSRKGEKLLGNRYWY FDVWGAGTSVTVSS |
| 128 | FN18 VL | hybridoma | NA | gacattgtgatgtcacagtctc catcctccctagctgtgtcagt tggagagaaggttactatgagc tgcaagtccagtcagagccttt tatatagtagcaatcaaaagaa ctacttggcctggtaccagcag aagccagggcagtctcctaaat tgctgattaactgggcatccac cagggaatctggggtccctgat cgcttcacaggcagtggatcta ggacagatttcactctcaccat cagcagtgtgaaggctgaagac ctggcagtttatttctgtcagc aattttatagttatcctccgac gttcggtggaggcaccaagctg gaaatcaaa |
| 129 | FN18 VL | hybridoma | AA | DIVMSQSPSSLAVSVGEKVTMS CKSSQSLLYSSNQKNYLAWYQQ KPGQSPKLLINWASTRESGVPD RFTGSGSRTDFTLTISSVKAED LAVYFCQQFYSYPPTFGGGTKL EIK |
| 130 | FN18 VH-VL scFv | artificial | NA | caggtccagctgcagcagtctg aagctgaactggcaagacctgg ggcctcagtgaagatgtcctgc aaggcttctggctacaccttta ctgactacacgatacactggtt aaaacagaggcctggacaggt ctggactggattggatatttta |

APPENDIX-continued

| SEQ ID NO. | DESIGNATION | SOURCE | TYPE | SEQUENCE |
|---|---|---|---|---|
| | | | | atcctagcagtgaatctactga atacaatcggaaattcaaggac aggaccatattgactgcagaca gatcctcaaccacagcctacat gcaactgagcagcctgacatct gaggactctgcggtctattact gttcaaggaaaggggagaaact acttggtaaccgttactggtac ttcgatgtctggggcgcaggga cctcggtcaccgtctcctcagg tggtggtggttctggcggcggc ggctccggtggtggtggttctg acattgtgatgtcacagtctcc atcctccctagctgtgtcagtt ggagagaaggttactatgagct gcaagtccagtcagagccttt atatagtagcaatcaaaagaac tacttggcctggtaccagcaga agccagggcagtctcctaaatt gctgattaactgggcatccacc agggaatctggggtccctgatc gcttcacaggcagtggatctag gacagatttcactctcaccatc agcagtgtgaaggctgaagacc tggcagtttatttctgtcagca attttatagttatcctccgacg ttcggtggaggcaccaagctgg aaatcaaa |
| 131 | FN18 VH-VL scFv | artificial | AA | QVQLQQSEAELARPGASVKMSC KASGYTFTDYTIHWLKQRPGQG LDWIGYFNPSSESTEYNRKFKD RTILTADRSSTTAYMQLSSLTS EDSAVYYCSRKGEKLLGNRYWY FDVWGAGTSVTVSSGGGGSGGG GSGGGGSDIVMSQSPSSLAVSV GEKVTMSCKSSQSLLYSSNQKN YLAWYQQKPGQSPKLLINWAST RESGVPDRFTGSGSRTDFTLTI SSVKAEDLAVYFCQQFYSYPPT FGGGTKIEIK |
| 132 | FN18 VL-VH scFv | artificial | NA | gacattgtgatgtcacagtctc catcctccctagctgtgtcagt tggagagaaggttactatgagc tgcaagtccagtcagagccttt tatatagtagcaatcaaaagaa ctacttggcctggtaccagcag aagccagggcagtctcctaaat tgctgattaactgggcatccac cagggaatctggggtccctgat cgcttcacaggcagtggatcta ggacagatttcactctcaccat cagcagtgtgaaggctgaagac ctggcagtttatttctgtcagc aattttatagttatcctccgac gttcggtggaggcaccaagctg gaaatcaaaggtggtggttctggcggcggcggctccggtgg tggtggttctcaggtccagctg cagcagtctgaagctgaactgg caagacctcagtgaa gatgtcctgcaaggcttctggc tacacctttactgactacacga tacactggttaaaacagaggcc tggacagggtctggactggatt ggatattttaatcctagcagtg aatctactgaatacaatcggaa attcaaggacaggaccatattg actgcagacagatcctcaacca cagcctacatgcaactgagcag cctgacatctgaggactctgcg gtctattactgttcaaggaaag |

APPENDIX-continued

| SEQ ID NO. | DESIGNATION | SOURCE | TYPE | SEQUENCE |
|---|---|---|---|---|
| | | | | gggagaaactacttggtaaccg ttactggtacttcgatgtctgg ggcgcaggacctcggtcaccg tctcctca |
| 133 | FN18 VL-VH scFv | artificial | AA | DIVMSQSPSSLAVSVGEKVTMS CKSSQSLLYSSNQKNYLAWYQQ KPGQSPKLLINWASTRESGVPD RFTGSGSRTDFTLTISSVKAED LAVYFCQQFYSYPPTFGGGTKL EIKGGGSGGGGSGGGGSQVQL QQSEAELARPGASVKMSCKASG YTFTDYTIHWLKQRPGQGLDWI GYFNPSSESTEYNRKFKDRTIL TADRSSTTAYMQLSSLTSEDSA VYYCSRKGEKLLGNRYWYFDVW GAGTSVTVSS |
| 134 | CD3 epsilon extracellular portion | human cDNA; NM_000733 | AA | QDGNEEMGGITQTPYKVSISGT TVILTCPQYPGSEILWQHNDKN IGGDEDDKNIGSDEDHLSLKEF SELEQSGYYVCYPRGSKPEDAN FYLYLRARVCENCMEMD |
| 135 | CD3 epsilon extracellular portion FN18+ | Cynomolgus cDNA; AB 073993 | AA | QDGNEEMGSITQTPYQVSISGT TVILTCSQHLGSEAQWQHNGKN KEDSGDRLFLPEFSEMEQSGYY VCYPRGSNPEDASHHLYLKARV CENCMEMD |
| 136 | CD3 epsilon extracellular portion FN18− | Cynomolgus cDNA; AB 073994 | AA | QDGNEEMGSITQTPYQVSISGT TVILTCSQHLGSEAQWQHNGKN KGDSGDQLFLPEFSEMEQSGYY VCYPRGSNPEDASHHLYLKARV CENCMEMD |
| 137 | EpCAM extracellular portion | human cDNA | AA | QEECVCENYKLAVNCFVNNNRQ CQCTSVGAQNTVICSKLAAKCL VMKAEMNGSKLGRRAKPEGALQ NNDGLYDPDCDESGLFKAKQCN GTSTCWCVNTAGVRRTDKDTEI TCSERVRTYWIIIELKHKAREK PYDSKSLRTALQKEITTRYQLD PKFITSILYENNVITIDLVQNS SQKTQNDVDIADVAYYFEKDVK GESLFHSKKMDLTVNGEQLDLD PGQTLIYYVDEKAPEFSMQGLK |
| 138 | EpCAM extracellular portion | chimp cDNA | AA | QEECVCENYKLAVNCFVNNNHQ CQCTSIGAQNTVICSKLAAKCL VMKAEMNGSKLGRRAKPEGALQ NNDGLYDPDCDESGLFKAKQCN GTSTCWCVNTAGVRRTDKDTEI TCSERVRTYWIIIELKHKAREK PYDGKSLRTALQKEITTRYQLD PKFITNILYENNVITIDLVQNS SQKTQNDVDIADVAYYFEKDVK GESLFHSKKMDLTVNGEQLDLD PGQTLIYYVDEKAPEFSMQGLK |
| 139 | EpCAM extracellular portion | rhesus cDNA | AA | IDENTICAL WITH CYNO-MOLGUS EPCAM SHOWN IN FIG. 6 AND SEQ ID NO. 48 |
| 142 | human CD3 gamma extracellular portion | human cDNA; NM_000073 | AA | QSIKGNHLVKVYDYQEDGSVLL TCDAEAKNITWFKDGKMIGFLT EDKKKWNLGSNAKDPRGMYQCK GSQNKSKPLQVYYRMCQNCIEL N |
| 143 | human CD3 delta extracellular portion | human cDNA; NM_000732 | AA | FKIPIEELEDRVFVNCNTSITW VEGTVGTLLSDITRLDLGKRIL DPRGIYRCNGTDIYKDKESTVQ VHYRMCQSCVELDPAT |
| 144 | cynomolgus CD3 gamma extracellular portion | cynomolgus cDNA; AB073992 | AA | QSFEENRKLNVYNQEDGSVLLT CHVKNTNITWFKEGKMIDILTA HKNKWNLGSNTKDPRGVYQCKG SKDKSKTLQVYYRMCQNCIELN |
| 145 | cynomolgus CD3 delta extracellular portion | cynomolgus cDNA; AB073991 | AA | FKIPVEELEDRVFVKCNTSVTW VEGTVGTLLTNNTRLDLGKRIL DPRGIYRCNGTDIYKDKESAVQ VHYRMCQNCVELDPAT |
| 146 | Human-like VH (SEQ ID NO.110) x murine VL (SEQ ID NO. 148) scFv | artificial | AA | EVQLLESGGGLVQPGGSLKLSC AASGFTFNTYAMNWVRQAPGKG LEWVARIRSKYNNYATYYADSV KDRFTISRDDSKNTAYLQMNNL KTEDTAVYYCVRHGNFGNSYVS WFAYWGQGTLVTVSSGGGGSGG GGSGGGGSELVVTQESALTTSP GETVTLTCRSSTGAVTTSNYAN WVQEKPDHLFTGLIGGTNKRAP GVPARFSGSLIGDKAALTITGA QTEDEAIYFCALWYSNLWVFGG GTKLTVL |
| 147 | Human-like VH (SEQ ID NO.110) x murine VL (SEQ ID NO. 148) scFv | artificial | NA | gaggtgcagctgctcgagtctg gaggaggattggtgcagcctgg agggtcattgaaactctcatgt gcagcctctggattcaccttca atacctacgccatgaactgggt ccgccaggctccaggaaaggt ttggaatgggttgctcgcataa gaagtaaatataataattatgc aacatattatgccgattcagtg aaagacaggttcaccatctcca gagatgattcaaaaaacactgc ctatctacaaatgaacaacttg aaaactgaggacactgccgtgt actactgtgtgagacatgggaa cttcggtaatagctacgtttcc tggtttgcttactggggccaag ggactctggtcaccgtctcctc aggtggtggtggttctggcggc ggcggctccggtggtggtggtt ctgagctcgttgtgactcagga atctgcactcaccacatccct ggtgaaacagtcacactcactt gtcgctcaagtactgggctgt tacaactagtaactatgccaac tgggtccaagaaaaaccagatc atttattcactggtctaatagg tggtaccaacaagcgagcacca ggtgtgcctgccagattctcag gctccctgattggagacaaggc tgccctcaccatcacaggggca cagactgaggatgaggcaatat atttctgtgctctatggtacag caacctctgggtgttcggtgga ggaaccaaactgactgtccta |

APPENDIX-continued

| SEQ ID NO. | DESIGNATION | SOURCE | TYPE | SEQUENCE |
|---|---|---|---|---|
| 148 | murine VL VL [identical to VL of SEQ ID NO. 4, with exception of the first two amino acid residues] | artificial | AA | ELVVTQESALTTSPGETVTLTC RSSTGAVTTSNYANWVQEKPDH LFTGLIGGTNKRAPGVPARFSG SLIGDKAALTITGAQTEDEAIY FCALWYSNLWVFGGGTKLTVL |
| 149 | murine VL VL [identical to VL of SEQ ID NO. 4, with exception of nucleotides encoding the first two amino acid residues] | artificial | NA | Gagctcgttgtgactcaggaat ctgcactcaccacatcacctgg tgaaacagtcacactcacttgt cgctcaagtactggggctgtta caactagtaactatgccaactg ggtccaagaaaaaccagatcat ttattcactggtctaataggtg gtaccaacaagcgagcaccagg tgtgcctgccagattctcaggc tccctgattggagacaaggctg ccctcaccatcacaggggcaca gactgaggatgaggcaatatat ttctgtgctctatggtacagca acctctgggtgttcggtggagg aaccaaactgactgtccta |
| 150 | CAIX LH scFv | artificial | NA | gacattgtgatgacccagtctc aaagattcatgtccacaacagt aggagacagggtcagcatcacc tgcaaggccagtcagaatgtgg tttctgctgttgcctggtatca acagaaaccaggacaatctcct aaactactgatttactcagcat ccaatcggtacactggagtccc tgatcgcttcacaggcagtgga tctgggacagatttcactctca ccattagcaatatgcagtctga agacctggctgatttttttctgt caacaatatagcaactatccgt ggacgttcggtggaggcaccaa gctggaaatcaaaggtggtggt ggttctggcggcggcggctccg gtggtggtggttctgacgtgaa gctcgtggagtctgggggaggc ttagtgaagcttggagggtccc tgaaactctcctgtgcagcctc tggattcactttcagtaactat acatgtcttgggttcgccaga ctccagagaagaggctggagtt ggtcgcagccattaatagtgat ggtggtatcacctactatcag acactgtgaagggccgattcac catttcaagagacaatgccaag aacaccctgtacctgcaaatga gcagtctgaaagtctgaggacac agccttgttttactgtgcaaga caccgctcgggctacttttcta tggactactggggtcaaggaac ctcagtcaccgtctcctcc |
| 151 | CAIX LH scFv | artificial | AA | DIVMTQSQRFMSTTVGDRVSIT CKASQNVVSAVAWYQQKPGQSP KLLIYSASNRYTGVPDRFTGSG SGTDFTLTISNMQSEDLADFFC QQYSNYPWTFGGGTKLEIKGGG GSGGGGSGGGGSDVKLVESGGG LVKLGGSLKLSCAASGFTFSNY YMSWVRQTPEKRLELVAAINSD GGITYYLDTVKGRFTISRDNAK NTLYLQMSSLKSEDTALFYCAR HRSGYFSMDYWGQGTSVTVSS |
| 152 | EGFR21 LH scFv | artificial | NA | gacattgtgctgacacagtctc ctgcttcctacctgtgtctct ggggcagagggccaccatctca tgcagggccagccaaagtgtca gttcatctacttatagttatat acactggtaccaacagaaacca ggacagccacccaaactcctca tcacgtatgcatccaacctaga atctggggtccctgccaggttc agtggcagtgggtctgggacag acttcaccctcgacatccatcc tgtggaggaggatgattcttca acatattactgtcagcacagtt gggagattccatttacgttcgg ctcggggacaaagttggaaata aaaggtggtggtggttctggcg gcggcggctccggtggtggtgg ttctcaggttcagctgcagcag tctggacctgatctggtgaagc ctggggcctcagtgaagatgtc ctgcaaggcttctggacacact ttcactgactgtgttataatct gggtgaaacagagagctggaca gggccttgagtggattggacag atttatccagggactggtcgtt cttactacaatgagattttcaa gggcaaggccacactgactgca gacaaatcctccaacacagtcc acattcaactcagcagcctgac atctgaggactctgcggtctat ttctgtgccctatctactctta ttcacgggacctggttttctta ttggggccaagggactctggtc actgtctcttcc |
| 153 | EGFR21 LH scFv | artificial | AA | DIVLTQSPASLPVSLGQRATIS CRASQSVSSSTYSYIHWYQQKP GQPPKLLITYASNLESGVPARF SGSGSGTDFTLDIHPVEEDDSS TYYCQHSWEIPFTFGSGTKLEI KGGGGSGGGGSGGGGSQVQLQQ SGPDLVKPGASVKMSCKASGHT FTDCVIIWVKQRAGQGLEWIGQ IYPGTGRSYYNEIFKGKATLTA DKSSNTVHIQLSSLTSEDSAVY FCALSTLIHGTWFSYWGQGTLV TVSS |
| 154 | EGFRvIII-LH scFv | artificial | NA | gatgttgtgatgacccagactc cactcactttgtcggttaccat tggacaaccagcctctatctct tgcaagtcaagtcagagcctct tatatagtaatggaaaaaccta tttgaattggttattacagagg ccaggccagtctccaaagcgcc taatctatctggtatctaaact ggactctggagtccctgacagg ttcactggcagtggatcaggaa cagatttacactgaaaatcag cagagtggaggctgaggatttg ggaatttattactgcgtgcaag atacacattttcctcagacatt cggtggaggcaccaagctggaa atcaaggtggtggtggttctg gcggcggcggctccggtggtgg tggttctgaggtccagctgcaa cagtctggacctgagctgctga agcctggggcttcagtgaagat atcctgcaagacttctggatac acattcactgaatacaccatac actgggtgaagcagagccatgg aaagggccttgagtggattgga ggtattgatcctaacaatggtg gtactatgtataaccaaaaatt caagggcaaggccacattgact gtagacaagtcttccagcacag |

APPENDIX-continued

| SEQ ID NO. | DESIGNATION | SOURCE | TYPE | SEQUENCE |
|---|---|---|---|---|
| | | | | cctacacggacctccgcagcct |
| | | | | gacgtctgaggattctgcagtc |
| | | | | tattactgcacaagagcagagg |
| | | | | ctatggactactggggtcaagg |
| | | | | aacctcagtcaccgtctcctcc |
| 155 | EGFRvIII-LH scFv | artificial | AA | DVVMTQTPLTLSVTIGQPASIS CKSSQSLLYSNGKTYLNWLLQR PGQSPKRLIYLVSKLDSGVPDR FTGSGSGTDFTLKISRVEAEDL GIYYCVQDTHFPQTFGGGTKLE IKGGGGSGGGGSGGGGSEVQLQ QSGPELLKPGASVKISCKTSGY TFTEYTIHWVKQSHGKSLEWIG GIDPNNGGTMYNQKFKGKATLT VDKSSSTAYTDLRSLTSEDSAV YYCTRAEAMDYWGQGTSVTVSS |
| 156 | CAIX LHx SEQ ID NO. 10 | artificial | NA | gacattgtgatgacccagtctc aaagattcatgtccacaacagt aggagacagggtcagcatcacc tgcaaggccagtcagaatgtgg tttctgctgttgcctggtatca acagaaaccaggacaatctcct aaactactgatttactcagcat ccaatcggtacactggagtccc tgatcgcttcacaggcagtgga tctgggacagatttcactctca ccattagcaatatgcagtctga agacctggctgattttttctgt caacaatatagcaactatccgt ggacgttcggtggaggcaccaa gctggaaatcaaaggtggtggt ggttctggcggcggcggctccg gtggtggtggttctgacgtgaa gctcgtggagtctgggggaggc ttagtgaagcttggagggtccc tgaaactctcctgtgcagcctc tggattcacttttcagtaactat tacatgtcttgggttcgccaga ctccagagaagaggctggagtt ggtcgcagccattaatagtgat ggtggtatcacctactatctag acactgtgaagggccgattcac catttcaagagacaatgccaag aacaccctgtacctgcaaatga gcagtctgaagtctgaggacac agccttgttttactgtgcaaga caccgctcgggctactttctac tggactactggggtcaaggaac ctcagtcaccgtctcctccgga ggtggtggatccgaggtgaagc ttctcgagtctggaggaggatt ggtgcagcctaaagggtcattg aaactctcatgtgcagcctctg gattcaccttcaatacctacgc catgaactgggtccgccaggct ccaggaaagggtttggaatggg ttgctcgcataagaagtaaata taataattatgcaacatattat gccgattcagtgaagacaggt tcaccatctccagagatgattc acaaagcattctctatctacaa atgaacaacttgaaaactgagg acacagccatgtactactgtgt gagacatgggaacttcggtaat agctacgttcctggttttgctt actggggccaagggactctggt cactgtctctgcaggtggtggt ggttctggcggcggcggctccg gtggtggtggttctcaggctgt tgtgactcaggaatctgcactc accacatcacctggtgaaacag tcacactcacttgtcgctcaag tactggggctgttacaactagt aactatgccaactgggtccaag |
| | | | | aaaaaccagatcattttattcac tggtctaataggtggtaccaac aagcgagctccaggtgtgcctg ccagattctcaggctccctgat tggagacaaggctgccctcacc atcacaggggcacagactgagg atgaggcaatatatttctgtgc tctatggtacagcaacctctgg gtgttcggtggaggaaccaaac tgactgtccta |
| 157 | CAIX LHx SEQ ID NO. 10 | artificial | AA | DIVMTQSQRFMSTTVGDRVSIT CKASQNVVSAVAWYQQKPGQSP KLLIYSASNRYTGVPDRFTGSG SGTDFTLTISNMQSEDLADFFC QQYSNYPWTFGGGTKLEIKGGG GSGGGGSGGGGSDVKLVESGGG LVKLGGSLKLSCAASGFTFSNY YMSWVRQTPEKRLELVAAINSD GGITYYLDTVKGRFTISRDNAK NTLYLQMSSLKSEDTALFYCAR HRSGYFSMDYWGQGTSVTVSSG GGGSEVKLLESGGGLVQPKGSL KLSCAASGFTFNTYAMNWVRQA PGKGLEWVARIRSKYNNYATYY ADSVKDRFTISRDDSQSILYLQ MNNLKTEDTAMYYCVRHGNFGN SYVSWFAYWGQGTLVTVSAGGG GSGGGGSGGGGSQAVVTQESAL TTSPGETVTLTCRSSTGAVTTS NYANWVQEKPDHLFTGLIGGTN KRAPGVPARFSGSLIGDKAALT ITGAQTEDEAIYFCALWYSNLW VFGGGTKLTVL |
| 158 | EGFR21 LHx SEQ ID NO. 10 | artificial | NA | gacattgtgctgacacagtctc ctgcttccttacctgtgtctct ggggcagagggccaccatctca tgcagggccagcaaaagtgtca gttcatctacttatagttatat acactggtaccaacagaaacca ggacagccaccccaaactcctca tcacgtatgcatccaacctaga atctggggtccctgccaggttc agtggcagtgggtctgggacag acttcaccctcgacatccatcc tgtggaggaggatgattcttca acatattactgtcagcacagtt gggagattccatttacgttcgg ctcggggacaaagttggaaata aaaggtggtggtggttctggcg gcggcggctccggtggtggtgg ttctcaggttcagctgcagcag tctggacctgatctggtgaagc ctgggcctcagtgaagatgtc ctgcaaggcttctggacacact ttcactgactgtgttataatct gggtgaaacagagagctggaca gggccttgagtggattggacag atttatccagggactggtcgtt cttactacaatgagattttcaa gggcaaggccacactgactgca gacaaatcctccaacacagtcc acattcaactcagcagcctgac atctgaggactctgcggtctat ttctgtgcccatctactcttta ttcacggacctggttttctta ttggggccaagggactctggtc actgtctcttccggaggtggtg gatccgaggtgaagcttctcga gtctggaggaggattggtgcag cctaaagggtcattgaaactct catgtgcagcctctggattcac cttcaatacctacgccatgaac tgggtccgccaggctccaggaa agggtttggaatgggttgctcg |

APPENDIX-continued

| SEQ ID NO. | DESIGNATION | SOURCE | TYPE | SEQUENCE |
|---|---|---|---|---|
| | | | | cataagaagtaaatataataat tatgcaacatattatgccgatt cagtgaaagacaggttcaccat ctccagagatgattcacaaagc attctctatctacaaatgaaca acttgaaaactgaggacacagc catgtactactgtgtgagacat gggaacttcggtaatagctacg tttcctggttttgcttactgggg ccaagggactctggtcactgtc tctgcaggtggtggtggttctg gcggcggcggctccggtggtgg tggttctcaggctgttgtgact caggaatctgcactcaccacat cacctggtgaaacagtcacact cacttgtcgctcaagtactggg gctgttacaactagtaactatg ccaactgggtccaagaaaaacc agatcatttattcactggtcta ataggtggtaccaacaagcgag ctccaggtgtgcctgccagatt ctcaggctccctgattggagac aaggctgccctcaccatcacag gggcacagactgaggatgaggc aatatatttctgtgctctatgg tacagcaacctctgggtgttcg gtggaggaaccaaactgactgt ccta |
| 159 | EGFR21LHx SEQ ID NO. 10 | artificial | AA | DIVLTQSPASLPVSLGQRATIS CRASQSVSSSTYSYIHWYQQKP GQPPKLLITYASNLESGVPARF SGSGSGTDFTLDIHPVEEDDSS TYYCQHSWEIPFTFGSGTKLEI KGGGGSGGGGSGGGGSQVQLQQ SGPDLVKPGASVKMSCKASGHT FTDCVIIWVKQRAGQGLEWIGQ IYPGTGRSYYNEIFKGKATLTA DKSSNTVHIQLSSLTSEDSAVY FCALSTLIHGTWFSYWGQGTLV TVSSGGGGSEVKLLESGGGLVQ PKGSLKLSCAASGFTFNTYAMN WVRQAPGKGLEWVARIRSKYNN YATYYADSVKDRFTISRDDSQS ILYLQMNNLKTEDTAMYYCVRH GNFGNSYVSWFAYWGQGTLVTV SAGGGGSGGGGSGGGGSQAVVT QESALTTSPGETVTLTCRSSTG AVTTSNYANWVQEKPDHLFTGL IGGTNKRAPGVPARFSGSLIGD KAALTITGAQTEDEAIYFCALW YSNLWVFGGGTKLTVL |
| 160 | EGFRvIII-LHx SEQ ID NO. 10 | artificial | NA | gatgttgtgatgacccagactc cactcactttgtcggttaccat tggacaaccagcctctatctct tgcaagtcaagtcagagcctct tatatagtaatggaaaaaccta tttgaattggttattacagagg ccaggccagtctccaaagcgcc taatctatctggtatctaaact ggactctggagtccctgacagg ttcactggcagtggatcaggaa cagattttacactgaaaatcag cagagtggaggctgaggatttg ggaatttattactgcgtgcaag atacacatttcctcagacatt cggtggaggcaccaagctggaa atcaaaggtggtggtggttctg gcggcggcggctccggtggtgg tggttctgaggtcaagcttgaa cagtctggacctgagctgctga agcctggggcttcagtgaagat atcctgcaagacttctggatac acattcactgaatacaccatac actgggtgaagcagagccatgg | | | | aaagagccttgagtggattgga ggtattgatcctaacaatggtg gtactatgtataaccaaaaatt caagggcaaggccacattgact gtagacaagtcttccagcacag cctacacggaccctcgcagcct gacgtctgaggattctgcagtc tattactgcacaagagcagagg ctatggactactggggtcaagg aacctcagtcaccgtctcctcc ggaggtggtggatccgaggtga agcttctcgagtctggaggagg attggtgcagcctaaagggtca ttgaaactctcatgtgcagcct ctggattcaccttcaatacctacgccatgaactgggtccgccag gctccaggaaagggtttggaat gggttgctcgcataagaagtaa atataataattatgcaacatat tatgccgattcagtgaaagaca ggttcaccatctccagagatga ttcacaaagcattctctatcta caaatgaacaacttgaaaactg aggacacagccatgtactactg tgtgagacatgggaacttcggt aatagctacgtttcctggttttg cttactggggccaagggactct ggtcactgtctctgcaggtggt ggtggttctggcggcggcggct ccggtggtggtggttctcaggc tgttgtgactcaggaatctgca ctcaccacatcacctggtgaaa cagtcacactcacttgtcgctc aagtactggggctgttacaact agtaactatgccaactgggtcc aagaaaaaccagatcatttatt cactggtctaataggtggtacc aacaagcgagctccaggtgtgc ctgccagattctcaggctccct gattggagacaaggctgccctc accatcacaggggcacagactg aggatgaggcaatatatttctg tgctctatggtacagcaacctc tgggtgttcggtggaggaacca aactgactgtccta |
| 161 | EGFRvIII-LHx SEQ ID NO. 10 | artificial | AA | DVVMTQTPLTLSVTIGQPASIS CKSSQSLLYSNGKTYLNWLLQR PGQSPKRLIYLVSKLDSGVPDR FTGSGSGTDFTLKISRVEAEDL GIYYCVQDTHFPQTFGGGTKLE IKGGGGSGGGGSGGGGSEVQLQ QSGPELLKPGASVKISCKTSGY TFTEYTIHWVKQSHGKSLEWIG GIDPNNGGTMYNQKFKGKATLT VDKSSSTAYTDLRSLTSEDSAV YYCTRAEAMDYWGQGTSVTVSS GGGGSEVKLLESGGGLVQPKGS LKLSCAASGFTFNTYAMNWVRQ APGKGLEWVARIRSKYNNYATY YADSVKDRFTISRDDSQSILYL QMNNLKTEDTAMYYCVRHGNFG NSYVSWFAYWGQGTLVTVSAGG GGSGGGGSGGGGSQAVVTQESA LTTSPGETVTLTCRSSTGAVTT SNYANWVQEKPDHLFTGLIGGT NKRAPGVPARFSGSLIGDKAAL TITGAQTEDEAIYFCALWYSNL WVFGGGTKLTVL |
| 162 | anti CD3 (as used in WO 99/54440) | artificial | AA | DIKLQQSGAELARPGASVKMSC KTSGYTFTRYTMHWVKQRPGQG LEWIGYINPSRGYTNYNQKFKD KATLTTDKSSSTAYMQLSSLTS EDSAVYYCARYYDDHYCLDYWG QGTTLTVSSVEGGSGGSGGSGG |

APPENDIX-continued

| SEQ ID NO. | DESIG- NATION | SOURCE | TYPE | SEQUENCE |
|---|---|---|---|---|
| | | | | SGGVDDIQLTQSPAIMSASPGE KVTMTCRASSSVSYMNWYQQKS GTSPKRWIYDTSKVASGVPYRF SGSGSGTSYSLTISSMEAEDAA TYYCQQWSSNPLTFGAGTKLEL K |
| 163 | deimmunised (di)-anti CD3 | arti- ficial | AA | DVQLVQSGAEVKKPGASVKVSC KASGYTFTRYTMHWVRQAPGQG LEWIGYINPSRGYTNYADSVKG RFTITTDKSTSTAYMELSSLRS EDTATYYCARYDDHYCLDYWG QGTTVTVSSGEGTSTGSGGSGG SGGADDIVLTQSPATLSLSPGE RATLSCRASQSVSYMNWYQQKP GKAPKRWIYDTSKVASGVPARY SGSGSGTDYSLTINSLEAEDAA TYYCQQWSSNPLTFGGGTKVEI K |
| 164 | VL: CDR3 | murine | AA | QQWSRNPPT |
| 165 | VL: CDR2 | murine | AA | DSSKLAS |
| 166 | VL: CDR1 | murine | AA | SASSSVSYMN |
| 167 | Human-like VL | arti- ficial | NA | gagctcgttgtgactcaggaac cttcactcaccgtatcacctgg tggaacagtcacactcacttgt cgctcgtcgactgggctgtta caactagcaactatgccaactg ggtccaacaaaaaccaggtcag gcacccgtggtctaataggtg gtaccaacaagcgcgcaccag tactcctgccagattctcaggc tccctgcttggaggcaaggctg ccctcaccctctcaggggtaca gccagaggatgaggcagaatat tactgtgctctatggtacagca acctctgggtgttcggtggagg aaccaaactgactgtccta |
| 168 | Human-like VL | arti- ficial | AA | ELVVTQEPSLTVSPGGTVTLTC RSSTGAVTTSNYANWVQQKPGQ APRGLIGGTNKRAPGTPARFSG SLLGGKAALTLSGVQPEDEAEY YCALWYSNLWvFGGGTKLTVL |
| 169 | Human-like VH (SEQ ID NO. 110) x Human- like VL (SEQ ID NO. 168) scFv | arti- ficial | NA | gaggtgcagctgctcgagtctg gaggaggattggtgcagcctgg aggtcattgaaactctcatgt gcagcctctggattcaccttca atacctacgccatgaactgggt ccgccaggctccaggaaaggt ttggaatgggttgctcgcataa gaagtaaatataattatgc aacatattatgccgattcagtg aaagacaggttcaccatctcca gagatgattcaaaaaacactgc ctatctacaaatgaacaacttg aaaactgaggacactgccgtgt actactgtgtgagacatggaa cttcggtaatagctacgtttcc tggtttgcttactggggccaag ggactctggtcaccgtctcctc aggtggtggtggttctggcggc ggcggctccggtggtggtggtt ctgagctcgttgtgactcagga accttcactcaccgtatcacct ggtggaacagtcacactcactt gtcgctcgtcgactgggctgt tacaactagcaactatgccaac tgggtccaacaaaaaccaggtc aggcacccgtggtctaatagg tggtaccaacaagcgcgcacca ggtactcctgccagattctcag |
| 170 | Human-like VH (SEQ ID NO. 110) x Human- like VL (SEQ ID NO. 168) scFv | arti- ficial | AA | EVQLLESGGGLVQPGGSLKLSC AASGFTFNTYAMNWVRQAPGKG LEWVARIRSKYNNYATYYADSV KDRFTISRDDSKNTAYLQMNNL KTEDTAVYYCVRHGNFGNSYVS WFAYWGQGTLVTVSSGGGGSGG GGSGGGGSELVVTQEPSLTVSP GGTVTLTCRSSTGAVTTSNYAN WVQQKPGQAPRGLIGGTNKRAP GTPARFSGSLLGGKAALTLSGV QPEDEAEYYCALWYSNLWVFGG GTKLTVL |
| 171 | EGFR HL x SEQ ID NO. 170 | arti- ficial | NA | caggtgcagctgcagcagtctg ggcctgatctggtgaagcctgg ggcctcagtgaagatgtcctgc aaggcttctggacacactttca ctgactgtgttataatctgggt gaaacagagagctggacaggc cttgagtggattggacagattt atccagggactggtcgttctta ctacaatgagattttcaaggc aaggccacactgactgcagaca atcctccaacacagtccacat tcaactccagcagcctgacatct gaggactctgcggtctatttct gtgccctatctactcttattca cgggacctggttttcttattgg ggccaagggactctggtcactg tctcttccggtggtggtggttc tggcggcggcggctccggtggt ggtggttctgacattgtactga cccagtctccagcttccttacc tgtgtctctggggcagagggcc accatctcatgcagggccagcc aaagtgtcagttcatctactta tagttatatacactggtaccaa cagaaaccaggacagccaccca aactcctcatcacgtatgcatc caacctagaatctggggtccct gccaggttcagtggcagtgggt ctgggacagacttcaccctcga catccatcctgtgaggaggat gattcttcaacatattactgtc agcacagttgggagattccatt tacgttcggctcggggacaaag ttggaaataaaatccggaggtg gtggctccgaggtgcagctggt ggagtctggaggaggattggtg cagcctggaggtcattgaaac tctcatgtgcagcctctggatt caccttcaataacctacgccatg aactgggtccgccaggctccag gaaaggggtttggaatgggttgc tcgcataagaagtaaatataat aattatgcaacatattatgccg attcagtgaaagacaggttcac catctccagagatgattcaaaa aacactgcctatctacaaatga acaacttgaaaactgaggacac tgccgtgtactactgtgtgaga catgggaacttcggtaatagct acgttcctggttgcttactg gggccaagggactctggtcacc gtctcctcaggtggtggtggtt ctggcggcggcggctccggtgg tggtggttctgacccgttgtg actcaggaaccttcactcaccg tatcacctggtggaacagtcac |

APPENDIX-continued

| SEQ ID NO. | DESIGNATION | SOURCE | TYPE | SEQUENCE |
|---|---|---|---|---|
| | | | | actcacttgtcgctcgtccact ggggctgttacaactagcaact atgccaactgggtccaacaaaa accaggtcaggcacccgtggt ctaataggtggtaccaacaagc gcgcaccaggtactcctgccag attctcaggctccctgcttgga ggcaaggctgccctcaccctct caggggtacagccagaggatga ggcagaatattactgtgctcta tggtacagcaacctctgggtgt tcggtggaggaaccaaactgac tgtcctacatcatcaccatcat cattaggtcgac |
| 172 | EGFR HL x SEQ ID NO. 170 | artificial | AA | QVQLQQSGPDLVKPGASVKMSC KASGHTFTDCVIIWVKQRAGQG LEWIGQIYPGTGRSYYNEIFKG KATLTADKSSNTVHIQLSSLTS EDSAVYFCALSTLIHGTWFSYW GQGTLVTVSSGGGGSGGGGSGG GGSDIVLTQSPASLPVSLGQRA TISCRASQSVSSSTYSYIHWYQ QKPGQPPKLLITYASNLESGVP ARFSGSGSGTDFTLDIHPVEED DSSTYYCQHSWEIPFTFGSGTK LEIKSGGGGSEVQLVESGGGLV QPGGSLKLSCAASGFTFNTYAM NWVRQAPGKGLEWVARIRSKYN NYATYYADSVKDRFTISRDDSK NTAYLQMNNLKTEDTAVYYCVR HGNFGNSYVSWFAYWGQGTLVT VSSGGGGSGGGGSGGGGSQTVV TQEPSLTVSPGGTVTLTCRSST GAVTTSNYANWVQQKPGQAPRG LIGGTNKRAPGTPARFSGSLLG GKAALTLSGVQPEDEAEYYCAL WYSNLWVFGGGTKLTVLHHHHH H*VD |
| 173 | EGFR LH x SEQ ID NO. 170 | artificial | NA | gacattgtgctgacacagtctc ctgcttccttacctgtgtctct ggggcagagggccaccatctca tgcagggccagccaaagtgtca gttcatctacttatagttatat acactggtaccaacagaaacca ggacagccacccaaactcctca tcacgtatgcatccaacctaga atctggggtccctgccaggttc agtggcagtgggtctgggacag acttcaccctcgacatccatcc tgtgaggaggatgattcttca acatattactgtcagcacagtt gggagattccatttacgttcgg ctcggggacaaagttggaaata aaaggtggtggtggttctggcg gcggcggctccggtggtggtgg ttctcaggttcagctgcagcag tctggacctgatctggtgaagc ctggggcctcagtgaagatgtc ctgcaaggcttctggacacact ttcactgactgtgttataatct gggtgaaacagagagctggaca gggccttgagtggattggacag atttatccagggactggtcgtt cttactacaatgagattttcaa gggcaaggccacactgactgca gacaaatcctccaacacagtcc acattcaactcagcagcctgac atctgaggactctgcggtctat ttctgtgccctatctactcctta ttcacgggacctggttttctta ttggggccaagggactctggtc actgtctcttccgaggtggtg gctccgaggtgcagctggtgga gtctggaggaggattggtgcag |
| | | | | cctggagggtcattgaaactct catgtgcagcctctggattcac cttcaatacctacgccatgaac tgggtccgccaggctccaggaa agggtttggaatgggttgctcg cataagaagtaaatataataat tatgcaacatattatgccgatt cagtgaaagcaggttccaccat ctccagagatgattcaaaaaac actgcctatctacaaatgaaca acttgaaaactgaggacactgc cgtgtactactgtgtgagacat gggaacttcggtaatagctacg tttcctggtttgcttactgggg ccaagggactctggtcaccgtc tcctcaggtggtggtggttctg gcggcggcggctccggtggtgg tggttctcagaccgttgtgact caggaaccttcactcaccgtat cacctggtggaacagtcacact cacttgtcgctcgtccactggg gctgttacaactagcaactatg ccaactgggtccaacaaaaacc aggtcaggcacccgtggtcta ataggtggtaccaacaagcgcg caccaggtactcctgccagatt ctcaggctccctgcttggaggc aaggctgccctcaccctctcag gggtacagccagaggatgaggc agaatattactgtgctctatgg tacagcaacctctgggtgttcg gtggaggaaccaaactgactgt cctacatcatcaccatcatcat taggtcgac |
| 174 | EGFR LH x SEQ ID NO. 170 | artificial | AA | DIVLTQSPASLPVSLGQRATIS CRASQSVSSSTYSYIHWYQQKP GQPPKLLITYASNLESGVPARF SGSGSGTDFTLDIHPVEEDDSS TYYCQHSWEIPFTFGSGTKLEI KGGGGSGGGGSGGGGSQVQLQQ SGPDLVKPGASVKMSCKASGHT FTDCVIIWVKQRAGQGLEWIGQ IYPGTGRSYYNEIFKGKATLTA DKSSNTVHIQLSSLTSEDSAVY FCALSTLIHGTWFSYWGQGTLV TVSSGGGGSEVQLVESGGGLVQ PGGSLKLSCAASGFTFNTYAMN WVRQAPGKGLEWVARIRSKYNN YATYYADSVKDRFTISRDDSKN TAYLQMNNLKTEDTAVYYCVRH GNFGNSYVSWFAYWGQGTLVTV SSGGGGSGGGGSGGGGSQTVVT QEPSLTVSPGGTVTLTCRSSTG AVTTSNYANWVQQKPGQAPRGL IGGTNKRAPGTPARFSGSLLGG KAALTLSGVQPEDEAEYYCALW YSNLWVFGGGTKLTVLHHHHH *VD |
| 175 | EGFR HL x SEQ ID NO. 194 | artificial | NA | caggtgcagctgcagcagtctg gacctgatctggtgaagcctgg ggcctcagtgaagatgtcctgc aaggcttctggacacactttca ctgactgtgttataatctgggt gaaacagagagctggacagggc cttgagtggattggacagattt atccagggactggtcgttctta ctacaatgagattttcaagggc aaggccacactgactgcagaca aatcctccaacacagtccacat tcaactcagcagcctgacatct gaggactctgcggtctatttct gtgccctatctactcttattca cgggacctggttttcttattgg ggccaagggactctggtcactg |

APPENDIX-continued

| SEQ ID NO. | DESIGNATION | SOURCE | TYPE | SEQUENCE |
|---|---|---|---|---|
| | | | | tctcttccggtggtggtggttc tggcggcggcggctccggtggt ggtggttctgacattgtactga cccagtctccagcttccttacc tgtgtctctggggcagagggcc accatctcatgcagggccagcc aaagtgtcagttcatctactta tagttatatacactggtaccaa cagaaaccaggacagccaccca aactcctcatcacgtatgcatc caacctagaatctggggtccct gccaggttcagtggcagtgggt ctgggacagacttcaccctcga catccatcctgtggaggaggat gattcttcaacatattactgtc agcacagttgggagattccatt tacgttcggctcggggacaaag ttggaaataaaatccggaggtg gtggctcccagaccgttgtgac tcaggaaccttcactcaccgta tcacctggtggaacagtcacac tcacttgtcgctcgtccactgg ggctgttacaactagcaactat gccaactgggtccaacaaaaac caggtcaggcaccccgtggtct aataggtggtaccaacaagcgc gcaccaggtactcctgccagat tctcaggctccctgcttggagg caaggctgccctcaccctctca ggggtacagcagaggatgagg cagaatattactgtgctctatg gtacagcaacctctgggtgttc ggtggaggaaccaaactgactg tcctaggtggtggtggttctgg cggcggcggctccggtggtggt ggttctgaggtgcagctggtgg agtctggaggaggattggtgca gcctggagggtcattgaaactc tcatgtgcagcctctggattca ccttcaatacctacgccatgaa ctgggtccgccaggctccagga aagggtttggaatgggttgctc gcataagaagtaaatataataa ttatgcaacatattatgccgat tcagtgaaagacaggttcacca tctccagagatgattcaaaaaa cactgcctatctacaaatgaac aacttgaaaactgaggacactg ccgtgtactactgtgtgagaca tgggaacttcggtaatagctac gtttcctggttttgcttactggg gccaagggactctggtcaccgt ctcctcacatcatcaccatcat cattaggtcgac |
| 176 | EGFR HL x SEQ ID NO. 194 | artificial | AA | QVQLQQSGPDLVKPGASVKMSC KASGHTFTDCVIIWVKQRAGQG LEWIGQIYPGTGRSYYNEIFKG KATLTADKSSNTVHIQLSSLTS EDSAVYFCALSTLIHGTWFSYW GQGTLVTVSSGGGGSGGGGSGG GGSDIVLTQSPASLPVSLGQRA TISCRASQSVSSSTYSYIHWYQ QKPGQPPKLLITYASNLESGVP ARFSGSGSGTDFTLDIHPVEED DSSTYYCQHSWEIPFTFGSGTK LEIKSGGGGSQTVVTQEPSLTV SPGGTVTLTCRSSTGAVTTSNY ANWVQQKPGQAPRGLIGGTNKR APGTPARFSGSLLGGKAALTLS GVQPEDEAEYYCALWYSNLWVF GGGTKLTVLGGGGSGGGGSGGG GSEVQLVESGGGLVQPGGSLKL SCAASGFTFNTYAMNWVRQAPG KGLEWVARIRSKYNNYATYYAD SVKDRFTISRDDSKNTAYLQMN NLKTEDTAVYYCVRHGNFGNSY VSWFAYWGQGTLVTVSSHHHHH H\*VD |
| 177 | EGFR LH x SEQ ID NO. 194 | artificial | NA | gacattgtgctgacacagtctc ctgcttccttacctgtgtctct ggggcagagggccaccatctca tgcagggccagccaaagtgtca gttcatctacttatagttatat acactggtaccaacagaaacca ggacagccacccaaactcctca tcacgtatgcatccaacctaga atctggggtccctgccaggttc agtggcagtgggtctgggacag acttcaccctcgacatccatcc tgtggaggaggatgattcttca acatattactgtcagcacagtt gggagattccatttacgttcgg ctcggggacaaagttggaaata aaaggtggtggtggttctggcg gcggcggctccggtggtggtgg ttctcaggttcagctgcagcag tctggacctgatctggtgaagc ctggggcctcagtgaagatgtc ctgcaaggcttctggacacact ttcactgactgtgttataatct gggtgaaacagagagctggaca gggccttgagtggattggacag atttatccagggactggtcgtt cttactacaatgagattttcaa gggcaaggccacactgactgca gacaaatcctccaacacagtcc acattcaactcagcagcctgac atctgaggactctgcggtctat ttctgtgcctatctactctta ttcacgggacctggttttctta ttggggccaagggactctggtc actgtctcttcctccggaggtg gtggctcccagaccgttgtgac tcaggaaccttcactcaccgta tcacctggtggaacagtcacac tcacttgtcgctcgtccactgg ggctgttacaactagcaactat gccaactgggtccaacaaaaac caggtcaggcaccccgtggtct aataggtggtaccaacaagcgc gcaccaggtactcctgccagat tctcaggctccctgcttggagg caaggctgccctcaccctctca ggggtacagcagaggatgagg cagaatattactgtgctctatg gtacagcaacctctgggtgttc ggtggaggaaccaaactgactg tcctaggtggtggtggttctgg cggcggcggctccggtggtggt ggttctgaggtgcagctggtgg agtctggaggaggattggtgca gcctggagggtcattgaaactc tcatgtgcagcctctggattca ccttcaatacctacgccatgaa ctgggtccgccaggctccagga aagggtttggaatgggttgctc gcataagaagtaaatataataa ttatgcaacatattatgccgat tcagtgaaagacaggttcacca tctccagagatgattcaaaaaa cactgcctatctacaaatgaac aacttgaaaactgaggacactg ccgtgtactactgtgtgagaca tgggaacttcggtaatagctac gtttcctggttttgcttactggg gccaagggactctggtcaccgt ctcctcacatcatcaccatcat cattaggtcgac |

| SEQ ID NO. | DESIG- NATION | SOURCE | TYPE | SEQUENCE |
|---|---|---|---|---|
| 178 | EGFR LH x SEQ ID NO. 194 | arti- ficial | AA | DIVLTQSPASLPVSLGQRATIS CRASQSVSSSTYSYIHWYQQKP GQPPKLLITYASNLESGVPARF SGSGSGTDFTLDIHPVEEDDSS TYYCQHSWEIPFTFGSGTKLEI KGGGGSGGGGSGGGGSQVQLQQ SGPDLVKPGASVKMSCKASGHT FTDCVIIWVKQRAGQGLEWIGQ IYPGTGRSYYNEIFKGKATLTA DKSSNTVHIQLSSLTSEDSAVY FCALSTLIHGTWFSYWGQGTLV TVSSSGGGGSQTVVTQEPSLTV SPGGTVTLTCRSSTGAVTTSNY ANWVQQKPGQAPRGLIGGTNKR APGTPARFSGSLLGGKAALTLS GVQPEDEAEYYCALWYSNLWVF GGGTKLTVLGGGGSGGGGSGGG GSEVQLVESGGGLVQPGGSLKL SCAASGFTFNTYAMNWVRQAPG KGLEWVARIRSKYNNYATYYAD SVKDRFTISRDDSKNTAYLQMN NLKTEDTAVYYCVRHGNFGNSY VSWFAYWGQGTLVTVSSHHHHH H*VD |
| 179 | SEQ ID NO. 170 x EGFR HL | arti- ficial | NA | gaggtgcagctggtggagtctg gaggaggattggtgcagcctgg agggtcattgaaactctcatgt gcagcctctggattcaccttca atacctacgccatgaactgggt ccgccaggctccaggaaagggt ttggaatgggttgctcgcataa gaagtaaatataataattatgc aacatattatgccgattcagtg aaagacaggttcaccatctcca gagatgattcaaaaaacactgc ctatctacaaatgaacaacttg aaaactgaggacactgccgtgt actactgtgtgagacatgggaa cttcggtaatagctacgtttcc tggtttgcttactggggccaag ggactctggtcaccgtctcctc aggtggtggtggttctggcggc ggcggctccggtggtggtggtt ctcagaccgttgtgactcagga accttcactcaccgtatcacct ggtggaacagtcacactcactt gtcgctcgtccactggggctgt tacaactagcaactatgccaac tgggtccaacaaaaaccaggtc aggcaccccgtggtctaatagg tggtaccaacaagcgcgcacca ggtactcctgccagattctcag gctcccctgcttggaggcaagg tgccctcaccctctcagggta cagccagaggatgaggcagaat attactgtgctctatggtacag caacctctgggtgttcggtgga ggaaccaaactgactgtcctat ccggaggtggtggctcccaggt gcagctgcagcagtctgggcct gatctggtgaagcctggggcct cagtgaagatgtcctgcaaggc ttctggacacactttcactgac tgtgttataatctgggtgaaac agagagctgacaaaggccttga gtggattggacagatttatcca gggactggtcgttcttactaca atgagattttcaagggcaaggc cacactgactgcagacaaatcc tccaacacagtccacattcaac tcagcagcctgacatctgagga ctctgcggtctatttctgtgcc ctatctactcttattcacggga cctggttttcttattgggggcca | agggactctggtcactgtctct tccggtggtggtggttctggcg gcggcggctccggtggtggtgg ttctgacattgtactgacccag tctccagcttccttacctgtgt ctctggggcagagggccaccat ctcatgcagggccagccaaagt gtcagttcatctacttatagtt atatacactggtaccaacagaa accaggacagccacccaaactc ctcatcacgtatgcatccaacc tagaatctggggtccctgccag gttcagtggcagtgggtctggg acagacttcaccctcgacatcc atcctgtggaggaggatgattc ttcaacatattactgtcagcac agttgggagattccatttacgt tcggctcggggacaaagttgga aataaaacatcatcaccatcat cattaggtcgac |
| 180 | SEQ ID NO. 170 x EGFR HL | arti- ficial | AA | EVQLVESGGGLVQPGGSLKLSC AASGFTFNTYAMNWVRQAPGKG LEWVARIRSKYNNYATYYADSV KDRFTISRDDSKNTAYLQMNNL KTEDTAVYYCVRHGNFGNSYVS WFAYWGQGTLVTVSSGGGGSGG GGSGGGGSQTVVTQEPSLTVSP GGTVTLTCRSSTGAVTTSNYAN WVQQKPGQAPRGLIGGTNKRAP GTPARFSGSLLGGKAALTLSGV QPEDEAEYYCALWYSNLWVFGG GTKLTVLGGGGSQVQLQQSGP DLVKPGASVKMSCKASGHTFTD CVIIWVKQRAGQGLEWIGQIYP GTGRSYYNEIFKGKATLTADKS SNTVHIQLSSLTSEDSAVYFCA LSTLIHGTWFSYWGQGTLVTVS SGGGGSGGGGSGGGGSDIVLTQ SPASLPVSLGQRATISCRASQS VSSSTYSYIHWYQQKPGQPPKL LITYASNLESGVPARFSGSGSG TDFTLDIHPVEEDDSSTYYCQH SWEIPFTFGSGTKLEIKHHHHH H*VD |
| 181 | SEQ ID NO. 194 x EGFR HL | arti- ficial | NA | cagaccgttgtgactcaggaac cttcactcaccgtatcacctgg tggaacagtcacactcacttgt cgctcgtccactggggctgtta caactagcaactatgccaactg ggtccaacaaaaaccaggtcag gcaccccgtggtctaataggtg gtaccaacaagcgcgcaccagg tactcctgccagattctcaggc tcccctgcttggaggcaaggctg ccctcaccctctcagggtaca gccagaggatgaggcagaatat tactgtgctctatggtacagca acctctgggtgttcggtggagg aaccaaactgactgtcctaggt ggtggtggttctggcggcggcg gctccggtggtggtggttctga ggtgcagctggtggagtctgga ggaggattggtgcagcctggag ggtcattgaaactctcatgtgc agcctctggattcaccttcaat acctacgccatgaactgggtcc gccaggctccaggaaagggttt ggaatgggttgctcgcataaga agtaaatataataattatgcaa catattatgccgattcagtgaa agacaggttcaccatctccaga gatgattcaaaaaacactgcct atctacaaatgaacaacttgaa aactgaggacactgccgtgtac |

APPENDIX-continued

| SEQ ID NO. | DESIGNATION | SOURCE | TYPE | SEQUENCE |
|---|---|---|---|---|
| | | | | tactgtgtgagacatgggaact |
| | | | | tcggtaatagctacgtttcctg |
| | | | | gtttgcttactggggccaaggg |
| | | | | actctggtcaccgtctcctcat |
| | | | | ccggaggtggtggctcccagt |
| | | | | gcagctgcagcagtctgggcct |
| | | | | gatctggtgaagcctggggcct |
| | | | | cagtgaagatgtcctgcaaggc |
| | | | | ttctggacacactttcactgac |
| | | | | tgtgttataatctgggtgaaac |
| | | | | agagagctggacagggccttga |
| | | | | gtggattggacagatttatcca |
| | | | | gggactggtcgttcttactaca |
| | | | | atgagattttcaagggcaaggc |
| | | | | cacactgactgcagacaaatcc |
| | | | | tccaacacagtccacattcaac |
| | | | | tcagcagcctgacatctgagga |
| | | | | ctctgcggtctatttctgtgcc |
| | | | | ctatctactcttattcacggga |
| | | | | cctggttttcttattgggcca |
| | | | | agggactctggtcactgtctct |
| | | | | tccggtggtggtggttctggcg |
| | | | | gcggcggctccggtggtggtgg |
| | | | | ttctgacattgtactgacccag |
| | | | | tctccagcttccttacctgtgt |
| | | | | ctctggggcagagggccaccat |
| | | | | ctcatgcagggccagccaaagt |
| | | | | gtcagttcatctacttatagtt |
| | | | | atatacactggtaccaacagaa |
| | | | | accaggacagccacccaaactc |
| | | | | ctcatcacgtatgcatccaacc |
| | | | | tagaatctggggtccctgccag |
| | | | | gttcagtggcagtgggtctggg |
| | | | | acagacttcaccctcgacatcc |
| | | | | atcctgtggaggaggatgattc |
| | | | | ttcaacatattactgtcagcac |
| | | | | agttgggagattccatttacgt |
| | | | | tcggctcggggacaaagttgga |
| | | | | aataaaacatcatcaccatcat |
| | | | | cattaggtcgac |
| 182 | SEQ ID NO. 194 x EGFR HL | artificial | AA | QTVVTQEPSLTVSPGGTVTLTC RSSTGAVTTSNYANWVQQKPGQ APRGLIGGTNKRAPGTPARFSG SLLGGKAALTLSGVQPEDEAEY YCALWYSNLWVFGGGTKLTVLG GGGSGGGGSGGGGSEVQLVESG GGLVQPGGSLKLSCAASGFTFN TYAMNWVRQAPGKGLEWVARIR SKYNNYATYYADSVKDRFTISR DDSKNTAYLQMNNLKTEDTAVY YCVRHGNFGNSYVSWFAYWGQG TLVTVSSSGGGGSQVQLQQSGP DLVKPGASVKMSCKASGHTFTD CVIIWVKQRAGQGLEWIGQIYP GTGRSYYNEIFKGKATLTADKS SNTVHIQLSSLTSEDSAVYFCA LSTLIHGTWFSYWGQGTLVTVS SGGGGSGGGGSGGGGSDIVLTQ SPASLPVSLGQRATISCRASQS VSSSTYSYIHWYQQKGQPPKLL ITYASNLESGVPARFSGSGSGT DFTLDIHPVEEDDSSTYYCQHS WEIPFTFGSGTKLEIKHHHHHH *VD |
| 183 | SEQ ID NO. 170 x EGFR HL | artificial | NA | gaggtgcagctggtggagtctg gaggaggattggtgcagcctgg agggtcattgaaactctcatgt gcagcctctggattcaccttca atacctacgccatgaactgggt ccgccaggctccaggaaaggt ttggaatgggttgctcgcataa gaagtaaatataataattatgc aacatattatgccgattcagtg aaagacaggttcaccatctcca gagatgattcaaaaacactgc ctatctacaaatgaacaacttg aaaactgaggacactgccgtgt actactgtgtgagacatgggaa cttcggtaatagctacgtttcc tggtttgcttactggggccaag ggactctggtcaccgtctcctc aggtggtggtggttctggcggc ggcggctccggtggtggtggtt ctcagaccgttgtgactcagga accttcactcaccgtatcacct ggtggaacagtcacactcactt gtcgctcgtccactgggcgtgt tacaactagcaactatgccaac tgggtccaacaaaaaccaggtc aggcacccgtggtctaatagg tggtaccaacaagcgcgcacca ggtactcctgccagattctcag gctccctgcttggaggcaaggc tgccctcaccctctcaggggta cagaggatgaggcagaat attactgtgctctatggtacag caacctctgggtgttcggtgga ggaaccaaactgactgtcctat ccggaggtggtggctccgacat tgtgctgacacagtctcctgct tccttacctgtgtctctggggc agagggccaccatctcatgcag ggccagccaaagtgtcagttca tctacttatagttatatacact ggtaccaacagaaaccaggaca gccacccaaactcctcatcacg tatgcatccaacctagaatctg gggtccctgccaggttcagtgg cagtgggtctgggacagacttc accctcgacatccatcctgtgg aggaggatgattcttcaacata ttactgtcagcacagttgggag attccatttacgttcggctcgg ggacaaagttggaaataaaagg tggtggtggttctggcggcggc ggctccggtggtggtggttctc aggttcagctgcagcagtctgg acctgatctggtgaagcctggg gcctcagtgaagatgtcctgca aggcttctggacacactttcac tgactgtgttataatctgggtg aaacagagagctggacagggcc ttgagtggattggacagatttac tccagggactggtcgttcttac tacaatgagattttcaagggca aggccacactgactgcagacaa atcctccaacacagtccacatt caactcagcagcctgacatctg aggactctgcggtctatttctg tgccctatctactcttattcac gggactggttttcttattggg gccaagggactctggtcactgt ctcttcccatcatcaccatcat cattaggtcgac |
| 184 | SEQ ID NO. 170 x EGFR HL | artificial | AA | EVQLVESGGGLVQPGGSLKLSC AASGFTFNTYAMNWVRQAPGKG LEWVARIRSKYNNYATYYADSV KDRFTISRDDSKNTAYLQMNNL KTEDTAVYYCVRHGNFGNSYVS WFAYWGQGTLVTVSSGGGGSGG GGSGGGGSQTVVTQEPSLTVSP GGTVTLTCRSSTGAVTTSNYAN WVQQKPGQAPRGLIGGTNKRAP GTPARFSGSLLGGKAALTLSGV QPEDEAEYYCALWYSNLWVFGG GTKLTVLGGGGSDIVLTQSPA SLPVSLGQRATISCRASQSVSS STYSYIHWYQQKGQPPKLLIT YASNLESGVPARFSGSGSGTDF |

APPENDIX-continued

| SEQ ID NO. | DESIGNATION | SOURCE | TYPE | SEQUENCE |
|---|---|---|---|---|
| | | | | TLDIHPVEEDDSSTYYCQHSWE IPFTFGSGTKLEIKGGGGSGGG GSGGGGSQVQLQQSGPDLVKPG ASVKMSCKASGHTFTDCVIIWV KQRAGQGLEWIGQIYPGTGRSY YNEIFKGKATLTADKSSNTVHI QLSSLTSEDSAVYFCALSTLIH GTWFSYWGQGTLVTVSSHHHHH H*VD |
| 185 | SEQ ID NO. 194 x EGFR HL | artificial | NA | cagaccgttgtgactcaggaac cttcactcaccgtatcacctgg tggaacagtcacactcacttgt cgctcgtccactgggctgtta caactagcaactatgccaactg ggtccaacaaaaaccaggtcag gcaccccgttggtctaataggt gtaccaacaagcgcgcaccagg tactcctgccagattctcaggc tccctgcttggaggcaaggctg ccctcaccctctcagggtaca gccagaggatgaggcagaatat tactgtgctctatggtacagca acctctgggtgttcggtggagg aaccaaactgactgtcctaggt ggtggtggttctggcggcggcg gctccggtggtggtggttctga ggtgcagctggtgagtctgga ggaggattggtgcagcctggag ggtcattgaaactctcatgtgc agcctctggattcaccttcaat acctacgccatgaactgggtcc gccaggctccaggaaagggttt ggaatggggttgctcgcataaga agtaaatataataattatgcaa catattatgccgattcagtgaa agacaggttcaccatctccaga gatgattcaaaaaacactgcct atctacaaatgaacaacttgaa aactgaggacactgccgtgtac tactgtgtgagacatgggaact tcggtaatagctacgtttcctg gtttgcttactggggccaaggg actctggtcaccgtctcctcat ccggaggtggtggctccgacat tgtgctgacagtcctcctgct tccttacctgtgtctctgggc agagggccaccatctcatgcag ggccagccaaagtgtcagttca tctacttatagttatatacact ggtaccaacagaaaccaggaca gccacccaaactcctcatcacg tatgcatccaacctagaatctg gggtccctgccaggttcagtgg cagtgggtctgggacagacttc accctcgacatccatcctgtgg aggaggatgattcttcaacata ttactgtcagcacagttgggag attccatttacgttcggctcgg ggacaaagttggaaataaaagg tggtggtggttctggcggcggc ggctccggtggtggtggttctc aggttcagctgcagcagtctgg acctgatctggtgaagcctggg gcctcagtgaagatgtcctgca aggcttctggacacactttcac tgactgttataatctgggtg aaacagagagctggacagggcc ttgagtggattggacagattta tccaggactggtcgttcttac tacaatgagattttcaagggga aggccacactgactgcagacaa atcctccaacacagtccacatt caactcagcagcctgacatctg aggactctgcggtctatttctg tgccctatctactcttattcac |

| SEQ ID NO. | DESIGNATION | SOURCE | TYPE | SEQUENCE |
|---|---|---|---|---|
| | | | | gggacctggttttcttattggg gccaagggactctggtcactgt ctcttccatcatcaccatcat cattaggtcgac |
| 186 | SEQ ID NO. 194 x EGFR HL | artificial | AA | QTVVTQEPSLTVSPGGTVTLTC RSSTGAVTTSNYANWVQQKPGQ APRGLIGGTNKRAPGTPARFSG SLLGGKAALTLSGVQPEDEAEY YCALWYSNLWVFGGGTKLTVLG GGGSGGGGSGGGGSEVQLVESG GGLVQPGGSLKLSCAASGFTFN TYAMNWVRQAPGKGLEWVARIR SKYNNYATYYADSVKDRFTISR DDSKNTAYLQMNNLKTEDTAVY YCVRHGNFGNSYVSWFAYWGQG TLVTVSSSGGGGSDIVLTQSPA SLPVSLGQRATISCRASQSVSS STYSYIHWYQQKPGQPPKLLIT YASNLESGVPARFSGSGSGTDF TLDIHPVEEDDSSTYYCQHSWE IPFTFGSGTKLEIKGGGGSGGG GSGGGGSQVQLQQSGPDLVKPG ASVKMSCKASGHTFTDCVIIWV KQRAGQGLEWIGQIYPGTGRSY YNEIFKGKATLTADKSSNTVHI QLSSLTSEDSAVYFCALSTLIH GTWFSYWGQGTLVTVSSHHHHH H*VD |
| 187 | CAIX HL x SEQ ID NO. 194 | artificial | NA | gacgtgaagctcgtggagtctg ggggaggcttagtgaagcttgg agggtccctgaaactctcctgt gcagcctctggattcactttca gtaactattacatgtcttggt tcgccagactccagagaagagg ctggagttggtcgcagccatta atagtgatggtggtatcaccta ctatctagacactgtgaagggc cgattcaccatttcaagagaca atgccaagaacaccctgtacct gcaaatgagcagtctgaagtct gaggacacagccttgttttact gtgcaagacaccgctcgggcta cttttctatggactactgggt caaggaacctcagtcaccgtct cctcaggtggtggtggttctgg cggcggcggctccggtggtggt ggttctgacattgtgatgaccc agtctcaaagattcatgtccac aacagtaggagacagggtcagc atcacctgcaaggccagtcaga atgtggtttctgctgttgcctg gtatcaacagaaaccaggacaa tctcctaaaactactgatttact cagcatccaatcggtacactgg agtccctgatcgcttcacaggc agtggatctgggacagatttca ctctcaccattagcaatatgca gtctgaagacctggctgatttt ttctgtcaacaatatagcaact atccgtggacgttcggtggagg caccaagctggaaatcaaatcc ggaggtggtggctcccagaccg ttgtgactcaggaaccttcact caccgtatcacctggtggaaca gtcacactcacttgtcgctcgt ccactggggctgttacaactag caactatgccaactgggtccaa caaaaaccaggtcaggcacccc gttggtctaataggtgtaccaa caagcgcgcaccaggtactcct gccagattctcaggctccctgc ttggaggcaaggctgccctcac cctctcaggggtacagccagag gatgaggcagaatattactgtg |

APPENDIX-continued

| SEQ ID NO. | DESIGNATION | SOURCE | TYPE | SEQUENCE |
|---|---|---|---|---|
| | | | | ctctatggtacagcaacctctg ggtgttcggtggaggaaccaaa ctgactgtcctaggtggtggtg gttctggcggcggcggctccgg tggtggtggttctgaggtgcag ctggtggagtctgaggaggat tggtgcagcctggagggtcatt gaaactctcatgtgcagcctct ggattcaccttcaatacctacg ccatgaactgggtccgccaggc tccaggaaagggtttggaatgg gttgctcgcataagaagtaaat ataataattatgcaacatatta tgccgattcagtgaaagacagg ttcaccatctccagagatgatt caaaaaacactgcctatctaca aatgaacaacttgaaaactgag gacactgccgtgtactactgtg tgagacatgggaacttcggtaa tagctacgtttcctggtttgct tactggggccaagggactctgg tcaccgtctcctcacatcatca ccatcatcattaggtcgac |
| 188 | CAIX HL x SEQ ID NO. 194 | artificial | AA | DVKLVESGGGLVKLGGSLKLSC AASGFTFSNYYMSWVRQTPEKR LELVAAINSDGGITYYLDTVKG RFTISRDNAKNTLYLQMSSLKS EDTALFYCARHRSGYFSMDYWG QGTSVTVSSGGGGSGGGGSGGG GSDIVMTQSQRFMSTTVGDRVS ITCKASQNVVSAVAWYQQKPGQ SPKLLIYSASNRYTGVPDRFTG SGSGTDFTLTISNMQSEDLADF FCQQYSNYPWTFGGGTKLEIKS GGGGSQTVVTQEPSLTVSPGGT VTLTCRSSTGAVTTSNYANWVQ QKPGQAPRGLIGGTNKRAPGTP ARFSGSLLGGKAALTLSGVQPE DEAEYYCALWYSNLWVFGGGTK LTVLGGGGSGGGGSGGGGSEVQ LVESGGGLVQPGGSLKLSCAAS GFTFNTYAMNWVRQAPGKGLEW VARIRSKYNNYATYYADSVKDR FTISRDDSKNTAYLQMNNLKTE DTAVYYCVRHGNFGNSYVSWFA YWGQGTLVTVSSHHHHHH*VD |
| 189 | CAIX HL x SEQ ID NO. 170 | artificial | NA | gacgtgaagctcgtggagtctg ggggaggcttagtgaagcttgg agggtccctgaaactctcctgt gcagcctctggattcacttttca gtaactattacatgtcttggt tcgccagactccagagaagagg ctggagttggtcgcagccatta atagtgatggtggtatcacccta ctatctagacactgtgaagggc cgattcaccatttcaagagaca atgccaagaacaccctgtacct gcaaatgagcagtctgaagtct gaggacacagccttgttttact gtgcaagacaccgctcgggcta cttttctatggactactggggt caaggaacctcagtcaccgtct cctcaggtggtggtggttctgg cggcggcggctccggtggtggt ggttctgacattgtgatgaccc agtctcaaagattcatgtccac aacagtaggagacagggtcagc atcacctgcaaggccagtcaga atgtggtttctgctgttgcctg gtatcaacagaaaccaggacaa tctcctaaactactgatttact cagcatccaatcggtacactgg agtccctgatcgcttcacaggc agtggatctgggacagatttca |
| | | | | ctctcaccattagcaatatgca gtctgaagacctggctgatttt ttctgtcaacaatatagcaact atccgtggacgttcggtggagg caccaagctggaaatcaaatcc ggaggtggtggctccgaggtgc agctggtggagtctgaggagg attggtgcagcctggagggtca ttgaaactctcatgtgcagcct ctggattcaccttcaatacctcta cgccatgaactgggtccgccag gctccaggaaagggtttggaat gggttgctcgcataagaagtaa atataataattatgcaacatat tatgccgattcagtgaaagaca ggttcaccatctccagagatga ttcaaaaaacactgcctatcta caaatgaacaacttgaaaactg aggacactgccgtgtactactg tgtgagacatgggaacttcggt aatagctacgtttcctggtttg cttactggggccaagggactct ggtcaccgtctcctcaggtggt ggtggttctggcggcggcggct ccggtggtggtggttctgagac cgttgtgactcaggaacctttca ctcaccgtatcacctggtggaa cagtcacactcacttgtcgctc gtccactgggctgttacaact agcaactatgccaactgggtcc aacaaaaaccaggtcaggcacc ccgtggtctaataggtggtacc aacaagcgcgcaccaggtactc ctgccagattctcaggctccct gcttggaggcaaggctgccctc accctctcaggggtacagccag aggatgaggcagaatattactg tgctctatggtacagcaacctc tggggtgttcggtggaggaacca aactgactgtcctacatcatca ccatcatcattaggtcgac |
| 190 | CAIX HL x SEQ ID NO. 170 | artificial | AA | DVKLVESGGGLVKLGGSLKLSC AASGFTFSNYYMSWVRQTPEKR LELVAAINSDGGITYYLDTVKG RFTISRDNAKNTLYLQMSSLKS EDTALFYCARHRSGYFSMDYWG QGTSVTVSSGGGGSGGGGSGGG GSDIVMTQSQRFMSTTVGDRVS ITCKASQNVVSAVAWYQQKPGQ SPKLLIYSASNRYTGVPDRFTG SGSGTDFTLTISNMQSEDLADF FCQQYSNYPWTFGGGTKLEIKS GGGGSEVQLVESGGGLVQPGGS LKLSCAASGFTFNTYAMNWVRQ APGKGLEWVARIRSKYNNYATY YADSVKDRFTISRDDSKNTAYL QMNNLKTEDTAVYYCVRHGNFG NSYVSWFAYWGQGTLVTVSSGG GGSGGGGSGGGGSQTVVTQEPS LTVSPGGTVTLTCRSSTGAVTT SNYANWVQQKPGQAPRGLIGGT NKRAPGTPARFSGSLLGGKAAL TLSGVQPEDEAEYYCALWYSNL WVFGGGTKLTVLHHHHHH*VD |
| 191 | CAIX LH x SEQ ID NO. 170 | artificial | NA | gacattgtgatgacccagtctc aaagattcatgtccacaacagt aggagacagggtcagcatcacc tgcaaggccagtcagaatgtgg tttctgctgttgcctgg tatca acagaaaccaggacaatctcct aaactactgatttactcagcat ccaatcggtacactggagtccc tgatcgcttcacaggcagtgga tctgggacagatttcactctca |

APPENDIX-continued

| SEQ ID NO. | DESIGNATION | SOURCE | TYPE | SEQUENCE |
|---|---|---|---|---|
| | | | | ccattagcaatatgcagtctga agacctggctgatttttctgt caacaatatagcaactatccgt ggacgttcggtggaggcaccaa gctggaaatcaaaggtggtggt ggttctggcggcggcggctccg gtggtggtggttctgacgtgaa gctcgtggagtctgggggaggc ttagtgaagcttggagggtccc tgaaactctcctgtgcagcctc tggattcactttcagtaactat tacatgtcttgggttcgcaga ctccagagaaggctggagtt ggtcgcagccattaatagtgat ggtggtatcacctactatctag acactgtgaagggccgattcac catttcaagagacaatgccaag aacaccctgtacctgcaaatga gcagtctgaagtctgaggacac agccttgttttactgtgcaaga caccgctcgggctacttttcta tggactactggggtcaaggaac ctcagtcaccgtctcctcctcc ggaggtggtggctccgaggtgc agctggtggagtctggaggagg attggtgcagcctggggctca ttgaaactctcatgtgcagcct ctggattccttcaataccta cgccatgaactgggtccgccag gctccaggaaagggtttggaat gggttgctcgcataagaagtaa atataataattatgcaacatat tatgccgattcagtgaaagaca ggttcaccatctccagagatga ttcaaaaaacactgcctatcta caaatgaacaacttgaaaactg aggacactgccgtgtactactg tgtgagacatgggaacttcggt aatagctacgttctggtttg cttactggggccaagggactct ggtcaccgtctcctcaggtggt ggttctggcggcggcggct ccggtggtggtggttctcagac cgttgtgactcaggaaccttca ctcaccgtatcacctggtggaa cagtcacactcacttgtcgctc gtccactggggctgttacaact agcaactatgccaactgggtcc aacaaaaaccaggtcaggcacc ccgtggtctaataggtggtacc aacaagcgcgcaccaggtactc ctgccagattctcaggctcct gcttggaggcaaggctgccctc accctctcaggggtacagccag aggatgaggcagaatattactg tgctctatggtacagcaacctc tgggtgttcggtggaggaacca aactgactgtcctacatcatca ccatcatcattaggtcgac |
| 192 | CAIX LH × SEQ ID NO. 170 | artificial | AA | DIVMTQSQRFMSTTVGDRVSIT CKASQNVVSAVAWYQQKPGQSP KLLIYSASNRYTGVPDRFTGSG SGTDFTLTISNMQSEDLADFFC QQYSNYPWTFGGGTKLEIKGGG GSGGGGSGGGGSDVKLVESGGG LVKLGGSLKLSCAASGFTFSNY YMSWVRQTPEKRLELVAAINSD GGITYYLDTVKGRFTISRDNAK NTLYLQMSSLKSEDTALFYCAR HRSGYFSMDYWGQGTSVTVSSS GGGGSEVQLVESGGGLVQPGGS LKLSCAASGFTFNTYAMNWVRQ APGKGLEWVARIRSKYNNYATY YADSVKDRFTISRDDSKNTAYL QMNNLKTEDTAVYYCVRHGNFG NSYVSWFAYWGQGTLVTVSSGG GGSGGGGSGGGGSQTVVTQEPS LTVSPGGTVTLTCRSSTGAVTT SNYANWVQQKPGQAPRGLIGGT NKRAPGTPARFSGSLLGGKAAL TLSGVQPEDEAEYYCALWYSNL WVFGGGTKLTVLHHHHHH*VD |
| 193 | Human-like VL (SEQ ID NO. 168) × Human-like VH (SEQ ID NO. 110) scFv | artificial | NA | cagaccgttgtgactcaggaac cttcactcaccgtatcacctgg tggaacagtcacactcacttgt cgctcgtccactggggctgtta caactagcaactatgccaactg ggtccaacaaaaaccaggtcag gcaccccgtggtctaataggtg gtaccaacaagcgcgcaccagg tactcctgccagattctcaggc tccctgcttggaggcaaggctg ccctcaccctctcaggggtaca gccagaggatgaggcagaatat tactgtgctctatggtacagca acctctgggtgttcggtggagg aaccaaactgactgtcctaggt ggtggttctggcggcggcg gctccggtggtggtggttctga ggtgcagctggtggagtctgga ggaggattggtgcagcctggag ggtcattgaaactctcatgtgc agcctctggattccacttcaat acctacgccatgaactgggtcc gccaggctccaggaaagggttt ggaatgggttgctcgcataaga gtaaatataataattatgcaa catattatgccgattcagtgaa agacaggttcaccatctccaga gatgattcaaaaaacactgcct atctacaaatgaacaacttgaa aactgaggacactgccgtgtac tactgtgtgagacatgggaact tcggtaatagctacgtttcctg gtttgcttactggggccaaggg actctggtcaccgtctcctca |
| 194 | Human-like VL (SEQ ID NO. 168) × Human-like VH (SEQ ID NO. 110) scFv | artificial | AA | QTVVTQEPSLTVSPGGTVTLTC RSSTGAVTTSNYANWVQQKPGQ APRGLIGGTNKRAPGTPARFSG SLLGGKAALTLSGVQPEDEAEY YCALWYSNLWVFGGGTKLTVLG GGGSGGGGSGGGGSEVQLVESG GGLVQPGGSLKLSCAASGFTFN TYAMNWVRQAPGKGLEWVARIR SKYNNYATYYADSVKDRFTISR DDSKNTAYLQMNNLKTEDTAVY YCVRHGNFGNSYVSWFAYWGQG TLVTVSS |
| 195 | epitope | artificial | AA | EFSELEQSGYYVC |
| 196 | epitope | artificial | AA | EFSELEQSGYYVK |
| 197 | 5' EGFR XbaI | artificial | NA | GGTCTAGAGCATGCGACCCTCC GGGACGGCCGGG |
| 198 | 3' EGFR SalI | artificial | NA | TTTTAAGTCGACTCATGCTCCA ATAAATTCACTGCT |
| 199 | epitope | artificial | AA | QDGNEEMGSITQT |

APPENDIX-continued

| SEQ ID NO. | DESIGNATION | SOURCE | TYPE | SEQUENCE |
|---|---|---|---|---|
| 200 | epitope | artificial | AA | YVVSYPRGSNPED |
| 201 | epitope | artificial | AA | EFSEMEQSGYYVC |
| 202 | epitope | artificial | AA | FSEXE; X as in SEQ ID NO: 204 |
| 203 | epitope | artificial | AA | QYPGSEILWQHND |
| 204 | epitope | artificial | AA | FSEXE, wherein X represents L (Leucine) or M (Methionine) |
| 205 | epitope | artificial | AA | FSELE |
| 206 | epitope | artificial | AA | FSEME |
| 207 | epitope | artificial | AA | EFSEXEQSGYYVC, wherein X represents L (Leucine) or M (Methionine) |

Abbreviations:
scFv = single chain Fv
AA = amino acid sequence
NA = nuclei acid sequence
L = VL region
H = VH region
Single letter code as used in the sequence listing:
B = C or G or T
D = A or G or T
H = A or C or T
K = G or T?
M = A or C
N = A or C or G or T
R = A or G
S = C or G
V = A or C or G
W = A or T
Y = C or T

The invention claimed is:

1. A bispecific single chain antibody comprising:
   (i) a first binding domain which binds to primate CD3 comprising
      CDR-L1 (SEQ ID NO: 118), CDR-L2 (SEQ ID NO: 117), and CDR-L3 (SEQ ID NO: 116) and CDR-H1 (SEQ ID NO: 115), CDR-H2 (SEQ ID NO: 114) and CDR-H3 (SEQ ID NO: 112) or (SEQ ID NO: 113),
      wherein the first binding domain comprises a VH region comprising the amino acid sequence set forth in SEQ ID NO: 110 and/or a VL region comprising the amino acid sequence set forth in SEQ ID NO: 168; and
   (ii) a second binding domain binding to a cell surface antigen.

2. The bispecific single chain antibody of claim 1, wherein said first binding domain binds to an epitope of human and non-chimpanzee primate CD3 comprising the amino acid sequence of "FSEXE" (SEQ ID NO: 204), wherein "X" represents L (Leucine) or M (Methionine).

3. The bispecific single chain antibody of claim 1, wherein said first binding domain is located C-terminally or N-terminally to the second binding domain.

4. The bispecific single chain antibody of claim 1, wherein the second binding domain binds to a human cell surface antigen and to a non-chimpanzee primate homolog of the cell surface antigen.

5. The bispecific single chain antibody of claim 1, wherein the cell surface antigen is a tumor antigen.

6. The bispecific single chain antibody of claim 1, wherein the first binding domain comprises a VH region comprising the amino acid sequence set forth in SEQ ID NO: 110.

7. The bispecific single chain antibody of claim 1, wherein the first binding domain comprises a VL region comprising the amino acid sequence set forth in SEQ ID NO: 168.

8. The bispecific single chain antibody of claim 1, wherein the VH region of the first binding domain comprises or consists of the amino acid sequence set forth in SEQ ID NO: 110 and the VL region of the first binding domain comprises or consists of the amino acid sequence set forth in SEQ ID NO: 168.

9. The bispecific single chain antibody of claim 5, wherein said tumor antigen is EpCAM, EGFR, EGFRvIII or Carboanhydrase IX (MN/CA IX).

10. The bispecific single chain antibody of claim 1, wherein the primate is a baboon, marmoset or an old world monkey.

11. The bispecific single chain antibody of claim 10, wherein the old world monkey is a monkey of the macaque genus.

12. The bispecific single chain antibody of claim 1, wherein the primate CD3 comprises or consists of the amino acid sequence set forth in SEQ ID NO: 135, 136, 144 or 145.

13. The bispecific single chain antibody of claim 1, wherein at least one of said first or second binding domains is human, humanized, CDR-grafted and/or deimmunized.

14. A composition comprising the bispecific single chain antibody of claim 1 and a carrier, stabilizer, and/or excipient.

15. The bispecific single chain antibody of claim 1, wherein the first binding domain comprises a single chain antibody fragment (scFv) comprising:
   (a) the amino acid sequence set forth in SEQ ID NO: 170; or
   (b) an amino acid sequence encoded by the nucleotide sequence set forth in SEQ ID NO: 169.

16. A bispecific single chain antibody comprising:
   (i) a first binding domain which binds to primate CD3 comprising CDR-L1 (SEQ ID NO: 118), CDR-L2 (SEQ ID NO: 117), and CDR-L3 (SEQ ID NO: 116) and CDR-H1 (SEQ ID NO: 115), CDR-H2 (SEQ ID NO: 114) and CDR-H3 (SEQ ID NO: 112) or (SEQ ID NO: 113),
      wherein the first binding domain comprises a single chain antibody fragment (scFv) comprising:
      (a) the amino acid sequence set forth in SEQ ID NO: 194; or
      (b) an amino acid sequence encoded by the nucleotide sequence set forth in SEQ ID NO: 193; and
   (ii) a second binding domain binding to a cell surface antigen.

* * * * *

SEQUENCE LISTING

<160> NUMBER OF SEQ ID NOS: 207

<210> SEQ ID NO 1
<211> LENGTH: 375
<212> TYPE: DNA
<213> ORGANISM: mus musculus
<220> FEATURE:
<221> NAME/KEY: misc_feature
<222> LOCATION: (1)..(375)
<223> OTHER INFORMATION: VH region

<400> SEQUENCE: 1

```
gaggtgaagc ttctcgagtc tggaggagga ttggtgcagc ctaaagggtc attgaaactc    60
tcatgtgcag cctctggatt caccttcaat acctacgcca tgaactgggt ccgccaggct   120
ccaggaaagg gtttggaatg ggttgctcgc ataagaagta aatataataa ttatgcaaca   180
tattatgccg attcagtgaa agacaggttc accatctcca gagatgattc acaaagcatt   240
ctctatctac aaatgaacaa cttgaaaact gaggacacag ccatgtacta ctgtgtgaga   300
catgggaact tcggtaatag ctacgtttcc tggtttgctt actggggcca agggactctg   360
gtcactgtct ctgca                                                    375
```

<210> SEQ ID NO 2
<211> LENGTH: 125
<212> TYPE: PRT
<213> ORGANISM: mus musculus
<220> FEATURE:
<221> NAME/KEY: misc_feature
<222> LOCATION: (1)..(125)
<223> OTHER INFORMATION: VH region

<400> SEQUENCE: 2

```
Glu Val Lys Leu Leu Glu Ser Gly Gly Gly Leu Val Gln Pro Lys Gly
 1               5                  10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
```

```
                  35                  40                  45
Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Gln Ser Ile
 65                 70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
            115                 120                 125

<210> SEQ ID NO 3
<211> LENGTH: 327
<212> TYPE: DNA
<213> ORGANISM: MUS MUSCULUS
<220> FEATURE:
<221> NAME/KEY: misc_feature
<222> LOCATION: (1)..(327)
<223> OTHER INFORMATION: VL region

<400> SEQUENCE: 3
caggctgttg tgactcagga atctgcactc accacatcac ctggtgaaac agtcacactc     60
acttgtcgct caagtactgg ggctgttaca actagtaact atgccaactg gtccaagaa    120 aaaccagatc atttattcac tggtctaata ggtggtacca acaagcgagc tccaggtgtg    180
cctgccagat tctcaggctc cctgattgga gacaaggctg ccctcaccat cacaggggca    240
cagactgagg atgaggcaat atatttctgt gctctatggt acagcaacct ctgggtgttc    300
ggtggaggaa ccaaactgac tgtccta                                        327

<210> SEQ ID NO 4
<211> LENGTH: 109
<212> TYPE: PRT
<213> ORGANISM: mus musculus
<220> FEATURE:
<221> NAME/KEY: misc_feature
<222> LOCATION: (1)..(109)
<223> OTHER INFORMATION: VL region

<400> SEQUENCE: 4

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
 65                 70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 5
<211> LENGTH: 363
<212> TYPE: DNA
<213> ORGANISM: MUS MUSCULUS
```

```
<220> FEATURE:
<221> NAME/KEY: misc_feature
<222> LOCATION: (1)..(363)
<223> OTHER INFORMATION: VH region

<400> SEQUENCE: 5
caggtccagc tgcagcagtc tggggctgaa ctggcaagac ctggggcctc agtgaagatg      60
tcctgcaagg cttctggcta cacctttact agatctacga tgcactgggt aaaacagagg     120
cctggacagg gtctggaatg gattggatac attaatccta gcagtgctta tactaattac     180
aatcagaaat tcaaggacaa ggccacattg actgcagaca atcctccag tacagcctac      240 atgcaactga gtagcctgac atctgaggac tctgcagtct attactgtgc aagtccgcaa     300
gtccactatg attacaacgg gtttccttac tggggccaag ggactctggt cactgtctct     360
gca                                                                   363

<210> SEQ ID NO 6
<211> LENGTH: 121
<212> TYPE: PRT
<213> ORGANISM: mus musculus
<220> FEATURE:
<221> NAME/KEY: misc_feature
<222> LOCATION: (1)..(121)
<223> OTHER INFORMATION: VH region

<400> SEQUENCE: 6

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Ser Pro Gln Val His Tyr Asp Tyr Asn Gly Phe Pro Tyr Trp Gly
        100                 105                 110

Gln Gly Thr Leu Val Thr Val Ser Ala
    115                 120

<210> SEQ ID NO 7
<211> LENGTH: 318
<212> TYPE: DNA
<213> ORGANISM: MUS MUSCULUS
<220> FEATURE:
<221> NAME/KEY: misc_feature
<222> LOCATION: (1)..(318)
<223> OTHER INFORMATION: VL region

<400> SEQUENCE: 7
caagttgttc tcacccagtc tccagcaatc atgtctgcat ttccagggga gaaggtcacc      60
atgacctgca gtgccagctc aagtgtaagt tacatgaact ggtaccagca gaagtcaggc     120
acctccccca aaagatggat ttatgactca tccaaactgg cttctggagt ccctgctcgc     180
ttcagtggca gtgggtctgg gacctcttat tctctcacaa tcagcagcat ggagactgaa     240
gatgctgcca cttattactg ccagcagtgg agtcgtaacc cacccacgtt cggaggggg       300
```
accaagctac aaattaca 318

<210> SEQ ID NO 8
<211> LENGTH: 106
<212> TYPE: PRT
<213> ORGANISM: mus musculus
<220> FEATURE:
<221> NAME/KEY: misc_feature
<222> LOCATION: (1)..(106)
<223> OTHER INFORMATION: VL region

<400> SEQUENCE: 8

Gln Val Val Leu Thr Gln Ser Pro Ala Ile Met Ser Ala Phe Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Arg Asn Pro Pro Thr
                85                  90                  95

Phe Gly Gly Gly Thr Lys Leu Gln Ile Thr
            100                 105

<210> SEQ ID NO 9
<211> LENGTH: 747
<212> TYPE: DNA
<213> ORGANISM: ARTIFICIAL SEQUENCE
<220> FEATURE:
<223> OTHER INFORMATION: VH-VL scFV single chain Fv

<400> SEQUENCE: 9
gaggtgaagc ttctcgagtc tggaggagga ttggtgcagc ctaaagggtc attgaaactc     60
tcatgtgcag cctctggatt caccttcaat acctacgcca tgaactgggt ccgccaggct    120
ccaggaaagg gtttggaatg ggttgctcgc ataagaagta aatataataa ttatgcaaca    180
tattatgccg attcagtgaa agacaggttc accatctcca gagatgattc acaaagcatt    240
ctctatctac aaatgaacaa cttgaaaact gaggacacag ccatgtacta ctgtgtgaga    300
catgggaact tcggtaatag ctacgtttcc tggtttgctt actggggcca agggactctg    360
gtcactgtct ctgcaggtgg tggtggttct ggcggcggcg gctccggtgg tggtggttct    420
caggctgttg tgactcagga atctgcactc accacatcac ctggtgaaac agtcacactc    480
acttgtcgct caagtactgg ggctgttaca actagtaact atgccaactg ggtccaagaa    540
aaaccagatc atttattcac tggtctaata ggtggtacca acaagcgagc tccaggtgtg    600
cctgccagat tctcaggctc cctgattgga acaaggctg ccctcaccat cacaggggca    660
cagactgagg atgaggcaat atatttctgt gctctatggt acagcaacct ctgggtgttc    720
ggtggaggaa ccaaactgac tgtccta    747

<210> SEQ ID NO 10
<211> LENGTH: 249
<212> TYPE: PRT
<213> ORGANISM: artificial sequence
<220> FEATURE:
<223> OTHER INFORMATION: VH-VL scFv single chain Fv

<400> SEQUENCE: 10

| | | | | | | | | | | | | | | |
|---|---|---|---|---|---|---|---|---|---|---|---|---|---|---|
| Glu | Val | Lys | Leu | Leu | Glu | Ser | Gly | Gly | Gly | Leu | Val | Gln | Pro | Lys | Gly |
| 1 | | | | 5 | | | | | 10 | | | | | 15 |
| Ser | Leu | Lys | Leu | Ser | Cys | Ala | Ala | Ser | Gly | Phe | Thr | Phe | Asn | Thr | Tyr |
| | | | 20 | | | | | 25 | | | | | 30 | |
| Ala | Met | Asn | Trp | Val | Arg | Gln | Ala | Pro | Gly | Lys | Gly | Leu | Glu | Trp | Val |
| | | 35 | | | | | 40 | | | | | 45 | | |
| Ala | Arg | Ile | Arg | Ser | Lys | Tyr | Asn | Asn | Tyr | Ala | Thr | Tyr | Tyr | Ala | Asp |
| | 50 | | | | | 55 | | | | | 60 | | | | |
| Ser | Val | Lys | Asp | Arg | Phe | Thr | Ile | Ser | Arg | Asp | Asp | Ser | Gln | Ser | Ile |
| 65 | | | | | 70 | | | | | 75 | | | | | 80 |
| Leu | Tyr | Leu | Gln | Met | Asn | Asn | Leu | Lys | Thr | Glu | Asp | Thr | Ala | Met | Tyr |
| | | | | 85 | | | | | 90 | | | | | 95 | |
| Tyr | Cys | Val | Arg | His | Gly | Asn | Phe | Gly | Asn | Ser | Tyr | Val | Ser | Trp | Phe |
| | | | 100 | | | | | 105 | | | | | 110 | | |
| Ala | Tyr | Trp | Gly | Gln | Gly | Thr | Leu | Val | Thr | Val | Ser | Ala | Gly | Gly | Gly |
| | | 115 | | | | | 120 | | | | | 125 | | | |
| Gly | Ser | Gly | Gly | Gly | Gly | Ser | Gly | Gly | Gly | Gly | Ser | Gln | Ala | Val | Val |
| | 130 | | | | | 135 | | | | | 140 | | | | |
| Thr | Gln | Glu | Ser | Ala | Leu | Thr | Thr | Ser | Pro | Gly | Glu | Thr | Val | Thr | Leu |
| 145 | | | | | 150 | | | | | 155 | | | | | 160 |
| Thr | Cys | Arg | Ser | Ser | Thr | Gly | Ala | Val | Thr | Thr | Ser | Asn | Tyr | Ala | Asn |
| | | | | 165 | | | | | 170 | | | | | 175 | |
| Trp | Val | Gln | Glu | Lys | Pro | Asp | His | Leu | Phe | Thr | Gly | Leu | Ile | Gly | Gly |
| | | | 180 | | | | | 185 | | | | | 190 | | |
| Thr | Asn | Lys | Arg | Ala | Pro | Gly | Val | Pro | Ala | Arg | Phe | Ser | Gly | Ser | Leu |
| | | 195 | | | | | 200 | | | | | 205 | | | |
| Ile | Gly | Asp | Lys | Ala | Ala | Leu | Thr | Ile | Thr | Gly | Ala | Gln | Thr | Glu | Asp |
| | | 210 | | | | | 215 | | | | | 220 | | | |
| Glu | Ala | Ile | Tyr | Phe | Cys | Ala | Leu | Trp | Tyr | Ser | Asn | Leu | Trp | Val | Phe |
| 225 | | | | | 230 | | | | | 235 | | | | | 240 |
| Gly | Gly | Gly | Thr | Lys | Leu | Thr | Val | Leu | | | | | | | |
| | | | | 245 | | | | | | | | | | | |

<210> SEQ ID NO 11
<211> LENGTH: 747
<212> TYPE: DNA
<213> ORGANISM: ARTIFICIAL SEQUENCE
<220> FEATURE:
<223> OTHER INFORMATION: VL-VH scFv single chain Fv

<400> SEQUENCE: 11

```
caggctgttg tgactcagga atctgcactc accacatcac ctggtgaaac agtcacactc      60
acttgtcgct caagtactgg ggctgttaca actagtaact atgccaactg ggtccaagaa     120
aaaccagatc atttattcac tggtctaata ggtggtacca acaagcgagc tccaggtgtg     180
cctgccagat tctcaggctc cctgattgga gacaaggctg ccctcaccat cacagggca      240
cagactgagg atgaggcaat atatttctgt gctctatggt acagcaacct ctgggtgttc     300
ggtggaggaa ccaaactgac tgtcctaggt ggtggtggtt ctggcggcgg cggctccggt     360
ggtggtggtt ctgaggtgaa gcttctcgag tctggaggag gattggtgca gcctaaaggg     420
tcattgaaac tctcatgtgc agcctctgga ttcaccttca ataccctacgc catgaactgg     480
gtccgccagg ctccaggaaa gggtttggaa tgggttgctc gcataagaag taaatataat     540
aattatgcaa catattatgc cgattcagtg aaagacaggt tcaccatctc cagagatgat     600
```

-continued

```
tcacaaagca ttctctatct acaaatgaac aacttgaaaa ctgaggacac agccatgtac    660
tactgtgtga catgggaa cttcggtaat agctacgttt cctggtttgc ttactggggc     720
caagggactc tggtcactgt ctctgca                                       747
```

<210> SEQ ID NO 12
<211> LENGTH: 249
<212> TYPE: PRT
<213> ORGANISM: artificial sequence
<220> FEATURE:
<223> OTHER INFORMATION: VL-VH scFv single chain Fv

<400> SEQUENCE: 12

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Lys Leu
        115                 120                 125

Leu Glu Ser Gly Gly Gly Leu Val Gln Pro Lys Gly Ser Leu Lys Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Gln Ser Ile Leu Tyr Leu Gln
        195                 200                 205

Met Asn Asn Leu Lys Thr Glu Asp Thr Ala Met Tyr Tyr Cys Val Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ala
                245
```

<210> SEQ ID NO 13
<211> LENGTH: 726
<212> TYPE: DNA
<213> ORGANISM: ARTIFICIAL SEQUENCE
<220> FEATURE:
<223> OTHER INFORMATION: VH-VL scFv single chain Fv

<400> SEQUENCE: 13

```
caggtccagc tgcagcagtc tggggctgaa ctggcaagac ctggggcctc agtgaagatg    60
tcctgcaagg cttctggcta cacctttact agatctacga tgcactgggt aaaacagagg   120
```

```
cctggacagg gtctggaatg gattggatac attaatccta gcagtgctta tactaattac    180
aatcagaaat tcaaggacaa ggccacattg actgcagaca atcctccag tacagcctac     240 atgcaactga gtagcctgac atctgaggac tctgcagtct attactgtgc aagtccgcaa    300
gtccactatg attaacgg gtttccttac tggggccaag ggactctggt cactgtctct      360
gcaggtggtg gtggttctgg cggcggcggc tccggtggtg gtggttctca gttgttctc     420 acccagtctc cagcaatcat gtctgcattt ccaggggaga aggtcaccat gacctgcagt    480
gccagctcaa gtgtaagtta catgaactgg taccagcaga agtcaggcac ctcccccaaa    540
agatggattt atgactcatc caaactggct tctggagtcc ctgctcgctt cagtggcagt    600
gggtctggga cctcttattc tctcacaatc agcagcatgg agactgaaga tgctgccact    660
tattactgcc agcagtggag tcgtaaccca cccacgttcg gagggggac caagctacaa     720 attaca                                                               726
```

<210> SEQ ID NO 14
<211> LENGTH: 242
<212> TYPE: PRT
<213> ORGANISM: artificial sequence
<220> FEATURE:
<223> OTHER INFORMATION: VH-VL scFv single chain Fv

<400> SEQUENCE: 14

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ala Gly Gly Gly Ser Gly Gly
        115                 120                 125

Gly Gly Ser Gly Gly Gly Ser Gln Val Val Leu Thr Gln Ser Pro
    130                 135                 140

Ala Ile Met Ser Ala Phe Pro Gly Glu Lys Val Thr Met Thr Cys Ser
145                 150                 155                 160

Ala Ser Ser Ser Val Ser Tyr Met Asn Trp Tyr Gln Gln Lys Ser Gly
                165                 170                 175

Thr Ser Pro Lys Arg Trp Ile Tyr Asp Ser Ser Lys Leu Ala Ser Gly
            180                 185                 190

Val Pro Ala Arg Phe Ser Gly Ser Gly Ser Gly Thr Ser Tyr Ser Leu
        195                 200                 205

Thr Ile Ser Ser Met Glu Thr Glu Asp Ala Ala Thr Tyr Tyr Cys Gln
    210                 215                 220

Gln Trp Ser Arg Asn Pro Pro Thr Phe Gly Gly Thr Lys Leu Gln
225                 230                 235                 240

Ile Thr
```

<210> SEQ ID NO 15
<211> LENGTH: 726
<212> TYPE: DNA
<213> ORGANISM: ARTIFICIAL SEQUENCE
<220> FEATURE:
<223> OTHER INFORMATION: VL-VH scFv single chain Fv

<400> SEQUENCE: 15

```
caagttgttc tcacccagtc tccagcaatc atgtctgcat ttccagggga gaaggtcacc    60
atgacctgca gtgccagctc aagtgtaagt tacatgaact ggtaccagca gaagtcaggc   120
acctccccca aaagatggat ttatgactca tccaaactgg cttctggagt ccctgctcgc   180
ttcagtggca gtgggtctgg gacctcttat tctctcacaa tcagcagcat ggagactgaa   240
gatgctgcca cttattactg ccagcagtgg agtcgtaacc cacccacgtt cggagggggg   300
accaagctac aaattacagg tggtggtggt tctggcggcg gcggctccgg tggtggtggt   360
tctcaggtcc agctgcagca gtctggggct gaactggcaa gacctggggc ctcagtgaag   420
atgtcctgca aggcttctgg ctacaccttt actagatcta cgatgcactg ggtaaaacag   480
aggcctggac agggtctgga atggattgga tacattaatc ctagcagtgc ttatactaat   540
tacaatcaga aattcaagga caaggccaca ttgactgcag acaaatcctc cagtacagcc   600
tacatgcaac tgagtagcct gacatctgag gactctgcag tctattactg tgcaagtccg   660
caagtccact atgattacaa cgggtttcct tactggggcc aagggactct ggtcactgtc   720
tctgca                                                              726
```

<210> SEQ ID NO 16
<211> LENGTH: 242
<212> TYPE: PRT
<213> ORGANISM: artificial sequence
<220> FEATURE:
<223> OTHER INFORMATION: VL-VH scFv single chain Fv

<400> SEQUENCE: 16

```
Gln Val Val Leu Thr Gln Ser Pro Ala Ile Met Ser Ala Phe Pro Gly
1               5                   10                  15
Glu Lys Val Thr Met Thr Cys Ser Ala Ser Ser Ser Val Ser Tyr Met
            20                  25                  30
Asn Trp Tyr Gln Gln Lys Ser Gly Thr Ser Pro Lys Arg Trp Ile Tyr
        35                  40                  45
Asp Ser Ser Lys Leu Ala Ser Gly Val Pro Ala Arg Phe Ser Gly Ser
    50                  55                  60
Gly Ser Gly Thr Ser Tyr Ser Leu Thr Ile Ser Ser Met Glu Thr Glu
65                  70                  75                  80
Asp Ala Ala Thr Tyr Tyr Cys Gln Gln Trp Ser Arg Asn Pro Pro Thr
                85                  90                  95
Phe Gly Gly Gly Thr Lys Leu Gln Ile Thr Gly Gly Gly Gly Ser Gly
            100                 105                 110
Gly Gly Gly Ser Gly Gly Gly Gly Ser Gln Val Gln Leu Gln Gln Ser
        115                 120                 125
Gly Ala Glu Leu Ala Arg Pro Gly Ala Ser Val Lys Met Ser Cys Lys
    130                 135                 140
Ala Ser Gly Tyr Thr Phe Thr Arg Ser Thr Met His Trp Val Lys Gln
145                 150                 155                 160
Arg Pro Gly Gln Gly Leu Glu Trp Ile Gly Tyr Ile Asn Pro Ser Ser
                165                 170                 175
```

```
Ala Tyr Thr Asn Tyr Asn Gln Lys Phe Lys Asp Lys Ala Thr Leu Thr
            180                 185                 190

Ala Asp Lys Ser Ser Ser Thr Ala Tyr Met Gln Leu Ser Ser Leu Thr
        195                 200                 205

Ser Glu Asp Ser Ala Val Tyr Tyr Cys Ala Ser Pro Gln Val His Tyr
    210                 215                 220

Asp Tyr Asn Gly Phe Pro Tyr Trp Gly Gln Gly Thr Leu Val Thr Val
225                 230                 235                 240

Ser Ala

<210> SEQ ID NO 17
<211> LENGTH: 47
<212> TYPE: DNA
<213> ORGANISM: ARTIFICIAL SEQUENCE
<220> FEATURE:
<223> OTHER INFORMATION: 5' LH oligonucleotide

<400> SEQUENCE: 17
acatccggag gtggtggatc ccaggctgtt gtgactcagg aatctgc                    47

<210> SEQ ID NO 18
<211> LENGTH: 51
<212> TYPE: DNA
<213> ORGANISM: artificial sequence
<220> FEATURE:
<223> OTHER INFORMATION: 3' VL Linker oligonucleotide

<400> SEQUENCE: 18
ggagccgccg ccgccagaac caccaccacc taggacagtc agtttggttc c              51

<210> SEQ ID NO 19
<211> LENGTH: 70
<212> TYPE: DNA
<213> ORGANISM: artificial sequence
<220> FEATURE:
<223> OTHER INFORMATION: 5' VH Linker oligonucleotide

<400> SEQUENCE: 19
tctggcggcg gcggctccgg tggtggtggt tctgaggtga agcttctcga gtctggagga     60
ggattggtgc                                                            70

<210> SEQ ID NO 20
<211> LENGTH: 56
<212> TYPE: DNA
<213> ORGANISM: artificial sequence
<220> FEATURE:
<223> OTHER INFORMATION: 3' LH oligonucleotide

<400> SEQUENCE: 20
agtgggtcga cctaatgatg atggtgatga tgtgcagaga cagtgaccag agtccc         56

<210> SEQ ID NO 21
<211> LENGTH: 58
<212> TYPE: DNA
<213> ORGANISM: artificial sequence
<220> FEATURE:
<223> OTHER INFORMATION: 5' HL oligonucleotide

<400> SEQUENCE: 21
acatccggag gtggtggatc cgaggtgaag cttctcgagt ctggaggagg attggtgc       58

<210> SEQ ID NO 22
<211> LENGTH: 54
```

```
<212> TYPE: DNA
<213> ORGANISM: artificial sequence
<220> FEATURE:
<223> OTHER INFORMATION: 3' VH Linker oligonucleotide

<400> SEQUENCE: 22
ggagccgccg ccgccagaac caccaccacc tgcagagaca gtgaccagag tccc        54

<210> SEQ ID NO 23
<211> LENGTH: 59
<212> TYPE: DNA
<213> ORGANISM: artificial sequence
<220> FEATURE:
<223> OTHER INFORMATION: 5' VL Linker oligonucleotide

<400> SEQUENCE: 23
tctggcggcg gcggctccgg tggtggtggt tctcaggctg ttgtgactca ggaatctgc   59

<210> SEQ ID NO 24
<211> LENGTH: 56
<212> TYPE: DNA
<213> ORGANISM: artificial sequence
<220> FEATURE:
<223> OTHER INFORMATION: 3' HL oligonucleotide

<400> SEQUENCE: 24
agtgggtcga cctaatgatg atggtgatga tgtaggacag tcagtttggt tcctcc      56

<210> SEQ ID NO 25
<211> LENGTH: 44
<212> TYPE: DNA
<213> ORGANISM: artificial sequence
<220> FEATURE:
<223> OTHER INFORMATION: 5' LH oligonucleotide

<400> SEQUENCE: 25
acatccggag gtggtggatc ccaagttgtt ctcacccagt ctcc                   44

<210> SEQ ID NO 26
<211> LENGTH: 53
<212> TYPE: DNA
<213> ORGANISM: artificial sequence
<220> FEATURE:
<223> OTHER INFORMATION: 3' VL Linker oligonucleotide

<400> SEQUENCE: 26
ggagccgccg ccgccagaac caccaccacc tgtaatttgt agcttggtcc ccc          53

<210> SEQ ID NO 27
<211> LENGTH: 56
<212> TYPE: DNA
<213> ORGANISM: artificial sequence
<220> FEATURE:
<223> OTHER INFORMATION: 5' VH Linker oligonucleotide

<400> SEQUENCE: 27
tctggcggcg gcggctccgg tggtggtggt tctcaggtcc agctgcagca gtctgg      56

<210> SEQ ID NO 28
<211> LENGTH: 55
<212> TYPE: DNA
<213> ORGANISM: artificial sequence
<220> FEATURE:
<223> OTHER INFORMATION: 3' LH oligonucleotide

<400> SEQUENCE: 28
```

```
agtgggtcga cctaatgatg atggtgatga tgtgcagaga cagtgaccag agtcc        55

<210> SEQ ID NO 29
<211> LENGTH: 44
<212> TYPE: DNA
<213> ORGANISM: artificial sequence
<220> FEATURE:
<223> OTHER INFORMATION: 5' HL oligonucleotide

<400> SEQUENCE: 29
acatccggag gtggtggatc ccaggtccag ctgcagcagt ctgg                    44

<210> SEQ ID NO 30
<211> LENGTH: 53
<212> TYPE: DNA
<213> ORGANISM: artificial sequence
<220> FEATURE:
<223> OTHER INFORMATION: 3' VH Linker oligonucleotide

<400> SEQUENCE: 30
ggagccgccg ccgccagaac caccaccacc tgcagagaca gtgaccagag tcc          53

<210> SEQ ID NO 31
<211> LENGTH: 56
<212> TYPE: DNA
<213> ORGANISM: artificial sequence
<220> FEATURE:
<223> OTHER INFORMATION: 5' VL Linker oligonucleotide

<400> SEQUENCE: 31
tctggcggcg gcggctccgg tggtggtggt tctcaagttg ttctcaccca gtctcc       56

<210> SEQ ID NO 32
<211> LENGTH: 55
<212> TYPE: DNA
<213> ORGANISM: artificial sequence
<220> FEATURE:
<223> OTHER INFORMATION: 3' HL oligonucleotide

<400> SEQUENCE: 32
agtgggtcga cctaatgatg atggtgatga tgtgtaattt gtagcttggt ccccc        55

<210> SEQ ID NO 33
<211> LENGTH: 744
<212> TYPE: DNA
<213> ORGANISM: artificial sequence
<220> FEATURE:
<223> OTHER INFORMATION: 5-10 LH scFv single chain Fv

<400> SEQUENCE: 33
gagctcgtga tgacacagtc tccatcctcc ctgactgtga cagcaggaga gaaggtcact   60
atgagctgca agtccagtca gagtctgtta aacagtggaa atcaaaagaa ctacttgacc  120
tggtaccagc agaaaccagg gcagcctcct aaactgttga tctactgggc atccactagg  180
gaatctgggg tccctgatcg cttcacaggc agtggatctg gaacagattt cactctcacc  240
atcagcagtg tgcaggctga agacctggca gtttattact gtcagaatga ttatagttat  300
ccgctcacgt tcggtgctgg gaccaagctt gagatcaaag gtggtggtgg ttctggcggc  360
ggcggctccg gtggtggtgg ttctgaggtg cagctgctcg agcagtctgg agctgagctg  420
gtaaggcctg ggacttcagt gaagatatcc tgcaaggctt ctggatacgc cttcactaac  480
tactggctag gttgggtaaa gcagaggcct ggacatggac ttgagtggat tggagatatt  540
ttccctggaa gtggtaatat ccactacaat gagaagttca aggcaaagc cacactgact  600
```

```
gcagacaaat cttcgagcac agcctatatg cagctcagta gcctgacatt tgaggactct    660
gctgtctatt tctgtgcaag actgaggaac tgggacgagc ctatggacta ctggggccaa    720
gggaccacgg tcaccgtctc ctcc                                          744
```

<210> SEQ ID NO 34
<211> LENGTH: 248
<212> TYPE: PRT
<213> ORGANISM: artificial sequence
<220> FEATURE:
<223> OTHER INFORMATION: 5-10 LH scFv single chain Fv

<400> SEQUENCE: 34

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser
                245
```

<210> SEQ ID NO 35
<211> LENGTH: 57
<212> TYPE: DNA
<213> ORGANISM: MUS MUSCULUS
<220> FEATURE:
<221> NAME/KEY: misc_feature
<222> LOCATION: (1)..(57)
<223> OTHER INFORMATION: leader peptide

<400> SEQUENCE: 35

```
atgggatgga gctgtatcat cctcttcttg gtagcaacag ctacaggtgt acactcc    57
```

<210> SEQ ID NO 36
<211> LENGTH: 19
<212> TYPE: PRT
<213> ORGANISM: mus musculus
<220> FEATURE:
<221> NAME/KEY: misc_feature
<222> LOCATION: (1)..(19)
<223> OTHER INFORMATION: leader peptide

<400> SEQUENCE: 36

Met Gly Trp Ser Cys Ile Ile Leu Phe Leu Val Ala Thr Ala Thr Gly
1               5                   10                  15

Val His Ser

<210> SEQ ID NO 37
<211> LENGTH: 1506
<212> TYPE: DNA
<213> ORGANISM: ARTIFICIAL SEQUENCE
<220> FEATURE:
<223> OTHER INFORMATION: 5-10 LHxSEQ ID NO: 12 ; Bispecific single chain
      antibody

<400> SEQUENCE: 37

| | | | | | |
|---|---|---|---|---|---|
| gagctcgtga | tgacacagtc | tccatcctcc | ctgactgtga | cagcaggaga | gaaggtcact | 60 |
| atgagctgca | agtccagtca | gagtctgtta | aacagtggaa | atcaaaagaa | ctacttgacc | 120 |
| tggtaccagc | agaaaccagg | gcagcctcct | aaactgttga | tctactgggc | atccactagg | 180 |
| gaatctgggg | tccctgatcg | cttcacaggc | agtggatctg | gaacagattt | cactctcacc | 240 |
| atcagcagtg | tgcaggctga | agacctggca | gtttattact | gtcagaatga | ttatagttat | 300 |
| ccgctcacgt | tcggtgctgg | gaccaagctt | gagatcaaag | gtggtggtgg | ttctggcggc | 360 |
| ggcggctccg | gtggtggtgg | ttctgaggtg | cagctgctcg | agcagtctgg | agctgagctg | 420 |
| gtaaggcctg | ggacttcagt | gaagatatcc | tgcaaggctt | ctggatacgc | cttcactaac | 480 |
| tactggctag | ttgggtaaa | gcagaggcct | ggacatggac | ttgagtggat | tggagatatt | 540 |
| ttccctggaa | gtggtaatat | ccactacaat | gagaagttca | agggcaaagc | cacactgact | 600 |
| gcagacaaat | cttcgagcac | agcctatatg | cagctcagta | gcctgacatt | tgaggactct | 660 |
| gctgtctatt | tctgtgcaag | actgaggaac | tgggacgagc | ctatggacta | ctggggccaa | 720 |
| gggaccacgg | tcaccgtctc | ctccggaggt | ggtggatccc | aggctgttgt | gactcaggaa | 780 |
| tctgcactca | ccacatcacc | tggtgaaaca | gtcacactca | cttgtcgctc | aagtactggg | 840 |
| gctgttacaa | ctagtaacta | tgccaactgg | gtccaagaaa | aaccagatca | tttattcact | 900 |
| ggtctaatag | gtggtaccaa | caagcgagct | ccaggtgtgc | ctgccagatt | ctcaggctcc | 960 |
| ctgattggag | acaaggctgc | cctcaccatc | acagggcac | agactgagga | tgaggcaata | 1020 |
| tatttctgtg | ctctatggta | cagcaacctc | tgggtgttcg | gtggaggaac | caaactgact | 1080 |
| gtcctaggtg | gtggtggttc | tggcggcggc | ggctccggtg | gtggtggttc | tgaggtgaag | 1140 |
| cttctcgagt | ctggaggagg | attggtgcag | cctaaagggt | cattgaaact | ctcatgtgca | 1200 |
| gcctctggat | tcaccttcaa | tacctacgcc | atgaactggg | tccgccaggc | tccaggaaag | 1260 |
| ggtttggaat | gggttgctcg | cataagaagt | aaatataata | attatgcaac | atattatgcc | 1320 |
| gattcagtga | aagacaggtt | caccatctcc | agagatgatt | cacaaagcat | tctctatcta | 1380 |
| caaatgaaca | acttgaaaac | tgaggacaca | gccatgtact | actgtgtgag | acatgggaac | 1440 |
| tcggtaata | gctacgtttc | ctggtttgct | tactggggcc | aagggactct | ggtcactgtc | 1500 |
| tctgca | | | | | | 1506 |

<210> SEQ ID NO 38
<211> LENGTH: 502
<212> TYPE: PRT
<213> ORGANISM: artificial sequence
<220> FEATURE:
<223> OTHER INFORMATION: 5-10 LHxSEQ ID NO: 12 ; Bispecific single chain antibody

<400> SEQUENCE: 38

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Gln Ala Val
                245                 250                 255

Val Thr Gln Glu Ser Ala Leu Thr Thr Ser Pro Gly Glu Thr Val Thr
            260                 265                 270

Leu Thr Cys Arg Ser Ser Thr Gly Ala Val Thr Thr Ser Asn Tyr Ala
        275                 280                 285

Asn Trp Val Gln Glu Lys Pro Asp His Leu Phe Thr Gly Leu Ile Gly
290                 295                 300

Gly Thr Asn Lys Arg Ala Pro Gly Val Pro Ala Arg Phe Ser Gly Ser
305                 310                 315                 320

Leu Ile Gly Asp Lys Ala Ala Leu Thr Ile Thr Gly Ala Gln Thr Glu
                325                 330                 335

Asp Glu Ala Ile Tyr Phe Cys Ala Leu Trp Tyr Ser Asn Leu Trp Val
            340                 345                 350

Phe Gly Gly Gly Thr Lys Leu Thr Val Leu Gly Gly Gly Gly Ser Gly
```

```
                355                 360                 365
Gly Gly Gly Ser Gly Gly Gly Ser Glu Val Lys Leu Leu Glu Ser
            370                 375                 380

Gly Gly Gly Leu Val Gln Pro Lys Gly Ser Leu Lys Leu Ser Cys Ala
385                 390                 395                 400

Ala Ser Gly Phe Thr Phe Asn Thr Tyr Ala Met Asn Trp Val Arg Gln
                405                 410                 415

Ala Pro Gly Lys Gly Leu Glu Trp Val Ala Arg Ile Arg Ser Lys Tyr
            420                 425                 430

Asn Asn Tyr Ala Thr Tyr Tyr Ala Asp Ser Val Lys Asp Arg Phe Thr
        435                 440                 445

Ile Ser Arg Asp Asp Ser Gln Ser Ile Leu Tyr Leu Gln Met Asn Asn
    450                 455                 460

Leu Lys Thr Glu Asp Thr Ala Met Tyr Tyr Cys Val Arg His Gly Asn
465                 470                 475                 480

Phe Gly Asn Ser Tyr Val Ser Trp Phe Ala Tyr Trp Gly Gln Gly Thr
                485                 490                 495

Leu Val Thr Val Ser Ala
            500

<210> SEQ ID NO 39
<211> LENGTH: 1506
<212> TYPE: DNA
<213> ORGANISM: ARTIFICIAL SEQUENCE
<220> FEATURE:
<223> OTHER INFORMATION: 5-10 LHx SEQ ID NO: 10 ; bispecific single
      chain antibdoy

<400> SEQUENCE: 39
gagctcgtga tgacacagtc tccatcctcc ctgactgtga cagcaggaga gaaggtcact      60
atgagctgca agtccagtca gagtctgtta acagtggaaa tcaaaagaa ctacttgacc     120 tggtaccagc agaaaccagg gcagcctcct aaactgttga tctactgggc atccactagg     180
gaatctgggg tccctgatcg cttcacaggc agtggatctg aacagattt cactctcacc     240 atcagcagtg tgcaggctga agacctggca gtttattact gtcagaatga ttatagttat     300
ccgctcacgt tcggtgctgg gaccaagctt gagatcaaag gtggtggtgg ttctggcggc     360
ggcggctccg gtggtggtgg ttctgaggtg cagctgctcg agcagtctgg agctgagctg     420
gtaaggcctg ggacttcagt gaagatatcc tgcaaggctt ctggatacgc cttcactaac     480
tactggctag ttgggtaaa gcagaggcct ggacatggac ttgagtggat tggagatatt     540
ttccctggaa gtggtaatat ccactacaat gagaagttca gggcaaagc cacactgact     600 gcagacaaat cttcgagcac agcctatatg cagctcagta gcctgacatt tgaggactct     660
gctgtctatt tctgtgcaag actgaggaac tgggacgagc tatggactac tggggccaa     720 gggaccacgg tcaccgtctc ctccggaggt ggtggatccg aggtgaagct tctcgagtct     780
ggaggaggat tggtgcagcc taaagggtca ttgaaactct catgtgcagc ctctggattc     840
accttcaata cctacgccat gaactgggtc cgccaggctc aggaagggg tttggaatgg     900 gttgctcgca taagaagtaa atataataat tatgcaacat attatgccga ttcagtgaaa     960
gacaggttca ccatctccag agatgattca caaagcattc tctatctaca aatgaacaac    1020
ttgaaaactg aggacacagc catgtactac tgtgtgagac atgggaactt cggtaatagc    1080
tacgtttcct ggtttgctta ctggggccaa gggactctgg tcactgtctc tgcaggtggt    1140
ggtggttctg gcggcggcgg ctccggtggt ggtggttctc aggctgttgt gactcaggaa    1200
```

-continued

```
tctgcactca ccacatcacc tggtgaaaca gtcacactca cttgtcgctc aagtactggg    1260
gctgttacaa ctagtaacta tgccaactgg gtccaagaaa aaccagatca tttattcact    1320
ggtctaatag gtggtaccaa caagcgagct ccaggtgtgc ctgccagatt ctcaggctcc    1380
ctgattggag acaaggctgc cctcaccatc acagggcac agactgagga tgaggcaata    1440
tatttctgtg ctctatggta cagcaacctc tgggtgttcg gtggaggaac caaactgact    1500
gtccta                                                              1506
```

<210> SEQ ID NO 40
<211> LENGTH: 502
<212> TYPE: PRT
<213> ORGANISM: artificial sequence
<220> FEATURE:
<223> OTHER INFORMATION: 5-10 LHx SEQ ID NO: 10 ; bispecific single chain antibody

<400> SEQUENCE: 40

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Glu Val Lys
                245                 250                 255

Leu Leu Glu Ser Gly Gly Gly Leu Val Gln Pro Lys Gly Ser Leu Lys
            260                 265                 270

Leu Ser Cys Ala Ala Ser Gly Phe Thr Phe Asn Thr Tyr Ala Met Asn
        275                 280                 285

Trp Val Arg Gln Ala Pro Gly Lys Gly Leu Glu Trp Val Ala Arg Ile
```

```
                    290                 295                 300
Arg Ser Lys Tyr Asn Asn Tyr Ala Thr Tyr Tyr Ala Asp Ser Val Lys
305                 310                 315                 320

Asp Arg Phe Thr Ile Ser Arg Asp Ser Gln Ser Ile Leu Tyr Leu
                325                 330                 335

Gln Met Asn Asn Leu Lys Thr Glu Asp Thr Ala Met Tyr Tyr Cys Val
                340                 345                 350

Arg His Gly Asn Phe Gly Asn Ser Tyr Val Ser Trp Phe Ala Tyr Trp
                355                 360                 365

Gly Gln Gly Thr Leu Val Thr Val Ser Ala Gly Gly Gly Ser Gly
370                 375                 380

Gly Gly Gly Ser Gly Gly Gly Ser Gln Ala Val Val Thr Gln Glu
385                 390                 395                 400

Ser Ala Leu Thr Thr Ser Pro Gly Glu Thr Val Thr Leu Thr Cys Arg
                405                 410                 415

Ser Ser Thr Gly Ala Val Thr Thr Ser Asn Tyr Ala Asn Trp Val Gln
                420                 425                 430

Glu Lys Pro Asp His Leu Phe Thr Gly Leu Ile Gly Gly Thr Asn Lys
                435                 440                 445

Arg Ala Pro Gly Val Pro Ala Arg Phe Ser Gly Ser Leu Ile Gly Asp
                450                 455                 460

Lys Ala Ala Leu Thr Ile Thr Gly Ala Gln Thr Glu Asp Glu Ala Ile
465                 470                 475                 480

Tyr Phe Cys Ala Leu Trp Tyr Ser Asn Leu Trp Val Phe Gly Gly Gly
                485                 490                 495

Thr Lys Leu Thr Val Leu
                500

<210> SEQ ID NO 41
<211> LENGTH: 1485
<212> TYPE: DNA
<213> ORGANISM: ARTIFICIAL SEQUENCE
<220> FEATURE:
<223> OTHER INFORMATION: 5-10 LHx SEQ ID NO: 16 ; bispecific single
      chain antibody

<400> SEQUENCE: 41
gagctcgtga tgacacagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttatagttat     300
ccgctcacgt tcggtgctgg gaccaagctt gagatcaaag gtggtggtgg ttctggcggc     360
ggcggctccg gtggtggtgg ttctgaggtg cagctgctcg agcagtctgg agctgagctg     420
gtaaggcctg ggacttcagt gaagatatcc tgcaaggctt ctggatacgc cttcactaac     480
tactggctag gttgggtaaa gcagaggcct ggacatggac ttgagtggat tggagatatt     540
ttccctggaa gtggtaatat ccactacaat gagaagttca gggcaaagc cacactgact     600 gcagacaaat cttcgagcac agcctatatg cagctcagta gcctgacatt tgaggactct     660
gctgtctatt tctgtgcaag actgaggaac tgggacgagc ctatggacta ctggggccaa     720
gggaccacgg tcaccgtctc ctccggaggt ggtggatccc aagttgttct cacccagtct     780
ccagcaatca tgtctgcatt tccaggggag aaggtcacca tgacctgcag tgccagctca     840
```

```
agtgtaagtt acatgaactg gtaccagcag aagtcaggca cctcccccaa aagatggatt    900
tatgactcat ccaaactggc ttctggagtc cctgctcgct tcagtggcag tgggtctggg    960
acctcttatt ctctcacaat cagcagcatg gagactgaag atgctgccac ttattactgc   1020
cagcagtgga gtcgtaaccc acccacgttc ggaggggggga ccaagctaca aattacaggt   1080
ggtggtggtt ctggcggcgg cggctccggt ggtggtggtt ctcaggtcca gctgcagcag   1140 tctgggctg aactgcaag acctggggcc tcagtgaaga tgtcctgcaa ggcttctggc     1200 tacacctta ctagatctac gatgcactgg gtaaaacaga ggcctggaca gggtctggaa    1260
tggattggat acattaatcc tagcagtgct tatactaatt acaatcagaa attcaaggac   1320
aaggccacat tgactgcaga caaatcctcc agtacagcct acatgcaact gagtagcctg   1380
acatctgagg actctgcagt ctattactgt gcaagtccgc aagtccacta tgattacaac   1440
gggtttcctt actggggcca agggactctg gtcactgtct ctgca                   1485
```

<210> SEQ ID NO 42
<211> LENGTH: 495
<212> TYPE: PRT
<213> ORGANISM: artificial sequence
<220> FEATURE:
<223> OTHER INFORMATION: 5-10 LHxSEQ ID NO: 16 ; bispecific single chain antibody

<400> SEQUENCE: 42

```
Glu Leu Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240
```

Gly Thr Thr Val Thr Val Ser Ser Gly Gly Gly Ser Gln Val Val
                245                 250                 255

Leu Thr Gln Ser Pro Ala Ile Met Ser Ala Phe Pro Gly Glu Lys Val
            260                 265                 270

Thr Met Thr Cys Ser Ala Ser Ser Val Ser Tyr Met Asn Trp Tyr
        275                 280                 285

Gln Gln Lys Ser Gly Thr Ser Pro Lys Arg Trp Ile Tyr Asp Ser Ser
    290                 295                 300

Lys Leu Ala Ser Gly Val Pro Ala Arg Phe Ser Gly Ser Gly Ser Gly
305                 310                 315                 320

Thr Ser Tyr Ser Leu Thr Ile Ser Ser Met Glu Thr Glu Asp Ala Ala
                325                 330                 335

Thr Tyr Tyr Cys Gln Gln Trp Ser Arg Asn Pro Pro Thr Phe Gly Gly
            340                 345                 350

Gly Thr Lys Leu Gln Ile Thr Gly Gly Gly Ser Gly Gly Gly Gly
        355                 360                 365

Ser Gly Gly Gly Gly Ser Gln Val Gln Leu Gln Gln Ser Gly Ala Glu
    370                 375                 380

Leu Ala Arg Pro Gly Ala Ser Val Lys Met Ser Cys Lys Ala Ser Gly
385                 390                 395                 400

Tyr Thr Phe Thr Arg Ser Thr Met His Trp Val Lys Gln Arg Pro Gly
                405                 410                 415

Gln Gly Leu Glu Trp Ile Gly Tyr Ile Asn Pro Ser Ser Ala Tyr Thr
            420                 425                 430

Asn Tyr Asn Gln Lys Phe Lys Asp Lys Ala Thr Leu Thr Ala Asp Lys
        435                 440                 445

Ser Ser Ser Thr Ala Tyr Met Gln Leu Ser Ser Leu Thr Ser Glu Asp
    450                 455                 460

Ser Ala Val Tyr Tyr Cys Ala Ser Pro Gln Val His Tyr Asp Tyr Asn
465                 470                 475                 480

Gly Phe Pro Tyr Trp Gly Gln Gly Thr Leu Val Thr Val Ser Ala
                485                 490                 495

<210> SEQ ID NO 43
<211> LENGTH: 1485
<212> TYPE: DNA
<213> ORGANISM: ARTIFICIAL SEQUENCE
<220> FEATURE:
<223> OTHER INFORMATION: 5-10 LHxSEQ ID NO: 14 ; bispecific single chain
      antibody

<400> SEQUENCE: 43
gagctcgtga tgacacagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttatagttat     300
ccgctcacgt tcggtgctgg gaccaagctt gagatcaaag gtggtggtgg ttctggcggc     360
ggcggctccg gtggtggtgg ttctgagtgt cagctgctcg agcagtctgg agctgagctg     420
gtaaggcctg ggacttcagt gaagatatcc tgcaaggctt ctggatacgc cttcactaac     480
tactggctag gttgggtaaa gcagaggcct ggacatggac ttgagtggat tggagatatt     540
ttccctggaa gtggtaatat ccactacaat gagaagttca gggcaaagc cacactgact     600

```
gcagacaaat cttcgagcac agcctatatg cagctcagta gcctgacatt tgaggactct    660
gctgtctatt tctgtgcaag actgaggaac tgggacgagc ctatggacta ctggggccaa    720
gggaccacgg tcaccgtctc ctccggaggt ggtggatccc aggtccagct gcagcagtct    780
ggggctgaac tggcaagacc tgggccctca gtgaagatgt cctgcaaggc ttctggctac    840
acctttacta gatctacgat gcactgggta aaacagaggc ctggacaggg tctggaatgg    900
attggataca ttaatcctag cagtgcttat actaattaca atcagaaatt caaggacaag    960
gccacattga ctgcagacaa atcctccagt acagcctaca tgcaactgag tagcctgaca   1020
tctgaggact ctgcagtcta ttactgtgca agtccgcaag tccactatga ttacaacggg   1080
tttccttact ggggccaagg gactctggtc actgtctctg caggtggtgg tggttctggc   1140
ggcggcggct ccggtggtgg tggttctcaa gttgttctca cccagtctcc agcaatcatg   1200
tctgcatttc caggggagaa ggtcaccatg acctgcagtg ccagctcaag tgtaagttac   1260
atgaactggt accagcagaa gtcaggcacc tcccccaaaa gatggattta tgactcatcc   1320
aaactggctt ctggagtccc tgctcgcttc agtggcagtg gtctgggac ctcttattct    1380 ctcacaatca gcagcatgga gactgaagat gctgccactt attactgcca gcagtggagt   1440
cgtaacccac ccacgttcgg agggggggacc aagctacaaa ttaca                   1485
```

<210> SEQ ID NO 44
<211> LENGTH: 495
<212> TYPE: PRT
<213> ORGANISM: artificial sequence
<220> FEATURE:
<223> OTHER INFORMATION: 5-10 LHxSEQ ID NO: 14 ; bispecific single chain
      antibody

<400> SEQUENCE: 44

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Ser Gly Gly Gly Ser Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205
```

-continued

```
Tyr Met Gln Leu Ser Ser Leu Thr Phe Glu Asp Ser Ala Val Tyr Phe
            210                 215                 220
Cys Ala Arg Leu Arg Asn Trp Asp Glu Pro Met Asp Tyr Trp Gly Gln
225                 230                 235                 240
Gly Thr Thr Val Thr Val Ser Ser Gly Gly Gly Gly Ser Gln Val Gln
                245                 250                 255
Leu Gln Gln Ser Gly Ala Glu Leu Ala Arg Pro Gly Ala Ser Val Lys
            260                 265                 270
Met Ser Cys Lys Ala Ser Gly Tyr Thr Phe Thr Arg Ser Thr Met His
        275                 280                 285
Trp Val Lys Gln Arg Pro Gly Gln Gly Leu Glu Trp Ile Gly Tyr Ile
    290                 295                 300
Asn Pro Ser Ser Ala Tyr Thr Asn Tyr Asn Gln Lys Phe Lys Asp Lys
305                 310                 315                 320
Ala Thr Leu Thr Ala Asp Lys Ser Ser Ser Thr Ala Tyr Met Gln Leu
                325                 330                 335
Ser Ser Leu Thr Ser Glu Asp Ser Ala Val Tyr Tyr Cys Ala Ser Pro
            340                 345                 350
Gln Val His Tyr Asp Tyr Asn Gly Phe Pro Tyr Trp Gly Gln Gly Thr
        355                 360                 365
Leu Val Thr Val Ser Ala Gly Gly Gly Ser Gly Gly Gly Gly Ser
    370                 375                 380
Gly Gly Gly Gly Ser Gln Val Val Leu Thr Gln Ser Pro Ala Ile Met
385                 390                 395                 400
Ser Ala Phe Pro Gly Glu Lys Val Thr Met Thr Cys Ser Ala Ser Ser
                405                 410                 415
Ser Val Ser Tyr Met Asn Trp Tyr Gln Gln Lys Ser Gly Thr Ser Pro
            420                 425                 430
Lys Arg Trp Ile Tyr Asp Ser Ser Lys Leu Ala Ser Gly Val Pro Ala
        435                 440                 445
Arg Phe Ser Gly Ser Gly Ser Gly Thr Ser Tyr Ser Leu Thr Ile Ser
    450                 455                 460
Ser Met Glu Thr Glu Asp Ala Ala Thr Tyr Tyr Cys Gln Gln Trp Ser
465                 470                 475                 480
Arg Asn Pro Pro Thr Phe Gly Gly Gly Thr Lys Leu Gln Ile Thr
                485                 490                 495

<210> SEQ ID NO 45
<211> LENGTH: 43
<212> TYPE: DNA
<213> ORGANISM: ARTIFICIAL SEQUENCE
<220> FEATURE:
<223> OTHER INFORMATION: 5' EpCAM oligonucleotide

<400> SEQUENCE: 45
ggttctagac caccatggcg cccccgcagg tcctcgcgtt cgg        43

<210> SEQ ID NO 46
<211> LENGTH: 42
<212> TYPE: DNA
<213> ORGANISM: artificial sequence
<220> FEATURE:
<223> OTHER INFORMATION: 3' EpCAM oligonucleotide

<400> SEQUENCE: 46
agtgggtcga cttatgcatt gagttcccta tgcatctcac cc         42
```

<210> SEQ ID NO 47
<211> LENGTH: 726
<212> TYPE: DNA
<213> ORGANISM: Macaca fascicularis
<220> FEATURE:
<221> NAME/KEY: misc_feature
<222> LOCATION: (1)..(726)
<223> OTHER INFORMATION: cynomolgus EpCAM extracellular portion

<400> SEQUENCE: 47

```
cagaaagaat gtgtctgtga aaactacaag ctggccgtaa actgcttttt gaatgacaat      60
ggtcaatgcc agtgtacttc gattggtgca caaaatactg tcctttgctc aaagctggct    120
gccaaatgtt tggtgatgaa ggcagaaatg aacggctcaa aacttgggag aagagcgaaa    180
cctgaagggg ctctccagaa caatgatggc ctttacgatc ctgactgcga tgagagcggg    240
ctctttaagg ccaagcagtg caacggcacc tccacgtgct ggtgtgtgaa cactgctggg    300
gtcagaagaa ctgacaagga cactgaaata acctgctctg agcgagtgag aacctactgg    360
atcatcattg aattaaaaca caagcaaga gaaaaacctt atgatgttca agtttgcgg      420
actgcacttg aggaggcgat caaaacgcgt tatcaactgg atccaaaatt tatcacaaat    480
attttgtatg aggataatgt tatcactatt gatctggttc aaaattcttc tcagaaaact    540
cagaatgatg tggacatagc tgatgtggct tattattttg aaaaagatgt taaggtgaa     600
tccttgtttc attctaagaa aatggacctg agagtaaatg gggaacaact ggatctggat    660
cctggtcaaa ctttaattta ttatgtcgat gaaaaagcac tgaattctc aatgcagggt    720
ctaaaa                                                                726
```

<210> SEQ ID NO 48
<211> LENGTH: 242
<212> TYPE: PRT
<213> ORGANISM: Macaca fascicularis
<220> FEATURE:
<221> NAME/KEY: misc_feature
<222> LOCATION: (1)..(242)
<223> OTHER INFORMATION: cynomolgus EpCAM extracellular portion

<400> SEQUENCE: 48

```
Gln Lys Glu Cys Val Cys Glu Asn Tyr Lys Leu Ala Val Asn Cys Phe
1               5                   10                  15

Leu Asn Asp Asn Gly Gln Cys Gln Cys Thr Ser Ile Gly Ala Gln Asn
            20                  25                  30

Thr Val Leu Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Thr Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
        115                 120                 125

Ala Arg Glu Lys Pro Tyr Asp Val Gln Ser Leu Arg Thr Ala Leu Glu
    130                 135                 140

Glu Ala Ile Lys Thr Arg Tyr Gln Leu Asp Pro Lys Phe Ile Thr Asn
145                 150                 155                 160
```

Ile Leu Tyr Glu Asp Asn Val Ile Thr Ile Asp Leu Val Gln Asn Ser
            165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
            195                 200                 205

Asp Leu Arg Val Asn Gly Glu Gln Leu Asp Leu Asp Pro Gly Gln Thr
            210                 215                 220

Leu Ile Tyr Tyr Val Asp Glu Lys Ala Pro Glu Phe Ser Met Gln Gly
225                 230                 235                 240

Leu Lys

<210> SEQ ID NO 49
<211> LENGTH: 366
<212> TYPE: DNA
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(366)
<223> OTHER INFORMATION: 2G8 VH VH region of monoclonal antibody 2G8

<400> SEQUENCE: 49
gaggttcagc tgcagcagtc tggggcagag cttgtgaggt caggggcctc agtcaagttg     60
tcctgcacag cttctggctt caacattaaa gactactatt tgcactgggt gaagcagagg    120
cctgaacagg gcctggagtg gattgcctgg attgatcttg agaatggtga tattaaatat    180
gccccgaagt tcagggcaa ggccactata actgcagaca catcctccaa cacagcctac     240
ctgcagctca gcagcctgac atctgaggac actgccgtct attactgtaa tccctattac    300
tacggtagta actacgacta tgctatggac tactggggtc aaggaacctc agtcaccgtc    360
tcctca                                                               366

<210> SEQ ID NO 50
<211> LENGTH: 122
<212> TYPE: PRT
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(122)
<223> OTHER INFORMATION: 2G8 VH VH region of monoclonal antibody 2G8

<400> SEQUENCE: 50

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
            35                  40                  45

Ala Trp Ile Asp Leu Glu Asn Gly Asp Ile Lys Tyr Ala Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Pro Tyr Tyr Tyr Gly Ser Asn Tyr Asp Tyr Ala Met Asp Tyr Trp

```
                      100                 105                 110
Gly Gln Gly Thr Ser Val Thr Val Ser Ser
        115                 120

<210> SEQ ID NO 51
<211> LENGTH: 336
<212> TYPE: DNA
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(336)
<223> OTHER INFORMATION: 2G8 VL VL region of monoclonal antibody 2G8

<400> SEQUENCE: 51
gatgttgtga tgacccagac tccactcact ttgtcggtta ccattggaca accagcctct      60
atctcttgca agtcaagtca gagcctctta tatagtaatg aaaaaccta tttgaactgg     120 atattacaga ggccaggcca gtctccaaag cgcctaatct atctggtgtc taaactggac     180
tctggagtcc ctgacaggtt cactggcagt ggatcaggaa cagatttac gctgaaaatc     240 agcagagtgg aggctgagga tttgggagtt tattactgcg tgcaaggtac acattttcct     300
ctcacgttcg gtgctgggac caagctggag ctgaaa                              336

<210> SEQ ID NO 52
<211> LENGTH: 112
<212> TYPE: PRT
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(112)
<223> OTHER INFORMATION: 2G8 VL VL region of monoclonal antibody 2G8

<400> SEQUENCE: 52

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Ile Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Leu Thr Phe Gly Ala Gly Thr Lys Leu Glu Leu Lys
            100                 105                 110

<210> SEQ ID NO 53
<211> LENGTH: 747
<212> TYPE: DNA
<213> ORGANISM: artificial sequence
<220> FEATURE:
<223> OTHER INFORMATION: 2G8VH-VL scFv single chain Fv

<400> SEQUENCE: 53
gaggttcagc tgcagcagtc tggggcagag cttgtgaggt caggggcctc agtcaagttg      60
tcctgcacag cttctggctt caacattaaa gactactatt tgcactgggt gaagcagagg    120
```

```
cctgaacagg gcctggagtg gattgcctgg attgatcttg agaatggtga tattaaatat    180
gccccgaagt tcagggcaa ggccactata actgcagaca catcctccaa cacagcctac    240
ctgcagctca gcagcctgac atctgaggac actgccgtct attactgtaa tccctattac    300
tacggtagta actacgacta tgctatggac tactggggtc aaggaacctc agtcaccgtc    360
tcctcaggtg gtggtggttc tggcggcggc ggctccggtg gtggtggttc tgatgttgtg    420
atgacccaga ctccactcac tttgtcggtt accattggac aaccagcctc tatctcttgc    480
aagtcaagtc agagcctctt atatagtaat ggaaaaacct atttgaactg gatattacag    540
aggccaggcc agtctccaaa gcgcctaatc tatctggtgt ctaaactgga ctctggagtc    600
cctgacaggt tcactggcag tggatcagga acagatttta cgctgaaaat cagcagagtg    660
gaggctgagg atttgggagt ttattactgc gtgcaaggta cacattttcc tctcacgttc    720
ggtgctggga ccaagctgga gctgaaa                                        747

<210> SEQ ID NO 54
<211> LENGTH: 249
<212> TYPE: PRT
<213> ORGANISM: artificial sequence
<220> FEATURE:
<223> OTHER INFORMATION: 2G8VH-VL scFv single chain Fv

<400> SEQUENCE: 54

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Ala Trp Ile Asp Leu Glu Asn Gly Asp Ile Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Pro Tyr Tyr Tyr Gly Ser Asn Tyr Asp Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Ser Gly Gly Gly Gly Ser Asp Val Val Met Thr Gln Thr
    130                 135                 140

Pro Leu Thr Leu Ser Val Thr Ile Gly Gln Pro Ala Ser Ile Ser Cys
145                 150                 155                 160

Lys Ser Ser Gln Ser Leu Leu Tyr Ser Asn Gly Lys Thr Tyr Leu Asn
                165                 170                 175

Trp Ile Leu Gln Arg Pro Gly Gln Ser Pro Lys Arg Leu Ile Tyr Leu
            180                 185                 190

Val Ser Lys Leu Asp Ser Gly Val Pro Asp Arg Phe Thr Gly Ser Gly
        195                 200                 205

Ser Gly Thr Asp Phe Thr Leu Lys Ile Ser Arg Val Glu Ala Glu Asp
    210                 215                 220

Leu Gly Val Tyr Tyr Cys Val Gln Gly Thr His Phe Pro Leu Thr Phe
225                 230                 235                 240

Gly Ala Gly Thr Lys Leu Glu Leu Lys
```

<210> SEQ ID NO 55
<211> LENGTH: 747
<212> TYPE: DNA
<213> ORGANISM: ARTIFICIAL SEQUENCE
<220> FEATURE:
<223> OTHER INFORMATION: 2G8VL-VH scFv single chain Fv

<400> SEQUENCE: 55

```
gatgttgtga tgacccagac tccactcact ttgtcggtta ccattggaca accagcctct    60
atctcttgca agtcaagtca gagcctctta tatagtaatg gaaaaaccta tttgaactgg   120
atattacaga ggccaggcca gtctccaaag cgcctaatct atctggtgtc taaactggac   180
tctggagtcc ctgacaggtt cactggcagt ggatcaggaa cagattttac gctgaaaatc   240
agcagagtgg aggctgagga tttgggagtt tattactgcg tgcaaggtac acattttcct   300
ctcacgttcg gtgctgggac caagctggag ctgaaggtg gtggtggttc tggcggcggc   360
ggctccggtg gtggtggttc tgaggttcag ctgcagcagt ctggggcaga gcttgtgagg   420
tcagggcct cagtcaagtt gtcctgcaca gcttctggct tcaacattaa agactactat   480
ttgcactggg tgaagcagag gcctgaacag ggcctggagt ggattgcctg gattgatctt   540
gagaatggtg atattaaata tgccccgaag tttcagggca aggccactat aactgcagac   600
acatcctcca acacagccta cctgcagctc agcagcctga catctgagga cactgccgtc   660
tattactgta atccctatta ctacggtagt aactacgact atgctatgga ctactgggt   720
caaggaacct cagtcaccgt ctcctcc                                        747
```

<210> SEQ ID NO 56
<211> LENGTH: 249
<212> TYPE: PRT
<213> ORGANISM: artificial sequence
<220> FEATURE:
<223> OTHER INFORMATION: 2G8VL-VH scFv single chain Fv

<400> SEQUENCE: 56

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Ile Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Leu Thr Phe Gly Ala Gly Thr Lys Leu Glu Leu Lys
            100                 105                 110

Gly Gly Gly Gly Ser Gly Gly Gly Ser Gly Gly Gly Ser Glu
        115                 120                 125

Val Gln Leu Gln Gln Ser Gly Ala Glu Leu Val Arg Ser Gly Ala Ser
    130                 135                 140

Val Lys Leu Ser Cys Thr Ala Ser Gly Phe Asn Ile Lys Asp Tyr Tyr
145                 150                 155                 160

Leu His Trp Val Lys Gln Arg Pro Glu Gln Gly Leu Glu Trp Ile Ala

```
              165                 170                 175
Trp Ile Asp Leu Glu Asn Gly Asp Ile Lys Tyr Ala Pro Lys Phe Gln
            180                 185                 190

Gly Lys Ala Thr Ile Thr Ala Asp Thr Ser Ser Asn Thr Ala Tyr Leu
        195                 200                 205

Gln Leu Ser Ser Leu Thr Ser Glu Asp Thr Ala Val Tyr Tyr Cys Asn
    210                 215                 220

Pro Tyr Tyr Tyr Gly Ser Asn Tyr Asp Tyr Ala Met Asp Tyr Trp Gly
225                 230                 235                 240

Gln Gly Thr Ser Val Thr Val Ser Ser
                245
```

<210> SEQ ID NO 57
<211> LENGTH: 49
<212> TYPE: DNA
<213> ORGANISM: ARTIFICIAL SEQUENCE
<220> FEATURE:
<223> OTHER INFORMATION: 5'2G8 LH oligonucleotide

<400> SEQUENCE: 57
aggtgtacac tccgatgttg tgatgaccca gactccactc actttgtcg          49

<210> SEQ ID NO 58
<211> LENGTH: 54
<212> TYPE: DNA
<213> ORGANISM: artificial sequence
<220> FEATURE:
<223> OTHER INFORMATION: 3'2G8 VL Linker oligonucleotide

<400> SEQUENCE: 58
ggagccgccg ccgccagaac caccaccacc tttcagctcc agcttggtcc cagc     54

<210> SEQ ID NO 59
<211> LENGTH: 56
<212> TYPE: DNA
<213> ORGANISM: artificial sequence
<220> FEATURE:
<223> OTHER INFORMATION: 5'2G8 VH Linker oligonucleotide

<400> SEQUENCE: 59
tctggcggcg gcggctccgg tggtggtggt tctgaggttc agctgcagca gtctgg   56

<210> SEQ ID NO 60
<211> LENGTH: 30
<212> TYPE: DNA
<213> ORGANISM: artificial sequence
<220> FEATURE:
<223> OTHER INFORMATION: 3'2G8 LH oligonucleotide

<400> SEQUENCE: 60
acatccggag gagacggtga ctgaggttcc                               30

<210> SEQ ID NO 61
<211> LENGTH: 37
<212> TYPE: DNA
<213> ORGANISM: artificial sequence
<220> FEATURE:
<223> OTHER INFORMATION: 5' 2G8 HL oligonucleotide

<400> SEQUENCE: 61
aggtgtacac tccgaggttc agctgcagca gtctggg                       37

<210> SEQ ID NO 62

```
<211> LENGTH: 54
<212> TYPE: DNA
<213> ORGANISM: artificial sequence
<220> FEATURE:
<223> OTHER INFORMATION: 3' 2G8 VH Linker oligonucleotide

<400> SEQUENCE: 62
ggagccgccg ccgccagaac caccaccacc tgaggagacg gtgactgagg ttcc          54

<210> SEQ ID NO 63
<211> LENGTH: 69
<212> TYPE: DNA
<213> ORGANISM: artificial sequence
<220> FEATURE:
<223> OTHER INFORMATION: 5' 2G8 VL Linker oligonucleotide

<400> SEQUENCE: 63
tctggcggcg gcggctccgg tggtggtggt tctgatgttg tgatgaccca gactccactc    60
actttgtcg                                                            69

<210> SEQ ID NO 64
<211> LENGTH: 33
<212> TYPE: DNA
<213> ORGANISM: artificial sequence
<220> FEATURE:
<223> OTHER INFORMATION: 3' 2G8 HL oligonucleotide

<400> SEQUENCE: 64
acatccggat tcagctcca gcttggtccc agc                                  33

<210> SEQ ID NO 65
<211> LENGTH: 1509
<212> TYPE: DNA
<213> ORGANISM: artificial sequence
<220> FEATURE:
<223> OTHER INFORMATION: 2G8LHxSEQ ID NO: 12 ; bispecific single chain
      antibody

<400> SEQUENCE: 65
gatgttgtga tgacccagac tccactcact ttgtcggtta ccattggaca accagcctct    60
atctcttgca agtcaagtca gagcctctta tatagtaatg gaaaaaccta tttgaactgg   120
atattacaga ggccaggcca gtctccaaag cgcctaatct atctggtgtc taaactggac   180
tctggagtcc ctgacaggtt cactggcagt ggatcaggaa cagattttac gctgaaaatc   240
agcagagtgg aggctgagga tttgggagtt tattactgcg tgcaaggtac acattttcct   300
ctcacgttcg gtgctgggac caagctggag ctgaaaggtg gtggtggttc tggcggcggc   360
ggctccggtg gtggtggttc tgaggttcag ctgcagcagt ctggggcaga gcttgtgagg   420 tcagggcct cagtcaagtt gtcctgcaca gcttctggct tcaacattaa agactactat   480
ttgcactggg tgaagcagag gcctgaacag ggcctggagt ggattgcctg gattgatctt   540
gagaatggtg atattaaata tgccccgaag tttcagggca aggccactat aactgcagac   600
acatcctcca acacagccta cctgcagctc agcagcctga catctgagga cactgccgtc   660
tattactgta atccctatta ctacggtagt aactacgact atgctatgga ctactggggt   720
caaggaacct cagtcaccgt ctcctccgga ggtggtggat cccaggctgt tgtgactcag   780
gaatctgcac tcaccacatc acctggtgaa acagtcacac tcacttgtcg ctcaagtact   840
ggggctgtta caactagtaa ctatgccaac tgggtccaag aaaaaccaga tcatttattc   900
actggtctaa taggtggtac caacaagcga gctccaggtg tgcctgccag attctcaggc   960
```

-continued

```
tccctgattg gagacaaggc tgccctcacc atcacagggg cacagactga ggatgaggca    1020
atatatttct gtgctctatg gtacagcaac ctctgggtgt tcggtggagg aaccaaactg    1080
actgtcctag gtggtggtgg ttctggcggc ggcggctccg gtggtggtgg ttctgaggtg    1140
aagcttctcg agtctggagg aggattggtg cagcctaaag ggtcattgaa actctcatgt    1200
gcagcctctg gattcacctt caataccta gccatgaact gggtccgcca ggctccagga    1260
aagggtttgg aatgggttgc tcgcataaga agtaaatata ataattatgc aacatattat    1320
gccgattcag tgaaagacag gttcaccatc tccagagatg attcacaaag cattctctat    1380
ctacaaatga caacttgaa aactgaggac acagccatgt actactgtgt gagacatggg    1440
aacttcggta atagctacgt ttcctggttt gcttactggg gccaagggac tctggtcact    1500
gtctctgca                                                            1509
```

<210> SEQ ID NO 66
<211> LENGTH: 503
<212> TYPE: PRT
<213> ORGANISM: artificial sequence
<220> FEATURE:
<223> OTHER INFORMATION: 2G8LHxSEQ ID NO: 12 ; bispecific single chain antibody

<400> SEQUENCE: 66

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Ile Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Leu Thr Phe Gly Ala Gly Thr Lys Leu Glu Leu Lys
            100                 105                 110

Gly Gly Gly Gly Ser Gly Gly Gly Ser Gly Gly Gly Ser Glu
        115                 120                 125

Val Gln Leu Gln Gln Ser Gly Ala Glu Leu Val Arg Ser Gly Ala Ser
    130                 135                 140

Val Lys Leu Ser Cys Thr Ala Ser Gly Phe Asn Ile Lys Asp Tyr Tyr
145                 150                 155                 160

Leu His Trp Val Lys Gln Arg Pro Glu Gln Gly Leu Glu Trp Ile Ala
                165                 170                 175

Trp Ile Asp Leu Glu Asn Gly Asp Ile Lys Tyr Ala Pro Lys Phe Gln
            180                 185                 190

Gly Lys Ala Thr Ile Thr Ala Asp Thr Ser Ser Asn Thr Ala Tyr Leu
        195                 200                 205

Gln Leu Ser Ser Leu Thr Ser Glu Asp Thr Ala Val Tyr Tyr Cys Asn
    210                 215                 220

Pro Tyr Tyr Tyr Gly Ser Asn Tyr Asp Tyr Ala Met Asp Tyr Trp Gly
225                 230                 235                 240

Gln Gly Thr Ser Val Thr Val Ser Ser Gly Gly Gly Ser Gln Ala
                245                 250                 255
```

```
Val Val Thr Gln Glu Ser Ala Leu Thr Thr Ser Pro Gly Glu Thr Val
            260                 265                 270

Thr Leu Thr Cys Arg Ser Ser Thr Gly Ala Val Thr Thr Ser Asn Tyr
        275                 280                 285

Ala Asn Trp Val Gln Glu Lys Pro Asp His Leu Phe Thr Gly Leu Ile
    290                 295                 300

Gly Gly Thr Asn Lys Arg Ala Pro Gly Val Pro Ala Arg Phe Ser Gly
305                 310                 315                 320

Ser Leu Ile Gly Asp Lys Ala Ala Leu Thr Ile Thr Gly Ala Gln Thr
                325                 330                 335

Glu Asp Glu Ala Ile Tyr Phe Cys Ala Leu Trp Tyr Ser Asn Leu Trp
            340                 345                 350

Val Phe Gly Gly Gly Thr Lys Leu Thr Val Leu Gly Gly Gly Gly Ser
        355                 360                 365

Gly Gly Gly Gly Ser Gly Gly Gly Ser Glu Val Lys Leu Leu Glu
370                 375                 380

Ser Gly Gly Gly Leu Val Gln Pro Lys Gly Ser Leu Lys Leu Ser Cys
385                 390                 395                 400

Ala Ala Ser Gly Phe Thr Phe Asn Thr Tyr Ala Met Asn Trp Val Arg
                405                 410                 415

Gln Ala Pro Gly Lys Gly Leu Glu Trp Val Ala Arg Ile Arg Ser Lys
            420                 425                 430

Tyr Asn Asn Tyr Ala Thr Tyr Tyr Ala Asp Ser Val Lys Asp Arg Phe
        435                 440                 445

Thr Ile Ser Arg Asp Asp Ser Gln Ser Ile Leu Tyr Leu Gln Met Asn
    450                 455                 460

Asn Leu Lys Thr Glu Asp Thr Ala Met Tyr Tyr Cys Val Arg His Gly
465                 470                 475                 480

Asn Phe Gly Asn Ser Tyr Val Ser Trp Phe Ala Tyr Trp Gly Gln Gly
                485                 490                 495

Thr Leu Val Thr Val Ser Ala
            500

<210> SEQ ID NO 67
<211> LENGTH: 1509
<212> TYPE: DNA
<213> ORGANISM: ARTIFICIAL SEQUENCE
<220> FEATURE:
<223> OTHER INFORMATION: 2G8LHx SEQ ID NO: 10 ; bispecific single chain
      antibody

<400> SEQUENCE: 67
gatgttgtga tgacccagac tccactcact ttgtcggtta ccattggaca accagcctct    60
atctcttgca agtcaagtca gagcctctta tatagtaatg aaaaaaccta tttgaactgg   120
atattacaga ggccaggcca gtctccaaag cgcctaatct atctggtgtc taaactggac   180
tctggagtcc ctgacaggtt cactggcagt ggatcaggaa cagattttac gctgaaaatc   240
agcagagtgg aggctgagga tttgggagtt tattactgcg tgcaaggtac acatttttcct   300 ctcacgttcg gtgctgggac caagctggag ctgaaaggtg gtggtggttc tggcggcggc   360
ggctccggtg gtggtggttc tgaggttcag ctgcagcagt ctggggcaga gcttgtgagg   420 tcagggggcct cagtcaagtt gtcctgcaca gcttctggct tcaacattaa agactactat   480
ttgcactggg tgaagcagag gcctgaacag ggcctggagt ggattgcctg gattgatctt   540
gagaatggtg atattaaata tgcccccgaag tttcagggca aggccactat aactgcagac   600
```

```
acatcctcca acacagccta cctgcagctc agcagcctga catctgagga cactgccgtc    660
tattactgta atccctatta ctacggtagt aactacgact atgctatgga ctactggggt    720
caaggaacct cagtcaccgt ctcctccgga ggtggtggat ccgaggtgaa gcttctcgag    780
tctggaggag gattggtgca gcctaaaggg tcattgaaac tctcatgtgc agcctctgga    840
ttcaccttca atacctacgc catgaactgg gtccgccagg ctccaggaaa gggtttggaa    900
tgggttgctc gcataagaag taaatataat aattatgcaa catattatgc cgattcagtg    960
aaagacaggt tcaccatctc cagagatgat tcacaaagca ttctctatct acaaatgaac   1020
aacttgaaaa ctgaggacac agccatgtac tactgtgtga gacatgggaa cttcggtaat   1080
agctacgttt cctggtttgc ttactggggc caagggactc tggtcactgt ctctgcaggt   1140
ggtggtggtt ctggcggcgg cggctccggt ggtggtggtt ctcaggctgt tgtgactcag   1200
gaatctgcac tcaccacatc acctggtgaa acagtcacac tcacttgtcg ctcaagtact   1260
ggggctgtta caactagtaa ctatgccaac tgggtccaag aaaaaccaga tcatttattc   1320
actggtctaa taggtggtac caacaagcga gctccaggtg tgcctgccag attctcaggc   1380
tccctgattg gagacaaggc tgccctcacc atcacagggg cacagactga ggatgaggca   1440
atatatttct gtgctctatg gtacagcaac ctctgggtgt tcggtggagg aaccaaactg   1500
actgtccta                                                           1509

<210> SEQ ID NO 68
<211> LENGTH: 503
<212> TYPE: PRT
<213> ORGANISM: artificial sequence
<220> FEATURE:
<223> OTHER INFORMATION: 2G8LHxSEQ ID NO: 10 ; bispecific single chain
      antibody

<400> SEQUENCE: 68

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Ile Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Leu Thr Phe Gly Ala Gly Thr Lys Leu Glu Leu Lys
            100                 105                 110

Gly Gly Gly Gly Ser Gly Gly Gly Gly Ser Gly Gly Gly Gly Ser Glu
        115                 120                 125

Val Gln Leu Gln Gln Ser Gly Ala Glu Leu Val Arg Ser Gly Ala Ser
    130                 135                 140

Val Lys Leu Ser Cys Thr Ala Ser Gly Phe Asn Ile Lys Asp Tyr Tyr
145                 150                 155                 160

Leu His Trp Val Lys Gln Arg Pro Glu Gln Gly Leu Glu Trp Ile Ala
                165                 170                 175

Trp Ile Asp Leu Glu Asn Gly Asp Ile Lys Tyr Ala Pro Lys Phe Gln
            180                 185                 190
```

Gly Lys Ala Thr Ile Thr Ala Asp Thr Ser Ser Asn Thr Ala Tyr Leu
            195                 200                 205
Gln Leu Ser Ser Leu Thr Ser Glu Asp Thr Ala Val Tyr Tyr Cys Asn
        210                 215                 220
Pro Tyr Tyr Tyr Gly Ser Asn Tyr Asp Tyr Ala Met Asp Tyr Trp Gly
225                 230                 235                 240
Gln Gly Thr Ser Val Thr Val Ser Ser Gly Gly Gly Ser Glu Val
            245                 250                 255
Lys Leu Leu Glu Ser Gly Gly Gly Leu Val Gln Pro Lys Gly Ser Leu
        260                 265                 270
Lys Leu Ser Cys Ala Ala Ser Gly Phe Thr Phe Asn Thr Tyr Ala Met
    275                 280                 285
Asn Trp Val Arg Gln Ala Pro Gly Lys Gly Leu Glu Trp Val Ala Arg
290                 295                 300
Ile Arg Ser Lys Tyr Asn Asn Tyr Ala Thr Tyr Tyr Ala Asp Ser Val
305                 310                 315                 320
Lys Asp Arg Phe Thr Ile Ser Arg Asp Asp Ser Gln Ser Ile Leu Tyr
            325                 330                 335
Leu Gln Met Asn Asn Leu Lys Thr Glu Asp Thr Ala Met Tyr Tyr Cys
        340                 345                 350
Val Arg His Gly Asn Phe Gly Asn Ser Tyr Val Ser Trp Phe Ala Tyr
    355                 360                 365
Trp Gly Gln Gly Thr Leu Val Thr Val Ser Ala Gly Gly Gly Gly Ser
    370                 375                 380
Gly Gly Gly Gly Ser Gly Gly Gly Ser Gln Ala Val Val Thr Gln
385                 390                 395                 400
Glu Ser Ala Leu Thr Thr Ser Pro Gly Glu Thr Val Thr Leu Thr Cys
            405                 410                 415
Arg Ser Ser Thr Gly Ala Val Thr Thr Ser Asn Tyr Ala Asn Trp Val
        420                 425                 430
Gln Glu Lys Pro Asp His Leu Phe Thr Gly Leu Ile Gly Gly Thr Asn
    435                 440                 445
Lys Arg Ala Pro Gly Val Pro Ala Arg Phe Ser Gly Ser Leu Ile Gly
450                 455                 460
Asp Lys Ala Ala Leu Thr Ile Thr Gly Ala Gln Thr Glu Asp Glu Ala
465                 470                 475                 480
Ile Tyr Phe Cys Ala Leu Trp Tyr Ser Asn Leu Trp Val Phe Gly Gly
            485                 490                 495
Gly Thr Lys Leu Thr Val Leu
            500

<210> SEQ ID NO 69
<211> LENGTH: 1488
<212> TYPE: DNA
<213> ORGANISM: ARTIFICIAL SEQUENCE
<220> FEATURE:
<223> OTHER INFORMATION: 2G8LHxSEQ ID NO: 16 ; bispecific single chain
      antibody

<400> SEQUENCE: 69
gatgttgtga tgacccagac tccactcact tgtcggtta ccattggaca accagcctct      60
atctcttgca agtcaagtca gagcctctta tatagtaatg gaaaaaccta tttgaactgg    120
atattacaga ggccaggcca gtctccaaag cgcctaatct atctggtgtc taaactggac    180
tctggagtcc ctgacaggtt cactggcagt ggatcaggaa cagattttac gctgaaaatc    240

-continued

```
agcagagtgg aggctgagga tttgggagtt tattactgcg tgcaaggtac acattttcct    300
ctcacgttcg gtgctggac  caagctggag ctgaaaggtg gtggtggttc tggcggcggc    360
ggctccggtg gtggtggttc tgaggttcag ctgcagcagt ctggggcaga gcttgtgagg    420
tcagggcct  cagtcaagtt gtcctgcaca gcttctggct tcaacattaa agactactat    480
ttgcactggg tgaagcagag gcctgaacag ggcctggagt ggattgcctg gattgatctt    540
gagaatggtg atattaaata tgccccgaag tttcagggca aggccactat aactgcagac    600
acatcctcca acacagccta cctgcagctc agcagcctga catctgagga cactgccgtc    660
tattactgta atccctatta ctacggtagt aactacgact atgctatgga ctactgggt    720
caaggaacct cagtcaccgt ctcctccgga ggtggtggat cccaagttgt tctcacccag    780
tctccagcaa tcatgtctgc atttccaggg gagaaggtca ccatgacctg cagtgccagc    840
tcaagtgtaa gttacatgaa ctggtaccag cagaagtcag gcacctcccc caaaagatgg    900
atttatgact catccaaact ggcttctgga gtccctgctc gcttcagtgg cagtgggtct    960
gggacctctt attctctcac aatcagcagc atggagactg aagatgctgc cacttattac   1020
tgccagcagt ggagtcgtaa cccacccacg ttcggagggg ggaccaagct acaaattaca   1080
ggtggtggtg gttctggcgg cggcggctcc ggtggtggtg gttctcaggt ccagctgcag   1140
cagtctgggg ctgaactggc aagacctggg gcctcagtga agatgtcctg caaggcttct   1200
ggctacacct ttactagatc tacgatgcac tgggtaaaac agaggcctgg acagggtctg   1260
gaatggattg gatacattaa tcctagcagt gcttatacta attacaatca gaaattcaag   1320
gacaaggcca cattgactgc agacaaatcc tccagtacag cctacatgca actgagtagc   1380
ctgacatctg aggactctgc agtctattac tgtgcaagtc cgcaagtcca ctatgattac   1440
aacgggtttc cttactgggg ccaagggact ctggtcactg tctctgca                1488
```

<210> SEQ ID NO 70
<211> LENGTH: 496
<212> TYPE: PRT
<213> ORGANISM: artificial sequence
<220> FEATURE:
<223> OTHER INFORMATION: 2G8LHxSEQ ID NO: 16 ; bispecific single chain antibody

<400> SEQUENCE: 70

```
Asp Val Val Met Thr Gln Thr Pro Leu Thr Leu Ser Val Thr Ile Gly
  1               5                  10                  15

Gln Pro Ala Ser Ile Ser Cys Lys Ser Ser Gln Ser Leu Leu Tyr Ser
             20                  25                  30

Asn Gly Lys Thr Tyr Leu Asn Trp Ile Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                 85                  90                  95

Thr His Phe Pro Leu Thr Phe Gly Ala Gly Thr Lys Leu Glu Leu Lys
            100                 105                 110

Gly Gly Gly Gly Ser Gly Gly Gly Ser Gly Gly Gly Ser Glu
        115                 120                 125

Val Gln Leu Gln Gln Ser Gly Ala Glu Leu Val Arg Ser Gly Ala Ser
    130                 135                 140
```

```
Val Lys Leu Ser Cys Thr Ala Ser Gly Phe Asn Ile Lys Asp Tyr Tyr
145                 150                 155                 160

Leu His Trp Val Lys Gln Arg Pro Glu Gln Gly Leu Glu Trp Ile Ala
                165                 170                 175

Trp Ile Asp Leu Glu Asn Gly Asp Ile Lys Tyr Ala Pro Lys Phe Gln
            180                 185                 190

Gly Lys Ala Thr Ile Thr Ala Asp Thr Ser Ser Asn Thr Ala Tyr Leu
        195                 200                 205

Gln Leu Ser Ser Leu Thr Ser Glu Asp Thr Ala Val Tyr Tyr Cys Asn
    210                 215                 220

Pro Tyr Tyr Tyr Gly Ser Asn Tyr Asp Tyr Ala Met Asp Tyr Trp Gly
225                 230                 235                 240

Gln Gly Thr Ser Val Thr Val Ser Ser Gly Gly Gly Ser Gln Val
                245                 250                 255

Val Leu Thr Gln Ser Pro Ala Ile Met Ser Ala Phe Pro Gly Glu Lys
            260                 265                 270

Val Thr Met Thr Cys Ser Ala Ser Ser Ser Val Ser Tyr Met Asn Trp
        275                 280                 285

Tyr Gln Gln Lys Ser Gly Thr Ser Pro Lys Arg Trp Ile Tyr Asp Ser
    290                 295                 300

Ser Lys Leu Ala Ser Gly Val Pro Ala Arg Phe Ser Gly Ser Gly Ser
305                 310                 315                 320

Gly Thr Ser Tyr Ser Leu Thr Ile Ser Ser Met Glu Thr Glu Asp Ala
                325                 330                 335

Ala Thr Tyr Tyr Cys Gln Gln Trp Ser Arg Asn Pro Pro Thr Phe Gly
            340                 345                 350

Gly Gly Thr Lys Leu Gln Ile Thr Gly Gly Gly Ser Gly Gly Gly
        355                 360                 365

Gly Ser Gly Gly Gly Gly Ser Gln Val Gln Leu Gln Gln Ser Gly Ala
    370                 375                 380

Glu Leu Ala Arg Pro Gly Ala Ser Val Lys Met Ser Cys Lys Ala Ser
385                 390                 395                 400

Gly Tyr Thr Phe Thr Arg Ser Thr Met His Trp Val Lys Gln Arg Pro
                405                 410                 415

Gly Gln Gly Leu Glu Trp Ile Gly Tyr Ile Asn Pro Ser Ser Ala Tyr
            420                 425                 430

Thr Asn Tyr Asn Gln Lys Phe Lys Asp Lys Ala Thr Leu Thr Ala Asp
        435                 440                 445

Lys Ser Ser Ser Thr Ala Tyr Met Gln Leu Ser Ser Leu Thr Ser Glu
    450                 455                 460

Asp Ser Ala Val Tyr Tyr Cys Ala Ser Pro Gln Val His Tyr Asp Tyr
465                 470                 475                 480

Asn Gly Phe Pro Tyr Trp Gly Gln Gly Thr Leu Val Thr Val Ser Ala
                485                 490                 495

<210> SEQ ID NO 71
<211> LENGTH: 1488
<212> TYPE: DNA
<213> ORGANISM: ARTIFICIAL SEQUENCE
<220> FEATURE:
<223> OTHER INFORMATION: 2G8LHxSEQ ID NO: 14 ; bispecific single chain
      antibody

<400> SEQUENCE: 71
gatgttgtga tgacccagac tccactcact ttgtcggtta ccattggaca accagcctct    60
```

```
atctcttgca agtcaagtca gagcctctta tatagtaatg gaaaaaccta tttgaactgg      120
atattacaga ggccaggcca gtctccaaag cgcctaatct atctggtgtc taaactggac      180
tctggagtcc ctgacaggtt cactggcagt ggatcaggaa cagattttac gctgaaaatc      240
agcagagtgg aggctgagga tttgggagtt tattactgcg tgcaaggtac acattttcct      300
ctcacgttcg gtgctgggac caagctggag ctgaaaggtg gtggtggttc tggcggcggc      360
ggctccggtg gtggtggttc tgaggttcag ctgcagcagt ctggggcaga gcttgtgagg      420
tcagggggcct cagtcaagtt gtcctgcaca gcttctggct tcaacattaa agactactat      480
ttgcactggg tgaagcagag gcctgaacag ggcctggagt ggattgcctg gattgatctt      540
gagaatggtg atattaaata tgccccgaag tttcagggca aggccactat aactgcagac      600
acatcctcca acacagccta cctgcagctc agcagcctga catctgagga cactgccgtc      660
tattactgta atccctatta ctacggtagt aactacgact atgctatgga ctactggggt      720
caaggaacct cagtcaccgt ctcctccgga ggtggtggat cccaggtcca gctgcagcag      780
tctggggctg aactggcaag acctggggcc tcagtgaaga tgtcctgcaa ggcttctggc      840
tacaccttta ctagatctac gatgcactgg gtaaaacaga ggcctggaca gggtctggaa      900
tggattggat acattaatcc tagcagtgct tatactaatt acaatcagaa attcaaggac      960
aaggccacat tgactgcaga caaatcctcc agtacagcct acatgcaact gagtagcctg     1020
acatctgagg actctgcagt ctattactgt gcaagtccgc aagtccacta tgattacaac     1080
gggtttcctt actggggcca agggactctg gtcactgtct ctgcaggtgg tggtggttct     1140
ggcggcggcg gctccggtgg tggtggttct caagttgttc tcacccagtc tccagcaatc     1200
atgtctgcat ttccagggga aaggtcacc atgacctgca gtgccagctc aagtgtaagt     1260
tacatgaact ggtaccagca gaagtcaggc acctccccca aaagatggat ttatgactca     1320
tccaaactgg cttctggagt ccctgctcgc ttcagtggca gtgggtctgg gacctcttat     1380
tctctcacaa tcagcagcat ggagactgaa gatgctgcca cttattactg ccagcagtgg     1440
agtcgtaacc cacccacgtt cggagggggg accaagctac aaattaca                  1488
```

<210> SEQ ID NO 72
<211> LENGTH: 496
<212> TYPE: PRT
<213> ORGANISM: artificial sequence
<220> FEATURE:
<223> OTHER INFORMATION: 2G8LHxSEQ ID NO: 14 ; bispecific single chain antibody

<400> SEQUENCE: 72

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Ile Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Leu Thr Phe Gly Ala Gly Thr Lys Leu Glu Leu Lys
```

```
            100             105             110
Gly Gly Gly Gly Ser Gly Gly Gly Ser Gly Gly Gly Ser Glu
        115             120             125

Val Gln Leu Gln Gln Ser Gly Ala Glu Leu Val Arg Ser Gly Ala Ser
    130             135             140

Val Lys Leu Ser Cys Thr Ala Ser Gly Phe Asn Ile Lys Asp Tyr Tyr
145             150             155             160

Leu His Trp Val Lys Gln Arg Pro Glu Gln Gly Leu Glu Trp Ile Ala
            165             170             175

Trp Ile Asp Leu Glu Asn Gly Asp Ile Lys Tyr Ala Pro Lys Phe Gln
        180             185             190

Gly Lys Ala Thr Ile Thr Ala Asp Thr Ser Ser Asn Thr Ala Tyr Leu
        195             200             205

Gln Leu Ser Ser Leu Thr Ser Glu Asp Thr Ala Val Tyr Tyr Cys Asn
    210             215             220

Pro Tyr Tyr Tyr Gly Ser Asn Tyr Asp Tyr Ala Met Asp Tyr Trp Gly
225             230             235             240

Gln Gly Thr Ser Val Thr Val Ser Ser Gly Gly Gly Ser Gln Val
            245             250             255

Gln Leu Gln Gln Ser Gly Ala Glu Leu Ala Arg Pro Gly Ala Ser Val
        260             265             270

Lys Met Ser Cys Lys Ala Ser Gly Tyr Thr Phe Thr Arg Ser Thr Met
        275             280             285

His Trp Val Lys Gln Arg Pro Gly Gln Gly Leu Glu Trp Ile Gly Tyr
        290             295             300

Ile Asn Pro Ser Ser Ala Tyr Thr Asn Tyr Asn Gln Lys Phe Lys Asp
305             310             315             320

Lys Ala Thr Leu Thr Ala Asp Lys Ser Ser Ser Thr Ala Tyr Met Gln
            325             330             335

Leu Ser Ser Leu Thr Ser Glu Asp Ser Ala Val Tyr Tyr Cys Ala Ser
        340             345             350

Pro Gln Val His Tyr Asp Tyr Asn Gly Phe Pro Tyr Trp Gly Gln Gly
        355             360             365

Thr Leu Val Thr Val Ser Ala Gly Gly Gly Ser Gly Gly Gly Gly
        370             375             380

Ser Gly Gly Gly Gly Ser Gln Val Val Leu Thr Gln Ser Pro Ala Ile
385             390             395             400

Met Ser Ala Phe Pro Gly Glu Lys Val Thr Met Thr Cys Ser Ala Ser
            405             410             415

Ser Ser Val Ser Tyr Met Asn Trp Tyr Gln Gln Lys Ser Gly Thr Ser
            420             425             430

Pro Lys Arg Trp Ile Tyr Asp Ser Ser Lys Leu Ala Ser Gly Val Pro
        435             440             445

Ala Arg Phe Ser Gly Ser Gly Ser Gly Thr Ser Tyr Ser Leu Thr Ile
        450             455             460

Ser Ser Met Glu Thr Glu Asp Ala Ala Thr Tyr Tyr Cys Gln Gln Trp
465             470             475             480

Ser Arg Asn Pro Pro Thr Phe Gly Gly Gly Thr Lys Leu Gln Ile Thr
            485             490             495

<210> SEQ ID NO 73
<211> LENGTH: 1512
<212> TYPE: DNA
<213> ORGANISM: ARTIFICIAL SEQUENCE
```

<220> FEATURE:
<223> OTHER INFORMATION: 2G8HLxSEQ ID NO: 12 ; bispecific single chain antibody

<400> SEQUENCE: 73

```
gaggttcagc tgcagcagtc tggggcagag cttgtgaggt caggggcctc agtcaagttg      60
tcctgcacag cttctggctt caacattaaa gactactatt tgcactgggt gaagcagagg     120
cctgaacagg gcctggagtg gattgcctgg attgatcttg agaatggtga tattaaatat     180
gccccgaagt tcagggcaa ggccactata actgcagaca catcctccaa cacagcctac      240
ctgcagctca gcagcctgac atctgaggac actgccgtct attactgtaa tccctattac     300
tacggtagta actacgacta tgctatggac tactggggtc aaggaacctc agtcaccgtc     360
tcctcaggtg gtggtggttc tggcggcggc ggctccggtg gtggtggttc tgatgttgtg     420
atgacccaga ctccactcac tttgtcggtt accattggac aaccagcctc tatctcttgc     480
aagtcaagtc agagcctctt atatagtaat ggaaaaacct atttgaactg gatattacag     540
aggccaggcc agtctccaaa gcgcctaatc tatctggtgt ctaaactgga ctctggagtc     600
cctgacaggt tcactggcag tggatcagga acagatttta cgctgaaaat cagcagagtg     660
gaggctgagg atttgggagt ttattactgc gtgcaaggta cacattttcc tctcacgttc     720
ggtgctggga ccaagctgga gctgaaatcc ggaggtggtg atcccaggc tgttgtgact      780
caggaatctg cactcaccac atcacctggt gaaacagtca cactcacttg tcgctcaagt     840
actggggctg ttacaactag taactatgcc aactgggtcc agaaaaaacc agatcattta     900
ttcactggtc taataggtgg taccaacaag cgagctccag gtgtgcctgc agattctca      960
ggctccctga ttggagacaa ggctgccctc accatcacag gggcacagac tgaggatgag    1020
gcaatatatt tctgtgctct atggtacagc aacctctggg tgttcggtgg aggaaccaaa    1080
ctgactgtcc taggtggtgg tggttctggc ggcggcggct ccggtggtgg tggttctgag    1140
gtgaagcttc tcgagtctgg aggaggattg gtgcagccta agggtcatt gaaactctca    1200
tgtgcagcct ctggattcac cttcaatacc tacgccatga ctgggtccg ccaggctcca    1260
ggaaagggtt tggaatgggt tgctcgcata agaagtaaat ataataatta tgcaacatat    1320
tatgccgatt cagtgaaaga caggttcacc atctccagag atgattcaca aagcattctc    1380
tatctacaaa tgaacaactt gaaaactgag gacacagcca tgtactactg tgtgagacat    1440
gggaacttcg gtaatagcta cgtttcctgg tttgcttact ggggccaagg gactctggtc    1500
actgtctctg ca                                                        1512
```

<210> SEQ ID NO 74
<211> LENGTH: 504
<212> TYPE: PRT
<213> ORGANISM: artificial sequence
<220> FEATURE:
<223> OTHER INFORMATION: 2G8HLxSEQ ID NO: 12 ; bispecific single chain antibody

<400> SEQUENCE: 74

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Ala Trp Ile Asp Leu Glu Asn Gly Asp Ile Lys Tyr Ala Pro Lys Phe
```

-continued

```
                50                  55                  60
Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Pro Tyr Tyr Tyr Gly Ser Asn Tyr Asp Tyr Ala Met Asp Tyr Trp
                100                 105                 110

Gly Gln Gly Thr Ser Val Thr Val Ser Ser Gly Gly Gly Gly Ser Gly
                115                 120                 125

Gly Gly Ser Gly Gly Gly Gly Ser Asp Val Val Met Thr Gln Thr
            130                 135                 140

Pro Leu Thr Leu Ser Val Thr Ile Gly Gln Pro Ala Ser Ile Ser Cys
145                 150                 155                 160

Lys Ser Ser Gln Ser Leu Leu Tyr Ser Asn Gly Lys Thr Tyr Leu Asn
                165                 170                 175

Trp Ile Leu Gln Arg Pro Gly Gln Ser Pro Lys Arg Leu Ile Tyr Leu
                180                 185                 190

Val Ser Lys Leu Asp Ser Gly Val Pro Asp Arg Phe Thr Gly Ser Gly
                195                 200                 205

Ser Gly Thr Asp Phe Thr Leu Lys Ile Ser Arg Val Glu Ala Glu Asp
            210                 215                 220

Leu Gly Val Tyr Tyr Cys Val Gln Gly Thr His Phe Pro Leu Thr Phe
225                 230                 235                 240

Gly Ala Gly Thr Lys Leu Glu Leu Lys Ser Gly Gly Gly Gly Ser Gln
                245                 250                 255

Ala Val Val Thr Gln Glu Ser Ala Leu Thr Thr Ser Pro Gly Glu Thr
            260                 265                 270

Val Thr Leu Thr Cys Arg Ser Ser Thr Gly Ala Val Thr Thr Ser Asn
            275                 280                 285

Tyr Ala Asn Trp Val Gln Glu Lys Pro Asp His Leu Phe Thr Gly Leu
            290                 295                 300

Ile Gly Gly Thr Asn Lys Arg Ala Pro Gly Val Pro Ala Arg Phe Ser
305                 310                 315                 320

Gly Ser Leu Ile Gly Asp Lys Ala Ala Leu Thr Ile Thr Gly Ala Gln
                325                 330                 335

Thr Glu Asp Glu Ala Ile Tyr Phe Cys Ala Leu Trp Tyr Ser Asn Leu
            340                 345                 350

Trp Val Phe Gly Gly Gly Thr Lys Leu Thr Val Leu Gly Gly Gly Gly
            355                 360                 365

Ser Gly Gly Gly Gly Ser Gly Gly Gly Gly Ser Glu Val Lys Leu Leu
            370                 375                 380

Glu Ser Gly Gly Gly Leu Val Gln Pro Lys Gly Ser Leu Lys Leu Ser
385                 390                 395                 400

Cys Ala Ala Ser Gly Phe Thr Phe Asn Thr Tyr Ala Met Asn Trp Val
                405                 410                 415

Arg Gln Ala Pro Gly Lys Gly Leu Glu Trp Val Ala Arg Ile Arg Ser
            420                 425                 430

Lys Tyr Asn Asn Tyr Ala Thr Tyr Tyr Ala Asp Ser Val Lys Asp Arg
            435                 440                 445

Phe Thr Ile Ser Arg Asp Asp Ser Gln Ser Ile Leu Tyr Leu Gln Met
        450                 455                 460

Asn Asn Leu Lys Thr Glu Asp Thr Ala Met Tyr Tyr Cys Val Arg His
465                 470                 475                 480
```

Gly Asn Phe Gly Asn Ser Tyr Val Ser Trp Phe Ala Tyr Trp Gly Gln
            485                 490                 495

Gly Thr Leu Val Thr Val Ser Ala
        500

<210> SEQ ID NO 75
<211> LENGTH: 1512
<212> TYPE: DNA
<213> ORGANISM: ARTIFICIAL SEQUENCE
<220> FEATURE:
<223> OTHER INFORMATION: 2G8HLxSEQ ID NO: 10 ; bispecific single chain
      antibody

<400> SEQUENCE: 75

| | | | | | |
|---|---|---|---|---|---|
| gaggttcagc | tgcagcagtc | tggggcagag | cttgtgaggt | caggggcctc | agtcaagttg | 60 |
| tcctgcacag | cttctggctt | caacattaaa | gactactatt | tgcactgggt | gaagcagagg | 120 |
| cctgaacagg | gcctggagtg | gattgcctgg | attgatcttg | agaatggtga | tattaaatat | 180 |
| gccccgaagt | tcagggcaa | ggccactata | actgcagaca | catcctccaa | cacagcctac | 240 |
| ctgcagctca | gcagcctgac | atctgaggac | actgccgtct | attactgtaa | tccctattac | 300 |
| tacggtagta | actacgacta | tgctatggac | tactggggtc | aaggaacctc | agtcaccgtc | 360 |
| tcctcaggtg | gtggtggttc | tggcggcggc | ggctccggtg | gtggtggttc | tgatgttgtg | 420 |
| atgacccaga | ctccactcac | tttgtcggtt | accattggac | aaccagcctc | tatctcttgc | 480 |
| aagtcaagtc | agagcctctt | atatagtaat | ggaaaaacct | atttgaactg | gatattacag | 540 |
| aggccaggcc | agtctccaaa | gcgcctaatc | tatctggtgt | ctaaactgga | ctctggagtc | 600 |
| cctgacaggt | tcactggcag | tggatcagga | acagatttta | cgctgaaaat | cagcagagtg | 660 |
| gaggctgagg | atttgggagt | ttattactgc | gtgcaaggta | cacattttcc | tctcacgttc | 720 |
| ggtgctggga | ccaagctgga | gctgaaatcc | ggaggtggtg | gatccgaggt | gaagcttctc | 780 |
| gagtctggag | gaggattggt | gcagcctaaa | gggtcattga | actctcatg | tgcagcctct | 840 |
| ggattcacct | tcaataccta | cgccatgaac | tgggtccgcc | aggctccagg | aaagggtttg | 900 |
| gaatgggttg | ctcgcataag | aagtaaatat | aataattatg | caacatatta | tgccgattca | 960 |
| gtgaaagaca | ggttcaccat | ctccagagat | gattcacaaa | gcattctcta | tctacaaatg | 1020 |
| aacaacttga | aaactgagga | cacagccatg | tactactgtg | tgagacatgg | gaacttcggt | 1080 |
| aatagctacg | tttcctggtt | tgcttactgg | ggccaaggga | ctctggtcac | tgtctctgca | 1140 |
| ggtggtggtg | gttctggcgg | cggcggctcc | ggtggtggtg | gttctcaggc | tgttgtgact | 1200 |
| caggaatctg | cactcaccac | atcacctggt | gaaacagtca | cactcacttg | tcgctcaagt | 1260 |
| actgggctg | ttacaactag | taactatgcc | aactgggtcc | aagaaaaacc | agatcattta | 1320 |
| ttcactggtc | taataggtgg | taccaacaag | cgagctccag | gtgtgcctgc | cagattctca | 1380 |
| ggctccctga | ttggagacaa | ggctgccctc | accatcacag | ggcacagac | tgaggatgag | 1440 |
| gcaatatatt | tctgtgctct | atggtacagc | aacctctggg | tgttcggtgg | aggaaccaaa | 1500 |
| ctgactgtcc | ta | | | | | 1512 |

<210> SEQ ID NO 76
<211> LENGTH: 504
<212> TYPE: PRT
<213> ORGANISM: artificial sequence
<220> FEATURE:
<223> OTHER INFORMATION: 2G8HLxSEQ ID NO: 10 ; bispecific single chain
      antibody

```
<400> SEQUENCE: 76

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Ala Trp Ile Asp Leu Glu Asn Gly Asp Ile Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Pro Tyr Tyr Tyr Gly Ser Asn Tyr Asp Tyr Ala Met Asp Tyr Trp
            100                 105                 110

Gly Gln Gly Thr Ser Val Thr Val Ser Ser Gly Gly Gly Gly Ser Gly
            115                 120                 125

Gly Gly Gly Ser Gly Gly Gly Ser Asp Val Val Met Thr Gln Thr
            130                 135                 140

Pro Leu Thr Leu Ser Val Thr Ile Gly Gln Pro Ala Ser Ile Ser Cys
145                 150                 155                 160

Lys Ser Ser Gln Ser Leu Leu Tyr Ser Asn Gly Lys Thr Tyr Leu Asn
                165                 170                 175

Trp Ile Leu Gln Arg Pro Gly Gln Ser Pro Lys Arg Leu Ile Tyr Leu
            180                 185                 190

Val Ser Lys Leu Asp Ser Gly Val Pro Asp Arg Phe Thr Gly Ser Gly
            195                 200                 205

Ser Gly Thr Asp Phe Thr Leu Lys Ile Ser Arg Val Glu Ala Glu Asp
            210                 215                 220

Leu Gly Val Tyr Tyr Cys Val Gln Gly Thr His Phe Pro Leu Thr Phe
225                 230                 235                 240

Gly Ala Gly Thr Lys Leu Glu Leu Lys Ser Gly Gly Gly Gly Ser Glu
            245                 250                 255

Val Lys Leu Leu Glu Ser Gly Gly Gly Leu Val Gln Pro Lys Gly Ser
            260                 265                 270

Leu Lys Leu Ser Cys Ala Ala Ser Gly Phe Thr Phe Asn Thr Tyr Ala
            275                 280                 285

Met Asn Trp Val Arg Gln Ala Pro Gly Lys Gly Leu Glu Trp Val Ala
            290                 295                 300

Arg Ile Arg Ser Lys Tyr Asn Asn Tyr Ala Thr Tyr Tyr Ala Asp Ser
305                 310                 315                 320

Val Lys Asp Arg Phe Thr Ile Ser Arg Asp Asp Ser Gln Ser Ile Leu
            325                 330                 335

Tyr Leu Gln Met Asn Asn Leu Lys Thr Glu Asp Thr Ala Met Tyr Tyr
            340                 345                 350

Cys Val Arg His Gly Asn Phe Gly Asn Ser Tyr Val Ser Trp Phe Ala
            355                 360                 365

Tyr Trp Gly Gln Gly Thr Leu Val Thr Val Ser Ala Gly Gly Gly Gly
            370                 375                 380

Ser Gly Gly Gly Gly Ser Gly Gly Gly Ser Gln Ala Val Val Thr
385                 390                 395                 400

Gln Glu Ser Ala Leu Thr Thr Ser Pro Gly Glu Thr Val Thr Leu Thr
            405                 410                 415
```

Cys Arg Ser Ser Thr Gly Ala Val Thr Thr Ser Asn Tyr Ala Asn Trp
            420                 425                 430

Val Gln Glu Lys Pro Asp His Leu Phe Thr Gly Leu Ile Gly Gly Thr
        435                 440                 445

Asn Lys Arg Ala Pro Gly Val Pro Ala Arg Phe Ser Gly Ser Leu Ile
    450                 455                 460

Gly Asp Lys Ala Ala Leu Thr Ile Thr Gly Ala Gln Thr Glu Asp Glu
465                 470                 475                 480

Ala Ile Tyr Phe Cys Ala Leu Trp Tyr Ser Asn Leu Trp Val Phe Gly
            485                 490                 495

Gly Gly Thr Lys Leu Thr Val Leu
            500

<210> SEQ ID NO 77
<211> LENGTH: 1491
<212> TYPE: DNA
<213> ORGANISM: ARTIFICIAL SEQUENCE
<220> FEATURE:
<223> OTHER INFORMATION: 2G8HLxSEQ ID NO: 16 ; bispecific single chain
      antibody

<400> SEQUENCE: 77

| | |
|---|---:|
| gaggttcagc tgcagcagtc tggggcagag cttgtgaggt caggggcctc agtcaagttg | 60 |
| tcctgcacag cttctggctt caacattaaa gactactatt tgcactgggt gaagcagagg | 120 |
| cctgaacagg gcctggagtg gattgcctgg attgatcttg agaatggtga tattaaatat | 180 |
| gccccgaagt tcagggcaa ggccactata actgcagaca catcctccaa cacagcctac | 240 |
| ctgcagctca gcagcctgac atctgaggac actgccgtct attactgtaa tccctattac | 300 |
| tacggtagta actacgacta tgctatggac tactggggtc aaggaacctc agtcaccgtc | 360 |
| tcctcaggtg gtggtggttc tggcggcggc ggctccggtg gtggtggttc tgatgttgtg | 420 |
| atgacccaga ctccactcac tttgtcggtt accattggac aaccagcctc tatctcttgc | 480 |
| aagtcaagtc agagcctctt atatagtaat ggaaaaacct atttgaactg gatattacag | 540 |
| aggccaggcc agtctccaaa gcgcctaatc tatctggtgt ctaaactgga ctctggagtc | 600 |
| cctgacaggt tcactggcag tggatcagga acagatttta cgctgaaaat cagcagagtg | 660 |
| gaggctgagg atttgggagt ttattactgc gtgcaaggta cacattttcc tctcacgttc | 720 |
| ggtgctggga ccaagctgga gctgaaatcc ggaggtggtg gatcccaagt tgttctcacc | 780 |
| cagtctccag caatcatgtc tgcatttcca ggggagaagg tcaccatgac ctgcagtgcc | 840 |
| agctcaagtg taagttacat gaactggtac cagcagaagt caggcacctc ccccaaaaga | 900 |
| tggatttatg actcatccaa actggcttct ggagtccctg ctcgcttcag tggcagtggg | 960 |
| tctgggacct cttattctct cacaatcagc agcatggaga ctgaagatgc tgccacttat | 1020 |
| tactgccagc agtggagtcg taacccaccc acgttcggag gggggaccaa gctacaaatt | 1080 |
| acaggtggtg gtggttctgg cggcggcggc tccggtggtg gtggttctca ggtccagctg | 1140 |
| cagcagtctg ggctgaact ggcaagacct ggggcctcag tgaagatgtc ctgcaaggct | 1200 |
| tctggctaca cctttactag atctacgatg cactgggtaa acagaggcc tggacagggt | 1260 |
| ctggaatgga ttggatacat taatcctagc agtgcttata ctaattacaa tcagaaattc | 1320 |
| aaggacaagg ccacattgac tgcagacaaa tcctccagta cagcctacat gcaactgagt | 1380 |
| agcctgacat ctgaggactc tgcagtctat tactgtgcaa gtccgcaagt ccactatgat | 1440 |
| tacaacgggt ttccttactg gggccaaggg actctggtca ctgtctctgc a | 1491 |

<210> SEQ ID NO 78
<211> LENGTH: 497
<212> TYPE: PRT
<213> ORGANISM: artificial sequence
<220> FEATURE:
<223> OTHER INFORMATION: 2G8HLxSEQ ID NO: 16 ; bispecific single chain antibody

<400> SEQUENCE: 78

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Ala Trp Ile Asp Leu Glu Asn Gly Asp Ile Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Pro Tyr Tyr Tyr Gly Ser Asn Tyr Asp Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Val Val Met Thr Gln Thr
    130                 135                 140

Pro Leu Thr Leu Ser Val Thr Ile Gly Gln Pro Ala Ser Ile Ser Cys
145                 150                 155                 160

Lys Ser Ser Gln Ser Leu Leu Tyr Ser Asn Gly Lys Thr Tyr Leu Asn
                165                 170                 175

Trp Ile Leu Gln Arg Pro Gly Gln Ser Pro Lys Arg Leu Ile Tyr Leu
            180                 185                 190

Val Ser Lys Leu Asp Ser Gly Val Pro Asp Arg Phe Thr Gly Ser Gly
        195                 200                 205

Ser Gly Thr Asp Phe Thr Leu Lys Ile Ser Arg Val Glu Ala Glu Asp
    210                 215                 220

Leu Gly Val Tyr Tyr Cys Val Gln Gly Thr His Phe Pro Leu Thr Phe
225                 230                 235                 240

Gly Ala Gly Thr Lys Leu Glu Leu Lys Ser Gly Gly Gly Gly Ser Gln
                245                 250                 255

Val Val Leu Thr Gln Ser Pro Ala Ile Met Ser Ala Phe Pro Gly Glu
            260                 265                 270

Lys Val Thr Met Thr Cys Ser Ala Ser Ser Ser Val Ser Tyr Met Asn
        275                 280                 285

Trp Tyr Gln Gln Lys Ser Gly Thr Ser Pro Lys Arg Trp Ile Tyr Asp
    290                 295                 300

Ser Ser Lys Leu Ala Ser Gly Val Pro Ala Arg Phe Ser Gly Ser Gly
305                 310                 315                 320

Ser Gly Thr Ser Tyr Ser Leu Thr Ile Ser Ser Met Glu Thr Glu Asp
                325                 330                 335

Ala Ala Thr Tyr Tyr Cys Gln Gln Trp Ser Arg Asn Pro Pro Thr Phe
            340                 345                 350

Gly Gly Gly Thr Lys Leu Gln Ile Thr Gly Gly Gly Gly Ser Gly Gly

|  |  |  | 355 |  |  |  | 360 |  |  |  | 365 |  |  |
|--|--|--|--|--|--|--|--|--|--|--|--|--|--|

Gly Gly Ser Gly Gly Gly Ser Gln Val Gln Leu Gln Gln Ser Gly
370                  375                  380

Ala Glu Leu Ala Arg Pro Gly Ala Ser Val Lys Met Ser Cys Lys Ala
385                  390                  395              400

Ser Gly Tyr Thr Phe Thr Arg Ser Thr Met His Trp Val Lys Gln Arg
                  405                  410                  415

Pro Gly Gln Gly Leu Glu Trp Ile Gly Tyr Ile Asn Pro Ser Ser Ala
        420                  425                  430

Tyr Thr Asn Tyr Asn Gln Lys Phe Lys Asp Lys Ala Thr Leu Thr Ala
                435                  440                  445

Asp Lys Ser Ser Ser Thr Ala Tyr Met Gln Leu Ser Ser Leu Thr Ser
        450                  455                  460

Glu Asp Ser Ala Val Tyr Tyr Cys Ala Ser Pro Gln Val His Tyr Asp
465                  470                  475              480

Tyr Asn Gly Phe Pro Tyr Trp Gly Gln Gly Thr Leu Val Thr Val Ser
                485                  490                  495

Ala

```
<210> SEQ ID NO 79
<211> LENGTH: 1491
<212> TYPE: DNA
<213> ORGANISM: ARTIFICIAL SEQUENCE
<220> FEATURE:
<223> OTHER INFORMATION: 2G8HLxSEQ ID NO: 14 ; bispecific single chain
      antibody

<400> SEQUENCE: 79
```

| | | | | | |
|---|---|---|---|---|---|
| gaggttcagc | tgcagcagtc | tggggcagag | cttgtgaggt | caggggcctc | agtcaagttg | 60 |
| tcctgcacag | cttctggctt | caacattaaa | gactactatt | tgcactgggt | gaagcagagg | 120 |
| cctgaacagg | gcctggagtg | gattgcctgg | attgatcttg | agaatggtga | tattaaatat | 180 |
| gccccgaagt | tcagggcaa | ggccactata | actgcagaca | catcctccaa | cacagcctac | 240 |
| ctgcagctca | gcagcctgac | atctgaggac | actgccgtct | attactgtaa | tccctattac | 300 |
| tacggtagta | actacgacta | tgctatggac | tactggggtc | aaggaacctc | agtcaccgtc | 360 |
| tcctcaggtg | gtggtggttc | tggcggcggc | ggctccggtg | gtggtggttc | tgatgttgtg | 420 |
| atgacccaga | ctccactcac | tttgtcggtt | accattggac | aaccagcctc | tatctcttgc | 480 |
| aagtcaagtc | agagcctctt | atatagtaat | ggaaaaacct | atttgaactg | gatattacag | 540 |
| aggccaggcc | agtctccaaa | gcgcctaatc | tatctggtgt | ctaaactgga | ctctggagtc | 600 |
| cctgacaggt | tcactggcag | tggatcagga | acagatttta | cgctgaaaat | cagcagagtg | 660 |
| gaggctgagg | atttgggagt | ttattactgc | gtgcaaggta | cacattttcc | tctcacgttc | 720 |
| ggtgctggga | ccaagctgga | gctgaaatcc | ggaggtggtg | gatcccaggt | ccagctgcag | 780 |
| cagtctgggg | ctgaactggc | aagacctggg | gcctcagtga | agatgtcctg | caaggcttct | 840 |
| ggctacacct | ttactagatc | tacgatgcac | tgggtaaaac | agaggcctgg | acagggtctg | 900 |
| gaatggattg | gatacattaa | tcctagcagt | gcttatacta | attacaatca | gaaattcaag | 960 |
| gacaaggcca | cattgactgc | agacaaatcc | tccagtacag | cctacatgca | actgagtagc | 1020 |
| ctgacatctg | aggactctgc | agtctattac | tgtgcaagtc | cgcaagtcca | ctatgattac | 1080 |
| aacgggtttc | cttactgggg | ccaagggact | ctggtcactg | tctctgcagg | tggtggtggt | 1140 |
| tctggcggcg | gcggctccgg | tggtggtggt | tctcaagttg | ttctcaccca | gtctccagca | 1200 |

-continued

```
atcatgtctg catttccagg ggagaaggtc accatgacct gcagtgccag ctcaagtgta   1260
agttacatga actggtacca gcagaagtca ggcacctccc ccaaaagatg gatttatgac   1320
tcatccaaac tggcttctgg agtccctgct cgcttcagtg gcagtgggtc tgggacctct   1380
tattctctca caatcagcag catggagact gaagatgctg ccacttatta ctgccagcag   1440
tggagtcgta acccacccac gttcggaggg gggaccaagc tacaaattac a            1491
```

<210> SEQ ID NO 80
<211> LENGTH: 497
<212> TYPE: PRT
<213> ORGANISM: Artificial sequence
<220> FEATURE:
<223> OTHER INFORMATION: 2G8HLxSEQ ID NO: 14 ; bispecific single chain antibody

<400> SEQUENCE: 80

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Ala Trp Ile Asp Leu Glu Asn Gly Asp Ile Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Pro Tyr Tyr Tyr Gly Ser Asn Tyr Asp Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Val Val Met Thr Gln Thr
    130                 135                 140

Pro Leu Thr Leu Ser Val Thr Ile Gly Gln Pro Ala Ser Ile Ser Cys
145                 150                 155                 160

Lys Ser Ser Gln Ser Leu Leu Tyr Ser Asn Gly Lys Thr Tyr Leu Asn
                165                 170                 175

Trp Ile Leu Gln Arg Pro Gly Gln Ser Pro Lys Arg Leu Ile Tyr Leu
            180                 185                 190

Val Ser Lys Leu Asp Ser Gly Val Pro Asp Arg Phe Thr Gly Ser Gly
        195                 200                 205

Ser Gly Thr Asp Phe Thr Leu Lys Ile Ser Arg Val Glu Ala Glu Asp
    210                 215                 220

Leu Gly Val Tyr Tyr Cys Val Gln Gly Thr His Phe Pro Leu Thr Phe
225                 230                 235                 240

Gly Ala Gly Thr Lys Leu Glu Leu Lys Ser Gly Gly Gly Gly Ser Gln
                245                 250                 255

Val Gln Leu Gln Gln Ser Gly Ala Glu Leu Ala Arg Pro Gly Ala Ser
            260                 265                 270

Val Lys Met Ser Cys Lys Ala Ser Gly Tyr Thr Phe Thr Arg Ser Thr
        275                 280                 285

Met His Trp Val Lys Gln Arg Pro Gly Gln Gly Leu Glu Trp Ile Gly
    290                 295                 300

Tyr Ile Asn Pro Ser Ser Ala Tyr Thr Asn Tyr Asn Gln Lys Phe Lys
```

```
              305              310             315            320
Asp Lys Ala Thr Leu Thr Ala Asp Lys Ser Ser Thr Ala Tyr Met
                    325              330             335
Gln Leu Ser Ser Leu Thr Ser Glu Asp Ser Ala Val Tyr Tyr Cys Ala
                340              345             350
Ser Pro Gln Val His Tyr Asp Tyr Asn Gly Phe Pro Tyr Trp Gly Gln
            355              360             365
Gly Thr Leu Val Thr Val Ser Ala Gly Gly Gly Ser Gly Gly Gly
    370              375             380
Gly Ser Gly Gly Gly Ser Gln Val Val Leu Thr Gln Ser Pro Ala
385              390              395             400
Ile Met Ser Ala Phe Pro Gly Glu Lys Val Thr Met Thr Cys Ser Ala
                405              410             415
Ser Ser Ser Val Ser Tyr Met Asn Trp Tyr Gln Gln Lys Ser Gly Thr
                420              425             430
Ser Pro Lys Arg Trp Ile Tyr Asp Ser Ser Lys Leu Ala Ser Gly Val
            435              440             445
Pro Ala Arg Phe Ser Gly Ser Gly Ser Gly Thr Ser Tyr Ser Leu Thr
        450              455             460
Ile Ser Ser Met Glu Thr Glu Asp Ala Ala Thr Tyr Tyr Cys Gln Gln
465              470              475             480
Trp Ser Arg Asn Pro Pro Thr Phe Gly Gly Gly Thr Lys Leu Gln Ile
                485              490             495
Thr

<210> SEQ ID NO 81
<211> LENGTH: 27
<212> TYPE: DNA
<213> ORGANISM: ARTIFICIAL SEQUENCE
<220> FEATURE:
<223> OTHER INFORMATION: 5' primer VH ; oligonucleotide

<400> SEQUENCE: 81
saggtgcagc tcgaggagtc aggacct                                          27

<210> SEQ ID NO 82
<211> LENGTH: 27
<212> TYPE: DNA
<213> ORGANISM: artificial sequence
<220> FEATURE:
<223> OTHER INFORMATION: 5' primer VH ; oligonucleotide

<400> SEQUENCE: 82
gaggtccagc tcgagcagtc tggacct                                          27

<210> SEQ ID NO 83
<211> LENGTH: 27
<212> TYPE: DNA
<213> ORGANISM: artificial sequence
<220> FEATURE:
<223> OTHER INFORMATION: 5' primer VH ; oligonucleotide

<400> SEQUENCE: 83
caggtccaac tcgagcagcc tggggct                                          27

<210> SEQ ID NO 84
<211> LENGTH: 27
<212> TYPE: DNA
<213> ORGANISM: artificial sequence
<220> FEATURE:
```

```
<223> OTHER INFORMATION: 5' primer VH ; oligonucleotide

<400> SEQUENCE: 84
gaggttcagc tcgagcagtc tggggca                                    27

<210> SEQ ID NO 85
<211> LENGTH: 27
<212> TYPE: DNA
<213> ORGANISM: artificial sequence
<220> FEATURE:
<223> OTHER INFORMATION: 5' primer VH ; oligonucleotide

<400> SEQUENCE: 85
gargtgaagc tcgaggagtc tggagga                                    27

<210> SEQ ID NO 86
<211> LENGTH: 27
<212> TYPE: DNA
<213> ORGANISM: artificial sequence
<220> FEATURE:
<223> OTHER INFORMATION: 5' primer VH ; oligonucleotide

<400> SEQUENCE: 86
gaggtgaagc ttctcgagtc tggaggt                                    27

<210> SEQ ID NO 87
<211> LENGTH: 27
<212> TYPE: DNA
<213> ORGANISM: artificial sequence
<220> FEATURE:
<223> OTHER INFORMATION: 5' primer VH ; oligonucleotide

<400> SEQUENCE: 87
gaagtgaagc tcgaggagtc tggggga                                    27

<210> SEQ ID NO 88
<211> LENGTH: 27
<212> TYPE: DNA
<213> ORGANISM: artificial sequence
<220> FEATURE:
<223> OTHER INFORMATION: 5' primer VH ; oligonucleotide

<400> SEQUENCE: 88
gaggttcagc tcgagcagtc tggagct                                    27

<210> SEQ ID NO 89
<211> LENGTH: 39
<212> TYPE: DNA
<213> ORGANISM: artificial sequence
<220> FEATURE:
<223> OTHER INFORMATION: 5' primer VH ; oligonucleotide

<400> SEQUENCE: 89
gggctcgagc accatggrat gsagctgkgt matsctctt                       39

<210> SEQ ID NO 90
<211> LENGTH: 39
<212> TYPE: DNA
<213> ORGANISM: artificial sequence
<220> FEATURE:
<223> OTHER INFORMATION: 5' primer VH ; oligonucleotide

<400> SEQUENCE: 90
gggctcgagc accatgract tcgggytgag ctkggtttt                       39
```

```
<210> SEQ ID NO 91
<211> LENGTH: 38
<212> TYPE: DNA
<213> ORGANISM: artificial sequence
<220> FEATURE:
<223> OTHER INFORMATION: 5' primer VH ; oligonucleotide

<400> SEQUENCE: 91
gggctcgagc accatggctg tcttggggct gctcttct                              38

<210> SEQ ID NO 92
<211> LENGTH: 34
<212> TYPE: DNA
<213> ORGANISM: artificial sequence
<220> FEATURE:
<223> OTHER INFORMATION: 3' primer VH ; oligonucleotide

<400> SEQUENCE: 92
gaggaattcg aactggacag ggatccagag ttcc                                  34

<210> SEQ ID NO 93
<211> LENGTH: 34
<212> TYPE: DNA
<213> ORGANISM: ARTIFICIAL SEQUENCE
<220> FEATURE:
<223> OTHER INFORMATION: 3' primer VH ; oligonucleotide

<400> SEQUENCE: 93
cggaattcga atgacatgga catctgggtc atcc                                  34

<210> SEQ ID NO 94
<211> LENGTH: 32
<212> TYPE: DNA
<213> ORGANISM: ARTIFICIAL SEQUENCE
<220> FEATURE:
<223> OTHER INFORMATION: 5' primer VL ; oligonucleotide

<400> SEQUENCE: 94
ccagttccga gctcgttgtg actcaggaat ct                                    32

<210> SEQ ID NO 95
<211> LENGTH: 32
<212> TYPE: DNA
<213> ORGANISM: artificial sequence
<220> FEATURE:
<223> OTHER INFORMATION: 5' primer VL ; oligonucleotide

<400> SEQUENCE: 95
ccagttccga gctcgtgttg acgcagccgc cc                                    32

<210> SEQ ID NO 96
<211> LENGTH: 32
<212> TYPE: DNA
<213> ORGANISM: artificial sequence
<220> FEATURE:
<223> OTHER INFORMATION: 5' primer VL ; oligonucleotide

<400> SEQUENCE: 96
ccagttccga gctcgtgctc acccagtctc ca                                    32

<210> SEQ ID NO 97
<211> LENGTH: 32
<212> TYPE: DNA
<213> ORGANISM: artificial sequence
<220> FEATURE:
<223> OTHER INFORMATION: 5' primer VL ; oligonucleotide
```

<400> SEQUENCE: 97
ccagttccga gctccagatg acccagtctc ca    32

<210> SEQ ID NO 98
<211> LENGTH: 32
<212> TYPE: DNA
<213> ORGANISM: artificial sequence
<220> FEATURE:
<223> OTHER INFORMATION: 5' primer VL ; oligonucleotide

<400> SEQUENCE: 98
ccagatgtga gctcgtgatg acccagactc ca    32

<210> SEQ ID NO 99
<211> LENGTH: 32
<212> TYPE: DNA
<213> ORGANISM: artificial sequence
<220> FEATURE:
<223> OTHER INFORMATION: 5' primer VL ; oligonucleotide

<400> SEQUENCE: 99
ccagatgtga gctcgtcatg acccagtctc ca    32

<210> SEQ ID NO 100
<211> LENGTH: 32
<212> TYPE: DNA
<213> ORGANISM: artificial sequence
<220> FEATURE:
<223> OTHER INFORMATION: 5' primer VL ; oligonucleotide

<400> SEQUENCE: 100
ccagttccga gctcgtgatg acacagtctc ca    32

<210> SEQ ID NO 101
<211> LENGTH: 38
<212> TYPE: DNA
<213> ORGANISM: artificial sequence
<220> FEATURE:
<223> OTHER INFORMATION: 5' primer VL ; oligonucleotide

<400> SEQUENCE: 101
ggggagctcc accatggaga cagacacact cctgctat    38

<210> SEQ ID NO 102
<211> LENGTH: 39
<212> TYPE: DNA
<213> ORGANISM: artificial sequence
<220> FEATURE:
<223> OTHER INFORMATION: 5' primer VL ; oligonucleotide

<400> SEQUENCE: 102
ggggagctcc accatggatt ttcaagtgca gattttcag    39

<210> SEQ ID NO 103
<211> LENGTH: 40
<212> TYPE: DNA
<213> ORGANISM: artificial sequence
<220> FEATURE:
<223> OTHER INFORMATION: 5' primer VL ; oligonucleotide

<400> SEQUENCE: 103
ggggagctcc accatggagw cacakwctca ggtctttrta    40

<210> SEQ ID NO 104
<211> LENGTH: 36

```
<212> TYPE: DNA
<213> ORGANISM: artificial sequence
<220> FEATURE:
<223> OTHER INFORMATION: 5' primer VL ; oligonucleotide

<400> SEQUENCE: 104
ggggagctcc accatgkccc cwrctcagyt yctkgt                            36

<210> SEQ ID NO 105
<211> LENGTH: 31
<212> TYPE: DNA
<213> ORGANISM: artificial sequence
<220> FEATURE:
<223> OTHER INFORMATION: 3' primer VL ; oligonucleotide

<400> SEQUENCE: 105
gaggaattcg aactgctcac tggatggtgg g                                 31

<210> SEQ ID NO 106
<211> LENGTH: 35
<212> TYPE: DNA
<213> ORGANISM: ARTIFICIAL SEQUENCE
<220> FEATURE:
<223> OTHER INFORMATION: 3' primer VL ; oligonucleotide

<400> SEQUENCE: 106
cggaattcga acaaactctt ctccacagtg tgacc                             35

<210> SEQ ID NO 107
<211> LENGTH: 30
<212> TYPE: DNA
<213> ORGANISM: ARTIFICIAL SEQUENCE
<220> FEATURE:
<223> OTHER INFORMATION: 3' primer VH ; oligonucleotide

<400> SEQUENCE: 107
tatgcaacta gtacaaccac aatccctggg                                   30

<210> SEQ ID NO 108
<211> LENGTH: 34
<212> TYPE: DNA
<213> ORGANISM: artificial sequence
<220> FEATURE:
<223> OTHER INFORMATION: 3' primer VL ; oligonucleotide

<400> SEQUENCE: 108
gcgccgtcta gaattaacac tcattcctgt tgaa                              34

<210> SEQ ID NO 109
<211> LENGTH: 496
<212> TYPE: PRT
<213> ORGANISM: artificial sequence
<220> FEATURE:
<223> OTHER INFORMATION: 5-10 LH x deimmunised (di) anti-CD3 ;
      bispecific single chain antibody

<400> SEQUENCE: 109

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

```
Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
        115                 120                 125

Glu Val Gln Leu Leu Glu Gln Ser Gly Ala Glu Leu Val Arg Pro Gly
        130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
        210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Ser Asp Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Tyr Thr Phe Thr Arg Tyr Thr Met His
        275                 280                 285

Trp Val Arg Gln Ala Pro Gly Gln Gly Leu Glu Trp Ile Gly Tyr Ile
        290                 295                 300

Asn Pro Ser Arg Gly Tyr Thr Asn Tyr Ala Asp Ser Val Lys Gly Arg
305                 310                 315                 320

Phe Thr Ile Thr Thr Asp Lys Ser Thr Ser Thr Ala Tyr Met Glu Leu
                325                 330                 335

Ser Ser Leu Arg Ser Glu Asp Thr Ala Thr Tyr Tyr Cys Ala Arg Tyr
            340                 345                 350

Tyr Asp Asp His Tyr Cys Leu Asp Tyr Trp Gly Gln Gly Thr Thr Val
        355                 360                 365

Thr Val Ser Ser Gly Glu Gly Thr Ser Thr Gly Ser Gly Ser Gly
        370                 375                 380

Gly Ser Gly Gly Ala Asp Asp Ile Val Leu Thr Gln Ser Pro Ala Thr
385                 390                 395                 400

Leu Ser Leu Ser Pro Gly Glu Arg Ala Thr Leu Ser Cys Arg Ala Ser
                405                 410                 415

Gln Ser Val Ser Tyr Met Asn Trp Tyr Gln Gln Lys Pro Gly Lys Ala
            420                 425                 430

Pro Lys Arg Trp Ile Tyr Asp Thr Ser Lys Val Ala Ser Gly Val Pro
        435                 440                 445

Ala Arg Phe Ser Gly Ser Gly Ser Gly Thr Asp Tyr Ser Leu Thr Ile
        450                 455                 460

Asn Ser Leu Glu Ala Glu Asp Ala Ala Thr Tyr Tyr Cys Gln Gln Trp
465                 470                 475                 480
```

```
Ser Ser Asn Pro Leu Thr Phe Gly Gly Gly Thr Lys Val Glu Ile Lys
            485                 490                 495

<210> SEQ ID NO 110
<211> LENGTH: 125
<212> TYPE: PRT
<213> ORGANISM: ARTIFICIAL SEQUENCE
<220> FEATURE:
<223> OTHER INFORMATION: Human-like VH VH region

<400> SEQUENCE: 110

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 111
<211> LENGTH: 375
<212> TYPE: DNA
<213> ORGANISM: artificial sequence
<220> FEATURE:
<223> OTHER INFORMATION: Human-like VH VH region

<400> SEQUENCE: 111
gaggtgcagc tgctcgagtc tggaggagga ttggtgcagc ctggagggtc attgaaactc      60
tcatgtgcag cctctggatt caccttcaat acctacgcca tgaactgggt ccgccaggct    120
ccaggaaagg gtttggaatg ggttgctcgc ataagaagta atataataa ttatgcaaca     180 tattatgccg attcagtgaa agacaggttc accatctcca gagatgattc aaaaaacact    240
gcctatctac aaatgaacaa cttgaaaact gaggacactg ccgtgtacta ctgtgtgaga    300
catgggaact tcggtaatag ctacgtttcc tggtttgctt actggggcca agggactctg    360
gtcaccgtct cctca                                                     375

<210> SEQ ID NO 112
<211> LENGTH: 14
<212> TYPE: PRT
<213> ORGANISM: MUS MUSCULUS
<220> FEATURE:
<221> NAME/KEY: misc_feature
<222> LOCATION: (1)..(1)
<223> OTHER INFORMATION: CDR3 of VH

<400> SEQUENCE: 112

His Gly Asn Phe Gly Asn Ser Tyr Val Ser Trp Phe Ala Tyr
1               5                   10

<210> SEQ ID NO 113
<211> LENGTH: 6
```

```
<212> TYPE: PRT
<213> ORGANISM: mus musculus
<220> FEATURE:
<221> NAME/KEY: misc_feature
<222> LOCATION: (1)..(6)
<223> OTHER INFORMATION: VH: short CDR3 short CDR3 of SEQ ID NO: 112

<400> SEQUENCE: 113

Val Ser Trp Phe Ala Tyr
1               5

<210> SEQ ID NO 114
<211> LENGTH: 19
<212> TYPE: PRT
<213> ORGANISM: mus musculus
<220> FEATURE:
<221> NAME/KEY: misc_feature
<222> LOCATION: (1)..(19)
<223> OTHER INFORMATION: CDR2 of VH

<400> SEQUENCE: 114

Arg Ile Arg Ser Lys Tyr Asn Asn Tyr Ala Thr Tyr Tyr Ala Asp Ser
1               5                   10                  15

Val Lys Asp

<210> SEQ ID NO 115
<211> LENGTH: 5
<212> TYPE: PRT
<213> ORGANISM: mus musculus
<220> FEATURE:
<221> NAME/KEY: misc_feature
<222> LOCATION: (1)..(5)
<223> OTHER INFORMATION: CDR1 of VH

<400> SEQUENCE: 115

Thr Tyr Ala Met Asn
1               5

<210> SEQ ID NO 116
<211> LENGTH: 9
<212> TYPE: PRT
<213> ORGANISM: mus musculus
<220> FEATURE:
<221> NAME/KEY: misc_feature
<222> LOCATION: (1)..(9)
<223> OTHER INFORMATION: CDR3 of VL

<400> SEQUENCE: 116

Ala Leu Trp Tyr Ser Asn Leu Trp Val
1               5

<210> SEQ ID NO 117
<211> LENGTH: 7
<212> TYPE: PRT
<213> ORGANISM: mus musculus
<220> FEATURE:
<221> NAME/KEY: misc_feature
<222> LOCATION: (1)..(7)
<223> OTHER INFORMATION: CDR2 of VL

<400> SEQUENCE: 117

Gly Thr Asn Lys Arg Ala Pro
1               5

<210> SEQ ID NO 118
<211> LENGTH: 14
<212> TYPE: PRT
<213> ORGANISM: mus musculus
```

-continued

```
<220> FEATURE:
<221> NAME/KEY: misc_feature
<222> LOCATION: (1)..(14)
<223> OTHER INFORMATION: CDR1 of VL

<400> SEQUENCE: 118

Arg Ser Ser Thr Gly Ala Val Thr Thr Ser Asn Tyr Ala Asn
1               5                   10

<210> SEQ ID NO 119
<211> LENGTH: 12
<212> TYPE: PRT
<213> ORGANISM: mus musculus
<220> FEATURE:
<221> NAME/KEY: misc_feature
<222> LOCATION: (1)..(12)
<223> OTHER INFORMATION: CDR3 of VH

<400> SEQUENCE: 119

Pro Gln Val His Tyr Asp Tyr Asn Gly Phe Pro Tyr
1               5                   10

<210> SEQ ID NO 120
<211> LENGTH: 17
<212> TYPE: PRT
<213> ORGANISM: mus musculus
<220> FEATURE:
<221> NAME/KEY: misc_feature
<222> LOCATION: (1)..(17)
<223> OTHER INFORMATION: CDR2 of VH

<400> SEQUENCE: 120

Tyr Ile Asn Pro Ser Ser Ala Tyr Thr Asn Tyr Asn Gln Lys Phe Lys
1               5                   10                  15

Asp

<210> SEQ ID NO 121
<211> LENGTH: 10
<212> TYPE: PRT
<213> ORGANISM: mus musculus
<220> FEATURE:
<221> NAME/KEY: misc_feature
<222> LOCATION: (1)..(10)
<223> OTHER INFORMATION: CDR1 of VH

<400> SEQUENCE: 121

Gly Tyr Thr Phe Thr Arg Ser Thr Met His
1               5                   10

<210> SEQ ID NO 122
<211> LENGTH: 509
<212> TYPE: PRT
<213> ORGANISM: artificial sequence
<220> FEATURE:
<223> OTHER INFORMATION: 2G8 LHx SEQ ID NO: 146 ; bispecific single
      chain antibody

<400> SEQUENCE: 122

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Ile Leu Gln Arg Pro Gly Gln Ser
        35                  40                  45

Pro Lys Arg Leu Ile Tyr Leu Val Ser Lys Leu Asp Ser Gly Val Pro
    50                  55                  60
```

```
Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                 85                  90                  95

Thr His Phe Pro Leu Thr Phe Gly Ala Gly Thr Lys Leu Glu Leu Lys
                100                 105                 110

Gly Gly Gly Gly Ser Gly Gly Gly Ser Gly Gly Gly Gly Ser Glu
                115                 120                 125

Val Gln Leu Gln Gln Ser Gly Ala Glu Leu Val Arg Ser Gly Ala Ser
130                 135                 140

Val Lys Leu Ser Cys Thr Ala Ser Gly Phe Asn Ile Lys Asp Tyr Tyr
145                 150                 155                 160

Leu His Trp Val Lys Gln Arg Pro Glu Gln Gly Leu Glu Trp Ile Ala
                165                 170                 175

Trp Ile Asp Leu Glu Asn Gly Asp Ile Lys Tyr Ala Pro Lys Phe Gln
                180                 185                 190

Gly Lys Ala Thr Ile Thr Ala Asp Thr Ser Ser Asn Thr Ala Tyr Leu
                195                 200                 205

Gln Leu Ser Ser Leu Thr Ser Glu Asp Thr Ala Val Tyr Tyr Cys Asn
210                 215                 220

Pro Tyr Tyr Tyr Gly Ser Asn Tyr Asp Tyr Ala Met Asp Tyr Trp Gly
225                 230                 235                 240

Gln Gly Thr Ser Val Thr Val Ser Ser Gly Gly Gly Ser Glu Val
                245                 250                 255

Lys Leu Leu Glu Ser Gly Gly Gly Leu Val Gln Pro Gly Gly Ser Leu
                260                 265                 270

Lys Leu Ser Cys Ala Ala Ser Gly Phe Thr Phe Asn Thr Tyr Ala Met
                275                 280                 285

Asn Trp Val Arg Gln Ala Pro Gly Lys Gly Leu Glu Trp Val Ala Arg
                290                 295                 300

Ile Arg Ser Lys Tyr Asn Asn Tyr Ala Thr Tyr Tyr Ala Asp Ser Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
                340                 345                 350

Val Arg His Gly Asn Phe Gly Asn Ser Tyr Val Ser Trp Phe Ala Tyr
                355                 360                 365

Trp Gly Gln Gly Thr Leu Val Thr Val Ser Ser Gly Gly Gly Gly Ser
                370                 375                 380

Gly Gly Gly Gly Ser Gly Gly Gly Ser Glu Leu Val Leu Thr Gln
385                 390                 395                 400

Glu Ser Ala Leu Thr Thr Ser Pro Gly Glu Thr Val Thr Leu Thr Cys
                405                 410                 415

Arg Ser Ser Thr Gly Ala Val Thr Thr Ser Asn Tyr Ala Asn Trp Val
                420                 425                 430

Gln Glu Lys Pro Asp His Leu Phe Thr Gly Leu Ile Gly Gly Thr Asn
                435                 440                 445

Lys Arg Ala Pro Gly Val Pro Ala Arg Phe Ser Gly Ser Leu Ile Gly
                450                 455                 460

Asp Lys Ala Ala Leu Thr Ile Thr Gly Ala Gln Thr Glu Asp Glu Ala
465                 470                 475                 480
```

Ile Tyr Phe Cys Ala Leu Trp Tyr Ser Asn Leu Trp Val Phe Gly Gly
                            485                 490                 495

Gly Thr Lys Leu Thr Val Leu His His His His His His
                        500                 505

<210> SEQ ID NO 123
<211> LENGTH: 1527
<212> TYPE: DNA
<213> ORGANISM: ARTIFICIAL SEQUENCE
<220> FEATURE:
<223> OTHER INFORMATION: 2G8 LHxSEQ ID NO: 146 ; bispecific single chain
      antibody

<400> SEQUENCE: 123

| | | | | | | |
|---|---|---|---|---|---|---|
| gatgttgtga | tgacccagac | tccactcact | ttgtcggtta | ccattggaca | accagcctct | 60 |
| atctcttgca | agtcaagtca | gagcctctta | tatagtaatg | aaaaaccta | tttgaactgg | 120 |
| atattacaga | ggccaggcca | gtctccaaag | cgcctaatct | atctggtgtc | taaactggac | 180 |
| tctggagtcc | ctgacaggtt | cactggcagt | ggatcaggaa | cagattttac | gctgaaaatc | 240 |
| agcagagtgg | aggctgagga | tttgggagtt | tattactgcg | tgcaaggtac | acattttcct | 300 |
| ctcacgttcg | gtgctgggac | caagctggag | ctgaaaggtg | gtggtggttc | tggcggcggc | 360 |
| ggctccggtg | gtggtggttc | tgaggttcag | ctgcagcagt | ctggggcaga | gcttgtgagg | 420 |
| tcagggcct | cagtcaagtt | gtcctgcaca | gcttctggct | tcaacattaa | agactactat | 480 |
| ttgcactggg | tgaagcagag | gcctgaacag | ggcctggagt | ggattgcctg | gattgatctt | 540 |
| gagaatggtg | atattaaata | tgccccgaag | tttcagggca | aggccactat | aactgcagac | 600 |
| acatcctcca | cacagcctta | cctgcagctc | agcagcctga | catctgagga | cactgccgtc | 660 |
| tattactgta | tccctatta | ctacggtagt | aactacgact | atgctatgga | ctactggggt | 720 |
| caaggaacct | cagtcaccgt | ctcctccgga | ggtggtggat | ccgaggtgaa | gcttctcgag | 780 |
| tctggaggag | gattggtgca | gcctggaggg | tcattgaaac | tctcatgtgc | agcctctgga | 840 |
| ttcaccttca | ataacctacgc | catgaactgg | gtccgccagg | ctccaggaaa | gggtttggaa | 900 |
| tgggttgctc | gcataagaag | taaatataat | aattatgcaa | catattatgc | cgattcagtg | 960 |
| aaagacaggt | tcaccatctc | cagagatgat | tcaaaaaaca | ctgcctatct | acaaatgaac | 1020 |
| aacttgaaaa | ctgaggacac | tgccgtgtac | tactgtgtga | catgggaa | cttcggtaat | 1080 |
| agctacgttt | cctggtttgc | ttactggggc | caagggactc | tggtcaccgt | ctcctcaggt | 1140 |
| ggtggtggtt | ctggcggcgg | cggctccggt | ggtggtggtt | ctgagctcgt | tgtgactcag | 1200 |
| gaatctgcac | tcaccacatc | acctggtgaa | acagtcacac | tcacttgtcg | ctcaagtact | 1260 |
| ggggctgtta | caactagtaa | ctatgccaac | tgggtccaag | aaaaaccaga | tcatttattc | 1320 |
| actggtctaa | taggtggtac | caacaagcga | gcaccaggtg | tgcctgccag | attctcaggc | 1380 |
| tccctgattg | gagacaaggc | tgccctcacc | atcacagggg | cacagactga | ggatgaggca | 1440 |
| atatatttct | gtgctctatg | gtacagcaac | ctctgggtgt | tcggtggagg | aaccaaactg | 1500 |
| actgtcctac | atcatcacca | tcatcat | | | | 1527 |

<210> SEQ ID NO 124
<211> LENGTH: 508
<212> TYPE: PRT
<213> ORGANISM: artificial sequence
<220> FEATURE:
<223> OTHER INFORMATION: 5-10 LHxSEQ ID NO: 146 ; bispecific single
      chain antibody

<400> SEQUENCE: 124

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
50                      55                  60

Pro Asp Arg Phe Thr Gly Ser Gly Ser Gly Thr Asp Phe Thr Leu Thr
65                      70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Gly Ser Gly Gly Gly Gly Ser
            115                 120                 125

Glu Val Gln Leu Leu Glu Gln Ser Gly Ala Glu Leu Val Arg Pro Gly
            130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
            165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
            195                 200                 205

Tyr Met Gln Leu Ser Ser Leu Thr Phe Glu Asp Ser Ala Val Tyr Phe
        210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Glu Val Lys
            245                 250                 255

Leu Leu Glu Ser Gly Gly Gly Leu Val Gln Pro Gly Gly Ser Leu Lys
            260                 265                 270

Leu Ser Cys Ala Ala Ser Gly Phe Thr Phe Asn Thr Tyr Ala Met Asn
            275                 280                 285

Trp Val Arg Gln Ala Pro Gly Lys Gly Leu Glu Trp Val Ala Arg Ile
            290                 295                 300

Arg Ser Lys Tyr Asn Asn Tyr Ala Thr Tyr Tyr Ala Asp Ser Val Lys
305                 310                 315                 320

Asp Arg Phe Thr Ile Ser Arg Asp Asp Ser Lys Asn Thr Ala Tyr Leu
            325                 330                 335

Gln Met Asn Asn Leu Lys Thr Glu Asp Thr Ala Val Tyr Tyr Cys Val
            340                 345                 350

Arg His Gly Asn Phe Gly Asn Ser Tyr Val Ser Trp Phe Ala Tyr Trp
            355                 360                 365

Gly Gln Gly Thr Leu Val Thr Val Ser Ser Gly Gly Gly Gly Ser Gly
            370                 375                 380

Gly Gly Gly Ser Gly Gly Gly Gly Ser Glu Leu Val Val Thr Gln Glu
385                 390                 395                 400

Ser Ala Leu Thr Thr Ser Pro Gly Glu Thr Val Thr Leu Thr Cys Arg
                405                 410                 415
```

```
Ser Ser Thr Gly Ala Val Thr Thr Ser Asn Tyr Ala Asn Trp Val Gln
            420                 425                 430

Glu Lys Pro Asp His Leu Phe Thr Gly Leu Ile Gly Gly Thr Asn Lys
        435                 440                 445

Arg Ala Pro Gly Val Pro Ala Arg Phe Ser Gly Ser Leu Ile Gly Asp
    450                 455                 460

Lys Ala Leu Thr Ile Thr Gly Ala Gln Thr Glu Asp Glu Ala Ile
465                 470                 475                 480

Tyr Phe Cys Ala Leu Trp Tyr Ser Asn Leu Trp Val Phe Gly Gly Gly
                485                 490                 495

Thr Lys Leu Thr Val Leu His His His His His
            500                 505

<210> SEQ ID NO 125
<211> LENGTH: 1524
<212> TYPE: DNA
<213> ORGANISM: ARTIFICIAL SEQUENCE
<220> FEATURE:
<223> OTHER INFORMATION: 5-10 LHxSEQ ID NO: 146 ; bispecific single
      chain antibody

<400> SEQUENCE: 125
gagctcgtga tgacacagtc tccatcctcc ctgactgtga cagcaggaga gaaggtcact    60
atgagctgca gtccagtca gagtctgtta acagtggaa atcaaaagaa ctacttgacc   120
tggtaccagc agaaaccagg gcagcctcct aaactgttga tctactgggc atccactagg   180
gaatctgggg tccctgatcg cttcacaggc agtggatctg gaacagattt cactctcacc   240
atcagcagtg tgcaggctga agacctggca gtttattact gtcagaatga ttatagttat   300
ccgctcacgt tcggtgctgg gaccaagctt gagatcaaag gtggtggtgg ttctggcggc   360
ggcggctccg gtggtggtgg ttctgaggtg cagctgctcg agcagtctgg agctgagctg   420
gtaaggcctg ggacttcagt gaagatatcc tgcaaggctt ctggatacgc cttcactaac   480
tactggctag gttgggtaaa gcagaggcct ggacatggac ttgagtggat tggagatatt   540
ttccctggaa gtggtaatat ccactacaat gagaagttca aggcaaagc cacactgact   600 gcagacaaat cttcgagcac agcctatatg cagctcagta gcctgacatt tgaggactct   660
gctgtctatt tctgtgcaag actgaggaac tgggacgagc ctatggacta ctggggccaa   720
gggaccacgg tcaccgtctc ctccggaggt ggtggatccg aggtgaagct tctcgagtct   780
ggaggaggat tggtgcagcc tggagggtca ttgaaactct catgtgcagc ctctggattc   840
accttcaata cctacgccat gaactgggtc cgccaggctc aggaaagggg tttggaatgg   900
gttgctcgca taagaagtaa atataataat tatgcaacat attatgccga ttcagtgaaa   960
gacaggttca ccatctccag agatgattca aaaacactg cctatctaca atgaacaac   1020 ttgaaaactg aggacactgc cgtgtactac tgtgtgagac atgggaactt cggtaatagc  1080
tacgtttcct ggtttgctta ctggggccaa gggactctgg tcaccgtctc tcaggtggt  1140 ggtggttctg gcggcggcgg ctccggtggt ggtggttctg agctcgttgt gactcaggaa  1200
tctgcactca ccacatcacc tggtgaaaca gtcacactca cttgtcgctc aagtactggg  1260
gctgttacaa ctagtaacta tgccaactgg gtccaagaaa accagatca tttattcact  1320 ggtctaatag gtggtaccaa caagcgagca ccaggtgtgc ctgccagatt ctcaggctcc  1380
ctgattggag acaaggctgc cctcaccatc acagggcac agactgagga tgaggcaata  1440
tatttctgtg ctctatggta cagcaacctc tgggtgttcg gtggaggaac caaactgact  1500
```

```
gtcctacatc atcaccatca tcat                                          1524
```

<210> SEQ ID NO 126
<211> LENGTH: 372
<212> TYPE: DNA
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(372)
<223> OTHER INFORMATION: FN18 VH VH region of monoclonal antibody FN18

<400> SEQUENCE: 126

```
caggtccagc tgcagcagtc tgaagctgaa ctggcaagac ctggggcctc agtgaagatg    60
tcctgcaagg cttctggcta cacctttact gactacacga tacactggtt aaaacagagg   120
cctggacagg gtctggactg gattggatat tttaatccta gcagtgaatc tactgaatac   180
aatcggaaat tcaaggacag gaccatattg actgcagaca gatcctcaac cacagcctac   240
atgcaactga gcagcctgac atctgaggac tctgcggtct attactgttc aaggaaaggg   300
gagaaactac ttggtaaccg ttactggtac ttcgatgtct ggggcgcagg gacctcggtc   360
accgtctcct ca                                                        372
```

<210> SEQ ID NO 127
<211> LENGTH: 124
<212> TYPE: PRT
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(124)
<223> OTHER INFORMATION: FN18 VH VH region of monoclonal antibody FN18

<400> SEQUENCE: 127

```
Gln Val Gln Leu Gln Gln Ser Glu Ala Glu Leu Ala Arg Pro Gly Ala
1               5                   10                  15

Ser Val Lys Met Ser Cys Lys Ala Ser Gly Tyr Thr Phe Thr Asp Tyr
            20                  25                  30

Thr Ile His Trp Leu Lys Gln Arg Pro Gly Gln Gly Leu Asp Trp Ile
        35                  40                  45

Gly Tyr Phe Asn Pro Ser Ser Glu Ser Thr Glu Tyr Asn Arg Lys Phe
    50                  55                  60

Lys Asp Arg Thr Ile Leu Thr Ala Asp Arg Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ser Arg Lys Gly Glu Lys Leu Leu Gly Asn Arg Tyr Trp Tyr Phe Asp
            100                 105                 110

Val Trp Gly Ala Gly Thr Ser Val Thr Val Ser Ser
        115                 120
```

<210> SEQ ID NO 128
<211> LENGTH: 339
<212> TYPE: DNA
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(339)
<223> OTHER INFORMATION: FN18 VL VL region of monoclonal antibody FN18

-continued

<400> SEQUENCE: 128

```
gacattgtga tgtcacagtc tccatcctcc ctagctgtgt cagttggaga gaaggttact    60
atgagctgca agtccagtca gagccttttta tatagtagca atcaaaagaa ctacttggcc   120
tggtaccagc agaagccagg gcagtctcct aaattgctga ttaactgggc atccaccagg   180
gaatctgggg tccctgatcg cttcacaggc agtggatcta ggacagattt cactctcacc   240
atcagcagtg tgaaggctga agacctggca gtttatttct gtcagcaatt ttatagttat   300
cctccgacgt tcggtggagg caccaagctg gaaatcaaa                          339
```

<210> SEQ ID NO 129
<211> LENGTH: 113
<212> TYPE: PRT
<213> ORGANISM: Artificial Sequence
<220> FEATURE:
<223> OTHER INFORMATION: Hybridoma
<220> FEATURE:
<221> NAME/KEY: misc_feature
<222> LOCATION: (1)..(113)
<223> OTHER INFORMATION: FN18 VL VL region of monoclonal antibody FN18

<400> SEQUENCE: 129

```
Asp Ile Val Met Ser Gln Ser Pro Ser Ser Leu Ala Val Ser Val Gly
1               5                   10                  15
Glu Lys Val Thr Met Ser Cys Lys Ser Ser Gln Ser Leu Leu Tyr Ser
            20                  25                  30
Ser Asn Gln Lys Asn Tyr Leu Ala Trp Tyr Gln Gln Lys Pro Gly Gln
        35                  40                  45
Ser Pro Lys Leu Leu Ile Asn Trp Ala Ser Thr Arg Glu Ser Gly Val
    50                  55                  60
Pro Asp Arg Phe Thr Gly Ser Gly Ser Arg Thr Asp Phe Thr Leu Thr
65                  70                  75                  80
Ile Ser Ser Val Lys Ala Glu Asp Leu Ala Val Tyr Phe Cys Gln Gln
                85                  90                  95
Phe Tyr Ser Tyr Pro Pro Thr Phe Gly Gly Gly Thr Lys Leu Glu Ile
            100                 105                 110
Lys
```

<210> SEQ ID NO 130
<211> LENGTH: 756
<212> TYPE: DNA
<213> ORGANISM: ARTIFICIAL SEQUENCE
<220> FEATURE:
<223> OTHER INFORMATION: FN18 VH-VL scFv ; single chain Fv

<400> SEQUENCE: 130

```
caggtccagc tgcagcagtc tgaagctgaa ctggcaagac ctggggcctc agtgaagatg    60
tcctgcaagg cttctggcta cacctttact gactacacga tacactggtt aaaacagagg   120
cctggacagg gtctggactg gattggatat tttaatccta gcagtgaatc tactgaatac   180
aatcggaaat tcaaggacag gaccatattg actgcagaca gatcctcaac cacagcctac   240
atgcaactga gcagcctgac atctgaggac tctgcggtct attactgttc aaggaaaggg   300
gagaaactac ttggtaaccg ttactggtac ttcgatgtct ggggcgcagg gacctcggtc   360
accgtctcct caggtggtgg tggttctggc ggcggcggct ccggtggtgg tggttctgac   420
attgtgatgt cacagtctcc atcctcccta gctgtgtcag ttggagagaa ggttactatg   480
agctgcaagt ccagtcagag ccttttatat agtagcaatc aaaagaacta cttggcctgg   540
```

```
taccagcaga agccagggca gtctcctaaa ttgctgatta actgggcatc caccagggaa    600
tctggggtcc ctgatcgctt cacaggcagt ggatctagga cagatttcac tctcaccatc    660
agcagtgtga aggctgaaga cctggcagtt tatttctgtc agcaatttta tagttatcct    720
ccgacgttcg gtggaggcac caagctggaa atcaaa                              756
```

<210> SEQ ID NO 131
<211> LENGTH: 252
<212> TYPE: PRT
<213> ORGANISM: artificial sequence
<220> FEATURE:
<223> OTHER INFORMATION: FN18 VH-VL scFv ; single chain Fv

<400> SEQUENCE: 131

```
Gln Val Gln Leu Gln Gln Ser Glu Ala Glu Leu Ala Arg Pro Gly Ala
1               5                   10                  15

Ser Val Lys Met Ser Cys Lys Ala Ser Gly Tyr Thr Phe Thr Asp Tyr
            20                  25                  30

Thr Ile His Trp Leu Lys Gln Arg Pro Gly Gln Gly Leu Asp Trp Ile
        35                  40                  45

Gly Tyr Phe Asn Pro Ser Ser Glu Ser Thr Glu Tyr Asn Arg Lys Phe
    50                  55                  60

Lys Asp Arg Thr Ile Leu Thr Ala Asp Arg Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ser Arg Lys Gly Glu Lys Leu Leu Gly Asn Arg Tyr Trp Tyr Phe Asp
            100                 105                 110

Val Trp Gly Ala Gly Thr Ser Val Thr Val Ser Ser Gly Gly Gly Gly
        115                 120                 125

Ser Gly Gly Gly Gly Ser Gly Gly Gly Gly Ser Asp Ile Val Met Ser
    130                 135                 140

Gln Ser Pro Ser Ser Leu Ala Val Ser Val Gly Glu Lys Val Thr Met
145                 150                 155                 160

Ser Cys Lys Ser Ser Gln Ser Leu Leu Tyr Ser Ser Asn Gln Lys Asn
                165                 170                 175

Tyr Leu Ala Trp Tyr Gln Gln Lys Pro Gly Gln Ser Pro Lys Leu Leu
            180                 185                 190

Ile Asn Trp Ala Ser Thr Arg Glu Ser Gly Val Pro Asp Arg Phe Thr
        195                 200                 205

Gly Ser Gly Ser Arg Thr Asp Phe Thr Leu Thr Ile Ser Ser Val Lys
    210                 215                 220

Ala Glu Asp Leu Ala Val Tyr Phe Cys Gln Gln Phe Tyr Ser Tyr Pro
225                 230                 235                 240

Pro Thr Phe Gly Gly Gly Thr Lys Leu Glu Ile Lys
                245                 250
```

<210> SEQ ID NO 132
<211> LENGTH: 756
<212> TYPE: DNA
<213> ORGANISM: ARTIFICIAL SEQUENCE
<220> FEATURE:
<223> OTHER INFORMATION: FN18 VL-VH scFv ; single chain Fv

<400> SEQUENCE: 132

```
gacattgtga tgtcacagtc tccatcctcc ctagctgtgt cagttggaga gaaggttact    60
```

```
atgagctgca agtccagtca gagccttta tatagtagca atcaaaagaa ctacttggcc    120
tggtaccagc agaagccagg gcagtctcct aaattgctga ttaactgggc atccaccagg    180
gaatctgggg tccctgatcg cttcacaggc agtggatcta ggacagattt cactctcacc    240
atcagcagtg tgaaggctga agacctggca gtttatttct gtcagcaatt ttatagttat    300
cctccgacgt tcggtggagg caccaagctg gaaatcaaag gtggtggtgg ttctggcggc    360
ggcggctccg gtggtggtgg ttctcaggtc cagctgcagc agtctgaagc tgaactggca    420
agacctgggg cctcagtgaa gatgtcctgc aaggcttctg gctacacctt tactgactac    480
acgatacact ggttaaaaca gaggcctgga cagggtctgg actggattgg atatttaat    540 cctagcagtg aatctactga atacaatcgg aaattcaagg acaggaccat attgactgca    600
gacagatcct caaccacagc ctacatgcaa ctgagcagcc tgacatctga ggactctgcg    660
gtctattact gttcaaggaa aggggagaaa ctacttggta accgttactg gtacttcgat    720
gtctggggcg cagggacctc ggtcaccgtc tcctca    756
```

<210> SEQ ID NO 133
<211> LENGTH: 252
<212> TYPE: PRT
<213> ORGANISM: artificial sequence
<220> FEATURE:
<223> OTHER INFORMATION: FN18 VL-VH scFv ; single chain Fv

<400> SEQUENCE: 133

```
Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Asn Trp Ala Ser Thr Arg Glu Ser Gly Val
    50                  55                  60

Pro Asp Arg Phe Thr Gly Ser Gly Ser Arg Thr Asp Phe Thr Leu Thr
65                  70                  75                  80

Ile Ser Ser Val Lys Ala Glu Asp Leu Ala Val Tyr Phe Cys Gln Gln
                85                  90                  95

Phe Tyr Ser Tyr Pro Pro Thr Phe Gly Gly Gly Thr Lys Leu Glu Ile
            100                 105                 110

Lys Gly Gly Gly Gly Ser Gly Gly Gly Gly Ser Gly Gly Gly Gly Ser
        115                 120                 125

Gln Val Gln Leu Gln Gln Ser Glu Ala Glu Leu Ala Arg Pro Gly Ala
    130                 135                 140

Ser Val Lys Met Ser Cys Lys Ala Ser Gly Tyr Thr Phe Thr Asp Tyr
145                 150                 155                 160

Thr Ile His Trp Leu Lys Gln Arg Pro Gly Gln Gly Leu Asp Trp Ile
                165                 170                 175

Gly Tyr Phe Asn Pro Ser Ser Glu Ser Thr Glu Tyr Asn Arg Lys Phe
            180                 185                 190

Lys Asp Arg Thr Ile Leu Thr Ala Asp Arg Ser Ser Thr Thr Ala Tyr
        195                 200                 205

Met Gln Leu Ser Ser Leu Thr Ser Glu Asp Ser Ala Val Tyr Tyr Cys
    210                 215                 220

Ser Arg Lys Gly Glu Lys Leu Leu Gly Asn Arg Tyr Trp Tyr Phe Asp
225                 230                 235                 240
```

```
Val Trp Gly Ala Gly Thr Ser Val Thr Val Ser Ser
            245                 250
```

<210> SEQ ID NO 134
<211> LENGTH: 105
<212> TYPE: PRT
<213> ORGANISM: HOMO SAPIENS
<220> FEATURE:
<221> NAME/KEY: misc_feature
<222> LOCATION: (1)..(105)
<223> OTHER INFORMATION: CD3 epsilon extracellular portion

<400> SEQUENCE: 134

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp
            100                 105
```

<210> SEQ ID NO 135
<211> LENGTH: 96
<212> TYPE: PRT
<213> ORGANISM: Macaca fascicularis
<220> FEATURE:
<221> NAME/KEY: misc_feature
<222> LOCATION: (1)..(96)
<223> OTHER INFORMATION: CD3 epsilon extracellular portion FN18+

<400> SEQUENCE: 135

```
Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95
```

<210> SEQ ID NO 136
<211> LENGTH: 96
<212> TYPE: PRT
<213> ORGANISM: Macaca fascicularis
<220> FEATURE:
<221> NAME/KEY: misc_feature
<222> LOCATION: (1)..(96)
<223> OTHER INFORMATION: CD3 epsilon extracellular portion FN18-

<400> SEQUENCE: 136

```
Gln Asp Gly Asn Glu Glu Met Gly Ser Ile Thr Gln Thr Pro Tyr Gln
```

```
                1               5                  10                 15
            Val Ser Ile Ser Gly Thr Thr Val Ile Leu Thr Cys Ser Gln His Leu
                            20                  25                  30

Gly Ser Glu Ala Gln Trp Gln His Asn Gly Lys Asn Lys Gly Asp Ser
                            35                  40                  45

Gly Asp Gln Leu Phe Leu Pro Glu Phe Ser Glu Met Glu Gln Ser Gly
                            50                  55                  60

Tyr Tyr Val Cys Tyr Pro Arg Gly Ser Asn Pro Glu Asp Ala Ser His
             65                 70                  75                  80

His Leu Tyr Leu Lys Ala Arg Val Cys Glu Asn Cys Met Glu Met Asp
                            85                  90                  95

<210> SEQ ID NO 137
<211> LENGTH: 242
<212> TYPE: PRT
<213> ORGANISM: HOMO SAPIENS
<220> FEATURE:
<221> NAME/KEY: misc_feature
<222> LOCATION: (1)..(242)
<223> OTHER INFORMATION: EpCAM extracellular portion

<400> SEQUENCE: 137

Gln Glu Glu Cys Val Cys Glu Asn Tyr Lys Leu Ala Val Asn Cys Phe
 1               5                  10                  15

Val Asn Asn Asn Arg Gln Cys Gln Cys Thr Ser Val Gly Ala Gln Asn
                20                  25                  30

Thr Val Ile Cys Ser Lys Leu Ala Ala Lys Cys Leu Val Met Lys Ala
                35                  40                  45

Glu Met Asn Gly Ser Lys Leu Gly Arg Arg Ala Lys Pro Glu Gly Ala
             50                  55                  60

Leu Gln Asn Asn Asp Gly Leu Tyr Asp Pro Asp Cys Asp Glu Ser Gly
 65                 70                  75                  80

Leu Phe Lys Ala Lys Gln Cys Asn Gly Thr Ser Thr Cys Trp Cys Val
                85                  90                  95

Asn Thr Ala Gly Val Arg Arg Thr Asp Lys Asp Thr Glu Ile Thr Cys
                100                 105                 110

Ser Glu Arg Val Arg Thr Tyr Trp Ile Ile Glu Leu Lys His Lys
                115                 120                 125

Ala Arg Glu Lys Pro Tyr Asp Ser Lys Ser Leu Arg Thr Ala Leu Gln
            130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
                180                 185                 190

Phe Glu Lys Asp Val Lys Gly Glu Ser Leu Phe His Ser Lys Lys Met
                195                 200                 205

Asp Leu Thr Val Asn Gly Glu Gln Leu Asp Leu Asp Pro Gly Gln Thr
            210                 215                 220

Leu Ile Tyr Tyr Val Asp Glu Lys Ala Pro Glu Phe Ser Met Gln Gly
225                 230                 235                 240

Leu Lys

<210> SEQ ID NO 138
<211> LENGTH: 242
```

```
<212> TYPE: PRT
<213> ORGANISM: Pan troglodytes
<220> FEATURE:
<221> NAME/KEY: misc_feature
<222> LOCATION: (1)..(242)
<223> OTHER INFORMATION: EpCAM extracellular portion

<400> SEQUENCE: 138

Gln Glu Glu Cys Val Cys Glu Asn Tyr Lys Leu Ala Val Asn Cys Phe
1               5                   10                  15

Val Asn Asn Asn His Gln Cys Gln Cys Thr Ser Ile Gly Ala Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Thr Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Ala Arg Glu Lys Pro Tyr Asp Gly Lys Ser Leu Arg Thr Ala Leu Gln
    130                 135                 140

Lys Glu Ile Thr Thr Arg Tyr Gln Leu Asp Pro Lys Phe Ile Thr Asn
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Thr Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys

<210> SEQ ID NO 139
<211> LENGTH: 242
<212> TYPE: PRT
<213> ORGANISM: Macaca mulatta
<220> FEATURE:
<221> NAME/KEY: misc_feature
<222> LOCATION: (1)..(242)
<223> OTHER INFORMATION: EpCAM extracellular portion

<400> SEQUENCE: 139

Gln Lys Glu Cys Val Cys Glu Asn Tyr Lys Leu Ala Val Asn Cys Phe
1               5                   10                  15

Leu Asn Asp Asn Gly Gln Cys Gln Cys Thr Ser Ile Gly Ala Gln Asn
            20                  25                  30

Thr Val Leu Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
50                  55                  60
```

```
Leu Gln Asn Asn Asp Gly Leu Tyr Asp Pro Asp Cys Asp Glu Ser Gly
 65                  70                  75                  80

Leu Phe Lys Ala Lys Gln Cys Asn Gly Thr Ser Thr Cys Trp Cys Val
                 85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Ala Arg Glu Lys Pro Tyr Asp Val Gln Ser Leu Arg Thr Ala Leu Glu
130                 135                 140

Glu Ala Ile Lys Thr Arg Tyr Gln Leu Asp Pro Lys Phe Ile Thr Asn
145                 150                 155                 160

Ile Leu Tyr Glu Asp Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Arg Val Asn Gly Glu Gln Leu Asp Leu Asp Pro Gly Gln Thr
210                 215                 220

Leu Ile Tyr Tyr Val Asp Glu Lys Ala Pro Glu Phe Ser Met Gln Gly
225                 230                 235                 240

Leu Lys

<210> SEQ ID NO 140
<211> LENGTH: 242
<212> TYPE: PRT
<213> ORGANISM: Pan troglodytes
<220> FEATURE:
<221> NAME/KEY: misc_feature
<222> LOCATION: (1)..(242)
<223> OTHER INFORMATION: EpCAM extracellular portion

<400> SEQUENCE: 140

Gln Glu Glu Cys Val Cys Glu Asn Tyr Lys Leu Ala Val Asn Cys Phe
1               5                   10                  15

Val Asn Asn Asn His Gln Cys Gln Cys Thr Ser Ile Gly Ala Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
 50                 55                  60

Leu Gln Asn Asn Asp Gly Leu Tyr Asp Pro Asp Cys Asp Glu Ser Gly
 65                 70                  75                  80

Leu Phe Lys Ala Lys Gln Cys Asn Gly Thr Ser Thr Cys Trp Cys Val
                 85                 90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Ile Glu Leu Lys His Lys
        115                 120                 125

Ala Arg Glu Lys Pro Tyr Asp Gly Lys Ser Leu Arg Thr Ala Leu Gln
130                 135                 140

Lys Glu Ile Thr Thr Arg Tyr Gln Leu Asp Pro Lys Phe Ile Thr Asn
145                 150                 155                 160

Ile Leu Tyr Glu Asn Asn Val Ile Thr Ile Asp Leu Val Gln Asn Ser
```

```
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Thr Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys

<210> SEQ ID NO 141
<211> LENGTH: 242
<212> TYPE: PRT
<213> ORGANISM: Macaca mulatta
<220> FEATURE:
<221> NAME/KEY: misc_feat
<222> LOCATION: (1)..(242)
<223> OTHER INFORMATION: EpCAM extracellular portion

<400> SEQUENCE: 141

Gln Lys Glu Cys Val Cys Glu Asn Tyr Lys Leu Ala Val Asn Cys Phe
1               5                   10                  15

Leu Asn Asp Asn Gly Gln Cys Gln Cys Thr Ser Ile Gly Ala Gln Asn
            20                  25                  30

Thr Val Leu Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Thr Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
        115                 120                 125

Ala Arg Glu Lys Pro Tyr Asp Val Gln Ser Leu Arg Thr Ala Leu Glu
    130                 135                 140

Glu Ala Ile Lys Thr Arg Tyr Gln Leu Asp Pro Lys Phe Ile Thr Asn
145                 150                 155                 160

Ile Leu Tyr Glu Asp Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Arg Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys

<210> SEQ ID NO 142
<211> LENGTH: 89
<212> TYPE: PRT
```

<213> ORGANISM: HOMO SAPIENS
<220> FEATURE:
<221> NAME/KEY: misc_feature
<222> LOCATION: (1)..(89)
<223> OTHER INFORMATION: human CD3 gamma extracellular portion

<400> SEQUENCE: 142

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn
                85

<210> SEQ ID NO 143
<211> LENGTH: 82
<212> TYPE: PRT
<213> ORGANISM: HOMO SAPIENS
<220> FEATURE:
<221> NAME/KEY: misc_feature
<222> LOCATION: (1)..(82)
<223> OTHER INFORMATION: human CD3 delta extracellular portion

<400> SEQUENCE: 143

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Cys Gln Ser Cys Val Glu Leu Asp Pro
65                  70                  75                  80

Ala Thr

<210> SEQ ID NO 144
<211> LENGTH: 88
<212> TYPE: PRT
<213> ORGANISM: Macaca fascicularis
<220> FEATURE:
<221> NAME/KEY: misc_feature
<222> LOCATION: (1)..(88)
<223> OTHER INFORMATION: cynomolgus CD3 gamma extracellular portion

<400> SEQUENCE: 144

Gln Ser Phe Glu Glu Asn Arg Lys Leu Asn Val Tyr Asn Gln Glu Asp
1               5                   10                  15

Gly Ser Val Leu Leu Thr Cys His Val Lys Asn Thr Asn Ile Thr Trp
            20                  25                  30

Phe Lys Glu Gly Lys Met Ile Asp Ile Leu Thr Ala His Lys Asn Lys
        35                  40                  45

Trp Asn Leu Gly Ser Asn Thr Lys Asp Pro Arg Gly Val Tyr Gln Cys
    50                  55                  60

```
Lys Gly Ser Lys Asp Lys Ser Lys Thr Leu Gln Val Tyr Tyr Arg Met
65                  70                  75                  80

Cys Gln Asn Cys Ile Glu Leu Asn
                85
```

<210> SEQ ID NO 145
<211> LENGTH: 82
<212> TYPE: PRT
<213> ORGANISM: Macaca fascicularis
<220> FEATURE:
<221> NAME/KEY: misc_feature
<222> LOCATION: (1)..(82)
<223> OTHER INFORMATION: cynomolgus CD3 delta extracellular portion

<400> SEQUENCE: 145

```
Phe Lys Ile Pro Val Glu Glu Leu Glu Asp Arg Val Phe Val Lys Cys
1               5                   10                  15

Asn Thr Ser Val Thr Trp Val Glu Gly Thr Val Gly Thr Leu Leu Thr
                20                  25                  30

Asn Asn Thr Arg Leu Asp Leu Gly Lys Arg Ile Leu Asp Pro Arg Gly
            35                  40                  45

Ile Tyr Arg Cys Asn Gly Thr Asp Ile Tyr Lys Asp Lys Glu Ser Ala
50                  55                  60

Val Gln Val His Tyr Arg Met Cys Gln Asn Cys Val Glu Leu Asp Pro
65                  70                  75                  80

Ala Thr
```

<210> SEQ ID NO 146
<211> LENGTH: 249
<212> TYPE: PRT
<213> ORGANISM: ARTIFICIAL SEQUENCE
<220> FEATURE:
<223> OTHER INFORMATION: Human-like VH (SEQ ID NO: 110) x murine VL (SEQ
      ID NO: 148) scFv ; single chain Fv

<400> SEQUENCE: 146

```
Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Glu Leu Val Val
130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
                165                 170                 175
```

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
        195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Ser Asn Leu Trp Val Phe
225                 230                 235                 240

Gly Gly Gly Thr Lys Leu Thr Val Leu
                245

<210> SEQ ID NO 147
<211> LENGTH: 747
<212> TYPE: DNA
<213> ORGANISM: ARTIFICIAL SEQUENCE
<220> FEATURE:
<223> OTHER INFORMATION: Human-like VH (SEQ ID NO: 110) x murine VL (SEQ
      ID NO: 148) scFv ; single chain Fv

<400> SEQUENCE: 147
gaggtgcagc tgctcgagtc tggaggagga ttggtgcagc ctggagggtc attgaaactc      60
tcatgtgcag cctctggatt cacctccaat acctacgcca tgaactgggt ccgccaggct     120
ccaggaaagg gtttggaatg ggttgctcgc ataagaagta aatataataa ttatgcaaca     180
tattatgccg attcagtgaa agacaggttc accatctcca gagatgattc aaaaaacact     240
gcctatctac aaatgaacaa cttgaaaact gaggacactg ccgtgtacta ctgtgtgaga     300
catgggaact tcgtaatag ctacgtttcc tggtttgctt actggggcca agggactctg     360
gtcaccgtct cctcaggtgg tggtggttct ggcggcggcg gctccggtgg tggtggttct     420
gagctcgttg tgactcagga atctgcactc accacatcac ctggtgaaac agtcacactc     480
acttgtcgct caagtactgg ggctgttaca actagtaact atgccaactg ggtccaagaa     540
aaaccagatc atttattcac tggtctaata ggtggtacca caagcgagc accaggtgtg      600 cctgccagat tctcaggctc cctgattgga gacaaggctg ccctcaccat cacaggggca     660
cagactgagg atgaggcaat atatttctgt gctctatggt acagcaacct ctgggtgttc     720
ggtggaggaa ccaaactgac tgtccta                                         747

<210> SEQ ID NO 148
<211> LENGTH: 109
<212> TYPE: PRT
<213> ORGANISM: artificial sequence
<220> FEATURE:
<223> OTHER INFORMATION: murine VL

<400> SEQUENCE: 148

Glu Leu Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
                100                 105

<210> SEQ ID NO 149
<211> LENGTH: 327
<212> TYPE: DNA
<213> ORGANISM: ARTIFICIAL SEQUENCE
<220> FEATURE:
<223> OTHER INFORMATION: murine VL

<400> SEQUENCE: 149
gagctcgttg tgactcagga atctgcactc accacatcac ctggtgaaac agtcacactc        60
acttgtcgct caagtactgg ggctgttaca actagtaact atgccaactg gtccaagaa       120
aaaccagatc atttattcac tggtctaata ggtggtacca caagcgagc accaggtgtg       180
cctgccagat tctcaggctc cctgattgga gacaaggctg ccctcaccat cacaggggca       240
cagactgagg atgaggcaat atatttctgt gctctatggt acagcaacct ctgggtgttc       300
ggtggaggaa ccaaactgac tgtccta                                          327

<210> SEQ ID NO 150
<211> LENGTH: 723
<212> TYPE: DNA
<213> ORGANISM: artificial sequence
<220> FEATURE:
<223> OTHER INFORMATION: CAIX LH scFv , single chain Fv

<400> SEQUENCE: 150
gacattgtga tgacccagtc tcaaagattc atgtccacaa cagtaggaga cagggtcagc        60
atcacctgca aggccagtca gaatgtggtt tctgctgttg cctggtatca acagaaacca       120
ggacaatctc ctaaaactact gatttactca gcatccaatc ggtacactgg agtccctgat       180
cgcttcacag gcagtggatc tgggacagat ttcactctca ccattagcaa tatgcagtct       240
gaagacctgg ctgattttt ctgtcaacaa tatagcaact atccgtggac gttcggtgga       300
ggcaccaagc tggaaatcaa aggtggtggt ggttctggcg gcggcggctc cggtggtggt       360
ggttctgacg tgaagctcgt ggagtctggg ggaggcttag tgaagcttgg agggtccctg       420
aaactctcct gtgcagcctc tggattcact ttcagtaact attacatgtc ttgggttcgc       480
cagactccag agaagaggct ggagttggtc gcagccatta atagtgatgg tggtatcacc       540
tactatctag acactgtgaa gggccgattc accatttcaa gagacaatgc caagaacacc       600
ctgtacctgc aaatgagcag tctgaagtct gaggacacag ccttgttta ctgtgcaaga       660
caccgctcgg gctacttttc tatggactac tggggtcaag aacctcagt caccgtctcc       720
tcc                                                                    723

<210> SEQ ID NO 151
<211> LENGTH: 241
<212> TYPE: PRT
<213> ORGANISM: artificial sequence
<220> FEATURE:
<223> OTHER INFORMATION: CAIX LH scFv ; single chain Fv

<400> SEQUENCE: 151

Asp Ile Val Met Thr Gln Ser Gln Arg Phe Met Ser Thr Thr Val Gly
1               5                  10                  15

Asp Arg Val Ser Ile Thr Cys Lys Ala Ser Gln Asn Val Val Ser Ala
            20                  25                  30

Val Ala Trp Tyr Gln Gln Lys Pro Gly Gln Ser Pro Lys Leu Leu Ile

```
               35                  40                  45
Tyr Ser Ala Ser Asn Arg Tyr Thr Gly Val Pro Asp Arg Phe Thr Gly
 50                  55                  60

Ser Gly Ser Gly Thr Asp Phe Thr Leu Thr Ile Ser Asn Met Gln Ser
 65                  70                  75                  80

Glu Asp Leu Ala Asp Phe Phe Cys Gln Gln Tyr Ser Asn Tyr Pro Trp
                 85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Asp Val Lys Leu Val Glu
        115                 120                 125

Ser Gly Gly Gly Leu Val Lys Leu Gly Gly Ser Leu Lys Leu Ser Cys
130                 135                 140

Ala Ala Ser Gly Phe Thr Phe Ser Asn Tyr Tyr Met Ser Trp Val Arg
145                 150                 155                 160

Gln Thr Pro Glu Lys Arg Leu Glu Leu Val Ala Ala Ile Asn Ser Asp
                165                 170                 175

Gly Gly Ile Thr Tyr Tyr Leu Asp Thr Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Leu Phe Tyr Cys Ala Arg His Arg Ser Gly
210                 215                 220

Tyr Phe Ser Met Asp Tyr Trp Gly Gln Gly Thr Ser Val Thr Val Ser
225                 230                 235                 240

Ser

<210> SEQ ID NO 152
<211> LENGTH: 738
<212> TYPE: DNA
<213> ORGANISM: ARTIFICIAL SEQUENCE
<220> FEATURE:
<223> OTHER INFORMATION: EGFR21 LH scFv ; single chain Fv

<400> SEQUENCE: 152
gacattgtgc tgacacagtc tcctgcttcc ttacctgtgt ctctgggca gagggccacc      60
atctcatgca gggccagcca agtgtcagt catctactt atagttatat acactggtac     120
caacagaaac caggacagcc acccaaactc ctcatcacgt atgcatccaa cctagaatct   180
ggggtccctg ccaggttcag tgcagtggg tctgggacag acttcaccct cgacatccat    240
cctgtggagg aggatgattc ttcaacatat tactgtcagc acagttggga gattccattt   300
acgttcggct cggggacaaa gttggaaata aaaggtggtg gtggttctgg cggcggcggc   360
tccggtggtg gtggttctca ggttcagctg cagcagtctg acctgatct ggtgaagcct    420
ggggcctcag tgaagatgtc ctgcaaggct tctggacaca ctttcactga ctgtgttata   480
atctgggtga aacagagagc tggacagggc cttagtgga ttggacagat ttatccaggg    540
actggtcgtt cttactacaa tgagattttc aagggcaagg ccacactgac tgcagacaaa   600
tcctccaaca cagtccacat tcaactcagc agcctgacat ctgaggactc tgcggtctat   660
ttctgtgccc tatctactct tattcacggg acctggtttt cttattgggg ccaagggact   720
ctggtcactg tctcttcc                                                 738

<210> SEQ ID NO 153
<211> LENGTH: 246
```

<212> TYPE: PRT
<213> ORGANISM: artificial sequence
<220> FEATURE:
<223> OTHER INFORMATION: EGFR21 LH scFv ; single chain Fv

<400> SEQUENCE: 153

```
Asp Ile Val Leu Thr Gln Ser Pro Ala Ser Leu Pro Val Ser Leu Gly
1               5                  10                  15

Gln Arg Ala Thr Ile Ser Cys Arg Ala Ser Gln Ser Val Ser Ser Ser
            20                  25                  30

Thr Tyr Ser Tyr Ile His Trp Tyr Gln Gln Lys Pro Gly Gln Pro Pro
        35                  40                  45

Lys Leu Leu Ile Thr Tyr Ala Ser Asn Leu Glu Ser Gly Val Pro Ala
    50                  55                  60

Arg Phe Ser Gly Ser Gly Ser Gly Thr Asp Phe Thr Leu Asp Ile His
65                  70                  75                  80

Pro Val Glu Glu Asp Asp Ser Ser Thr Tyr Tyr Cys Gln His Ser Trp
                85                  90                  95

Glu Ile Pro Phe Thr Phe Gly Ser Gly Thr Lys Leu Glu Ile Lys Gly
            100                 105                 110

Gly Gly Gly Ser Gly Gly Gly Gly Ser Gly Gly Gly Ser Gln Val
        115                 120                 125

Gln Leu Gln Gln Ser Gly Pro Asp Leu Val Lys Pro Gly Ala Ser Val
130                 135                 140

Lys Met Ser Cys Lys Ala Ser Gly His Thr Phe Thr Asp Cys Val Ile
145                 150                 155                 160

Ile Trp Val Lys Gln Arg Ala Gly Gln Gly Leu Glu Trp Ile Gly Gln
                165                 170                 175

Ile Tyr Pro Gly Thr Gly Arg Ser Tyr Tyr Asn Glu Ile Phe Lys Gly
            180                 185                 190

Lys Ala Thr Leu Thr Ala Asp Lys Ser Ser Asn Thr Val His Ile Gln
        195                 200                 205

Leu Ser Ser Leu Thr Ser Glu Asp Ser Ala Val Tyr Phe Cys Ala Leu
    210                 215                 220

Ser Thr Leu Ile His Gly Thr Trp Phe Ser Tyr Trp Gly Gln Gly Thr
225                 230                 235                 240

Leu Val Thr Val Ser Ser
                245
```

<210> SEQ ID NO 154
<211> LENGTH: 726
<212> TYPE: DNA
<213> ORGANISM: ARTIFICIAL SEQUENCE
<220> FEATURE:
<223> OTHER INFORMATION: EGFRvIII-LH scFv ; single chain Fv

<400> SEQUENCE: 154

```
gatgttgtga tgacccagac tccactcact ttgtcggtta ccattggaca accagcctct    60
atctcttgca agtcaagtca gagcctctta tatagtaatg gaaaaaccta tttgaattgg   120
ttattacaga ggccaggcca gtctccaaag cgcctaatct atctggtatc taaactggac   180
tctggagtcc ctgacaggtt cactggcagt ggatcaggaa cagattttac actgaaaatc   240
agcagagtgg aggctgagga tttgggaatt tattactgcg tgcaagatac acattttcct   300
cagacattcg gtgaggcac caagctggaa atcaaaggtg gtggtggttc tggcggcggc   360
ggctccggtg gtggtggttc tgaggtccag ctgcaacagt ctggacctga gctgctgaag   420
```

-continued

```
cctgggcttt cagtgaagat atcctgcaag acttctggat acacattcac tgaatacacc    480
atacactggg tgaagcagag ccatggaaag agccttgagt ggattggagg tattgatcct    540
aacaatggtg gtactatgta taaccaaaaa ttcaagggca aggccacatt gactgtagac    600
aagtcttcca gcacagccta cacggacctc gcagcctga cgtctgagga ttctgcagtc     660
tattactgca caagagcaga ggctatggac tactggggtc aaggaacctc agtcaccgtc    720
tcctcc                                                               726
```

<210> SEQ ID NO 155
<211> LENGTH: 242
<212> TYPE: PRT
<213> ORGANISM: artificial sequence
<220> FEATURE:
<223> OTHER INFORMATION: EGFRvIII-LH scFv ; single chain Fv

<400> SEQUENCE: 155

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Val Gln Asp
                85                  90                  95

Thr His Phe Pro Gln Thr Phe Gly Gly Gly Thr Lys Leu Glu Ile Lys
            100                 105                 110

Gly Gly Gly Gly Ser Gly Gly Gly Ser Gly Gly Gly Ser Glu
        115                 120                 125

Val Gln Leu Gln Gln Ser Gly Pro Glu Leu Leu Lys Pro Gly Ala Ser
    130                 135                 140

Val Lys Ile Ser Cys Lys Thr Ser Gly Tyr Thr Phe Thr Glu Tyr Thr
145                 150                 155                 160

Ile His Trp Val Lys Gln Ser His Gly Lys Ser Leu Glu Trp Ile Gly
                165                 170                 175

Gly Ile Asp Pro Asn Asn Gly Gly Thr Met Tyr Asn Gln Lys Phe Lys
            180                 185                 190

Gly Lys Ala Thr Leu Thr Val Asp Lys Ser Ser Ser Thr Ala Tyr Thr
        195                 200                 205

Asp Leu Arg Ser Leu Thr Ser Glu Asp Ser Ala Val Tyr Tyr Cys Thr
    210                 215                 220

Arg Ala Glu Ala Met Asp Tyr Trp Gly Gln Gly Thr Ser Val Thr Val
225                 230                 235                 240

Ser Ser

<210> SEQ ID NO 156
<211> LENGTH: 1485
<212> TYPE: DNA
<213> ORGANISM: ARTIFICIAL SEQUENCE
<220> FEATURE:
<223> OTHER INFORMATION: CAIX LHxSEQ ID NO: 10 ; bispecific single chain
      antibody

<400> SEQUENCE: 156

```
gacattgtga tgacccagtc tcaaagattc atgtccacaa cagtaggaga cagggtcagc      60
atcacctgca aggccagtca gaatgtggtt tctgctgttg cctggtatca acagaaacca     120
ggacaatctc ctaaactact gatttactca gcatccaatc ggtacactgg agtccctgat     180
cgcttcacag gcagtggatc tgggacagat ttcactctca ccattagcaa tatgcagtct     240
gaagacctgg ctgattttt ctgtcaacaa tatagcaact atccgtggac gttcggtgga      300
ggcaccaagc tggaaatcaa aggtggtggt ggttctggcg gcggcggctc cggtggtggt     360
ggttctgacg tgaagctcgt ggagtctggg ggaggcttag tgaagcttgg agggtccctg     420
aaactctcct gtgcagcctc tggattcact ttcagtaact attacatgtc ttgggttcgc     480
cagactccag agaagaggct ggagttggtc gcagccatta atagtgatgg tggtatcacc     540
tactatctag acactgtgaa gggccgattc accatttcaa gagacaatgc caagaacacc     600
ctgtacctgc aaatgagcag tctgaagtct gaggacacag ccttgtttta ctgtgcaaga     660
caccgctcgg gctactttc tatggactac tggggtcaag aacctcagt caccgtctcc       720
tccggaggtg gtggatccga ggtgaagctt ctcgagtctg gaggaggatt ggtgcagcct     780
aaagggtcat tgaaactctc atgtgcagcc tctggattca ccttcaatac ctacgccatg     840
aactgggtcc gccaggctcc aggaaagggt ttggaatggg ttgctcgcat aagaagtaaa     900
tataataatt atgcaacata ttatgccgat tcagtgaaag acaggttcac catctccaga     960
gatgattcac aaagcattct ctatctacaa atgaacaact gaaaactga ggacacagcc     1020
atgtactact gtgtgagaca tgggaacttc ggtaatagct acgtttcctg gtttgcttac    1080
tggggccaag ggactctggt cactgtctct gcaggtggtg gtggttctgg cggcggcggc    1140
tccggtggtg gtggttctca ggctgttgtg actcaggaat ctgcactcac cacatcacct    1200
ggtgaaacag tcacactcac ttgtcgctca agtactgggg ctgttacaac tagtaactat    1260
gccaactggg tccaagaaaa accagatcat ttattcactg gtctaatagg tggtaccaac    1320
aagcgagctc caggtgtgcc tgccagattc tcaggctccc tgattggaga caaggctgcc    1380
ctcaccatca caggggcaca gactgaggat gaggcaatat atttctgtgc tctatggtac    1440
agcaacctct gggtgttcgg tggaggaacc aaactgactg tccta                    1485
```

<210> SEQ ID NO 157
<211> LENGTH: 495
<212> TYPE: PRT
<213> ORGANISM: artificial sequence
<220> FEATURE:
<223> OTHER INFORMATION: CAIX LHxSEQ ID NO: 10 ; bispecific single chain
      antibody

<400> SEQUENCE: 157

Asp Ile Val Met Thr Gln Ser Gln Arg Phe Met Ser Thr Thr Val Gly
1               5                   10                  15

Asp Arg Val Ser Ile Thr Cys Lys Ala Ser Gln Asn Val Val Ser Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Phe Phe Cys Gln Gln Tyr Ser Asn Tyr Pro Trp
                85                  90                  95

Thr Phe Gly Gly Gly Thr Lys Leu Glu Ile Lys Gly Gly Gly Ser
                100                 105                 110

Gly Gly Gly Gly Ser Gly Gly Gly Ser Asp Val Lys Leu Val Glu
            115                 120                 125

Ser Gly Gly Gly Leu Val Lys Leu Gly Gly Ser Leu Lys Leu Ser Cys
130                 135                 140

Ala Ala Ser Gly Phe Thr Phe Ser Asn Tyr Tyr Met Ser Trp Val Arg
145                 150                 155                 160

Gln Thr Pro Glu Lys Arg Leu Glu Leu Val Ala Ala Ile Asn Ser Asp
                165                 170                 175

Gly Gly Ile Thr Tyr Tyr Leu Asp Thr Val Lys Gly Arg Phe Thr Ile
            180                 185                 190

Ser Arg Asp Asn Ala Lys Asn Thr Leu Tyr Leu Gln Met Ser Ser Leu
                195                 200                 205

Lys Ser Glu Asp Thr Ala Leu Phe Tyr Cys Ala Arg His Arg Ser Gly
210                 215                 220

Tyr Phe Ser Met Asp Tyr Trp Gly Gln Gly Thr Ser Val Thr Val Ser
225                 230                 235                 240

Ser Gly Gly Gly Gly Ser Glu Val Lys Leu Leu Glu Ser Gly Gly Gly
                245                 250                 255

Leu Val Gln Pro Lys Gly Ser Leu Lys Leu Ser Cys Ala Ala Ser Gly
                260                 265                 270

Phe Thr Phe Asn Thr Tyr Ala Met Asn Trp Val Arg Gln Ala Pro Gly
                275                 280                 285

Lys Gly Leu Glu Trp Val Ala Arg Ile Arg Ser Lys Tyr Asn Asn Tyr
            290                 295                 300

Ala Thr Tyr Tyr Ala Asp Ser Val Lys Asp Arg Phe Thr Ile Ser Arg
305                 310                 315                 320

Asp Asp Ser Gln Ser Ile Leu Tyr Leu Gln Met Asn Asn Leu Lys Thr
                325                 330                 335

Glu Asp Thr Ala Met Tyr Tyr Cys Val Arg His Gly Asn Phe Gly Asn
                340                 345                 350

Ser Tyr Val Ser Trp Phe Ala Tyr Trp Gly Gln Gly Thr Leu Val Thr
            355                 360                 365

Val Ser Ala Gly Gly Gly Gly Ser Gly Gly Gly Ser Gly Gly Gly
370                 375                 380

Gly Ser Gln Ala Val Val Thr Gln Glu Ser Ala Leu Thr Thr Ser Pro
385                 390                 395                 400

Gly Glu Thr Val Thr Leu Thr Cys Arg Ser Ser Thr Gly Ala Val Thr
                405                 410                 415

Thr Ser Asn Tyr Ala Asn Trp Val Gln Glu Lys Pro Asp His Leu Phe
                420                 425                 430

Thr Gly Leu Ile Gly Gly Thr Asn Lys Arg Ala Pro Gly Val Pro Ala
            435                 440                 445

Arg Phe Ser Gly Ser Leu Ile Gly Asp Lys Ala Ala Leu Thr Ile Thr
450                 455                 460

Gly Ala Gln Thr Glu Asp Glu Ala Ile Tyr Phe Cys Ala Leu Trp Tyr
465                 470                 475                 480

Ser Asn Leu Trp Val Phe Gly Gly Gly Thr Lys Leu Thr Val Leu
                485                 490                 495

<210> SEQ ID NO 158
<211> LENGTH: 1500

<212> TYPE: DNA
<213> ORGANISM: ARTIFICIAL SEQUENCE
<220> FEATURE:
<223> OTHER INFORMATION: EGFR21 LHxSEQ ID NO: 10 ; bispecific single chain antibody

<400> SEQUENCE: 158

```
gacattgtgc tgacacagtc tcctgcttcc ttacctgtgt ctctgggca gagggccacc      60
atctcatgca gggccagcca aagtgtcagt tcatctactt atagttatat acactggtac     120
caacagaaac caggacagcc acccaaactc ctcatcacgt atgcatccaa cctagaatct     180
ggggtccctg ccaggttcag tggcagtggg tctgggacag acttcaccct cgacatccat     240
cctgtggagg aggatgattc ttcaacatat tactgtcagc acagttggga gattccattt     300
acgttcggct cggggacaaa gttggaaata aaaggtggtg gtggttctgg cggcggcggc     360
tccggtggtg gtggttctca ggttcagctg cagcagtctg gacctgatct ggtgaagcct     420
ggggcctcag tgaagatgtc ctgcaaggct tctggacaca ctttcactga ctgtgttata     480
atctgggtga acagagagc tggacagggc cttgagtgga ttggacagat ttatccaggg     540
actggtcgtt cttactacaa tgagattttc aagggcaagg ccacactgac tgcagacaaa     600
tcctccaaca cagtccacat tcaactcagc agcctgacat ctgaggactc tgcggtctat     660
ttctgtgccc tatctactct tattcacggg acctggtttt cttattgggg ccaagggact     720
ctggtcactg tctcttccgg aggtggtgga tccgaggtga gcttctcga gtctggagga     780
ggattggtgc agcctaaagg gtcattgaaa ctctcatgtg cagcctctgg attcaccttc     840
aatacctacg ccatgaactg ggtccgccag gctccaggaa agggtttgga atgggttgct     900
cgcataagaa gtaaatataa taattatgca acatattatg ccgattcagt gaaagacagg     960
ttcaccatct ccagagatga ttcacaaagc attctctatc tacaaatgaa caacttgaaa    1020
actgaggaca cagccatgta ctactgtgtg agacatggga acttcggtaa tagctacgtt    1080
tcctggtttg cttactgggg ccaagggact ctggtcactg tctctgcagg tggtggtggt    1140
tctggcggcg gcggctccgg tggtggtggt tctcaggctg ttgtgactca ggaatctgca    1200
ctcaccacat cacctggtga aacagtcaca ctcacttgtc gctcaagtac tggggctgtt    1260
acaactagta actatgccaa ctgggtccaa gaaaaaccag atcatttatt cactggtcta    1320
ataggtggta ccaacaagcg agctccaggt gtgcctgcca gattctcagg ctccctgatt    1380
ggagacaagg ctgccctcac catcacaggg gcacagactg aggatgaggc aatatatttc    1440
tgtgctctat ggtacagcaa cctctgggtg ttcggtggag gaaccaaact gactgtccta    1500
```

<210> SEQ ID NO 159
<211> LENGTH: 500
<212> TYPE: PRT
<213> ORGANISM: artificial sequence
<220> FEATURE:
<223> OTHER INFORMATION: EGFR21 LHxSEQ ID NO: 10 ; bispecific single chain antibody

<400> SEQUENCE: 159

```
Asp Ile Val Leu Thr Gln Ser Pro Ala Ser Leu Pro Val Ser Leu Gly
1               5                   10                  15

Gln Arg Ala Thr Ile Ser Cys Arg Ala Ser Gln Ser Val Ser Ser Ser
            20                  25                  30

Thr Tyr Ser Tyr Ile His Trp Tyr Gln Gln Lys Pro Gly Gln Pro Pro
        35                  40                  45

Lys Leu Leu Ile Thr Tyr Ala Ser Asn Leu Glu Ser Gly Val Pro Ala
```

```
            50                  55                  60
Arg Phe Ser Gly Ser Gly Ser Gly Thr Asp Phe Thr Leu Asp Ile His
 65                  70                  75                  80

Pro Val Glu Glu Asp Asp Ser Thr Tyr Tyr Cys Gln His Ser Trp
                 85                  90                  95

Glu Ile Pro Phe Thr Phe Gly Ser Gly Thr Lys Leu Glu Ile Lys Gly
            100                 105                 110

Gly Gly Gly Ser Gly Gly Gly Gly Ser Gly Gly Gly Ser Gln Val
            115                 120                 125

Gln Leu Gln Gln Ser Gly Pro Asp Leu Val Lys Pro Gly Ala Ser Val
130                 135                 140

Lys Met Ser Cys Lys Ala Ser Gly His Thr Phe Thr Asp Cys Val Ile
145                 150                 155                 160

Ile Trp Val Lys Gln Arg Ala Gly Gln Gly Leu Glu Trp Ile Gly Gln
                165                 170                 175

Ile Tyr Pro Gly Thr Gly Arg Ser Tyr Tyr Asn Glu Ile Phe Lys Gly
            180                 185                 190

Lys Ala Thr Leu Thr Ala Asp Lys Ser Ser Asn Thr Val His Ile Gln
            195                 200                 205

Leu Ser Ser Leu Thr Ser Glu Asp Ser Ala Val Tyr Phe Cys Ala Leu
210                 215                 220

Ser Thr Leu Ile His Gly Thr Trp Phe Ser Tyr Trp Gly Gln Gly Thr
225                 230                 235                 240

Leu Val Thr Val Ser Ser Gly Gly Gly Ser Glu Val Lys Leu Leu
                245                 250                 255

Glu Ser Gly Gly Gly Leu Val Gln Pro Lys Gly Ser Leu Lys Leu Ser
            260                 265                 270

Cys Ala Ala Ser Gly Phe Thr Phe Asn Thr Tyr Ala Met Asn Trp Val
            275                 280                 285

Arg Gln Ala Pro Gly Lys Gly Leu Glu Trp Val Ala Arg Ile Arg Ser
290                 295                 300

Lys Tyr Asn Asn Tyr Ala Thr Tyr Tyr Ala Asp Ser Val Lys Asp Arg
305                 310                 315                 320

Phe Thr Ile Ser Arg Asp Asp Ser Gln Ser Ile Leu Tyr Leu Gln Met
                325                 330                 335

Asn Asn Leu Lys Thr Glu Asp Thr Ala Met Tyr Tyr Cys Val Arg His
            340                 345                 350

Gly Asn Phe Gly Asn Ser Tyr Val Ser Trp Phe Ala Tyr Trp Gly Gln
            355                 360                 365

Gly Thr Leu Val Thr Val Ser Ala Gly Gly Gly Ser Gly Gly Gly
            370                 375                 380

Gly Ser Gly Gly Gly Ser Gln Ala Val Val Thr Gln Glu Ser Ala
385                 390                 395                 400

Leu Thr Thr Ser Pro Gly Glu Thr Val Thr Leu Thr Cys Arg Ser Ser
                405                 410                 415

Thr Gly Ala Val Thr Thr Ser Asn Tyr Ala Asn Trp Val Gln Glu Lys
            420                 425                 430

Pro Asp His Leu Phe Thr Gly Leu Ile Gly Gly Thr Asn Lys Arg Ala
            435                 440                 445

Pro Gly Val Pro Ala Arg Phe Ser Gly Ser Leu Ile Gly Asp Lys Ala
450                 455                 460

Ala Leu Thr Ile Thr Gly Ala Gln Thr Glu Asp Glu Ala Ile Tyr Phe
465                 470                 475                 480
```

Cys Ala Leu Trp Tyr Ser Asn Leu Trp Val Phe Gly Gly Gly Thr Lys
              485                 490                 495

Leu Thr Val Leu
        500

<210> SEQ ID NO 160
<211> LENGTH: 1488
<212> TYPE: DNA
<213> ORGANISM: ARTIFICIAL SEQUENCE
<220> FEATURE:
<223> OTHER INFORMATION: EGFRvIII-LHxSEQ ID NO: 10 ; bispecific single
      chain antibody

<400> SEQUENCE: 160

```
gatgttgtga tgacccagac tccactcact ttgtcggtta ccattggaca accagcctct     60
atctcttgca agtcaagtca gagcctctta tatagtaatg gaaaaaccta tttgaattgg    120
ttattacaga ggccaggcca gtctccaaag cgcctaatct atctggtatc taaactggac    180
tctggagtcc ctgacaggtt cactggcagt ggatcaggaa cagattttac actgaaaatc    240
agcagagtgg aggctgagga tttgggaatt tattactgcg tgcaagatac acattttcct    300
cagacattcg gtgaggcac caagctgaa atcaaaggtg gtggtggttc tggcggcggc    360
ggctccggtg gtggtggttc tgaggtccag ctgcaacagt ctggacctga gctgctgaag    420
cctgggctt cagtgaagat atcctgcaag acttctggat acacattcac tgaatacacc    480
atacactggg tgaagcagag ccatggaaag agccttgagt ggattggagg tattgatcct    540
aacaatggtg gtactatgta taccaaaaaa ttcaagggca aggccacatt gactgtagac    600
aagtcttcca gcacagccta cacggacctc cgcagcctga cgtctgagga ttctgcagtc    660
tattactgca agagcaga ggctatgac tactggggtc aaggaacctc agtcaccgtc    720
tcctccggag gtggtggatc cgaggtgaag cttctcgagt ctggaggagg attggtgcag    780
cctaaagggt cattgaaact ctcatgtgca gcctctggat tcaccttcaa tacctacgcc    840
atgaactggg tccgccaggc tccaggaaag ggtttggaat gggttgctcg cataagaagt    900
aaatataata attatgcaac atattatgcc gattcagtga agacaggtt caccatctcc    960
agagatgatt cacaaagcat tctctatcta caaatgaaca acttgaaaac tgaggacaca   1020
gccatgtact actgtgtgag acatgggaac ttcggtaata gctacgtttc ctggtttgct   1080
tactggggcc aagggactct ggtcactgtc tctgcaggtg gtggtggttc tggcggcggc   1140
ggctccggtg gtggtggttc tcaggctgtt gtgactcagg aatctgcact caccacatca   1200
cctggtgaaa cagtcacact cacttgtcgc tcaagtactg gggctgttac aactagtaac   1260
tatgccaact gggtccaaga aaaaccagat catttattca ctggtctaat aggtggtacc   1320
aacaagcgag ctccaggtgt gcctgccaga ttctcaggct ccctgattgg agacaaggct   1380
gccctcacca tcacaggggc acagactgag gatgaggcaa tatatttctg tgctctatgg   1440
tacagcaacc tctgggtgtt cggtggagga accaaactga ctgtccta              1488
```

<210> SEQ ID NO 161
<211> LENGTH: 496
<212> TYPE: PRT
<213> ORGANISM: artificial sequence
<220> FEATURE:
<223> OTHER INFORMATION: EGFRvIII-LHxSEQ ID NO: 10 ; bispecific single
      chain antibody

<400> SEQUENCE: 161

-continued

```
Asp Val Val Met Thr Gln Thr Pro Leu Thr Leu Ser Val Thr Ile Gly
 1               5                  10                  15
Gln Pro Ala Ser Ile Ser Cys Lys Ser Ser Gln Ser Leu Leu Tyr Ser
             20                  25                  30
Asn Gly Lys Thr Tyr Leu Asn Trp Leu Leu Gln Arg Pro Gly Gln Ser
         35                  40                  45
Pro Lys Arg Leu Ile Tyr Leu Val Ser Lys Leu Asp Ser Gly Val Pro
     50                  55                  60
Asp Arg Phe Thr Gly Ser Gly Ser Gly Thr Asp Phe Thr Leu Lys Ile
 65                  70                  75                  80
Ser Arg Val Glu Ala Glu Asp Leu Gly Ile Tyr Tyr Cys Val Gln Asp
                 85                  90                  95
Thr His Phe Pro Gln Thr Phe Gly Gly Gly Thr Lys Leu Glu Ile Lys
             100                 105                 110
Gly Gly Gly Gly Ser Gly Gly Gly Gly Ser Gly Gly Gly Gly Ser Glu
         115                 120                 125
Val Gln Leu Gln Gln Ser Gly Pro Glu Leu Leu Lys Pro Gly Ala Ser
     130                 135                 140
Val Lys Ile Ser Cys Lys Thr Ser Gly Tyr Thr Phe Thr Glu Tyr Thr
145                 150                 155                 160
Ile His Trp Val Lys Gln Ser His Gly Lys Ser Leu Glu Trp Ile Gly
                 165                 170                 175
Gly Ile Asp Pro Asn Asn Gly Gly Thr Met Tyr Asn Gln Lys Phe Lys
             180                 185                 190
Gly Lys Ala Thr Leu Thr Val Asp Lys Ser Ser Ser Thr Ala Tyr Thr
         195                 200                 205
Asp Leu Arg Ser Leu Thr Ser Glu Asp Ser Ala Val Tyr Tyr Cys Thr
     210                 215                 220
Arg Ala Glu Ala Met Asp Tyr Trp Gly Gln Gly Thr Ser Val Thr Val
225                 230                 235                 240
Ser Ser Gly Gly Gly Gly Ser Glu Val Lys Leu Leu Glu Ser Gly Gly
                 245                 250                 255
Gly Leu Val Gln Pro Lys Gly Ser Leu Lys Leu Ser Cys Ala Ala Ser
             260                 265                 270
Gly Phe Thr Phe Asn Thr Tyr Ala Met Asn Trp Val Arg Gln Ala Pro
         275                 280                 285
Gly Lys Gly Leu Glu Trp Val Ala Arg Ile Arg Ser Lys Tyr Asn Asn
     290                 295                 300
Tyr Ala Thr Tyr Tyr Ala Asp Ser Val Lys Asp Arg Phe Thr Ile Ser
305                 310                 315                 320
Arg Asp Asp Ser Gln Ser Ile Leu Tyr Leu Gln Met Asn Asn Leu Lys
                 325                 330                 335
Thr Glu Asp Thr Ala Met Tyr Tyr Cys Val Arg His Gly Asn Phe Gly
             340                 345                 350
Asn Ser Tyr Val Ser Trp Phe Ala Tyr Trp Gly Gln Gly Thr Leu Val
         355                 360                 365
Thr Val Ser Ala Gly Gly Gly Ser Gly Gly Gly Ser Gly Gly
         370                 375                 380
Gly Gly Ser Gln Ala Val Val Thr Gln Glu Ser Ala Leu Thr Thr Ser
385                 390                 395                 400
Pro Gly Glu Thr Val Thr Leu Thr Cys Arg Ser Ser Thr Gly Ala Val
             405                 410                 415
Thr Thr Ser Asn Tyr Ala Asn Trp Val Gln Glu Lys Pro Asp His Leu
```

```
                    420             425             430
Phe Thr Gly Leu Ile Gly Gly Thr Asn Lys Arg Ala Pro Gly Val Pro
            435                 440                 445

Ala Arg Phe Ser Gly Ser Leu Ile Gly Asp Lys Ala Ala Leu Thr Ile
    450                 455                 460

Thr Gly Ala Gln Thr Glu Asp Glu Ala Ile Tyr Phe Cys Ala Leu Trp
465                 470                 475                 480

Tyr Ser Asn Leu Trp Val Phe Gly Gly Gly Thr Lys Leu Thr Val Leu
                485                 490                 495

<210> SEQ ID NO 162
<211> LENGTH: 243
<212> TYPE: PRT
<213> ORGANISM: ARTIFICIAL SEQUENCE
<220> FEATURE:
<223> OTHER INFORMATION: anti CD3

<400> SEQUENCE: 162

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 163
<211> LENGTH: 243
<212> TYPE: PRT
<213> ORGANISM: artificial sequence
<220> FEATURE:
<223> OTHER INFORMATION: deimmunised(di)-anti CD3 deimmunised single
      chain Fv
```

<400> SEQUENCE: 163

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

<210> SEQ ID NO 164
<211> LENGTH: 9
<212> TYPE: PRT
<213> ORGANISM: mus musculus

<400> SEQUENCE: 164

Gln Gln Trp Ser Arg Asn Pro Pro Thr
1               5

<210> SEQ ID NO 165
<211> LENGTH: 7
<212> TYPE: PRT
<213> ORGANISM: mus musculus

<400> SEQUENCE: 165

Asp Ser Ser Lys Leu Ala Ser
1               5

<210> SEQ ID NO 166
<211> LENGTH: 10
<212> TYPE: PRT
<213> ORGANISM: mus musculus

<400> SEQUENCE: 166

Ser Ala Ser Ser Ser Val Ser Tyr Met Asn
1               5                   10

<210> SEQ ID NO 167
<211> LENGTH: 327
<212> TYPE: DNA
<213> ORGANISM: artificial sequence
<220> FEATURE:
<223> OTHER INFORMATION: Human-like VL VL region

<400> SEQUENCE: 167
gagctcgttg tgactcagga accttcactc accgtatcac ctggtggaac agtcacactc    60
acttgtcgct cgtcgactgg ggctgttaca actagcaact atgccaactg gtccaacaa    120 aaaccaggtc aggcaccccg tggtctaata ggtggtacca acaagcgcgc accaggtact    180
cctgccagat tctcaggctc cctgcttgga ggcaaggctg ccctcaccct ctcagggta    240 cagccagagg atgaggcaga atattactgt gctctatggt acagcaacct ctgggtgttc    300
ggtggaggaa ccaaactgac tgtccta                                        327

<210> SEQ ID NO 168
<211> LENGTH: 109
<212> TYPE: PRT
<213> ORGANISM: artificial sequence
<220> FEATURE:
<223> OTHER INFORMATION: Human-like VL VL region

<400> SEQUENCE: 168

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 169
<211> LENGTH: 747
<212> TYPE: DNA
<213> ORGANISM: ARTIFICIAL SEQUENCE
<220> FEATURE:
<223> OTHER INFORMATION: Human-like VH (SEQ ID NO: 110) x Human-like VL
      (SEQ ID NO: 168) scFv ; single chain Fv

<400> SEQUENCE: 169
gaggtgcagc tgctcgagtc tggaggagga ttggtgcagc ctggagggtc attgaaactc    60
tcatgtgcag cctctggatt caccttcaat acctacgcca tgaactgggt ccgccaggct    120
ccaggaaagg gtttggaatg ggttgctcgc ataagaagta aatataataa ttatgcaaca    180
tattatgccg attcagtgaa agacaggttc accatctcca gagatgattc aaaaaacact    240
gcctatctac aaatgaacaa cttgaaaact gaggacactg ccgtgtacta ctgtgtgaga    300
catgggaact tcggtaatag ctacgtttcc tggtttgctt actggggcca aggactctg     360

```
gtcaccgtct cctcaggtgg tggtggttct ggcggcggcg gctccggtgg tggtggttct    420
gagctcgttg tgactcagga accttcactc accgtatcac ctggtggaac agtcacactc    480
acttgtcgct cgtcgactgg ggctgttaca actagcaact atgccaactg gtccaacaa     540 aaaccaggtc aggcaccccg tggtctaata ggtggtacca caagcgcgc accaggtact     600 cctgccagat tctcaggctc cctgcttgga ggcaaggctg ccctcaccct ctcaggggta    660
cagccagagg atgaggcaga atattactgt gctctatggt acagcaacct ctgggtgttc    720
ggtggaggaa ccaaactgac tgtccta                                        747
```

<210> SEQ ID NO 170
<211> LENGTH: 249
<212> TYPE: PRT
<213> ORGANISM: artificial sequence
<220> FEATURE:
<223> OTHER INFORMATION: Human-like VH (SEQ ID NO: 110) x Human-like VL
      (SEQ ID NO: 168) scFv ; single chain Fv

<400> SEQUENCE: 170

```
Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Leu Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
            180                 185                 190

Thr Asn Lys Arg Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Leu Trp Val Phe
225                 230                 235                 240

Gly Gly Gly Thr Lys Leu Thr Val Leu
                245
```

<210> SEQ ID NO 171
<211> LENGTH: 1530
<212> TYPE: DNA
<213> ORGANISM: ARTIFICIAL SEQUENCE

<220> FEATURE:
<223> OTHER INFORMATION: EGFR HL x SEQ ID NO: 170 ; bispecific single
    chain antibody

<400> SEQUENCE: 171

| | | | | | |
|---|---|---|---|---|---|
| caggtgcagc | tgcagcagtc | tgggcctgat | ctggtgaagc | ctggggcctc | agtgaagatg | 60 |
| tcctgcaagg | cttctggaca | cactttcact | gactgtgtta | taatctgggt | gaaacagaga | 120 |
| gctggacagg | gccttgagtg | gattggacag | atttatccag | ggactggtcg | ttcttactac | 180 |
| aatgagattt | tcaagggcaa | ggccacactg | actgcagaca | aatcctccaa | cacagtccac | 240 |
| attcaactca | gcagcctgac | atctgaggac | tctgcggtct | atttctgtgc | cctatctact | 300 |
| cttattcacg | ggacctggtt | ttcttattgg | ggccaaggga | ctctggtcac | tgtctcttcc | 360 |
| ggtggtggtg | gttctggcgg | cggcggctcc | ggtggtggtg | gttctgacat | tgtactgacc | 420 |
| cagtctccag | cttccttacc | tgtgtctctg | gggcagaggg | ccaccatctc | atgcagggcc | 480 |
| agccaaagtg | tcagttcatc | tacttatagt | tatatacact | ggtaccaaca | gaaaccagga | 540 |
| cagccaccca | aactcctcat | cacgtatgca | tccaacctag | aatctggggt | ccctgccagg | 600 |
| ttcagtggca | gtgggtctgg | gacagacttc | accctcgaca | tccatcctgt | ggaggaggat | 660 |
| gattcttcaa | catattactg | tcagcacagt | tgggagattc | catttacgtt | cggctcgggg | 720 |
| acaaagttgg | aaataaaatc | cggaggtggt | ggctccgagg | tgcagctggt | ggagtctgga | 780 |
| ggaggattgg | tgcagcctgg | agggtcattg | aaactctcat | gtgcagcctc | tggattcacc | 840 |
| ttcaatacct | acgccatgaa | ctgggtccgc | caggctccag | aaagggtttt | ggaatgggtt | 900 |
| gctcgcataa | gaagtaaata | taataattat | gcaacatatt | atgccgattc | agtgaaagac | 960 |
| aggttcacca | tctccagaga | tgattcaaaa | acactgcct | atctacaaat | gaacaacttg | 1020 |
| aaaactgagg | acactgccgt | gtactactgt | gtgagacatg | gaacttcgg | taatagctac | 1080 |
| gtttcctggt | ttgcttactg | gggccaaggg | actctggtca | ccgtctcctc | aggtggtggt | 1140 |
| ggttctggcg | gcggcggctc | cggtggtggt | ggttctcaga | ccgttgtgac | tcaggaacct | 1200 |
| tcactcaccg | tatcacctgg | tggaacagtc | acactcactt | gtcgctcgtc | cactgggggct | 1260 |
| gttacaacta | gcaactatgc | caactgggtc | caacaaaaac | caggtcaggc | accccgtggt | 1320 |
| ctaataggtg | gtaccaacaa | gcgcgcacca | ggtactcctg | ccagattctc | aggctccctg | 1380 |
| cttggaggca | aggctgccct | caccctctca | ggggtacagc | cagaggatga | ggcagaatat | 1440 |
| tactgtgctc | tatggtacag | caacctctgg | gtgttcggtg | gaggaaccaa | actgactgtc | 1500 |
| ctacatcatc | accatcatca | ttaggtcgac | | | | 1530 |

<210> SEQ ID NO 172
<211> LENGTH: 507
<212> TYPE: PRT
<213> ORGANISM: artificial sequence
<220> FEATURE:
<223> OTHER INFORMATION: EGFR HL x SEQ ID NO: 170 ; bispecific single
    chain antibody

<400> SEQUENCE: 172

Gln Val Gln Leu Gln Gln Ser Gly Pro Asp Leu Val Lys Pro Gly Ala
1               5                   10                  15

Ser Val Lys Met Ser Cys Lys Ala Ser Gly His Thr Phe Thr Asp Cys
            20                  25                  30

Val Ile Ile Trp Val Lys Gln Arg Ala Gly Gln Gly Leu Glu Trp Ile
        35                  40                  45

Gly Gln Ile Tyr Pro Gly Thr Gly Arg Ser Tyr Tyr Asn Glu Ile Phe

```
                50                  55                  60
Lys Gly Lys Ala Thr Leu Thr Ala Asp Lys Ser Ser Asn Thr Val His
 65                  70                  75                  80

Ile Gln Leu Ser Ser Leu Thr Ser Glu Asp Ser Ala Val Tyr Phe Cys
                     85                  90                  95

Ala Leu Ser Thr Leu Ile His Gly Thr Trp Phe Ser Tyr Trp Gly Gln
                100                 105                 110

Gly Thr Leu Val Thr Val Ser Ser Gly Gly Gly Ser Gly Gly Gly
                115                 120                 125

Gly Ser Gly Gly Gly Ser Asp Ile Val Leu Thr Gln Ser Pro Ala
            130                 135                 140

Ser Leu Pro Val Ser Leu Gly Gln Arg Ala Thr Ile Ser Cys Arg Ala
145                 150                 155                 160

Ser Gln Ser Val Ser Ser Thr Tyr Ser Tyr Ile His Trp Tyr Gln
                165                 170                 175

Gln Lys Pro Gly Gln Pro Pro Lys Leu Leu Ile Thr Tyr Ala Ser Asn
                180                 185                 190

Leu Glu Ser Gly Val Pro Ala Arg Phe Ser Gly Ser Gly Ser Gly Thr
                195                 200                 205

Asp Phe Thr Leu Asp Ile His Pro Val Glu Glu Asp Ser Ser Thr
210                 215                 220

Tyr Tyr Cys Gln His Ser Trp Glu Ile Pro Phe Thr Phe Gly Ser Gly
225                 230                 235                 240

Thr Lys Leu Glu Ile Lys Ser Gly Gly Gly Ser Glu Val Gln Leu
                245                 250                 255

Val Glu Ser Gly Gly Gly Leu Val Gln Pro Gly Gly Ser Leu Lys Leu
                260                 265                 270

Ser Cys Ala Ala Ser Gly Phe Thr Phe Asn Thr Tyr Ala Met Asn Trp
                275                 280                 285

Val Arg Gln Ala Pro Gly Lys Gly Leu Glu Trp Val Ala Arg Ile Arg
                290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
                340                 345                 350

His Gly Asn Phe Gly Asn Ser Tyr Val Ser Trp Phe Ala Tyr Trp Gly
                355                 360                 365

Gln Gly Thr Leu Val Thr Val Ser Ser Gly Gly Gly Gly Ser Gly Gly
                370                 375                 380

Gly Gly Ser Gly Gly Gly Gly Ser Gln Thr Val Thr Gln Glu Pro
385                 390                 395                 400

Ser Leu Thr Val Ser Pro Gly Gly Thr Val Thr Leu Thr Cys Arg Ser
                405                 410                 415

Ser Thr Gly Ala Val Thr Thr Ser Asn Tyr Ala Asn Trp Val Gln Gln
                420                 425                 430

Lys Pro Gly Gln Ala Pro Arg Gly Leu Ile Gly Gly Thr Asn Lys Arg
                435                 440                 445

Ala Pro Gly Thr Pro Ala Arg Phe Ser Gly Ser Leu Leu Gly Gly Lys
                450                 455                 460

Ala Ala Leu Thr Leu Ser Gly Val Gln Pro Glu Asp Glu Ala Glu Tyr
465                 470                 475                 480
```

Tyr Cys Ala Leu Trp Tyr Ser Asn Leu Trp Val Phe Gly Gly Gly Thr
                485                 490                 495

Lys Leu Thr Val Leu His His His His His
        500                 505

<210> SEQ ID NO 173
<211> LENGTH: 1527
<212> TYPE: DNA
<213> ORGANISM: artificial sequence
<220> FEATURE:
<223> OTHER INFORMATION: EGFR LH x SEQ ID NO: 170 ; bispecific single chain antibody

<400> SEQUENCE: 173

| | | | | | |
|---|---|---|---|---|---|
| gacattgtgc | tgacacagtc | tcctgcttcc | ttacctgtgt | ctctggggca | gagggccacc | 60 |
| atctcatgca | gggccagcca | aagtgtcagt | tcatctactt | atagttatat | acactggtac | 120 |
| caacagaaac | caggacagcc | acccaaactc | ctcatcacgt | atgcatccaa | cctagaatct | 180 |
| ggggtccctg | ccaggttcag | tggcagtggg | tctgggacag | acttcaccct | cgacatccat | 240 |
| cctgtggagg | aggatgattc | ttcaacatat | tactgtcagc | acagttggga | gattccattt | 300 |
| acgttcggct | cggggacaaa | gttggaaata | aaaggtggtg | gtggttctgg | cggcggcggc | 360 |
| tccggtggtg | gtggttctca | ggttcagctg | cagcagtctg | gacctgatct | ggtgaagcct | 420 |
| ggggcctcag | tgaagatgtc | ctgcaaggct | tctggacaca | cttcactga | ctgtgttata | 480 |
| atctgggtga | aacagagagc | tggacagggc | cttgagtgga | ttggacagat | ttatccaggg | 540 |
| actggtcgtt | cttactacaa | tgagattttc | aagggcaagg | ccacactgac | tgcagacaaa | 600 |
| tcctccaaca | cagtccacat | tcaactcagc | agcctgacat | ctgaggactc | tgcggtctat | 660 |
| ttctgtgccc | tatctactct | tattcacggg | acctggtttt | cttattgggg | ccaagggact | 720 |
| ctggtcactg | tctcttccgg | aggtggtggc | tccgaggtgc | agctggtgga | gtctggagga | 780 |
| ggattggtgc | agcctggagg | gtcattgaaa | ctctcatgtg | cagcctctgg | attccacttc | 840 |
| aataccctacg | ccatgaactg | ggtccgccag | gctccaggaa | agggtttgga | atgggttgct | 900 |
| cgcataagaa | gtaaatataa | taattatgca | acatattatg | ccgattcagt | gaaagacagg | 960 |
| ttcaccatct | ccagagatga | ttcaaaaaac | actgcctatc | tacaaatgaa | caacttgaaa | 1020 |
| actgaggaca | ctgccgtgta | ctactgtgtg | agacatggga | acttcggtaa | tagctacgtt | 1080 |
| tcctggtttg | cttactgggg | ccaagggact | ctggtcaccg | tctcctcagg | tggtggtggt | 1140 |
| tctgcggcg | cggctccgg | tggtggtggt | tctcagaccg | ttgtgactca | ggaaccttca | 1200 |
| ctcaccgtat | cacctggtgg | aacagtcaca | ctcacttgtc | gctcgtccac | tggggctgtt | 1260 |
| acaactagca | actatgccaa | ctgggtccaa | caaaaaccag | gtcaggcacc | ccgtggtcta | 1320 |
| ataggtggta | ccaacaagcg | cgcaccaggt | actcctgcca | gattctcagg | ctccctgctt | 1380 |
| ggaggcaagg | ctgccctcac | cctctcaggg | gtacagccag | aggatgaggc | agaatattac | 1440 |
| tgtgctctat | ggtacagcaa | cctctgggtg | ttcggtggag | gaaccaaact | gactgtccta | 1500 |
| catcatcacc | atcatcatta | ggtcgac | | | | 1527 |

<210> SEQ ID NO 174
<211> LENGTH: 506
<212> TYPE: PRT
<213> ORGANISM: artificial sequence
<220> FEATURE:
<223> OTHER INFORMATION: EGFR LH x SEQ ID NO: 170 ; bispecific single chain antibody

<400> SEQUENCE: 174

```
Asp Ile Val Leu Thr Gln Ser Pro Ala Ser Leu Pro Val Ser Leu Gly
1               5                   10                  15

Gln Arg Ala Thr Ile Ser Cys Arg Ala Ser Gln Ser Val Ser Ser Ser
            20                  25                  30

Thr Tyr Ser Tyr Ile His Trp Tyr Gln Gln Lys Pro Gly Gln Pro Pro
        35                  40                  45

Lys Leu Leu Ile Thr Tyr Ala Ser Asn Leu Glu Ser Gly Val Pro Ala
    50                  55                  60

Arg Phe Ser Gly Ser Gly Ser Gly Thr Asp Phe Thr Leu Asp Ile His
65              70                  75                  80

Pro Val Glu Glu Asp Asp Ser Thr Tyr Tyr Cys Gln His Ser Trp
                85                  90                  95

Glu Ile Pro Phe Thr Phe Gly Ser Gly Thr Lys Leu Glu Ile Lys Gly
            100                 105                 110

Gly Gly Gly Ser Gly Gly Gly Ser Gly Gly Gly Ser Gln Val
            115                 120                 125

Gln Leu Gln Gln Ser Gly Pro Asp Leu Val Lys Pro Gly Ala Ser Val
130                 135                 140

Lys Met Ser Cys Lys Ala Ser Gly His Thr Phe Thr Asp Cys Val Ile
145                 150                 155                 160

Ile Trp Val Lys Gln Arg Ala Gly Gln Gly Leu Glu Trp Ile Gly Gln
                165                 170                 175

Ile Tyr Pro Gly Thr Gly Arg Ser Tyr Tyr Asn Glu Ile Phe Lys Gly
            180                 185                 190

Lys Ala Thr Leu Thr Ala Asp Lys Ser Ser Asn Thr Val His Ile Gln
            195                 200                 205

Leu Ser Ser Leu Thr Ser Glu Asp Ser Ala Val Tyr Phe Cys Ala Leu
    210                 215                 220

Ser Thr Leu Ile His Gly Thr Trp Phe Ser Tyr Trp Gly Gln Gly Thr
225                 230                 235                 240

Leu Val Thr Val Ser Ser Gly Gly Gly Ser Glu Val Gln Leu Val
                245                 250                 255

Glu Ser Gly Gly Gly Leu Val Gln Pro Gly Gly Ser Leu Lys Leu Ser
            260                 265                 270

Cys Ala Ala Ser Gly Phe Thr Phe Asn Thr Tyr Ala Met Asn Trp Val
            275                 280                 285

Arg Gln Ala Pro Gly Lys Gly Leu Glu Trp Val Ala Arg Ile Arg Ser
290                 295                 300

Lys Tyr Asn Asn Tyr Ala Thr Tyr Tyr Ala Asp Ser Val Lys Asp Arg
305                 310                 315                 320

Phe Thr Ile Ser Arg Asp Asp Ser Lys Asn Thr Ala Tyr Leu Gln Met
            325                 330                 335

Asn Asn Leu Lys Thr Glu Asp Thr Ala Val Tyr Tyr Cys Val Arg His
            340                 345                 350

Gly Asn Phe Gly Asn Ser Tyr Val Ser Trp Phe Ala Tyr Trp Gly Gln
        355                 360                 365

Gly Thr Leu Val Thr Val Ser Ser Gly Gly Gly Ser Gly Gly Gly
    370                 375                 380

Gly Ser Gly Gly Gly Ser Gln Thr Val Val Thr Gln Glu Pro Ser
385                 390                 395                 400

Leu Thr Val Ser Pro Gly Gly Thr Val Thr Leu Thr Cys Arg Ser Ser
            405                 410                 415
```

```
Thr Gly Ala Val Thr Thr Ser Asn Tyr Ala Asn Trp Val Gln Gln Lys
            420                 425                 430
Pro Gly Gln Ala Pro Arg Gly Leu Ile Gly Gly Thr Asn Lys Arg Ala
            435                 440                 445
Pro Gly Thr Pro Ala Arg Phe Ser Gly Ser Leu Leu Gly Gly Lys Ala
            450                 455                 460
Ala Leu Thr Leu Ser Gly Val Gln Pro Glu Asp Glu Ala Glu Tyr Tyr
465                 470                 475                 480
Cys Ala Leu Trp Tyr Ser Asn Leu Trp Val Phe Gly Gly Gly Thr Lys
            485                 490                 495
Leu Thr Val Leu His His His His His His
            500                 505
```

<210> SEQ ID NO 175
<211> LENGTH: 1530
<212> TYPE: DNA
<213> ORGANISM: artificial sequence
<220> FEATURE:
<223> OTHER INFORMATION: EGFR HL x SEQ ID NO: 194 ; bispecific single chain antibody

<400> SEQUENCE: 175

```
caggtgcagc tgcagcagtc tgggcctgat ctggtgaagc ctggggcctc agtgaagatg    60
tcctgcaagg cttctggaca cactttcact gactgtgtta taatctgggt gaaacagaga   120
gctggacagg gccttgagtg gattggacag atttatccag ggactggtcg ttcttactac   180
aatgagattt caagggcaa ggccacactg actgcagaca atcctccaa cacagtccac    240
attcaactca gcagcctgac atctgaggac tctgcggtct atttctgtgc cctatctact   300
cttattcacg ggacctggtt ttcttattgg ggccaaggga ctctggtcac tgtctcttcc   360
ggtggtggtg gttctggcgg cggcggctcc ggtggtggtg gttctgacat tgtactgacc   420
cagtctccag cttccttacc tgtgtctctg ggcagaggg ccaccatctc atgcagggcc    480
agccaaagtg tcagttcatc tacttatagt tatatacact ggtaccaaca gaaaccagga   540
cagccaccca aactcctcat cacgtatgca tccaacctag aatctggggt ccctgccagg   600
ttcagtggca gtgggtctgg gacagacttc accctcgaca tccatcctgt ggaggaggat   660
gattcttcaa catattactg tcagcacagt tgggagattc catttacgtt cggctcgggg   720
acaaagttgg aaataaaatc cggaggtggt ggctcccaga ccgttgtgac tcaggaacct   780
tcactcaccg tatcacctgg tggaacagtc acactcactt gtcgctcgtc cactgggct    840
gttacaacta gcaactatgc caactgggtc aacaaaaaac caggtcaggc accccgtggt   900
ctaataggtg gtaccaacaa gcgcgcacca ggtactcctg ccagattctc aggctccctg   960
cttggaggca aggctgccct caccctctca ggggtacagc cagaggatga ggcagaatat  1020
tactgtgctc tatggtacag caacctctgg gtgttcggtg gaggaaccaa actgactgtc  1080
ctaggtggtg gtggttctgg cggcggcggc tccggtggtg gttctga ggtgcagctg  1140
gtggagtctg gaggaggatt ggtgcagcct ggagggtcat tgaaactctc atgtgcagcc  1200
tctggattca ccttcaatac ctacgccatg aactgggtcc gccaggctcc aggaaagggt  1260
ttggaatggg ttgctcgcat aagaagtaaa tataataatt atgcaacata ttatgccgat  1320
tcagtgaaag acaggttcac catctccaga gatgattcaa aaaacactgc ctatctacaa  1380
atgaacaact tgaaaactga ggacactgcc gtgtactact gtgtgagaca tgggaacttc  1440
ggtaatagct acgtttcctg gtttgcttac tggggccaag ggactctggt caccgtctcc  1500
```
tcacatcatc accatcatca ttaggtcgac                                      1530

<210> SEQ ID NO 176
<211> LENGTH: 507
<212> TYPE: PRT
<213> ORGANISM: artificial sequence
<220> FEATURE:
<223> OTHER INFORMATION: EGFR HL x SEQ ID NO: 194 ; bispecific single
      chain antibody

<400> SEQUENCE: 176

```
Gln Val Gln Leu Gln Gln Ser Gly Pro Asp Leu Val Lys Pro Gly Ala
1               5                   10                  15

Ser Val Lys Met Ser Cys Lys Ala Ser Gly His Thr Phe Thr Asp Cys
            20                  25                  30

Val Ile Ile Trp Val Lys Gln Arg Ala Gly Gln Gly Leu Glu Trp Ile
        35                  40                  45

Gly Gln Ile Tyr Pro Gly Thr Gly Arg Ser Tyr Tyr Asn Glu Ile Phe
    50                  55                  60

Lys Gly Lys Ala Thr Leu Thr Ala Asp Lys Ser Ser Asn Thr Val His
65                  70                  75                  80

Ile Gln Leu Ser Ser Leu Thr Ser Glu Asp Ser Ala Val Tyr Phe Cys
                85                  90                  95

Ala Leu Ser Thr Leu Ile His Gly Thr Trp Phe Ser Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Val Leu Thr Gln Ser Pro Ala
    130                 135                 140

Ser Leu Pro Val Ser Leu Gly Gln Arg Ala Thr Ile Ser Cys Arg Ala
145                 150                 155                 160

Ser Gln Ser Val Ser Ser Thr Tyr Ser Tyr Ile His Trp Tyr Gln
                165                 170                 175

Gln Lys Pro Gly Gln Pro Pro Lys Leu Leu Ile Thr Tyr Ala Ser Asn
            180                 185                 190

Leu Glu Ser Gly Val Pro Ala Arg Phe Ser Gly Ser Gly Ser Gly Thr
        195                 200                 205

Asp Phe Thr Leu Asp Ile His Pro Val Glu Glu Asp Asp Ser Ser Thr
    210                 215                 220

Tyr Tyr Cys Gln His Ser Trp Glu Ile Pro Phe Thr Phe Gly Ser Gly
225                 230                 235                 240

Thr Lys Leu Glu Ile Lys Ser Gly Gly Gly Ser Gln Thr Val Val
                245                 250                 255

Thr Gln Glu Pro Ser Leu Thr Val Ser Pro Gly Gly Thr Val Thr Leu
            260                 265                 270

Thr Cys Arg Ser Ser Thr Gly Ala Val Thr Thr Ser Asn Tyr Ala Asn
        275                 280                 285

Trp Val Gln Gln Lys Pro Gly Gln Ala Pro Arg Gly Leu Ile Gly Gly
    290                 295                 300

Thr Asn Lys Arg Ala Pro Gly Thr Pro Ala Arg Phe Ser Gly Ser Leu
305                 310                 315                 320

Leu Gly Gly Lys Ala Ala Leu Thr Leu Ser Gly Val Gln Pro Glu Asp
                325                 330                 335

Glu Ala Glu Tyr Tyr Cys Ala Leu Trp Tyr Ser Asn Leu Trp Val Phe
            340                 345                 350
```

Gly Gly Gly Thr Lys Leu Thr Val Leu Gly Gly Gly Ser Gly Gly
            355                 360                 365

Gly Gly Ser Gly Gly Gly Ser Glu Val Gln Leu Val Glu Ser Gly
        370                 375                 380

Gly Gly Leu Val Gln Pro Gly Gly Ser Leu Lys Leu Ser Cys Ala Ala
385                 390                 395                 400

Ser Gly Phe Thr Phe Asn Thr Tyr Ala Met Asn Trp Val Arg Gln Ala
                405                 410                 415

Pro Gly Lys Gly Leu Glu Trp Val Ala Arg Ile Arg Ser Lys Tyr Asn
            420                 425                 430

Asn Tyr Ala Thr Tyr Tyr Ala Asp Ser Val Lys Asp Arg Phe Thr Ile
                435                 440                 445

Ser Arg Asp Asp Ser Lys Asn Thr Ala Tyr Leu Gln Met Asn Asn Leu
        450                 455                 460

Lys Thr Glu Asp Thr Ala Val Tyr Tyr Cys Val Arg His Gly Asn Phe
465                 470                 475                 480

Gly Asn Ser Tyr Val Ser Trp Phe Ala Tyr Trp Gly Gln Gly Thr Leu
                485                 490                 495

Val Thr Val Ser Ser His His His His His His
            500                 505

<210> SEQ ID NO 177
<211> LENGTH: 1530
<212> TYPE: DNA
<213> ORGANISM: artificial sequence
<220> FEATURE:
<223> OTHER INFORMATION: EGFR LH x SEQ ID NO: 194 ; bispecific single
      chain antibody

<400> SEQUENCE: 177

```
gacattgtgc tgacacagtc tcctgcttcc ttacctgtgt ctctgggca gagggccacc      60
atctcatgca gggccagcca aagtgtcagt tcatctactt atagttatat acactggtac    120
caacagaaac aggacagcc acccaaactc ctcatcacgt atgcatccaa cctagaatct    180
ggggtccctg ccaggttcag tggcagtggg tctgggacag acttcaccct cgacatccat    240
cctgtggagg aggatgattc ttcaacatat tactgtcagc acagttggga gattccattt    300
acgttcggct cggggacaaa gttggaaata aaaggtggtg gtggttctgg cggcggcggc    360
tccggtggtg gtggttctca ggttcagctg cagcagtctg gacctgatct ggtgaagcct    420
ggggcctcag tgaagatgtc ctgcaaggct tctggacaca ctttcactga ctgtgttata    480
atctgggtga acagagagc tggacagggc cttgagtgga ttggacagat ttatccaggg    540
actggtcgtt cttactacaa tgagattttc aagggcaagg ccacactgac tgcagacaaa    600
tcctccaaca cagtccacat tcaactcagc agcctgacat ctgaggactc tgcggtctat    660
ttctgtgccc tatctactct tattcacggg acctggtttt cttattgggg ccaaggact    720
ctggtcactg tctcttcctc cggaggtggt ggctcccaga ccgttgtgac tcaggaacct    780
tcactcaccg tatcacctgg tggaacagtc acactcactt gtcgctcgtc cactggggct    840
gttacaacta gcaactatgc caactgggtc caacaaaaac aggtcaggc accccgtggt    900
ctaataggtg gtaccaacaa gcgcgcacca ggtactcctg ccagattctc aggctccctg    960
cttggaggca aggctgccct caccctctca ggggtacagc cagaggatga ggcagaatat   1020
tactgtgctc tatggtacag caacctctgg gtgttcggtg gaggaaccaa actgactgtc   1080
ctaggtggtg gtggttctgg cggcggcggc tccggtggtg gtggttctga ggtgcagctg   1140
```

-continued

```
gtggagtctg gaggaggatt ggtgcagcct ggagggtcat tgaaactctc atgtgcagcc    1200
tctggattca ccttcaatac ctacgccatg aactgggtcc gccaggctcc aggaaagggt    1260
ttggaatggg ttgctcgcat aagaagtaaa tataataatt atgcaacata ttatgccgat    1320
tcagtgaaag acaggttcac catctccaga gatgattcaa aaaacactgc ctatctacaa    1380
atgaacaact tgaaaactga ggacactgcc gtgtactact gtgtgagaca tgggaacttc    1440
ggtaatagct acgtttcctg gtttgcttac tggggccaag ggactctggt caccgtctcc    1500
tcacatcatc accatcatca ttaggtcgac                                     1530
```

<210> SEQ ID NO 178
<211> LENGTH: 507
<212> TYPE: PRT
<213> ORGANISM: artificial sequence
<220> FEATURE:
<223> OTHER INFORMATION: EGFR LH x SEQ ID NO: 194 ; bispecific single
      chain antibody <400> SEQUENCE: 178

```
Asp Ile Val Leu Thr Gln Ser Pro Ala Ser Leu Pro Val Ser Leu Gly
1               5                   10                  15

Gln Arg Ala Thr Ile Ser Cys Arg Ala Ser Gln Ser Val Ser Ser Ser
            20                  25                  30

Thr Tyr Ser Tyr Ile His Trp Tyr Gln Gln Lys Pro Gly Gln Pro Pro
        35                  40                  45

Lys Leu Leu Ile Thr Tyr Ala Ser Asn Leu Glu Ser Gly Val Pro Ala
    50                  55                  60

Arg Phe Ser Gly Ser Gly Ser Gly Thr Asp Phe Thr Leu Asp Ile His
65                  70                  75                  80

Pro Val Glu Glu Asp Asp Ser Ser Thr Tyr Tyr Cys Gln His Ser Trp
                85                  90                  95

Glu Ile Pro Phe Thr Phe Gly Ser Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Pro Asp Leu Val Lys Pro Gly Ala Ser Val
    130                 135                 140

Lys Met Ser Cys Lys Ala Ser Gly His Thr Phe Thr Asp Cys Val Ile
145                 150                 155                 160

Ile Trp Val Lys Gln Arg Ala Gly Gln Gly Leu Glu Trp Ile Gly Gln
                165                 170                 175

Ile Tyr Pro Gly Thr Gly Arg Ser Tyr Tyr Asn Glu Ile Phe Lys Gly
            180                 185                 190

Lys Ala Thr Leu Thr Ala Asp Lys Ser Ser Asn Thr Val His Ile Gln
        195                 200                 205

Leu Ser Ser Leu Thr Ser Glu Asp Ser Ala Val Tyr Phe Cys Ala Leu
    210                 215                 220

Ser Thr Leu Ile His Gly Thr Trp Phe Ser Tyr Trp Gly Gln Gly Thr
225                 230                 235                 240

Leu Val Thr Val Ser Ser Gly Gly Gly Gly Ser Gln Thr Val Val
                245                 250                 255

Thr Gln Glu Pro Ser Leu Thr Val Ser Pro Gly Gly Thr Val Thr Leu
            260                 265                 270

Thr Cys Arg Ser Ser Thr Gly Ala Val Thr Thr Ser Asn Tyr Ala Asn
        275                 280                 285
```

```
Trp Val Gln Gln Lys Pro Gly Gln Ala Pro Arg Gly Leu Ile Gly Gly
        290                 295                 300
Thr Asn Lys Arg Ala Pro Gly Thr Pro Ala Arg Phe Ser Gly Ser Leu
305                 310                 315                 320
Leu Gly Gly Lys Ala Ala Leu Thr Leu Ser Gly Val Gln Pro Glu Asp
                325                 330                 335
Glu Ala Glu Tyr Tyr Cys Ala Leu Trp Tyr Ser Asn Leu Trp Val Phe
            340                 345                 350
Gly Gly Gly Thr Lys Leu Thr Val Leu Gly Gly Gly Ser Gly Gly
        355                 360                 365
Gly Gly Ser Gly Gly Gly Ser Glu Val Gln Leu Val Glu Ser Gly
        370                 375                 380
Gly Gly Leu Val Gln Pro Gly Gly Ser Leu Lys Leu Ser Cys Ala Ala
385                 390                 395                 400
Ser Gly Phe Thr Phe Asn Thr Tyr Ala Met Asn Trp Val Arg Gln Ala
                405                 410                 415
Pro Gly Lys Gly Leu Glu Trp Val Ala Arg Ile Arg Ser Lys Tyr Asn
            420                 425                 430
Asn Tyr Ala Thr Tyr Tyr Ala Asp Ser Val Lys Asp Arg Phe Thr Ile
        435                 440                 445
Ser Arg Asp Asp Ser Lys Asn Thr Ala Tyr Leu Gln Met Asn Asn Leu
450                 455                 460
Lys Thr Glu Asp Thr Ala Val Tyr Tyr Cys Val Arg His Gly Asn Phe
465                 470                 475                 480
Gly Asn Ser Tyr Val Ser Trp Phe Ala Tyr Trp Gly Gln Gly Thr Leu
                485                 490                 495
Val Thr Val Ser Ser His His His His His His
            500                 505

<210> SEQ ID NO 179
<211> LENGTH: 1530
<212> TYPE: DNA
<213> ORGANISM: artificial sequence
<220> FEATURE:
<223> OTHER INFORMATION: SEQ ID NO: 170 x EGFR HL ; bispecific single
      chain antibody

<400> SEQUENCE: 179
gaggtgcagc tggtggagtc tggaggagga ttggtgcagc tggagggtc attgaaactc        60
tcatgtgcag cctctggatt caccttcaat acctacgcca tgaactgggt ccgccaggct       120
ccaggaaagg gtttggaatg ggttgctcgc ataagaagta aatataataa ttatgcaaca       180
tattatgccg attcagtgaa agacaggttc accatctcca gagatgattc aaaaaacact       240
gcctatctac aaatgaacaa cttgaaaact gaggacactg ccgtgtacta ctgtgtgaga       300
catgggaact tcggtaatag ctacgttttc tggtttgctt actggggcca agggactctg       360
gtcaccgtct cctcaggtgg tggtggttct ggcggcggcg gctccggtgg tggtggttct       420
cagaccgttg tgactcagga accttcactc accgtatcac tggtggaac agtcacactc       480
acttgtcgct cgtccactgg ggctgttaca actagcaact atgccaactg ggtccaacaa       540
aaaccaggtc aggcacccg tggtctaata ggtggtacca caagcgcgc accaggtact       600
cctgccagat ctcaggctc cctgcttgga ggcaaggctg ccctcaccct ctcaggggta       660
cagccagagg atgaggcaga atattactgt gctctatggt acagcaacct ctgggtgttc       720
ggtggaggaa ccaaactgac tgtcctatcc ggaggtggtg gctcccaggt gcagctgcag       780
```

-continued

```
cagtctgggc ctgatctggt gaagcctggg gcctcagtga agatgtcctg caaggcttct    840
ggacacactt tcactgactg tgttataatc tgggtgaaac agagagctgg acagggcctt    900
gagtggattg gacagattta tccagggact ggtcgttctt actacaatga gattttcaag    960
ggcaaggcca cactgactgc agacaaatcc tccaacacag tccacattca actcagcagc   1020
ctgacatctg aggactctgc ggtctatttc tgtgccctat ctactcttat tcacgggacc   1080
tggttttctt attggggcca agggactctg gtcactgtct cttccggtgg tggtggttct   1140
ggcggcggcg gctccggtgg tggtggttct gacattgtac tgacccagtc tccagcttcc   1200
ttacctgtgt ctctggggca gagggccacc atctcatgca gggccagcca aagtgtcagt   1260
tcatctactt atagttatat acactggtac caacagaaac aggacagcc  acccaaactc   1320 ctcatcacgt atgcatccaa cctagaatct ggggtccctg ccaggttcag tggcagtggg   1380
tctgggacag acttcaccct cgacatccat cctgtggagg aggatgattc ttcaacatat   1440
tactgtcagc acagttggga gattccattt acgttcggct cggggacaaa gttggaaata   1500
aaacatcatc accatcatca ttaggtcgac                                    1530
```

<210> SEQ ID NO 180
<211> LENGTH: 507
<212> TYPE: PRT
<213> ORGANISM: artificial sequence
<220> FEATURE:
<223> OTHER INFORMATION: SEQ ID NO: 170 x EGFR HL , bispecific single
      chain antibody

<400> SEQUENCE: 180

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
            180                 185                 190

Thr Asn Lys Arg Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Leu Trp Val Phe
225                 230                 235                 240

Gly Gly Gly Thr Lys Leu Thr Val Leu Ser Gly Gly Gly Gly Ser Gln
                245                 250                 255

Val Gln Leu Gln Gln Ser Gly Pro Asp Leu Val Lys Pro Gly Ala Ser
            260                 265                 270

Val Lys Met Ser Cys Lys Ala Ser Gly His Thr Phe Thr Asp Cys Val
        275                 280                 285

Ile Ile Trp Val Lys Gln Arg Ala Gly Gln Gly Leu Glu Trp Ile Gly
290                 295                 300

Gln Ile Tyr Pro Gly Thr Gly Arg Ser Tyr Asn Glu Ile Phe Lys
305                 310                 315                 320

Gly Lys Ala Thr Leu Thr Ala Asp Lys Ser Ser Asn Thr Val His Ile
                325                 330                 335

Gln Leu Ser Ser Leu Thr Ser Glu Asp Ser Ala Val Tyr Phe Cys Ala
            340                 345                 350

Leu Ser Thr Leu Ile His Gly Thr Trp Phe Ser Tyr Trp Gly Gln Gly
        355                 360                 365

Thr Leu Val Thr Val Ser Ser Gly Gly Gly Gly Ser Gly Gly Gly Gly
370                 375                 380

Ser Gly Gly Gly Gly Ser Asp Ile Val Leu Thr Gln Ser Pro Ala Ser
385                 390                 395                 400

Leu Pro Val Ser Leu Gly Gln Arg Ala Thr Ile Ser Cys Arg Ala Ser
                405                 410                 415

Gln Ser Val Ser Ser Thr Tyr Ser Tyr Ile His Trp Tyr Gln Gln
            420                 425                 430

Lys Pro Gly Gln Pro Pro Lys Leu Leu Ile Thr Tyr Ala Ser Asn Leu
        435                 440                 445

Glu Ser Gly Val Pro Ala Arg Phe Ser Gly Ser Gly Ser Gly Thr Asp
450                 455                 460

Phe Thr Leu Asp Ile His Pro Val Glu Glu Asp Asp Ser Ser Thr Tyr
465                 470                 475                 480

Tyr Cys Gln His Ser Trp Glu Ile Pro Phe Thr Phe Gly Ser Gly Thr
                485                 490                 495

Lys Leu Glu Ile Lys His His His His His His
            500                 505

<210> SEQ ID NO 181
<211> LENGTH: 1530
<212> TYPE: DNA
<213> ORGANISM: artificial sequence
<220> FEATURE:
<223> OTHER INFORMATION: SEQ ID NO: 194 x EGFR HL ; bispecific single
      chain antibody

<400> SEQUENCE: 181

```
cagaccgttg tgactcagga accttcactc accgtatcac ctggtggaac agtcacactc      60
acttgtcgct cgtccactgg ggctgttaca actagcaact atgccaactg gtccaacaa     120 aaaccaggtc aggcaccccg tgtctaata ggtggtacca caagcgcgc accaggtact     180 cctgccagat tctcaggctc cctgcttgga ggcaaggctg ccctcaccct ctcagggta     240 cagccgagg atgaggcaga atattactgt gctctatggt acagcaacct ctgggtgttc     300
ggtggaggaa ccaaactgac tgtcctaggt ggtggtggtt ctggcggcgg cggctccggt     360
ggtggtggtt ctgaggtgca gctggtggag tctggaggag gattggtgca gcctggaggg     420
```

```
tcattgaaac tctcatgtgc agcctctgga ttcaccttca ataccctacgc catgaactgg    480
gtccgccagg ctccaggaaa gggtttggaa tgggttgctc gcataagaag taaatataat    540
aattatgcaa catattatgc cgattcagtg aaagacaggt tcaccatctc cagagatgat    600
tcaaaaaaca ctgcctatct acaaatgaac aacttgaaaa ctgaggacac tgccgtgtac    660
tactgtgtga acatgggaa cttcggtaat agctacgttt cctggtttgc ttactggggc     720
caagggactc tggtcaccgt ctcctcatcc ggaggtggtg ctcccaggt gcagctgcag     780
cagtctgggc ctgatctggt gaagcctggg gcctcagtga agatgtcctg caaggcttct    840
ggacacactt tcactgactg tgttataatc tgggtgaaac agagagctgg acagggcctt    900
gagtggattg gacagattta tccagggact ggtcgttctt actacaatga gattttcaag    960
ggcaaggcca cactgactgc agacaaatcc tccaacacag tccacattca actcagcagc   1020
ctgacatctg aggactctgc ggtctatttc tgtgccctat ctactcttat tcacgggacc   1080
tggttttctt attggggcca agggactctg gtcactgtct cttccggtgg tggtggttct   1140
ggcggcggcg gctccggtgg tggtggttct gacattgtac tgacccagtc tccagcttcc   1200
ttacctgtgt ctctggggca gagggccacc atctcatgca gggccagcca aagtgtcagt   1260
tcatctactt atagttatat acactggtac caacagaaac aggacagcc acccaaactc    1320
ctcatcacgt atgcatccaa cctagaatct ggggtccctg ccaggttcag tggcagtggg   1380
tctgggacag acttcaccct cgacatccat cctgtggagg aggatgattc ttcaacatat   1440
tactgtcagc acagtgggga gattccattt acgttcggct cggggacaaa gttggaaata   1500
aaacatcatc accatcatca ttaggtcgac                                    1530
```

<210> SEQ ID NO 182
<211> LENGTH: 507
<212> TYPE: PRT
<213> ORGANISM: artificial sequence
<220> FEATURE:
<223> OTHER INFORMATION: SEQ ID NO: 194 x EGFR HL ; bispecific single chain antibody

<400> SEQUENCE: 182

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Thr Tyr Ala Met Asn Trp
145                 150                 155                 160
```

Val Arg Gln Ala Pro Gly Lys Gly Leu Glu Trp Val Ala Arg Ile Arg
            165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
            195                 200                 205

Met Asn Asn Leu Lys Thr Glu Asp Thr Ala Val Tyr Tyr Cys Val Arg
            210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser Gly Gly Gly Gly Ser Gln
            245                 250                 255

Val Gln Leu Gln Gln Ser Gly Pro Asp Leu Val Lys Pro Gly Ala Ser
            260                 265                 270

Val Lys Met Ser Cys Lys Ala Ser Gly His Thr Phe Thr Asp Cys Val
            275                 280                 285

Ile Ile Trp Val Lys Gln Arg Ala Gly Gln Gly Leu Glu Trp Ile Gly
            290                 295                 300

Gln Ile Tyr Pro Gly Thr Gly Arg Ser Tyr Tyr Asn Glu Ile Phe Lys
305                 310                 315                 320

Gly Lys Ala Thr Leu Thr Ala Asp Lys Ser Ser Asn Thr Val His Ile
            325                 330                 335

Gln Leu Ser Ser Leu Thr Ser Glu Asp Ser Ala Val Tyr Phe Cys Ala
            340                 345                 350

Leu Ser Thr Leu Ile His Gly Thr Trp Phe Ser Tyr Trp Gly Gln Gly
            355                 360                 365

Thr Leu Val Thr Val Ser Ser Gly Gly Gly Gly Ser Gly Gly Gly Gly
            370                 375                 380

Ser Gly Gly Gly Gly Ser Asp Ile Val Leu Thr Gln Ser Pro Ala Ser
385                 390                 395                 400

Leu Pro Val Ser Leu Gly Gln Arg Ala Thr Ile Ser Cys Arg Ala Ser
            405                 410                 415

Gln Ser Val Ser Ser Thr Tyr Ser Tyr Ile His Trp Tyr Gln Gln
            420                 425                 430

Lys Pro Gly Gln Pro Pro Lys Leu Leu Ile Thr Tyr Ala Ser Asn Leu
            435                 440                 445

Glu Ser Gly Val Pro Ala Arg Phe Ser Gly Ser Gly Ser Gly Thr Asp
450                 455                 460

Phe Thr Leu Asp Ile His Pro Val Glu Glu Asp Asp Ser Ser Thr Tyr
465                 470                 475                 480

Tyr Cys Gln His Ser Trp Glu Ile Pro Phe Thr Phe Gly Ser Gly Thr
            485                 490                 495

Lys Leu Glu Ile Lys His His His His His His
            500                 505

<210> SEQ ID NO 183
<211> LENGTH: 1530
<212> TYPE: DNA
<213> ORGANISM: artificial sequence
<220> FEATURE:
<223> OTHER INFORMATION: SEQ ID NO: 170 x EGFR LH ; bispecific single
      chain antibody

<400> SEQUENCE: 183
gaggtgcagc tggtggagtc tggaggagga ttggtgcagc ctggagggtc attgaaactc      60

```
tcatgtgcag cctctggatt caccttcaat acctacgcca tgaactgggt ccgccaggct    120
ccaggaaagg gtttggaatg ggttgctcgc ataagaagta aatataataa ttatgcaaca    180
tattatgccg attcagtgaa agacaggttc accatctcca gagatgattc aaaaaacact    240
gcctatctac aaatgaacaa cttgaaaact gaggacactg ccgtgtacta ctgtgtgaga    300
catgggaact tcggtaatag ctacgtttcc tggtttgctt actggggcca agggactctg    360
gtcaccgtct cctcaggtgg tggtggttct ggcggcggcg gctccggtgg tggtggttct    420
cagaccgttg tgactcagga accttcactc accgtatcac tggtggaaca gtcacactc     480 acttgtcgct cgtccactgg ggctgttaca actagcaact atgccaactg gtccaacaa     540 aaaccaggtc aggcaccccg tggtctaata ggtggtacca caagcgcgc accaggtact    600 cctgccagat tctcaggctc cctgcttgga ggcaaggctg ccctcaccct tcaggggta    660 cagccagagg atgaggcaga atattactgt gctctatggt acagcaacct ctgggtgttc    720
ggtggaggaa ccaaactgac tgtcctatcc ggaggtggtg gctccgacat tgtgctgaca    780
cagtctcctg cttccttacc tgtgtctctg ggcagaggg ccaccatctc atgcagggcc    840
agccaaagtg tcagttcatc tacttatagt tatatacact ggtaccaaca gaaaccagga    900
cagccaccca aactcctcat cacgtatgca tccaacctag aatctggggt ccctgccagg    960
ttcagtggca gtgggtctgg gacagacttc accctcgaca tccatcctgt ggaggaggat   1020
gattcttcaa catattactg tcagcacagt tgggagattc catttacgtt cggctcgggg   1080
acaaagttgg aaataaaagg tggtggtggt tctggcggcg gcggctccgg tggtggtggt   1140
tctcaggttc agctgcagca gtctggacct gatctggtga agcctggggc ctcagtgaag   1200
atgtcctgca aggcttctgg acacactttc actgactgtg ttataatctg ggtgaaacag   1260
agagctggac agggccttga gtggattgga cagatttatc cagggactgg tcgttcttac   1320
tacaatgaga ttttcaaggg caaggccaca ctgactgcag acaaatcctc caacacagtc   1380
cacattcaac tcagcagcct gacatctgag gactctgcgg tctatttctg tgccctatct   1440
actcttattc acgggacctg gttttcttat tggggccaag ggactctggt cactgtctct   1500
tcccatcatc accatcatca ttaggtcgac                                     1530
```

<210> SEQ ID NO 184
<211> LENGTH: 507
<212> TYPE: PRT
<213> ORGANISM: artificial sequence
<220> FEATURE:
<223> OTHER INFORMATION: SEQ ID NO: 170 x EGFR LH ; bispecific single
      chain antibody

<400> SEQUENCE: 184

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95
```

-continued

```
Tyr Cys Val Arg His Gly Asn Phe Gly Asn Ser Tyr Val Ser Trp Phe
                100                 105                 110
Ala Tyr Trp Gly Gln Gly Thr Leu Val Thr Val Ser Ser Gly Gly Gly
        115                 120                 125
Gly Ser Gly Gly Gly Gly Ser Gly Gly Gly Ser Gln Thr Val Val
    130                 135                 140
Thr Gln Glu Pro Ser Leu Thr Val Ser Pro Gly Gly Thr Val Thr Leu
145                 150                 155                 160
Thr Cys Arg Ser Ser Thr Gly Ala Val Thr Thr Ser Asn Tyr Ala Asn
                165                 170                 175
Trp Val Gln Gln Lys Pro Gly Gln Ala Pro Arg Gly Leu Ile Gly Gly
            180                 185                 190
Thr Asn Lys Arg Ala Pro Gly Thr Pro Ala Arg Phe Ser Gly Ser Leu
        195                 200                 205
Leu Gly Gly Lys Ala Ala Leu Thr Leu Ser Gly Val Gln Pro Glu Asp
    210                 215                 220
Glu Ala Glu Tyr Tyr Cys Ala Leu Trp Tyr Ser Asn Leu Trp Val Phe
225                 230                 235                 240
Gly Gly Gly Thr Lys Leu Thr Val Leu Ser Gly Gly Gly Gly Ser Asp
                245                 250                 255
Ile Val Leu Thr Gln Ser Pro Ala Ser Leu Pro Val Ser Leu Gly Gln
                260                 265                 270
Arg Ala Thr Ile Ser Cys Arg Ala Ser Gln Ser Val Ser Ser Ser Thr
        275                 280                 285
Tyr Ser Tyr Ile His Trp Tyr Gln Gln Lys Pro Gly Gln Pro Pro Lys
    290                 295                 300
Leu Leu Ile Thr Tyr Ala Ser Asn Leu Glu Ser Gly Val Pro Ala Arg
305                 310                 315                 320
Phe Ser Gly Ser Gly Ser Gly Thr Asp Phe Thr Leu Asp Ile His Pro
                325                 330                 335
Val Glu Glu Asp Asp Ser Ser Thr Tyr Tyr Cys Gln His Ser Trp Glu
                340                 345                 350
Ile Pro Phe Thr Phe Gly Ser Gly Thr Lys Leu Glu Ile Lys Gly Gly
        355                 360                 365
Gly Gly Ser Gly Gly Gly Gly Ser Gly Gly Gly Gly Ser Gln Val Gln
    370                 375                 380
Leu Gln Gln Ser Gly Pro Asp Leu Val Lys Pro Gly Ala Ser Val Lys
385                 390                 395                 400
Met Ser Cys Lys Ala Ser Gly His Thr Phe Thr Asp Cys Val Ile Ile
                405                 410                 415
Trp Val Lys Gln Arg Ala Gly Gln Gly Leu Glu Trp Ile Gly Gln Ile
            420                 425                 430
Tyr Pro Gly Thr Gly Arg Ser Tyr Tyr Asn Glu Ile Phe Lys Gly Lys
        435                 440                 445
Ala Thr Leu Thr Ala Asp Lys Ser Ser Asn Thr Val His Ile Gln Leu
    450                 455                 460
Ser Ser Leu Thr Ser Glu Asp Ser Ala Val Tyr Phe Cys Ala Leu Ser
465                 470                 475                 480
Thr Leu Ile His Gly Thr Trp Phe Ser Tyr Trp Gly Gln Gly Thr Leu
                485                 490                 495
Val Thr Val Ser Ser His His His His His
            500                 505
```

<210> SEQ ID NO 185
<211> LENGTH: 1530
<212> TYPE: DNA
<213> ORGANISM: artificial sequence
<220> FEATURE:
<223> OTHER INFORMATION: SEQ ID NO: 194 x EGFR LH ; bispecific single chain antibody

<400> SEQUENCE: 185

```
cagaccgttg tgactcagga accttcactc accgtatcac ctggtggaac agtcacactc      60
acttgtcgct cgtccactgg ggctgttaca actagcaact atgccaactg gtccaacaa     120
aaaccaggtc aggcacccg tggtctaata ggtggtacca caagcgcgc accaggtact     180
cctgccagat tctcaggctc cctgcttgga ggcaaggctg ccctcaccct ctcagggta     240
cagccagagg atgaggcaga atattactgt gctctatggt acagcaacct ctgggtgttc     300
ggtggaggaa ccaaactgac tgtcctaggt ggtggtggtt ctggcggcgg cggctccggt     360
ggtggtggtt ctgaggtgca gctggtggag tctggaggag gattggtgca gcctggaggg     420
tcattgaaac tctcatgtgc agcctctgga ttcaccttca atacctacgc catgaactgg     480
gtccgccagg ctccaggaaa gggttttgaa tgggttgctc gcataagaag taaatataat     540
aattatgcaa catattatgc cgattcagtg aaagacaggt tcaccatctc cagagatgat     600
tcaaaaaaca ctgcctatct acaaatgaac aacttgaaaa ctgaggacac tgccgtgtac     660
tactgtgtga catgggaa cttcggtaat agctacgttt cctggtttgc ttactggggc     720
caagggactc tggtcaccgt ctcctcatcc ggaggtggtg gctccgacat tgtgctgaca     780
cagtctcctg cttccttacc tgtgtctctg gggcagaggg ccaccatctc atgcagggcc     840
agccaaagtg tcagttcatc tacttatagt tatatacact ggtaccaaca gaaaccagga     900
cagccaccca aactcctcat cacgtatgca tccaacctag aatctggggt ccctgccagg     960
ttcagtggca gtgggtctgg gacagacttc accctcgaca tccatcctgt ggaggaggat    1020
gattcttcaa catattactg tcagcacagt tgggagattc catttacgtt cggctcgggg    1080
acaaagttgg aaataaaagg tggtggtggt tctggcggcg gcggctccgg tggtggtggt    1140
tctcaggttc agctgcagca gtctggacct gatctggtga gcctgggggc tcagtgaag    1200
atgtcctgca aggcttctgg acacactttc actgactgtg ttataatctg ggtgaaacag    1260
agagctggac agggccttga gtggattgga cagatttatc cagggactgg tcgttcttac    1320
taatgaga tttcaagggg caaggccaca ctgactgcag acaaatcctc caacacagtc    1380
cacattcaac tcagcagcct gacatctgag gactctgcgg tctatttctg tgccctatct    1440
actcttattc acgggacctg gttttcttat tggggccaag gactctggt cactgtctct    1500
tcccatcatc accatcatca ttaggtcgac                                    1530
```

<210> SEQ ID NO 186
<211> LENGTH: 507
<212> TYPE: PRT
<213> ORGANISM: artificial sequence
<220> FEATURE:
<223> OTHER INFORMATION: SEQ ID NO: 194 x EGFR LH ; bispecific single chain antibody

<400> SEQUENCE: 186

```
Gln Thr Val Val Thr Gln Glu Pro Ser Leu Thr Val Ser Pro Gly Gly
 1               5                  10                  15
Thr Val Thr Leu Thr Cys Arg Ser Ser Thr Gly Ala Val Thr Thr Ser
            20                  25                  30
```

```
Asn Tyr Ala Asn Trp Val Gln Gln Lys Pro Gly Gln Ala Pro Arg Gly
         35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gly Gly
                100                 105                 110

Gly Ser Gly Gly Gly Gly Ser Gly Gly Gly Gly Ser Glu Val Gln Leu
            115                 120                 125

Val Glu Ser Gly Gly Gly Leu Val Gln Pro Gly Gly Ser Leu Lys Leu
        130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Thr Ala Tyr Leu Gln
            195                 200                 205

Met Asn Asn Leu Lys Thr Glu Asp Thr Ala Val Tyr Tyr Cys Val Arg
        210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser Gly Gly Gly Gly Ser Asp
                245                 250                 255

Ile Val Leu Thr Gln Ser Pro Ala Ser Leu Pro Val Ser Leu Gly Gln
            260                 265                 270

Arg Ala Thr Ile Ser Cys Arg Ala Ser Gln Ser Val Ser Ser Ser Thr
        275                 280                 285

Tyr Ser Tyr Ile His Trp Tyr Gln Gln Lys Pro Gly Gln Pro Pro Lys
            290                 295                 300

Leu Leu Ile Thr Tyr Ala Ser Asn Leu Glu Ser Gly Val Pro Ala Arg
305                 310                 315                 320

Phe Ser Gly Ser Gly Ser Gly Thr Asp Phe Thr Leu Asp Ile His Pro
                325                 330                 335

Val Glu Glu Asp Asp Ser Ser Thr Tyr Tyr Cys Gln His Ser Trp Glu
                340                 345                 350

Ile Pro Phe Thr Phe Gly Ser Gly Thr Lys Leu Glu Ile Lys Gly Gly
            355                 360                 365

Gly Gly Ser Gly Gly Gly Gly Ser Gly Gly Gly Gly Ser Gln Val Gln
        370                 375                 380

Leu Gln Gln Ser Gly Pro Asp Leu Val Lys Pro Gly Ala Ser Val Lys
385                 390                 395                 400

Met Ser Cys Lys Ala Ser Gly His Thr Phe Thr Asp Cys Val Ile Ile
                405                 410                 415

Trp Val Lys Gln Arg Ala Gly Gln Gly Leu Glu Trp Ile Gly Gln Ile
            420                 425                 430

Tyr Pro Gly Thr Gly Arg Ser Tyr Tyr Asn Glu Ile Phe Lys Gly Lys
            435                 440                 445
```

```
Ala Thr Leu Thr Ala Asp Lys Ser Ser Asn Thr Val His Ile Gln Leu
            450                 455                 460

Ser Ser Leu Thr Ser Glu Asp Ser Ala Val Tyr Phe Cys Ala Leu Ser
465                 470                 475                 480

Thr Leu Ile His Gly Thr Trp Phe Ser Tyr Trp Gly Gln Gly Thr Leu
                485                 490                 495

Val Thr Val Ser Ser His His His His His His
            500                 505
```

<210> SEQ ID NO 187
<211> LENGTH: 1515
<212> TYPE: DNA
<213> ORGANISM: artificial sequence
<220> FEATURE:
<223> OTHER INFORMATION: CAIX HL x SEQ ID NO: 194 ; bispecific single
      chain antibody

<400> SEQUENCE: 187

```
gacgtgaagc tcgtggagtc tgggggaggc ttagtgaagc ttggagggtc cctgaaactc    60
tcctgtgcag cctctggatt cactttcagt aactattaca tgtcttgggt tcgccagact   120
ccagagaaga ggctggagtt ggtcgcagcc attaatagtg atggtggtat cacctactat   180
ctagacactg tgaagggccg attcaccatt tcaagagaca tgccaagaa cccctgtac   240
ctgcaaatga gcagtctgaa gtctgaggac acagccttgt tttactgtgc aagacaccgc   300
tcgggctact tttctatgga ctactggggt caaggaacct cagtcaccgt ctcctcaggt   360
ggtggtggtt ctggcggcgg cggctccggt ggtggtggtt ctgacattgt gatgacccag   420
tctcaaagat tcatgtccac aacagtagga gacagggtca gcatcacctg caaggccagt   480
cagaatgtgg tttctgctgt tgcctggtat aacagaaac caggacaatc tcctaaacta   540
ctgatttact cagcatccaa tcggtacact ggagtccctg atcgcttcac aggcagtgga   600
tctgggacag atttcactct caccattagc aatatgcagt ctgaagacct ggctgatttt   660
ttctgtcaac aatatagcaa ctatccgtgg acgttcggtg gaggcaccaa gctggaaatc   720
aaatccggag gtggtggctc cagaccgttt gtgactcagg aaccttcact caccgtatca   780
cctggtggaa cagtcacact cacttgtcgc tcgtccactg gggctgttac aactagcaac   840
tatgccaact gggtccaaca aaaaccaggt caggcacccc gtggtctaat aggtggtacc   900
aacaagcgcg caccaggtac tcctgccaga ttctcaggct ccctgcttgg aggcaaggct   960
gccctcaccc tctcaggggt acagccagag gatgaggcag aatattactg tgctctatgg  1020
tacagcaacc tctgggtgtt cggtggagga accaaactga ctgtcctagg tggtggtggt  1080
tctggcggcg gcggctccgg tggtggtggt tctgaggtgc agctggtgga gtctgggaga  1140
ggattggtgc agcctggagg gtcattgaaa ctctcatgtg cagcctctgg attcaccttc  1200
aatacctacg ccatgaactg ggtccgccag gctccaggaa agggtttgga atgggttgct  1260
cgcataagaa gtaaatataa taattatgca acatattatg ccgattcagt gaaagacagg  1320
ttcaccatct ccagagatga ttcaaaaaac actgcctatc tacaaatgaa caacttgaaa  1380
actgaggaca ctgccgtgta ctactgtgtg agacatggga acttcggtaa tagctacgtt  1440
tcctggtttg cttactgggg ccaagggact ctggtcaccg tctcctcaca tcatcaccat  1500
catcattagg tcgac                                                    1515
```

<210> SEQ ID NO 188
<211> LENGTH: 502
<212> TYPE: PRT

<213> ORGANISM: artificial sequence
<220> FEATURE:
<223> OTHER INFORMATION: CAIX HL x SEQ ID NO: 194 ; bispecific single
      chain antibody

<400> SEQUENCE: 188

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Thr Pro Glu Lys Arg Leu Glu Leu Val
        35                  40                  45

Ala Ala Ile Asn Ser Asp Gly Gly Ile Thr Tyr Tyr Leu Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Phe Tyr Cys
                85                  90                  95

Ala Arg His Arg Ser Gly Tyr Phe Ser Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Ile Val Met Thr Gln Ser Gln Arg Phe
    130                 135                 140

Met Ser Thr Thr Val Gly Asp Arg Val Ser Ile Thr Cys Lys Ala Ser
145                 150                 155                 160

Gln Asn Val Val Ser Ala Val Ala Trp Tyr Gln Gln Lys Pro Gly Gln
                165                 170                 175

Ser Pro Lys Leu Leu Ile Tyr Ser Ala Ser Asn Arg Tyr Thr Gly Val
            180                 185                 190

Pro Asp Arg Phe Thr Gly Ser Gly Ser Gly Thr Asp Phe Thr Leu Thr
        195                 200                 205

Ile Ser Asn Met Gln Ser Glu Asp Leu Ala Asp Phe Phe Cys Gln Gln
    210                 215                 220

Tyr Ser Asn Tyr Pro Trp Thr Phe Gly Gly Gly Thr Lys Leu Glu Ile
225                 230                 235                 240

Lys Ser Gly Gly Gly Gly Ser Gln Thr Val Val Thr Gln Glu Pro Ser
                245                 250                 255

Leu Thr Val Ser Pro Gly Gly Thr Val Thr Leu Thr Cys Arg Ser Ser
            260                 265                 270

Thr Gly Ala Val Thr Thr Ser Asn Tyr Ala Asn Trp Val Gln Gln Lys
        275                 280                 285

Pro Gly Gln Ala Pro Arg Gly Leu Ile Gly Gly Thr Asn Lys Arg Ala
    290                 295                 300

Pro Gly Thr Pro Ala Arg Phe Ser Gly Ser Leu Leu Gly Gly Lys Ala
305                 310                 315                 320

Ala Leu Thr Leu Ser Gly Val Gln Pro Glu Asp Glu Ala Glu Tyr Tyr
                325                 330                 335

Cys Ala Leu Trp Tyr Ser Asn Leu Trp Val Phe Gly Gly Gly Thr Lys
            340                 345                 350

Leu Thr Val Leu Gly Gly Gly Ser Gly Gly Gly Ser Gly Gly
        355                 360                 365

Gly Gly Ser Glu Val Gln Leu Val Glu Ser Gly Gly Gly Leu Val Gln
    370                 375                 380

```
Pro Gly Gly Ser Leu Lys Leu Ser Cys Ala Ala Ser Gly Phe Thr Phe
385                 390                 395                 400

Asn Thr Tyr Ala Met Asn Trp Val Arg Gln Ala Pro Gly Lys Gly Leu
            405                 410                 415

Glu Trp Val Ala Arg Ile Arg Ser Lys Tyr Asn Asn Tyr Ala Thr Tyr
        420                 425                 430

Tyr Ala Asp Ser Val Lys Asp Arg Phe Thr Ile Ser Arg Asp Asp Ser
        435                 440                 445

Lys Asn Thr Ala Tyr Leu Gln Met Asn Asn Leu Lys Thr Glu Asp Thr
    450                 455                 460

Ala Val Tyr Tyr Cys Val Arg His Gly Asn Phe Gly Asn Ser Tyr Val
465             470                 475                 480

Ser Trp Phe Ala Tyr Trp Gly Gln Gly Thr Leu Val Thr Val Ser Ser
            485                 490                 495

His His His His His His
            500
```

<210> SEQ ID NO 189
<211> LENGTH: 1515
<212> TYPE: DNA
<213> ORGANISM: artificial sequence
<220> FEATURE:
<223> OTHER INFORMATION: CAIX HL x SEQ ID NO: 170 ; bispecific single
      chain antibody

<400> SEQUENCE: 189

```
gacgtgaagc tcgtggagtc tgggggaggc ttagtgaagc ttggagggtc cctgaaactc      60
tcctgtgcag cctctggatt cactttcagt aactattaca tgtcttgggt tcgccagact     120
ccagagaaga ggctggagtt ggtcgcagcc attaatagtg atggtggtat cacctactat     180
ctagacactg tgaagggccg attcaccatt tcaagagaca atgccaagaa caccctgtac     240
ctgcaaatga gcagtctgaa gtctgaggac acagccttgt tttactgtgc aagacaccgc     300
tcgggctact tttctatgga ctactggggt caaggaacct cagtcaccgt ctcctcaggt     360
ggtggtggtt ctggcggcgg cggctccggt ggtggtggtt ctgacattgt gatgacccag     420
tctcaaagat tcatgtccac aacagtagga gacagggtca gcatcacctg caaggccagt     480
cagaatgtgg tttctgctgt tgcctggtat caacagaaac caggacaatc tcctaaacta     540
ctgatttact cagcatccaa tcggtacact ggagtccctg atcgcttcac aggcagtgga     600
tctgggacag atttcactct caccattagc aatatgcagt ctgaagacct ggctgatttt     660
ttctgtcaac aatatagcaa ctatccgtgg acgttcggtg aggcaccaa gctgaaatc      720 aaatccggag gtggtggctc cgaggtgcag ctggtggagt ctggaggagg attggtgcag     780 cctgagggt cattgaaact ctcatgtgca gcctctggat tcaccttcaa tacctacgcc     840
atgaactggg tccgccaggc tccaggaaag ggtttggaat gggttgctcg cataagaagt     900
aaatataata attatgcaac atattatgcc gattcagtga agacaggtt caccatctcc     960 agagatgatt caaaaacac tgcctatcta caaatgaaca acttgaaaac tgaggacact    1020
gccgtgtact actgtgtgag acatgggaac ttcggtaata gctacgtttc ctggtttgct    1080
tactggggcc aagggactct ggtcaccgtc tcctcaggtg gtggtggttc tggcggcggc    1140
ggctccggtg gtggtggttc tcagaccgtt gtgactcagg aaccttcact caccgtatca    1200
cctggtggaa cagtcacact cacttgtcgc tcgtccactg gggctgttac aactagcaac    1260
tatgccaact gggtccaaca aaaaccaggt caggcacccc gtggtctaat aggtggtacc    1320
```

-continued

```
aacaagcgcg caccaggtac tcctgccaga ttctcaggct ccctgcttgg aggcaaggct    1380
gccctcaccc tctcaggggt acagccagag gatgaggcag aatattactg tgctctatgg    1440
tacagcaacc tctgggtgtt cggtggagga accaaactga ctgtcctaca tcatcaccat    1500
catcattagg tcgac                                                      1515
```

<210> SEQ ID NO 190
<211> LENGTH: 502
<212> TYPE: PRT
<213> ORGANISM: artificial sequence
<220> FEATURE:
<223> OTHER INFORMATION: CAIX HL x SEQ ID NO: 170 ; bispecific single
      chain antibody

<400> SEQUENCE: 190

```
Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Asn Tyr
            20                  25                  30

Tyr Met Ser Trp Val Arg Gln Thr Pro Glu Lys Arg Leu Glu Leu Val
        35                  40                  45

Ala Ala Ile Asn Ser Asp Gly Gly Ile Thr Tyr Tyr Leu Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Phe Tyr Cys
                85                  90                  95

Ala Arg His Arg Ser Gly Tyr Phe Ser Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Ile Val Met Thr Gln Ser Gln Arg Phe
    130                 135                 140

Met Ser Thr Thr Val Gly Asp Arg Val Ser Ile Thr Cys Lys Ala Ser
145                 150                 155                 160

Gln Asn Val Val Ser Ala Val Ala Trp Tyr Gln Gln Lys Pro Gly Gln
                165                 170                 175

Ser Pro Lys Leu Leu Ile Tyr Ser Ala Ser Asn Arg Tyr Thr Gly Val
            180                 185                 190

Pro Asp Arg Phe Thr Gly Ser Gly Ser Gly Thr Asp Phe Thr Leu Thr
        195                 200                 205

Ile Ser Asn Met Gln Ser Glu Asp Leu Ala Asp Phe Phe Cys Gln Gln
    210                 215                 220

Tyr Ser Asn Tyr Pro Trp Thr Phe Gly Gly Gly Thr Lys Leu Glu Ile
225                 230                 235                 240

Lys Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Thr Tyr Ala Met Asn Trp Val Arg Gln Ala Pro
        275                 280                 285

Gly Lys Gly Leu Glu Trp Val Ala Arg Ile Arg Ser Lys Tyr Asn Asn
    290                 295                 300

Tyr Ala Thr Tyr Tyr Ala Asp Ser Val Lys Asp Arg Phe Thr Ile Ser
305                 310                 315                 320
```

| | | | | | | | | | | | | |
|---|---|---|---|---|---|---|---|---|---|---|---|---|
|Arg|Asp|Asp|Ser|Lys|Asn|Thr|Ala|Tyr|Leu|Gln|Met|Asn Asn Leu Lys|
| | | | |325| | | |330| | | |335|

Thr Glu Asp Thr Ala Val Tyr Tyr Cys Val Arg His Gly Asn Phe Gly
340 345 350

Asn Ser Tyr Val Ser Trp Phe Ala Tyr Trp Gly Gln Gly Thr Leu Val
355 360 365

Thr Val Ser Ser Gly Gly Gly Gly Ser Gly Gly Gly Gly Ser Gly Gly
370 375 380

Gly Gly Ser Gln Thr Val Val Thr Gln Glu Pro Ser Leu Thr Val Ser
385 390 395 400

Pro Gly Gly Thr Val Thr Leu Thr Cys Arg Ser Ser Thr Gly Ala Val
405 410 415

Thr Thr Ser Asn Tyr Ala Asn Trp Val Gln Gln Lys Pro Gly Gln Ala
420 425 430

Pro Arg Gly Leu Ile Gly Gly Thr Asn Lys Arg Ala Pro Gly Thr Pro
435 440 445

Ala Arg Phe Ser Gly Ser Leu Leu Gly Gly Lys Ala Ala Leu Thr Leu
450 455 460

Ser Gly Val Gln Pro Glu Asp Glu Ala Glu Tyr Tyr Cys Ala Leu Trp
465 470 475 480

Tyr Ser Asn Leu Trp Val Phe Gly Gly Gly Thr Lys Leu Thr Val Leu
485 490 495

His His His His His His
500

```
<210> SEQ ID NO 191
<211> LENGTH: 1515
<212> TYPE: DNA
<213> ORGANISM: artificial sequence
<220> FEATURE:
<223> OTHER INFORMATION: CAIX LH x SEQ ID NO: 170 ; bispecific single
      chain antibody

<400> SEQUENCE: 191
gacattgtga tgacccagtc tcaaagattc atgtccacaa cagtaggaga cagggtcagc      60
atcacctgca aggccagtca gaatgtggtt tctgctgttg cctggtatca acagaaacca     120
ggacaatctc ctaaactact gatttactca gcatccaatc ggtacactgg agtccctgat     180
cgcttcacag gcagtggatc tgggacagat ttcactctca ccattagcaa tatgcagtct     240
gaagacctgg ctgatttttt ctgtcaacaa tatagcaact atccgtggac gttcggtgga     300
ggcaccaagc tggaaatcaa aggtggtggt ggttctggcg gcggcggctc cggtggtggt     360
ggttctgacg tgaagctcgt ggagtctggg ggaggcttag tgaagcttgg agggtccctg     420
aaactctcct gtgcagcctc tggattcact ttcagtaact attacatgtc ttgggttcgc     480
cagactccag agaagaggct ggagttggtc gcagccatta atagtgatgg tggtatcacc     540
tactatctag acactgtgaa gggccgattc accatttcaa gagacaatgc caagaacacc     600
ctgtacctgc aaatgagcag tctgaagtct gaggacacag ccttgtttta ctgtgcaaga     660
caccgctcgg gctactttte tatggactac tggggtcaag gaacctcagt caccgtctcc     720
tcctccggag gtggtggctc cgaggtgcag ctggtggagt ctggaggagg attggtgcag     780
cctggagggt cattgaaact ctcatgtgca gcctctggat tcaccttcaa tacctacgcc     840
atgaactggg tccgccaggc tccaggaaag ggtttggaat gggttgctcg cataagaagt     900
aaatataata attatgcaac atattatgcc gattcagtga agacaggtt caccatctcc     960
```

```
agagatgatt caaaaaacac tgcctatcta caaatgaaca acttgaaaac tgaggacact    1020
gccgtgtact actgtgtgag acatgggaac ttcggtaata gctacgtttc ctggtttgct    1080
tactggggcc aagggactct ggtcaccgtc tcctcaggtg gtggtggttc tggcggcggc    1140
ggctccggtg gtggtggttc tcagaccgtt gtgactcagg aaccttcact caccgtatca    1200
cctggtggaa cagtcacact cacttgtcgc tcgtccactg gggctgttac aactagcaac    1260
tatgccaact gggtccaaca aaaaccaggt caggcacccc gtggtctaat aggtggtacc    1320
aacaagcgcg caccaggtac tcctgccaga ttctcaggct ccctgcttgg aggcaaggct    1380
gccctcaccc tctcagggct acagccagag gatgaggcag aatattactg tgctctatgg    1440
tacagcaacc tctgggtgtt cggtggagga accaaactga ctgtcctaca tcatcaccat    1500
catcattagg tcgac                                                    1515
```

<210> SEQ ID NO 192
<211> LENGTH: 502
<212> TYPE: PRT
<213> ORGANISM: artificial sequence
<220> FEATURE:
<223> OTHER INFORMATION: CAIX LH x SEQ ID NO: 170 ; bispecific single chain antibody

<400> SEQUENCE: 192

Asp Ile Val Met Thr Gln Ser Gln Arg Phe Met Ser Thr Thr Val Gly
1               5                   10                  15

Asp Arg Val Ser Ile Thr Cys Lys Ala Ser Gln Asn Val Val Ser Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Phe Phe Cys Gln Gln Tyr Ser Asn Tyr Pro Trp
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Asp Val Lys Leu Val Glu
        115                 120                 125

Ser Gly Gly Gly Leu Val Lys Leu Gly Gly Ser Leu Lys Leu Ser Cys
130                 135                 140

Ala Ala Ser Gly Phe Thr Phe Ser Asn Tyr Tyr Met Ser Trp Val Arg
145                 150                 155                 160

Gln Thr Pro Glu Lys Arg Leu Glu Leu Val Ala Ala Ile Asn Ser Asp
                165                 170                 175

Gly Gly Ile Thr Tyr Tyr Leu Asp Thr Val Lys Gly Arg Phe Thr Ile
            180                 185                 190

Ser Arg Asp Asn Ala Lys Asn Thr Leu Tyr Leu Gln Met Ser Ser Leu
        195                 200                 205

Lys Ser Glu Asp Thr Ala Leu Phe Tyr Cys Ala Arg His Arg Ser Gly
    210                 215                 220

Tyr Phe Ser Met Asp Tyr Trp Gly Gln Gly Thr Ser Val Thr Val Ser
225                 230                 235                 240

Ser Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Thr Tyr Ala Met Asn Trp Val Arg Gln Ala Pro
        275                 280                 285

Gly Lys Gly Leu Glu Trp Val Ala Arg Ile Arg Ser Lys Tyr Asn Asn
    290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Val Ser Trp Phe Ala Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Arg Ser Ser Thr Gly Ala Val
                405                 410                 415

Thr Thr Ser Asn Tyr Ala Asn Trp Val Gln Gln Lys Pro Gly Gln Ala
            420                 425                 430

Pro Arg Gly Leu Ile Gly Gly Thr Asn Lys Arg Ala Pro Gly Thr Pro
        435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Ala Leu Trp
465                 470                 475                 480

Tyr Ser Asn Leu Trp Val Phe Gly Gly Gly Thr Lys Leu Thr Val Leu
                485                 490                 495

His His His His His His
            500

<210> SEQ ID NO 193
<211> LENGTH: 747
<212> TYPE: DNA
<213> ORGANISM: artificial sequence
<220> FEATURE:
<223> OTHER INFORMATION: Human-like VL (SEQ ID NO: 168) x Human-like VH
      (SEQ ID NO: 110) scFv ; single chain Fv

<400> SEQUENCE: 193
cagaccgttg tgactcagga accttcactc accgtatcac ctggtggaac agtcacactc      60
acttgtcgct cgtccactgg ggctgttaca actagcaact atgccaactg ggtccaacaa     120
aaaccaggtc aggcaccccg tggtctaata ggtggtacca acaagcgcgc accaggtact     180
cctgccagat tctcaggctc cctgcttgga ggcaaggctg ccctcaccct ctcaggggta     240
cagccagagg atgaggcaga atattactgt gctctatggt acagcaacct ctgggtgttc     300
ggtggaggaa ccaaactgac tgtcctaggt ggtggtggtt ctggcggcgg cggctccggt     360
ggtggtggtt ctgagtgcag ctggtggag tctggaggag gattggtgca gcctggaggg     420
tcattgaaac tctcatgtgc agcctctgga ttcaccttca atacctacgc catgaactgg     480
gtccgccagg ctccaggaaa gggtttggaa tgggttgctc gcataagaag taaatataat     540
aattatgcaa catattatgc cgattcagtg aaagacaggt tcaccatctc cagagatgat     600

```
tcaaaaaaca ctgcctatct acaaatgaac aacttgaaaa ctgaggacac tgccgtgtac    660
tactgtgtga acatgggaa cttcggtaat agctacgttt cctggtttgc ttactggggc    720
caagggactc tggtcaccgt ctcctca                                        747
```

<210> SEQ ID NO 194
<211> LENGTH: 249
<212> TYPE: PRT
<213> ORGANISM: artificial sequence
<220> FEATURE:
<223> OTHER INFORMATION: Human-like VL (SEQ ID NO: 168) x Human-like VH
      (SEQ ID NO: 110) scFv ; single chain Fv

<400> SEQUENCE: 194

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser
                245

<210> SEQ ID NO 195
<211> LENGTH: 13
<212> TYPE: PRT
<213> ORGANISM: artificial sequence
<220> FEATURE:
<223> OTHER INFORMATION: epitope

<400> SEQUENCE: 195

Glu Phe Ser Glu Leu Glu Gln Ser Gly Tyr Tyr Val Cys
1               5                   10

```
<210> SEQ ID NO 196
<211> LENGTH: 13
<212> TYPE: PRT
<213> ORGANISM: artificial sequence
<220> FEATURE:
<223> OTHER INFORMATION: epitope

<400> SEQUENCE: 196

Glu Phe Ser Glu Leu Glu Gln Ser Gly Tyr Tyr Val Lys
1               5                   10

<210> SEQ ID NO 197
<211> LENGTH: 34
<212> TYPE: DNA
<213> ORGANISM: artificial sequence
<220> FEATURE:
<223> OTHER INFORMATION: 5' EGFR XbaI ; oligonucleotide

<400> SEQUENCE: 197
ggtctagagc atgcgaccct ccgggacggc cggg                               34

<210> SEQ ID NO 198
<211> LENGTH: 36
<212> TYPE: DNA
<213> ORGANISM: ARTIFICIAL SEQUENCE
<220> FEATURE:
<223> OTHER INFORMATION: 3' EGFR SalI ; oligonucleotide

<400> SEQUENCE: 198 tttttaagtcg actcatgctc caataaattc actgct                            36

<210> SEQ ID NO 199
<211> LENGTH: 13
<212> TYPE: PRT
<213> ORGANISM: artificial sequence
<220> FEATURE:
<223> OTHER INFORMATION: epitope

<400> SEQUENCE: 199

Gln Asp Gly Asn Glu Glu Met Gly Ser Ile Thr Gln Thr
1               5                   10

<210> SEQ ID NO 200
<211> LENGTH: 13
<212> TYPE: PRT
<213> ORGANISM: artificial sequence
<220> FEATURE:
<223> OTHER INFORMATION: epitope

<400> SEQUENCE: 200

Tyr Tyr Val Ser Tyr Pro Arg Gly Ser Asn Pro Glu Asp
1               5                   10

<210> SEQ ID NO 201
<211> LENGTH: 13
<212> TYPE: PRT
<213> ORGANISM: artificial sequence
<220> FEATURE:
<223> OTHER INFORMATION: epitope

<400> SEQUENCE: 201

Glu Phe Ser Glu Met Glu Gln Ser Gly Tyr Tyr Val Cys
1               5                   10

<210> SEQ ID NO 202
<211> LENGTH: 5
<212> TYPE: PRT
```

```
<213> ORGANISM: artificial sequence
<220> FEATURE:
<223> OTHER INFORMATION: epitope
<220> FEATURE:
<221> NAME/KEY: variation
<222> LOCATION: (4)..(4)
<223> OTHER INFORMATION: /replace= "Met"

<400> SEQUENCE: 202

Phe Ser Glu Leu Glu
1               5

<210> SEQ ID NO 203
<211> LENGTH: 13
<212> TYPE: PRT
<213> ORGANISM: artificial sequence
<220> FEATURE:
<223> OTHER INFORMATION: epitope

<400> SEQUENCE: 203

Gln Tyr Pro Gly Ser Glu Ile Leu Trp Gln His Asn Asp
1               5                   10

<210> SEQ ID NO 204
<211> LENGTH: 5
<212> TYPE: PRT
<213> ORGANISM: artificial sequence
<220> FEATURE:
<223> OTHER INFORMATION: epitope
<220> FEATURE:
<221> NAME/KEY: variation
<222> LOCATION: (4)..(4)
<223> OTHER INFORMATION: /replace="Met"

<400> SEQUENCE: 204

Phe Ser Glu Leu Glu
1               5

<210> SEQ ID NO 205
<211> LENGTH: 5
<212> TYPE: PRT
<213> ORGANISM: artificial sequence
<220> FEATURE:
<223> OTHER INFORMATION: epitope

<400> SEQUENCE: 205

Phe Ser Glu Leu Glu
1               5

<210> SEQ ID NO 206
<211> LENGTH: 5
<212> TYPE: PRT
<213> ORGANISM: artificial sequence
<220> FEATURE:
<223> OTHER INFORMATION: epitope

<400> SEQUENCE: 206

Phe Ser Glu Met Glu
1               5

<210> SEQ ID NO 207
<211> LENGTH: 13
<212> TYPE: PRT
<213> ORGANISM: artificial sequence
<220> FEATURE:
<223> OTHER INFORMATION: epitope
<220> FEATURE:
<221> NAME/KEY: variation
<222> LOCATION: (5)..(5)
```

```
<223> OTHER INFORMATION: /replace="Met"

<400> SEQUENCE: 207

Glu Phe Ser Glu Leu Glu Gln Ser Gly Tyr Tyr Val Cys
1               5                   10
```